US010760105B2

(12) United States Patent
Shaw, IV et al.

(10) Patent No.: US 10,760,105 B2
(45) Date of Patent: Sep. 1, 2020

(54) ENHANCED PRODUCTION OF CORE LIPIDS IN OLEAGINOUS YEASTS

(71) Applicant: NOVOGY, INC., Cambridge, MA (US)

(72) Inventors: Arthur J. Shaw, IV, Belmond, MA (US); Johannes Pieter Van Dijken, Leidschendam (NL); Annapurna Kamineni, Arlington, MA (US); Jonathan Friedlander, Cambridge, MA (US); Vasiliki Tsakraklides, Arlington, MA (US); Maureen Hamilton, Littleton, MA (US); Elena E. Brevnova, Belmont, MA (US)

(73) Assignee: NOVOGY, INC., Cambridge, MA (US)

( * ) Notice: Subject to any disclaimer, the term of this patent is extended or adjusted under 35 U.S.C. 154(b) by 44 days.

(21) Appl. No.: 15/540,916

(22) PCT Filed: Dec. 29, 2015

(86) PCT No.: PCT/US2015/067805

§ 371 (c)(1),
(2) Date: Jun. 29, 2017

(87) PCT Pub. No.: WO2016/109494

PCT Pub. Date: Jul. 7, 2016

(65) Prior Publication Data

US 2017/0369912 A1 Dec. 28, 2017

Related U.S. Application Data

(60) Provisional application No. 62/097,781, filed on Dec. 30, 2014.

(51) Int. Cl.

| | |
|---|---|
| ***C12N 15/63*** | (2006.01) |
| ***C12N 15/81*** | (2006.01) |
| ***C12P 7/64*** | (2006.01) |
| ***C12N 9/10*** | (2006.01) |
| ***C12N 9/12*** | (2006.01) |
| ***C12N 9/16*** | (2006.01) |
| ***C12N 9/88*** | (2006.01) |
| ***C12P 5/00*** | (2006.01) |
| ***C12P 7/04*** | (2006.01) |
| ***C12N 1/20*** | (2006.01) |

(52) U.S. Cl.

CPC .............. *C12P 7/6463* (2013.01); *C12N 1/20* (2013.01); *C12N 9/1029* (2013.01); *C12N 9/1205* (2013.01); *C12N 9/16* (2013.01); *C12N 9/88* (2013.01); *C12P 5/007* (2013.01); *C12P 7/04* (2013.01); *C12P 7/64* (2013.01); *C12P 7/6427* (2013.01)

(58) Field of Classification Search

None

See application file for complete search history.

(56) References Cited

U.S. PATENT DOCUMENTS

| | | | | |
|---|---|---|---|---|
| 2012/0005773 | A1 | 1/2012 | Aasen | 800/275 |
| 2013/0089906 | A1 | 4/2013 | Beck | 435/167 |
| 2013/0197247 | A1 | 8/2013 | Franklin | 554/1 |
| 2013/0344548 | A1 | 12/2013 | Stephanopoulos et al. | 435/134 |
| 2014/0248669 | A1* | 9/2014 | Marliere | C12N 9/88 435/92 |

FOREIGN PATENT DOCUMENTS

| | | |
|---|---|---|
| WO | WO/14/058295 | 4/2014 |
| WO | WO/14/081803 | 5/2014 |
| WO | WO/14/153036 | 9/2014 |

OTHER PUBLICATIONS

International Search Report and Written Opinion in International Application No. PCT/US2015/067805 dated Mar. 21, 2016.

International Preliminary Report on Patentability in International Application No. PCT/US2015/067805 dated Jul. 4, 2017.

* cited by examiner

*Primary Examiner* — Channing S Mahatan
(74) *Attorney, Agent, or Firm* — Albert Shung

(57) ABSTRACT

Disclosed are transformed cells comprising one or more genetic modifications that increase the lipid content of the cell, e.g., relative to an unmodified cell of the same type. Also disclosed are methods for increasing the lipid content of a cell by increasing the activity of one or more proteins in the cell and/or by decreasing the activity of one or more proteins in the cell.

21 Claims, 16 Drawing Sheets

Specification includes a Sequence Listing.

ENHANCED PRODUCTION OF CORE LIPIDS IN OLEAGINOUS YEASTS

RELATED APPLICATION

This application is a national phase application under 35 U.S.C. § 371 of International Application No. PCT/US2015/067805, filed Dec. 29, 2015, which claims the benefit of priority to U.S. Provisional Patent Application Ser. No. 62/097,781 filed Dec. 30, 2014. Both applications are incorporated into the present application by reference.

SEQUENCE LISTING

The instant application contains a Sequence Listing which has been submitted electronically in ASCII format and is hereby incorporated by reference in its entirety. Said ASCII copy, created on Dec. 11, 2015, is named NGX03825SL.txt and is 575,737 bytes in size.

BACKGROUND

Lipids are indispensable ingredients in the food and cosmetics industries, and they are important precursors in the biodiesel and biochemical industries. Many oleaginous microorganisms produce lipids, including the well-characterized yeast *Yarrowia lipolytica.*

Oleaginous microorganisms can be easily and cost-effectively grown on large scale, which suggests broad applicability for biodiesel and biochemical production. Microorganisms may also be engineered to produce high-value products for the food and beverage industries. Further, these products are typically sequestered within the microorganisms, which can facilitate their isolation and purification.

Microorganisms produce lipid products at different rates and with different efficiencies. Lipid production in eukaryotic organisms generally proceeds by the oxidation of pyruvate to acetyl-CoA in the mitochondria via pyruvate dehydrogenase and the subsequent export of acetyl-CoA to the cytosol via the metabolic intermediate citrate. Mitochondrial pyruvate oxidation and citrate export results in a net accumulation of reduced nicotinamide adenine dinucleotide (NADH) in the mitochondria. The accumulation of NADH in the mitochondria is suboptimal for lipid production, however, in part because mitochondrial NADH cannot reduce cytosolic ketones, which results in a lower overall lipid yield.

The lipid yield of oleaginous organisms can be increased by the up-regulation, down-regulation, or deletion of genes implicated in a lipid pathway. The successful modulation of enzymes, however, is unpredictable at best. For example, overexpressing the type 2 diacylglycerol acyltransferase from *Mortierella* alpine in *Y. lipolytica* has no significant effect on lipid content (U.S. Pat. No. 7,198,937; hereby incorporated by reference).

SUMMARY

In some aspects, the invention relates to a transformed cell, comprising a first genetic modification, and a second genetic modification, wherein said first genetic modification increases the activity of a phosphoketolase protein in the cell, and said second genetic modification increases the activity of a phosphate acetyltransferase protein in the cell.

In some embodiments, the invention relates to a transformed cell, comprising a first genetic modification, a second genetic modification, a third genetic modification, and a fourth genetic modification, wherein said first genetic modification increases the activity of a phosphoketolase protein in the cell, said second genetic modification increases the activity of a phosphate acetyltransferase protein in the cell, said third genetic modification increases the activity of a fructose-1,6-bisphosphatase protein in the cell, and said fourth genetic modification decreases the activity of a phosphofructokinase protein in the cell.

In some embodiments, the invention relates to a transformed cell, comprising a first genetic modification, a second genetic modification, and a third genetic modification, wherein said first genetic modification increases the activity of a pyruvate decarboxylase protein in the cell, said second genetic modification increases the activity of a phosphate acetyltransferase protein in the cell, and said third genetic modification increases the activity of an acetate kinase in the cell.

In some embodiments, the invention relates to a transformed cell, comprising a first genetic modification, a second genetic modification, and a third genetic modification, wherein said first genetic modification increases the activity of a citrate/oxaloacetate mitochondrial transporter protein in the cell, said second genetic modification increases the activity of a cytosolic malic enzyme protein in the cell, and said third genetic modification increases the activity of a cytosolic pyruvate carboxylase protein in the cell.

In some embodiments, the invention relates to a transformed cell, comprising a first genetic modification, and a second genetic modification, wherein said first genetic modification increases the activity of a citrate/oxaloacetate mitochondrial transporter protein in the cell, and said second genetic modification increases the NADH-specific enoyl acyl-carrier reductase activity of the cell.

In some aspects, the invention relates to a product derived from a transformed cell of the invention. In some embodiments, the product comprises an oil, lipid, fatty acid, fatty alcohol, triacylglyceride, isoprenoid, or farnesene. The product may comprise stearic acid, oleic acid, linoleic acid, capric acid, caprylic acid, caproic acid, lauric acid, myristic acid, palmitic acid, palmitoleic acid, or squalene. For example, the product may be oleic acid.

In some aspects, the invention relates to methods of increasing the lipid content of a cell, comprising transforming said cell with a first nucleotide sequence that encodes a phosphoketolase protein, and transforming said cell with a second nucleotide sequence that encodes a phosphate acetyltransferase protein.

In some embodiments, the invention relates to methods of increasing the lipid content of a cell, comprising transforming said cell with a first nucleotide sequence that encodes a phosphoketolase protein, transforming said cell with a second nucleotide sequence that encodes a phosphate acetyltransferase protein, transforming said cell with a third nucleotide sequence that encodes a fructose-1,6-bisphosphatase protein, and transforming said cell with a fourth nucleotide sequence that decreases that decreases the activity of a native phosphofructokinase protein in the cell.

In some embodiments, the invention relates to methods of increasing the lipid content of a cell, comprising transforming said cell with a first nucleotide sequence that encodes a pyruvate decarboxylase protein, transforming said cell with a second nucleotide sequence that encodes a phosphate acetyltransferase protein, and transforming said cell with a third nucleotide sequence that encodes an acetate kinase protein.

In some embodiments, the invention relates to methods of increasing the lipid content of a cell, comprising transforming said cell with a first nucleotide sequence that encodes a citrate/oxaloacetate mitochondrial transporter protein, transforming said cell with a second nucleotide sequence that encodes a cytosolic malic enzyme protein, and transforming said cell with a third nucleotide sequence that encodes a cytosolic pyruvate carboxylase protein.

In some embodiments, the invention relates to methods of increasing the lipid content of a cell, comprising transforming said cell with a first nucleotide sequence that encodes a citrate/oxaloacetate mitochondrial transporter protein, and transforming said cell with a second nucleotide sequence. The second nucleotide sequence may either encode a NADH specific enoyl acyl-carrier reductase protein, or the second nucleotide sequence may be capable of recombining with a nucleotide sequence in a native type I fatty acid synthase enoyl reductase gene; and transformation of the cell with the second nucleotide sequence may increase the NADH specific enoyl acyl-carrier reductase activity of the cell.

The transformed cell may be selected from the group consisting of algae, bacteria, molds, fungi, plants, and yeasts. The cell may be a yeast. For example, the cell may be a yeast selected from the group consisting of *Arxula adeninivorans, Saccharomyces cerevisiae*, and *Yarrowia lipolytica.*

These and other features, aspects, and advantages of the present invention will become better understood with reference to the following description, drawings, and claims.

DETAILED DESCRIPTION

Overview

In some aspects, the invention relates to the production of lipids (e.g., neutral lipids and triacylglycerols) in oleaginous yeasts, such as *Yarrowia lipolytica* and *Arxula adeninivorans*. In some aspects, the invention relates to a transformed cell comprising one or more genetic modifications that increase the yield of lipid from glucose in the cell relative to an unmodified cell of the same type. In some aspects, the invention relates to methods of increasing the lipid content of a cell by transforming the cell with one or more nucleotide sequences encoding proteins that increase the yield of lipid from glucose in the cell relative to an unmodified cell of the same type.

In some aspects, the invention relates to a transformed cell comprising one or more metabolically engineered pathways that more efficiently produce a metabolic precursor used to synthesize lipid molecules, e.g., acetyl co-enzyme A (acetyl-CoA), reduced nicotinamide adenine dinucleotide phosphate (NADPH), NADH, and adenosine triphosphate (ATP), relative to unmodified cells of the same type. In some aspects, the invention relates to methods of increasing the lipid content of a cell by transforming the cell with one or more nucleotide sequences that encode proteins that catalyze or otherwise accomplish one or more steps in a metabolic pathway that produces a metabolic precursor, e.g., acetyl-CoA, NADPH, NADH, or ATP.

Figure 1:
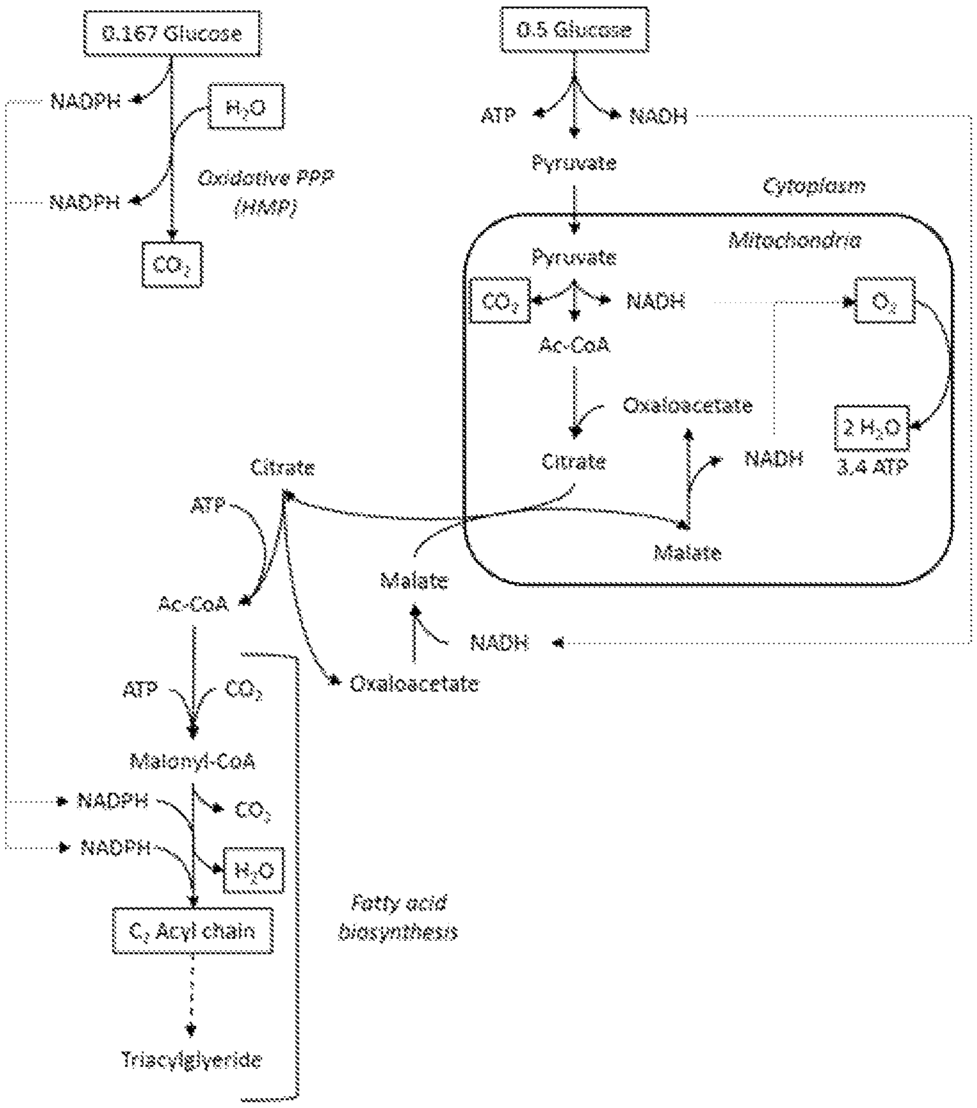
FIG. 1 depicts pathways for generation of acetyl-CoA and NADPH in unmodified yeast.

Pyruvate oxidation within the mitochondria and the export of acetyl-CoA via the metabolic intermediate citrate from the mitochondria to the cytosol results in net accumulation of NADH in the mitochondrion (FIG. 1). This accumulation is unfavorable for obtaining high cellular lipid contents as reducing equivalents (e.g., NADH and NADPH) must be available in the cytosol for the reduction of the acetyl group to an acyl group on the growing fatty acid chain. The preferred electron carrier for this reduction is NADPH, localized to the cytoplasm. In some aspects, the invention relates to a transformed cell comprising one or more genetic modifications that increase the NADPH production (e.g., cytosolic NADPH production) in the cell relative to an unmodified cell of the same type. In some aspects, the invention relates to methods of increasing the lipid content of a cell by transforming the cell with one or more nucleotide sequences encoding proteins that increase the NADPH production (e.g., cytosolic NADPH production) in the cell relative to an unmodified cell of the same type. In some aspects, the invention relates to transformed cells comprising one or more genetic modifications that increase the utilization of cytosolic NADH and/or cytosolic NADPH in lipid production relative to an unmodified cell of the same type. In some aspects, the invention relates to methods of increasing the lipid content of a cell by transforming the cell with one or more nucleotide sequences encoding proteins that increase the utilization of cytosolic NADH and/or cytosolic NADPH in lipid production.

Definitions

The articles "a" and "an" are used herein to refer to one or to more than one (i.e., to at least one) of the grammatical object of the article. By way of example, "an element" means one element or more than one element.

The term "activity" refers to the total capacity of a cell to perform a function. For example, a genetic modification that decreases the activity of an enzyme in a cell may reduce the amount of the enzyme in a cell or reduce the efficiency of the enzyme. A knockout reduces the activity of a protein by reducing the amount of the protein in the cell. Alternatively, a mutation to a gene may reduce the efficiency of its protein product with little effect on the amount of the protein in the cell. Mutations that reduce the efficiency of an enzyme may affect the active site, for example, by changing one or more active site residues; they may impair the enzyme's kinetics, for example, by sterically blocking substrates or products; they may affect protein folding or dynamics, for example, by reducing the proportion of properly-folded enzymes; they may affect protein localization, for example, by preventing the protein from localizing to lipid particles; or they may affect protein degradation, for example, by adding one or more protein cleavage sites or by adding one or more residues or amino acid sequences that target the protein for proteolysis. These mutations affect coding regions. Mutations that decrease the activity of a protein may instead affect the transcription or translation of the gene. For example, mutation of an enhancer or promoter can reduce the activity of a protein by reducing its expression. Mutating or deleting the non-coding portions of a gene, such as its introns, may also reduce transcription or translation. Additionally, mutations to the upstream regulators of a gene may affect the activity of its protein product; for example, the over-expression of one or more repressors may decrease the activity of a protein, and a knockout or mutation of one or more activators may similarly decrease the activity of a protein.

A genetic modification that increases the activity of a protein in a cell may increase the amount of the protein in the cell or increase the efficiency of the protein (e.g., the efficiency of an enzyme). For example, the genetic modification may simply insert an additional copy of the protein into the cell such that the additional copy is transcribed and translated into additional functional protein. The added gene can be native to the host organism or from a different organism. Alternatively, mutating or deleting the non-coding portions of a gene, such as its introns, may also increase translation. A native gene can be altered by adding a new promoter that causes more transcription. Similarly, enhancers may be added to the gene to increase transcription, or silencers may be mutated or deleted from the gene to increase transcription. Mutations to a native gene's coding region might also increase the activity of the protein, for example, by producing a protein variant that does not interact with inhibitory proteins or molecules. The over-expression of one or more activators may increase the activity of a protein by increasing the expression of the protein, and a knockout or mutation of one or more repressors may similarly increase the activity of the protein.

The term "biologically-active portion" refers to an amino acid sequence that is less than a full-length amino acid sequence, but exhibits at least one activity of the full length sequence. For example, a biologically-active portion of a phosphoketolase may refer to one or more domains of a phosphoketolase having biological activity for converting xylulose-5-phosphate to glyceraldehyde-3-phosphate. Biologically-active portions of a protein include peptides or polypeptides comprising amino acid sequences sufficiently identical to or derived from the amino acid sequence of the protein, e.g., the amino acid sequence set forth in SEQ ID NOs: 1, 3, 5, 7, 9, 11, 13, 15, 17, 19, 21, 23, 25, 27, 29, 31, 121, 123, or 125, which include fewer amino acids than the full length protein, and exhibit at least one activity of the protein. Similarly, biologically-active portions of a protein include peptides or polypeptides comprising amino acid sequences sufficiently identical to or derived from the amino acid sequence of the protein, e.g., an amino acid sequence set forth in SEQ ID NO: 1, 3, 5, 7, 9, 11, 13, 15, 17, 19, 21, 23, 25, 27, 29, 31, 121, 123, or 125, which include fewer amino acids than the full length protein, and exhibit at least one activity of the protein. A biologically-active portion of a protein may comprise, for example, at least 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700 or more amino acids. Typically, biologically-active portions comprise a domain or motif having a catalytic activity, such as catalytic activity for producing a molecule in a fatty acid biosynthesis pathway, or having a transporter activity, such as for mitochondrial transport. A biologically-active portion of a protein includes portions of the protein that have the same activity as the full-length peptide and every portion that has more activity than background. For example, a biologically-active portion of an enzyme may have 0.1%, 0.5%, 1%, 2%, 3%, 4%, 5%, 10%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5%, 99.6%, 99.7%, 99.8%, 99.9%, 100%, 100.1%, 100.2%, 100.3%, 100.4%, 100.5%, 100.6%, 100.7%, 100.8%, 100.9%, 101%, 105%, 110%, 115%, 120%, 125%, 130%, 135%, 140%, 145%, 150%, 160%, 170%, 180%, 190%, 200%, 220%, 240%, 260%, 280%, 300%, 320%, 340%, 360%, 380%, 400% or higher activity relative to the full-length enzyme. A biologically-active portion of a protein may include portions of a protein that lack a domain that targets the protein to a cellular compartment. A biologically active portion of a phosphate acetyltransferase protein can be a polypeptide which is, for example, 310 amino acids in length.

The term "domain" refers to a part of the amino acid sequence of a protein that is able to fold into a stable three-dimensional structure independent of the rest of the protein.

The term "drug" refers to any molecule that inhibits cell growth or proliferation, thereby providing a selective advantage to cells that contain a gene that confers resistance to the drug. Drugs include antibiotics, antimicrobials, toxins, and pesticides.

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

The term "encode" refers to nucleic acids that comprise a coding region, portion of a coding region, or compliments thereof. Both DNA and RNA may encode a gene. Both DNA and RNA may encode a protein.

The term "enzyme" as used herein refers to a protein that can catalyze a chemical reaction.

The term "exogenous" refers to anything that is introduced into a cell. An "exogenous nucleic acid" is a nucleic acid that entered a cell through the cell membrane. An exogenous nucleic acid may contain a nucleotide sequence that exists in the native genome of a cell and/or nucleotide sequences that did not previously exist in the cell's genome. Exogenous nucleic acids include exogenous genes. An "exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from the same or different species relative to the cell being transformed. Thus, an exogenous gene can include a native gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

The term "expression" refers to the amount of a nucleic acid or amino acid sequence (e.g., peptide, polypeptide, or protein) in a cell. The increased expression of a gene refers to the increased transcription of that gene. The increased expression of an amino acid sequence, peptide, polypeptide, or protein refers to the increased translation of a nucleic acid encoding the amino acid sequence, peptide, polypeptide, or protein.

The term "gene," as used herein, may encompass genomic sequences that contain exons, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence. In other embodiments, the genes are synthesized, non-native cDNA wherein the codons have been optimized for expression in *Y. lipolytica* based on codon usage. The term can further include nucleic acid molecules comprising upstream, downstream, and/or intron nucleotide sequences.

The term "genetic modification" refers to the result of a transformation. Every transformation causes a genetic modification by definition.

The term "homolog", as used herein, refers to (a) peptides, oligopeptides, polypeptides, proteins, and enzymes having amino acid substitutions, deletions and/or insertions relative to the unmodified protein in question and having similar biological and functional activity as the unmodified protein from which they are derived, and (b) nucleic acids which encode peptides, oligopeptides, polypeptides, proteins, and enzymes with the same characteristics described in (a).

"Inducible promoter" is a promoter that mediates the transcription of an operably linked gene in response to a particular stimulus.

The term "integrated" refers to a nucleic acid that is maintained in a cell as an insertion into the cell's genome, such as insertion into a chromosome, including insertions into a plastid genome.

"In operable linkage" refers to a functional linkage between two nucleic acid sequences, such a control sequence (typically a promoter) and the linked sequence (typically a sequence that encodes a protein, also called a coding sequence). A promoter is in operable linkage with a gene if it can mediate transcription of the gene.

The term "knockout mutation" or "knockout" refers to a genetic modification that prevents a native gene from being transcribed and translated into a functional protein.

The term "native" refers to the composition of a cell or parent cell prior to a transformation event. A "native gene" refers to a nucleotide sequence that encodes a protein that has not been introduced into a cell by a transformation event. A "native protein" refers to an amino acid sequence that is encoded by a native gene.

The terms "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The acronym "ORF" stands for open reading frame.

The term "parent cell" refers to every cell from which a cell descended. The genome of a cell is comprised of the parent cell's genome and any subsequent genetic modifications to parent the cell's genome.

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

The term "portion" refers to peptides, oligopeptides, polypeptides, protein domains, and proteins. A nucleotide sequence encoding a "portion of a protein" includes both nucleotide sequences that can be transcribed and/or translated and nucleotide sequences that must undergo one or more recombination events to be transcribed and/or translated. For example, a nucleic acid may comprise a nucleotide sequence encoding one or more amino acids of a selectable marker protein. This nucleic acid can be engineered to recombine with one or more different nucleotide sequences that encode the remaining portion of the protein. Such nucleic acids are useful for generating knockout mutations because only recombination with the target sequence is likely to reconstitute the full-length selectable marker gene whereas random-integration events are unlikely to result in a nucleotide sequence that can produce a functional marker protein.

A "promoter" is a nucleic acid control sequence that directs the transcription of a nucleic acid. As used herein, a promoter includes the necessary nucleic acid sequences near the start site of transcription. A promoter also optionally includes distal enhancer or repressor elements, which can be located as much as several thousand base pairs from the start site of transcription.

The term "protein" refers to molecules that comprise an amino acid sequence, wherein the amino acids are linked by peptide bonds.

"Recombinant" refers to a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The term "regulatory region" refers to nucleotide sequences that affect the transcription or translation of a gene but do not encode an amino acid sequence. Regulatory regions include promoters, operators, enhancers, and silencers.

The term "substantially identical" refers to a nucleotide or amino acid sequence that encodes a biologically-active portion of a protein, which has 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence identity with a reference sequence. For enzymes, a substantially identical sequence typically retains the enzymatic activity of the reference sequence. For example, a sequence is substantially identical to a reference sequence if it encodes an enzyme that has between 10% and 1,000% of the enzymatic activity of the reference enzyme.

"Transformation" refers to the transfer of a nucleic acid into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The terms "triacylglyceride," "triacylglycerol," "triglyceride," and "TAG" are esters comprised of glycerol and three fatty acids.

The term "vector" refers to the means by which a nucleic acid can be propagated and/or transferred between organisms, cells, or cellular components. Vectors include plasmids, linear DNA fragments, viruses, bacteriophage, proviruses, phagemids, transposons, and artificial chromosomes, and the like, that may or may not be able to replicate autonomously or integrate into a chromosome of a host cell.

Microbe Engineering

A. Overview

In certain embodiments of the invention, a microorganism is genetically modified to increase its lipid content.

Genes and gene products may be introduced into microbial host cells. Suitable host cells for expression of the genes and nucleic acid molecules are microbial hosts that can be found broadly within the fungal or bacterial families. Examples of suitable host strains include but are not limited to fungal or yeast species, such as *Arxula, Aspegillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia*, or bacterial species, such as members of proteobacteria and actinomycetes, as well as the genera *Acinetobacter, Arthrobacter, Brevibacterium, Acidovorax, Bacillus, Clostridia, Streptomyces, Escherichia, Salmonella, Pseudomonas*, and *Cornyebacterium*. *Yarrowia lipolytica* and *Arxula adeninivorans* are suited for use as a host microorganism because they can accumulate a large percentage of their weight as triacylglycerols.

Microbial expression systems and expression vectors containing regulatory sequences that direct high level expression of foreign proteins are known to those skilled in the art. Any of these could be used to construct chimeric genes to produce any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and an aforementioned starting parent strain as a host can be transformed with the resulting plasmid. This approach can increase the copy number of each of the genes encoding the enzymes and, as a result, the activities of the enzymes can be increased. The plasmid is not particularly limited so long as it renders a desired genetic modification inheritable to the microorganism's progeny.

Vectors or cassettes useful for the transformation of suitable host cells are well known in the art. Typically the vector or cassette contains sequences that direct the transcription and translation of the relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. It is preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (Green & Sambrook, *Molecular Cloning: A Laboratory Manual*, (4th ed., 2012); U.S. Pat. No. 4,683,202; incorporated by reference). Alternatively, elements can be generated synthetically using known methods (Gene 164:49-53 (1995)).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has many practical implications for what can be carried out at the molecular genetic level and is useful in the generation of a microbe that can produce a desired product. By its nature homologous recombination is a precise gene targeting event and, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements, such as promoters/UTRs, to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion, and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transforming microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in operable linkage with the coding sequence of interest, the coding sequence can be transformed into the cells such that it becomes operably linked to an endogenous promoter at the point of vector integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chen & Orozco, Nucleic Acids Research 16:8411 (1988)).

2. Genes and Codon Optimization

Typically, a gene includes a promoter, a coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA.

C. Transformation

Cells can be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of expression of transgenes in oleaginous yeast (e.g., *Yarrowia lipolytica*) can be found in the literature (Bordes et al., J. Microbiological Methods, 70:493 (2007); Chen et al., Applied Microbiology & Biotechnology 48:232 (1997)). Examples of expression of exogenous genes in bacteria such as *E. coli* are well known (Green & Sambrook, *Molecular Cloning: A Laboratory Manual*, (4th ed., 2012)).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

D. Nucleic Acids and Methods of Increasing the Activity of a Protein

The genes of the invention may comprise conservative substitutions, deletions, and/or insertions while still encoding a protein that has activity. For example, codons may be optimized for a particular host cell, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions.

Proteins may comprise conservative substitutions, deletions, and/or insertions while still maintaining activity. Conservative substitution tables are well known in the art (Creighton, *Proteins* (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

To determine the percent identity of two amino acid sequences or of two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences can be determined using the Needleman and Wunsch (J. Molecular Biology 48:444-453 (1970)) algorithm which has been incorporated into the GAP program in the GCG software package (available at the World Wide Web address: gcg.com), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences can be determined using the GAP program in the GCG software package (available at the World Wide Web address: gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0U), using a PAM120 weight residue table, a gap length penalty of 12 and a gap penalty of 4

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, e.g., ClustalW, ClustalX, and Clustal Omega.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

Amino acid and nucleotide sequences may be derived from oleaginous organisms having high, native levels of lipid accumulation. (Bioresource Technology 144:360-69 (2013); Progress Lipid Research 52:395-408 (2013); Applied Microbiology & Biotechnology 90:1219-27 (2011); European Journal Lipid Science & Technology 113:1031-51 (2011); Food Technology & Biotechnology 47:215-20 (2009); Advances Applied Microbiology 51:1-51 (2002); Lipids 11:837-44 (1976)). A list of organisms with a reported lipid content of about 50% and higher is shown in Table 1. *R. toruloides* and *L. starkeyi* have the highest lipid content.

TABLE 1

| List of oleaginous fungi with reported lipid contents of about 50% and above. Fungi with reported high lipid content |
|---|
| *Aspergillus terreus* |
| *Aurantiochytrium limacinum* |
| *Claviceps purpurea* |
| *Cryptococcus albidus* |
| *Cryptococcus curvatus* |
| *Cryptococcus ramirezgomezianus* |
| *Cryptococcus terreus* |
| *Cryptococcus wieringae* |
| *Cunninghamella echinulata* |
| *Cunninghamella japonica* |
| *Leucosporidiella creatinivora* |
| *Lipomyces lipofer* |
| *Lipomyces starkeyi* |
| *Lipomyces tetrasporus* |
| *Mortierella isabellina* |
| *Prototheca zopfii* |
| *Rhizopus arrhizus* |
| *Rhodosporidium babjevae* |
| *Rhodosporidium paludigenum* |
| *Rhodosporidium toruloides* |
| *Rhodotorula glutinis* |
| *Rhodotorulo mucilaginosa* |
| *Tremella enchepala* |
| *Trichosporon cutaneum* |
| *Trichosporon fermentans* |

A protein's activity may be increased by overexpressing the protein. Proteins may be overexpressed in a cell using a variety of genetic modifications. In some embodiments, the genetic modification increases the expression of a native protein. A native protein may be overexpressed by modifying the upstream transcription regulators of the gene that encodes the protein, for example, by increasing the expression of a transcription activator or decreasing the expression of a transcription repressor. Alternatively, the promoter of a native gene may be substituted with a constitutively active or inducible promoter by recombination with an exogenous nucleic acid.

In some embodiments, a genetic modification that increases the activity of a protein comprises transformation with a nucleic acid that comprises a gene that encodes the protein. The gene may be native to the cell or from a different species. In certain embodiments, the gene is inheritable to the progeny of a transformed cell. In some embodiments, the gene is inheritable because it resides on a plasmid. In certain embodiments, the gene is inheritable because it is integrated into the genome of the transformed cell.

E. Nucleic Acids and Methods of Decreasing the Activity of a Native Protein

In some embodiments, the transformed oleaginous cell comprises a genetic modification that decreases the activity of a native protein. Such genetic modifications may affect a protein that regulates the transcription of the native protein, including modifications that decrease the expression of a transcription activator and/or increase the expression of a transcription repressor. Modifications that affect a regulator protein may both decrease the expression of the native protein and alter other gene expression profiles that shift the cellular equilibrium toward increased oleic acid accumulation. Alternatively, the genetic modification may be the introduction of an interfering nucleic acid, such as a small interfering RNA, or a nucleic acid that encodes an interfering nucleic acid. In other embodiments, the genetic modification consists of the homologous recombination of a nucleic acid and the regulatory region of a gene that encodes the native protein. The regulatory region of the gene may include an operator, promoter, sequences upstream from the promoter, enhancers, and/or sequences downstream of the gene.

In some embodiments the transformed oleaginous cell comprises a genetic modification consisting of a homologous recombination event. In certain embodiments, the transformed cell comprises a genetic modification consisting of a homologous recombination event between a native gene and a nucleic acid. Thus, the genetic modification deletes the native gene, prevents its transcription, or prevents the transcription of a gene that can be translated into a fully-active protein. A homologous recombination event may mutate or delete a portion of a native gene. For example, the homologous recombination event may mutate one or more residues in the active site of a native enzyme, thereby reducing the efficiency of the enzyme or rendering it inactive. Alternatively, the homologous recombination event may affect post-translational modification, folding, stability, or localization within the cell. In some embodiments, the homologous recombination event replaces the promoter with a promoter that drives less transcription. In other embodiments, the homologous recombination event mutates the promoter to impair its ability to drive transcription. In certain embodiments, the genetic modification is a knockout mutation.

A knockout mutation may delete one or more genes. Additionally, the knockout mutation may substitute a native gene with an exogenous gene that encodes a different protein. The exogenous gene may be operably linked to an exogenous promoter. In certain embodiments, the gene is not linked to an exogenous promoter, and instead, the gene is configured to recombine with the native gene such that the native gene's promoter drives transcription of the exogenous gene. Thus, the gene is less likely to be expressed if it randomly integrates into the cell's genome. Methods for creating knockouts are well-known in the art (See, e.g., Fickers et al., J. Microbiological Methods 55:727 (2003)).

In certain embodiments, the genetic modification comprises two homologous recombination events. In the first event, a nucleic acid encoding a portion of a gene recombines with the native gene, and in the second event, a nucleic acid encoding the remaining portion of the gene recombines with the native gene. The two portions of the gene are designed such that neither portion is functional unless they recombine with each other. These two events further reduce the likelihood that the gene can be expressed following random integration events.

In certain embodiments, the gene encodes a marker protein, such as a dominant selectable marker. Thus, knockout cells may be selected by screening for the marker. In some embodiments, the dominant selectable marker is a drug resistance marker. A drug resistance marker is a dominant selectable marker that, when expressed by a cell, allows the cell to grow and/or survive in the presence of a drug that would normally inhibit cellular growth and/or survival. Cells expressing a drug resistance marker can be selected by growing the cells in the presence of the drug. In some embodiments, the drug resistance marker is an antibiotic resistance marker. In some embodiments, the drug resistance marker confers resistance to a drug selected from the group consisting of Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Benzoic acid, Ciclopirox, Flucytosine, 5-fluorocytosine, Griseofulvin, Haloprogin, Polygodial, Tolnaftate, Crystal violet, Amikacin, Gentamicin, Kanamycin, Neomycin, Netilmicin, Tobramycin, Paromomycin, Spectinomycin, Geldanamycin, Herbimycin, Rifaximin, Streptomycin, Loracarbef, Ertapenem, Doripenem, Imipenem, Meropenem, Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, clavulanate, sulbactam, tazobactam, clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole, Co-trimoxazole, Sulfonamidochrysoidine, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Metronidazole, Mupirocin, Platensimycin, Quinupristin, Dalfopristin, Thiamphenicol, Tigecycline, Tinidazole, Trimethoprim, Geneticin, Nourseothricin, Hygromycin, Bleomycin, and Puromycin.

In some embodiments, the dominant selectable marker is a nutritional marker. A nutritional marker is a dominant selectable marker that, when expressed by the cell, enables the cell to grow or survive using one or more particular nutrient sources. Cells expressing a nutritional marker can be selected by growing the cells under limiting nutrient conditions in which cells expressing the nutritional marker can survive and/or grow, but cells lacking the nutrient marker cannot. In some embodiments, the nutritional marker is selected from the group consisting of Orotidine 5-phosphate decarboxylase, Phosphite specific oxidoreductase, Alpha-ketoglutarate-dependent hypophosphite dioxygenase, Alkaline phosphatase, Cyanamide hydratase, Melamine deaminase, Cyanurate amidohydrolase, Biuret hydrolyase, Urea amidolyase, Ammelide aminohydrolase, Guanine deaminase, Phosphodiesterase, Phosphotriesterase, Phosphite hydrogenase, Glycerophosphodiesterase, Parathion hydrolyase, Phosphite dehydrogenase, Dibenzothiophene desulfurization enzyme, Aromatic desulfinase, FMN reductase, NADH-dependent FMN reductase, Aminopurine transporter, Hydroxylamine oxidoreductase, Invertase, Beta-glucosidase, Alpha-glucosidase, Beta-galactosidase, Alpha-galactosidase, Amylase, Cellulase, and Pullulonase.

Different approaches may be used to knockout a gene in a yeast cell (See, e.g., Dulermo et al., Biochimica Biophysica Acta 1831:1486 (2013)). The methods disclosed herein and other methods known in the art may be used to knockout different genes in other species, such as *Arxula adeninivorans*.

In some embodiments, a genetic modification decreases the expression of a native gene by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the efficiency of a native protein by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

In some embodiments, a genetic modification decreases the activity of a native protein by 0.1, 0.2, 0.3, 0.4, 0.5, 0.6, 0.7, 0.8, 0.9, 1, 2, 3, 4, 5, 6, 7, 8, 9, 10, 25, 30, 35, 40, 45, 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, or 100 percent.

Exemplary Cells, Nucleic Acids, and Methods

A. Transformed Cell

In some embodiments, the transformed cell is a prokaryotic cell, such as a bacterial cell. In some embodiments, the cell is a eukaryotic cell, such as a mammalian cell, a yeast cell, a filamentous fungi cell, a protist cell, an algae cell, an avian cell, a plant cell, or an insect cell. In some embodiments, the cell is a yeast. Those with skill in the art will recognize that many forms of filamentous fungi produce yeast-like growth, and the definition of yeast herein encompasses such cells.

The cell may be selected from the group consisting of *Arxula, Aspegillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia*.

In some embodiments, the cell is selected from the group of consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, and *Yarrowia lipolytica*.

In certain embodiments, the cell is *Saccharomyces cerevisiae, Yarrowia lipolytica*, or *Arxula adeninivorans*. In certain embodiments, the cell is not *Saccharomyces cerevisiae*.

In some embodiments, the cell is a yeast, fungus, or yeast-like algae. The cell may be selected from thraustochytrids (*Aurantiochytrium*) and achlorophylic unicellular algae (*Prototheca*).

In certain embodiments, the transformed cell comprises at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, or more lipid as measured by % dry cell weight.

B. Cells Comprising Phosphoketolase and Phosphate Acetyltransferase Activity

Figure 2:
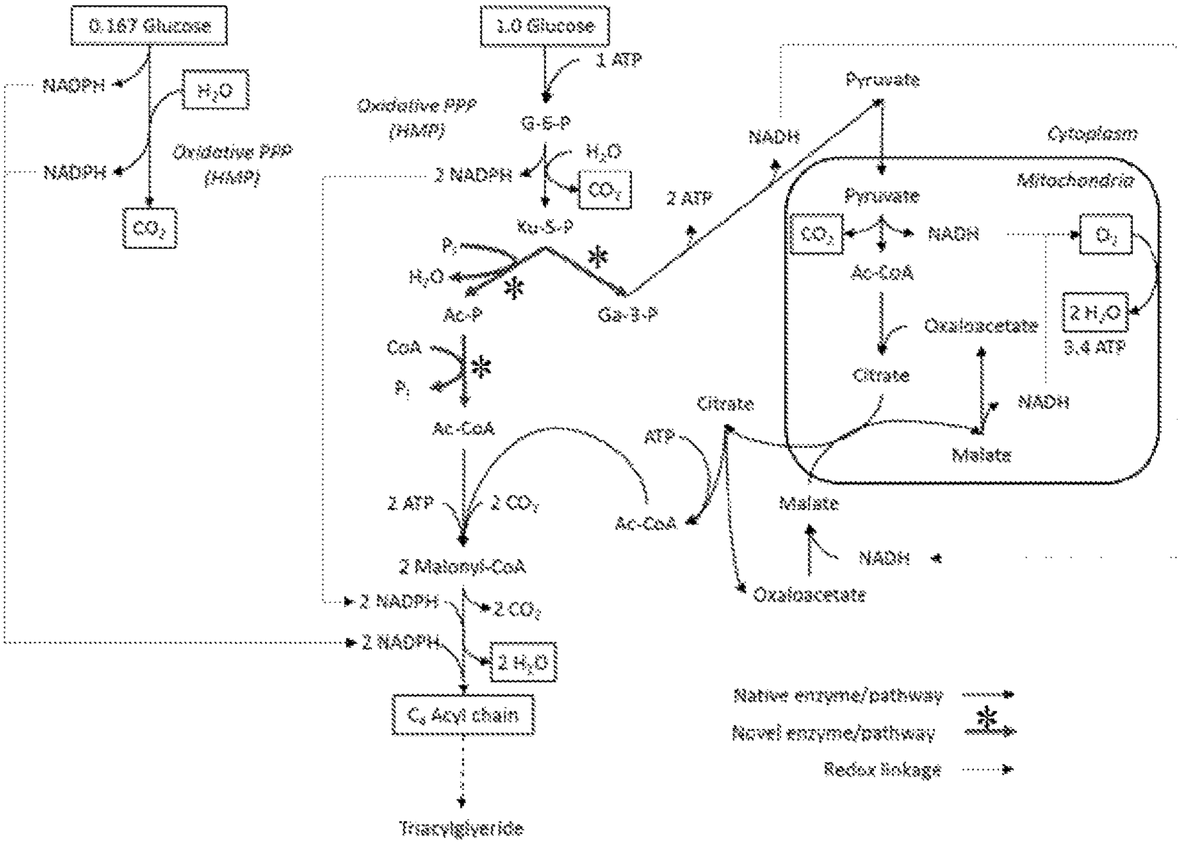
FIG. 2 depicts a novel phosphoketolase pathway.
Figure 3:
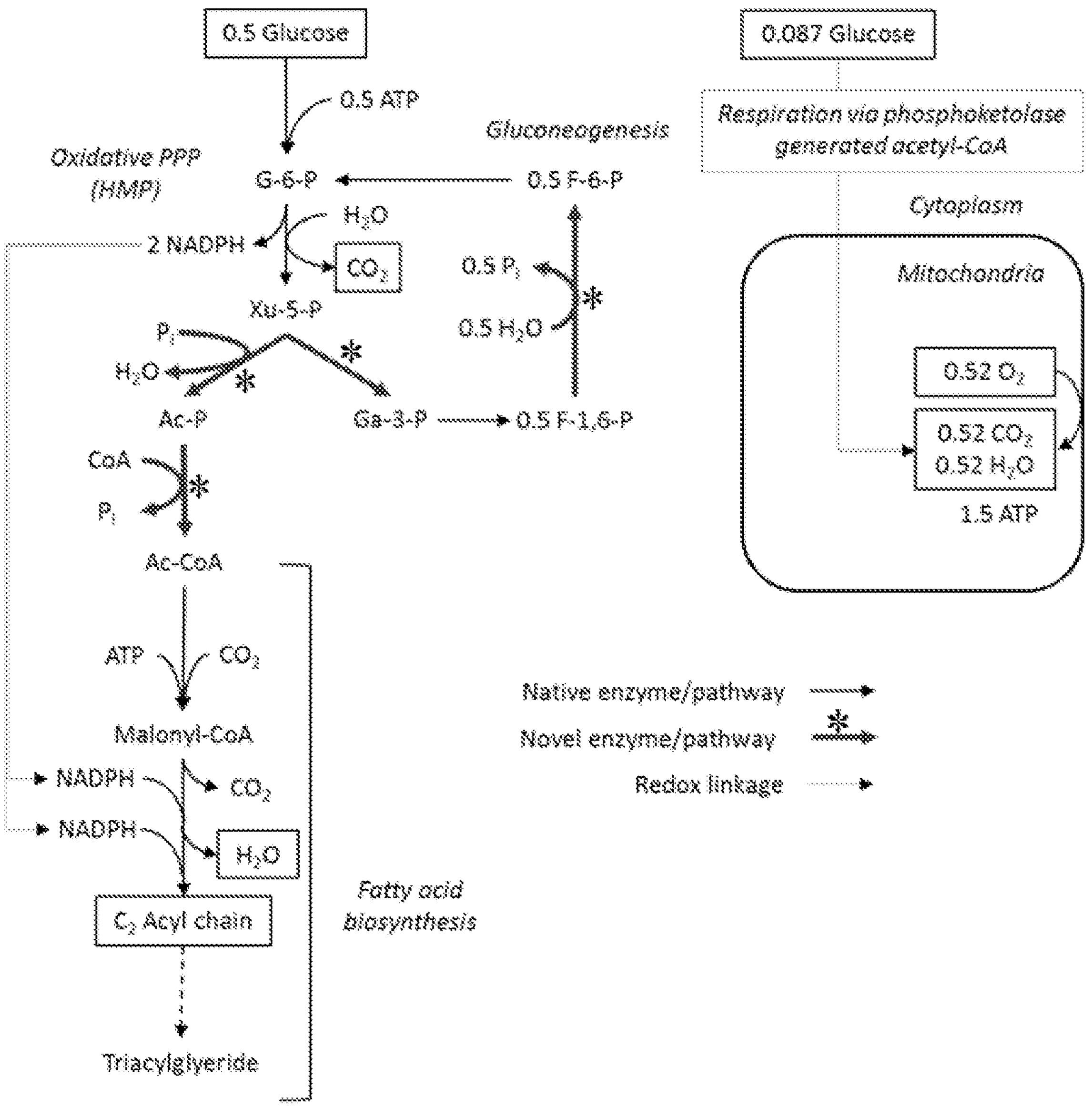
FIG. 3 depicts a novel phosphoketolase pathway.

Cells comprising phosphoketolase and phosphate acetyltransferase activity can catalyze the conversion of xylulose-5-phosphate to acetyl-CoA, which allows the cell to produce acetyl-CoA from glucose in the cytoplasm, thereby increasing cytosolic NADPH relative to cells that rely on the mitochondrial pathway (FIGS. 2 and 3).

Three versions of phosphoketolase exist, those acting on the five carbon xylulose-5-phosphate (X-5-P), EC 4.1.2.9, those acting on the six carbon fructose-6-phosphate (F-6-P), EC 4.1.2.22, and those with bifunctional activity on both substrates. The 6-carbon phosphoketolase together with a transketolase (EC 2.2.1.1), which is present in all microorganisms, catalyze reactions with the same net conversion of xylulose-5-phosphate to acetyl phosphate (Ac-P) and glyceraldehyde-3-phosphate (Ga-3-P) as the 5-carbon phosphoketolase. Transketolase coverts xylulose-5-phosphate (X-5-P) and erythrose-4-phosphate (E-4-P) to fructose-6-phosphate (F-6-P) and glyceraldehyde-3-phosphate (Ga-3-P).

i) EC 4.1.2.9 X-5-P+Pi→Ac-P+Ga-3-P+H2O ii) EC 4.1.2.22 F-6-P+Pi→Ac-P+E-4-P+H2O

EC 2.2.1.1 X-5-P+E-4-P→F-6-P+Ga-3-P

Net: X-5-P+Pi→Ac-P+Ga-3-P+H2O

Methods of introducing genes that encode phosphoketolase and phosphate acetyltransferase proteins into a cell are known in the art (See, e.g., U.S. Patent Application Publication No. 2012/0156735; hereby incorporated by reference).

In some embodiments, the invention relates to a transformed cell, comprising a first genetic modification, and a second genetic modification, wherein said first genetic modification increases the activity of a phosphoketolase protein in the cell, and said second genetic modification increases the activity of a phosphate acetyltransferase protein in the cell. In some embodiments, the transformed cell can catalyze the phosphoketolase/phosphate acetyltransferase pathway described above. In some embodiments, the transformed cell does not catalyze a phosphoketolase/phosphate acetyltransferase pathway, e.g., the cell may utilize either the phosphoketolase and/or phosphate acetyltransferase proteins to convert xylulose-5-phosphate, fructose-6-phosphate, or different substrates (e.g., different sugars) into acetyl phosphate and glyceraldehyde-3-phosphate or different products; or, e.g., the cell may serve as a host cell for molecular cloning.

In some embodiments, the invention relates to methods of increasing the lipid content of a cell, comprising transforming said cell with a first nucleotide sequence that encodes a phosphoketolase protein, and transforming said cell with a second nucleotide sequence that encodes a phosphate acetyltransferase protein. The method may increase the lipid content of the cell by completing the phosphoketolase/phosphate acetyltransferase pathway described above. In some embodiments, the method increases the lipid content of the cell through a molecular pathway other than the phosphoketolase/phosphate acetyltransferase pathway, e.g., the transformed cell may utilize either the phosphoketolase and/or phosphate acetyltransferase proteins to convert xylulose-5-phosphate, fructose-6-phosphate, or different substrates (e.g., different sugars) into acetyl phosphate and glyceraldehyde-3-phosphate or different products. The phosphoketolase and/or phosphate acetyltransferase may catalyze steps in a different metabolic pathway, for example, such as a metabolic pathway that tends to increase lipid biosynthesis or decrease lipid degradation.

In some embodiments, the phosphoketolase protein is classified by Enzyme Commission number EC 4.1.2.9 or EC 4.1.2.22.

The phosphoketolase protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, or a biologically active portion of any one of them. For example, the phosphoketolase protein may be substantially identical to SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, and retain the functional activity of the protein of SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, yet differ in amino acid sequence, e.g., due to either natural allelic variation or mutagenesis. In some embodiments, the phosphoketolase protein comprises the amino acid sequence set forth in SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125.

The first genetic modification may be transformation with a first nucleic acid, and the first nucleic acid may encode a phosphoketolase protein, i.e., the first nucleic acid may comprise a first nucleotide sequence that encodes a phosphoketolase protein.

In some embodiments, the first nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:22, SEQ ID NO:24, SEQ ID NO:26, SEQ ID NO:28, SEQ ID NO:30, SEQ ID NO:32, SEQ ID NO:122, SEQ ID NO:124, or SEQ ID NO:126. For example, the first nucleotide sequence may have the sequence set forth in SEQ ID NO:22, SEQ ID NO:24, SEQ ID NO:26, SEQ ID NO:28, SEQ ID NO:30, SEQ ID NO:32, SEQ ID NO:122, SEQ ID NO:124, or SEQ ID NO:126. In some embodiments, the first nucleotide sequence is substantially identical to the sequence set forth in SEQ ID NO:22, SEQ ID NO:24, SEQ ID NO:26, SEQ ID NO:28, SEQ ID NO:30, SEQ ID NO:32, SEQ ID NO:122, SEQ ID NO:124, or SEQ ID NO:126, and the first nucleotide sequence encodes a phosphoketolase protein that retains the activity of a protein encoded by SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, yet the first nucleotide sequence differs from the sequence set forth in SEQ ID NO:22, SEQ ID NO:24, SEQ ID NO:26, SEQ ID NO:28, SEQ ID NO:30, SEQ ID NO:32, SEQ ID NO:122, SEQ ID NO:124, or SEQ ID NO:126, e.g., due to either natural allelic variation or mutagenesis.

In some embodiments, the first nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, or a biologically active portion of any one of them. For example, the first nucleotide sequence may encode the amino acid sequence set forth in SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125. In some embodiments, the first nucleotide sequence encodes an amino acid sequence that is substantially identical to the sequence set forth in SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, and the first nucleotide sequence encodes a phosphoketolase protein that retains the activity of a protein encoded by SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, yet the first nucleotide sequence encodes an amino acid sequence that differs from the sequence set forth in SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125, e.g., due to either natural allelic variation or mutagenesis.

In some embodiments, the phosphate acetyltransferase protein is classified by Enzyme Commission number EC 2.3.1.8.

The phosphate acetyltransferase protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119 or a biologically active portion of any one of them. For example, the phosphate acetyltransferase protein may be substantially identical to SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, and retain the functional activity of the protein of SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, yet differ in amino acid sequence, e.g., due to either natural allelic variation or mutagenesis. In some embodiments, the phosphate acetyltransferase protein comprises the amino acid sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119.

The second genetic modification may be transformation with a second nucleic acid, and the second nucleic acid may encode a phosphate acetyltransferase protein, i.e., the second nucleic acid may comprise a second nucleotide sequence that encodes a phosphate acetyltransferase protein.

In some embodiments, the second nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, or SEQ ID NO:120. For example, the second nucleotide sequence may have the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, or SEQ ID NO:120. In some embodiments, the second nucleotide sequence is substantially identical to the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, or SEQ ID NO:120, and the second nucleotide sequence encodes a phosphate acetyltransferase protein that retains the activity of a protein encoded by SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, yet the second nucleotide sequence differs from the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, or SEQ ID NO:120, e.g., due to either natural allelic variation or mutagenesis.

In some embodiments, the second nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, or a biologically active portion of any one of them. For example, the second nucleotide sequence may encode the amino acid sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119. In some embodiments, the second nucleotide sequence encodes an amino acid sequence that is substantially identical to the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, and the second nucleotide sequence encodes a phosphate acetyltransferase protein that retains the activity of a protein encoded by SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, yet the second nucleotide sequence encodes an amino acid sequence that differs from the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, e.g., due to either natural allelic variation or mutagenesis.

In some embodiments, the transformed cell does not comprise a deletion, mutation, or substitution in a native pyruvate decarboxylase gene. In some embodiments, the transformed cell does not comprise a deletion, mutation, or substitution in a native gene encoding a polypeptide that converts pyruvate to acetaldehyde, acetyl-phosphate, or acetyl-CoA. In some embodiments, the transformed cell comprises a pyruvate decarboxylase protein.

1. Decreasing the Activity of a Phosphofructokinase Protein, Fructose-Bisphosphate Aldolase Protein, and/or Triose Phosphate Isomerase Protein Decreasing the activity of a native phosphofructokinase protein, a native fructose-bisphosphate aldolase protein, or a native triose phosphate isomerase protein obstructs a cellular pathway that competes with the phosphoketolase pathway, thereby increasing the utilization of the phosphoketolase pathway (FIG. 2).

a. Decreasing the Activity of a Phosphofructokinase Protein

In some embodiments, the transformed cell further comprises a genetic modification that decreases the activity of a native phosphofructokinase protein in the cell, e.g., the cell may comprise a knockout mutation in a native phosphofructokinase gene.

In some embodiments, the method further comprises transforming the cell with a nucleotide sequence that decreases the activity of a native phosphofructokinase protein in the cell. For example, the nucleotide sequence may be capable of recombining with a nucleotide sequence in a native phosphofructokinase gene and/or a nucleotide sequence in the regulatory region of a native phosphofructokinase gene.

The phosphofructokinase protein may be classified by Enzyme Commission number EC 2.7.1.11.

b. Decreasing the Activity of a Fructose-Bisphosphate Aldolase Protein

In some embodiments, the transformed cell further comprises a genetic modification that decreases the activity of a native fructose-bisphosphate aldolase protein in the cell, e.g., the cell may comprise a knockout mutation in a native fructose-bisphosphate aldolase gene.

In some embodiments, the method further comprises transforming the cell with a nucleotide sequence that decreases the activity of a native fructose-bisphosphate aldolase protein in the cell. For example, the nucleotide sequence may be capable of recombining with a nucleotide sequence in a native fructose-bisphosphate aldolase gene and/or a nucleotide sequence in the regulatory region of a native fructose-bisphosphate aldolase gene.

The fructose-bisphosphate aldolase protein may be classified by Enzyme Commission number EC 4.1.2.13.

c. Decreasing the Activity of a Triose Phosphate Isomerase Protein

In some embodiments, the transformed cell further comprises a genetic modification that decreases the activity of a native triose phosphate isomerase protein in the cell, e.g., the cell may comprise a knockout mutation in a native triose phosphate isomerase gene.

In some embodiments, the method further comprises transforming the cell with a nucleotide sequence that decreases the activity of a native triose phosphate isomerase protein in the cell. For example, the nucleotide sequence may be capable of recombining with a nucleotide sequence in a native triose phosphate isomerase gene and/or a nucleotide sequence in the regulatory region of a native triose phosphate isomerase gene.

The triose phosphate isomerase protein may be classified by Enzyme Commission number EC 5.3.1.1.

2. Increasing the Activity of a Fructose-1,6-Bisphosphatase Protein and Decreasing the Activity of a Phosphofructokinase Protein Increasing the activity of a fructose-1,6-bisphosphatase protein in a cell increases the conversion of glyceraldehyde-3-phosphate to glucose-6-phosphate, which provides a sink for the glyceraldehyde-3-phosphate product of the phosphoketolase reaction and increases the concentration of the glucose-6-phosphate precursor, thereby increasing the utilization of the phosphoketolase pathway (FIG. 3). Decreasing the activity of a native phosphofructokinase protein obstructs a cellular pathway that competes with the fructose-1,6-bisphosphatase pathway, thereby increasing the utilization of the fructose-1,6-bisphosphatase pathway.

a. Increasing the Activity of a Fructose-1,6-Bisphosphatase Protein

In some embodiments, the transformed cell comprises a third genetic modification, wherein said third genetic modification increases the activity of a fructose-1,6-bisphosphatase protein in the cell. The third genetic modification may be transformation with a third nucleic acid, and the third nucleic acid may encode a fructose-1,6-bisphosphatase protein.

In some embodiments, the method comprises transforming the cell with a third nucleotide sequence, wherein said third nucleotide sequence increases the activity of a fructose-1,6-bisphosphatase protein in the cell. For example, the third nucleotide sequence may encode a fructose-1,6-bisphosphatase protein.

The fructose-1,6-bisphosphatase protein may be classified by Enzyme Commission number EC 3.1.3.11.

b. Decreasing the Activity of a Phosphofructokinase Protein

In some embodiments, the transformed cell comprises a fourth genetic modification that decreases the activity of a native phosphofructokinase protein in the cell, e.g., the cell may comprise a knockout mutation in a native phosphofructokinase gene.

In some embodiments, the method further comprises transforming the cell with a fourth nucleotide sequence, wherein said fourth nucleotide sequence decreases the activity of a native phosphofructokinase protein in the cell. For example, the fourth nucleotide sequence may be capable of recombining with a nucleotide sequence in a native phosphofructokinase gene and/or a nucleotide sequence in the regulatory region of a native phosphofructokinase gene.

The phosphofructokinase protein may be classified by Enzyme Commission number EC 2.7.1.11.

c. Decreasing the Activity of a Transaldolase Protein

In some embodiments, the transformed cell further comprises a genetic modification that decreases the activity of a native transaldolase protein in the cell, e.g., the cell may comprise a knockout mutation in a native transaldolase gene.

In some embodiments, the method further comprises transforming the cell with a nucleotide sequence that decreases the activity of a native transaldolase protein in the cell. For example, the nucleotide sequence may be capable of recombining with a nucleotide sequence in a native transaldolase gene and/or a nucleotide sequence in the regulatory region of a native transaldolase gene.

The transaldolase protein may be classified by Enzyme Commission number EC 2.2.1.2.

d. Decreasing the Activity of a Glyceraldehyde 3-Phosphate Dehydrogenase Protein In some embodiments, the transformed cell further comprises a genetic modification that decreases the activity of a native glyceraldehyde 3-phosphate dehydrogenase protein in the cell, e.g., the cell may comprise a knockout mutation in a native glyceraldehyde 3-phosphate dehydrogenase gene.

In some embodiments, the method further comprises transforming the cell with a nucleotide sequence that decreases the activity of a native glyceraldehyde 3-phosphate dehydrogenase protein in the cell. For example, the nucleotide sequence may be capable of recombining with a nucleotide sequence in a native glyceraldehyde 3-phosphate dehydrogenase gene and/or a nucleotide sequence in the regulatory region of a native glyceraldehyde 3-phosphate dehydrogenase gene.

The glyceraldehyde 3-phosphate dehydrogenase protein may be classified by Enzyme Commission number EC 1.2.1.12.

e. Decreasing the Activity of a Phosphoglycerate Kinase Protein

In some embodiments, the transformed cell further comprises a genetic modification that decreases the activity of a native phosphoglycerate kinase protein in the cell, e.g., the cell may comprise a knockout mutation in a native phosphoglycerate kinase gene.

In some embodiments, the method further comprises transforming the cell with a nucleotide sequence that decreases the activity of a native phosphoglycerate kinase protein in the cell. For example, the nucleotide sequence may be capable of recombining with a nucleotide sequence in a native phosphoglycerate kinase gene and/or a nucleotide sequence in the regulatory region of a native phosphoglycerate kinase gene.

The phosphoglycerate kinase protein may be classified by Enzyme Commission number EC 2.7.2.3.

f. Decreasing the Activity of a Phosphoglycerate Mutase Protein

In some embodiments, the transformed cell further comprises a genetic modification that decreases the activity of a native phosphoglycerate mutase protein in the cell, e.g., the cell may comprise a knockout mutation in a native phosphoglycerate mutase gene.

In some embodiments, the method further comprises transforming the cell with a nucleotide sequence that decreases the activity of a native phosphoglycerate mutase protein in the cell. For example, the nucleotide sequence may be capable of recombining with a nucleotide sequence in a native phosphoglycerate mutase gene and/or a nucleotide sequence in the regulatory region of a native phosphoglycerate mutase gene.

The phosphoglycerate mutase protein may be classified by Enzyme Commission number EC 5.4.2.11.

g. Decreasing the Activity of an Enolase Protein

In some embodiments, the transformed cell further comprises a genetic modification that decreases the activity of a native enolase protein in the cell, e.g., the cell may comprise a knockout mutation in a native enolase gene.

In some embodiments, the method further comprises transforming the cell with a nucleotide sequence that decreases the activity of a native enolase protein in the cell. For example, the nucleotide sequence may be capable of recombining with a nucleotide sequence in a native enolase gene and/or a nucleotide sequence in the regulatory region of a native enolase gene.

The enolase protein may be classified by Enzyme Commission number EC 4.2.1.11.

h. Decreasing the Activity of a Pyruvate Kinase Protein

In some embodiments, the transformed cell further comprises a genetic modification that decreases the activity of a native pyruvate kinase protein in the cell, e.g., the cell may comprise a knockout mutation in a native pyruvate kinase gene.

In some embodiments, the method further comprises transforming the cell with a nucleotide sequence that decreases the activity of a native pyruvate kinase protein in the cell. For example, the nucleotide sequence may be capable of recombining with a nucleotide sequence in a native pyruvate kinase gene and/or a nucleotide sequence in the regulatory region of a native pyruvate kinase gene.

The pyruvate kinase protein may be classified by Enzyme Commission number EC 2.7.1.40.

i. Increasing the Activity of an Oxidoreductase Protein

In some embodiments, the transformed cell further comprises a genetic modification that increases the activity of a oxidoreductase protein in the cell. For example, the genetic modification may be transformation with a nucleic acid that encodes a oxidoreductase protein.

In some embodiments, the method further comprises transforming the cell with a nucleotide sequence that increases the activity of a oxidoreductase protein in the cell. For example, the nucleotide sequence may encode a oxidoreductase protein.

In some embodiments, the transformed cell further comprises a genetic modification that increases the activity of a NADPH external oxidoreductase protein in the cell. For example, the genetic modification may be transformation with a nucleic acid that encodes a NADPH external oxidoreductase protein.

In some embodiments, the method further comprises transforming the cell with a nucleotide sequence that increases the activity of a NADPH external oxidoreductase protein in the cell. For example, the nucleotide sequence may encode a NADPH external oxidoreductase protein.

j. Increasing the Activity of a Soluble Transhydrogenase Protein

In some embodiments, the transformed cell further comprises a genetic modification that increases the activity of a transhydrogenase protein in the cell. For example, the genetic modification may be transformation with a nucleic acid that encodes a transhydrogenase protein.

In some embodiments, the method further comprises transforming the cell with a nucleotide sequence that increases the activity of a transhydrogenase protein in the cell. For example, the nucleotide sequence may encode a transhydrogenase protein.

In some embodiments, the transformed cell further comprises a genetic modification that increases the activity of a soluble NADPH:NADH transhydrogenase protein in the cell. For example, the genetic modification may be transformation with a nucleic acid that encodes a soluble NADPH:NADH transhydrogenase protein.

In some embodiments, the method further comprises transforming the cell with a nucleotide sequence that increases the activity of a soluble NADPH:NADH transhydrogenase protein in the cell. For example, the nucleotide sequence may encode a soluble NADPH:NADH transhydrogenase protein.

Figure 4:
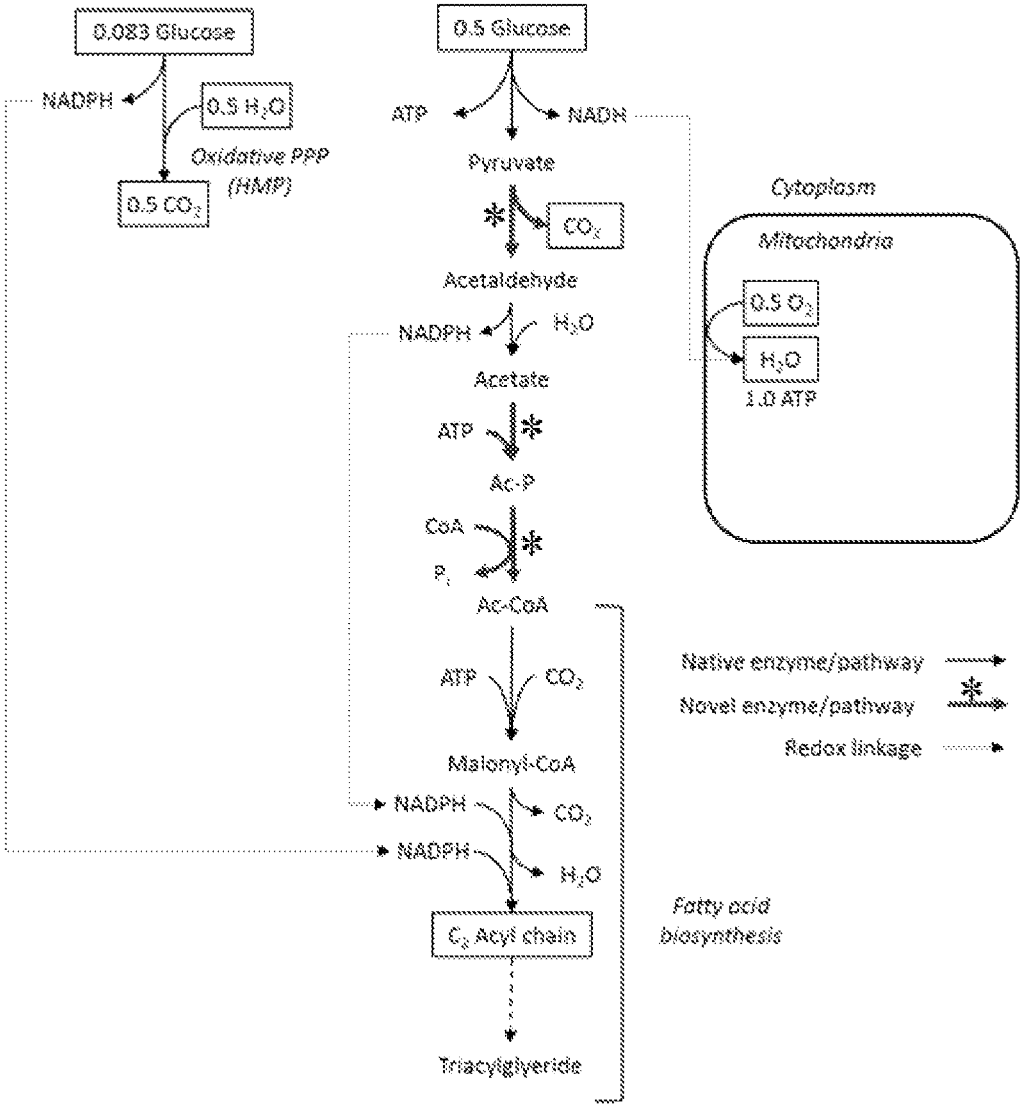
FIG. 4 depicts a novel pyruvate decarboxylase pathway.

C. Cells Comprising Pyruvate Decarboxylase Activity, Phosphate Acetyltransferase Activity, and Acetate Kinase Activity Increasing the activity of a pyruvate decarboxylase, phosphate acetyltransferase and acetate kinase in a cell allows the cell to produce acetyl-CoA from pyruvate in the cytosol (FIG. 4).

In some embodiments, the invention relates to a transformed cell, comprising a first genetic modification, a second genetic modification, and a third genetic modification, wherein said first genetic modification increases the activity of a pyruvate decarboxylase protein in the cell, said second genetic modification increases the activity of a phosphate acetyltransferase protein in the cell, and said third genetic modification increases the activity of an acetate kinase in the cell. In some embodiments, the transformed cell produces acetyl-CoA from pyruvate in the cytosol. In some embodiments, the transformed cell does not produce acetyl-CoA from pyruvate in the cytosol, e.g., the cell may convert pyruvate or a different substrate into acetyl-CoA or a different product; or, e.g., the cell may serve as a host cell for molecular cloning.

In some embodiments, the invention relates to methods of increasing the lipid content of a cell, comprising transforming said cell with a first nucleotide sequence that encodes a pyruvate decarboxylase protein, transforming said cell with a second nucleotide sequence that encodes a phosphate acetyltransferase protein, and transforming said cell with a third nucleotide sequence that encodes an acetate kinase protein. In some embodiments, the method increases the lipid content of a cell by the cytosolic production of acetyl-CoA from pyruvate. In some embodiments, the method increases the lipid content of a cell through a molecular pathway other than by the cytosolic production of acetyl-CoA from pyruvate, e.g., the transformed cell may utilize the pyruvate decarboxylase, phosphate acetyltransferase, and/or acetate kinase proteins to convert pyruvate or a different substrate into acetyl-CoA or a different product. For example, the pyruvate decarboxylase, phosphate acetyltransferase, and/or acetate kinase may catalyze steps in a different metabolic pathway that either increases lipid biosynthesis or decreases lipid degradation.

a. Increasing the Activity of a Pyruvate Decarboxylase Protein

In some embodiments, the pyruvate decarboxylase protein is classified by Enzyme Commission number EC 4.1.1.1.

The pyruvate decarboxylase protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:7, SEQ ID NO:9, or SEQ ID NO:11, or a biologically active portion of any one of them. For example, the pyruvate decarboxylase protein may be substantially identical to SEQ ID NO:7, SEQ ID NO:9, or SEQ ID NO:11, and retain the functional activity of the protein of SEQ ID NO:7, SEQ ID NO:9, or SEQ ID NO:11, yet differ in amino acid sequence, e.g., due to either natural allelic variation or mutagenesis. In some embodiments, the pyruvate decarboxylase protein comprises the amino acid sequence set forth in SEQ ID NO:7, SEQ ID NO:9, or SEQ ID NO:11.

The first genetic modification may be transformation with a first nucleic acid, and the first nucleic acid may encode a pyruvate decarboxylase protein, i.e., the first nucleic acid may comprise a first nucleotide sequence that encodes a pyruvate decarboxylase protein.

In some embodiments, the first nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:8, SEQ ID NO:10, or SEQ ID NO:12. For example, the first nucleotide sequence may have the sequence set forth in SEQ ID NO:8, SEQ ID NO:10, or SEQ ID NO:12. In some embodiments, the first nucleotide sequence is substantially identical to the sequence set forth in SEQ ID NO:8, SEQ ID NO:10, or SEQ ID NO:12, and the first nucleotide sequence encodes a pyruvate decarboxylase protein that retains the activity of a protein encoded by SEQ ID NO:7, SEQ ID NO:9, or SEQ ID NO:11, yet the first nucleotide sequence differs from the sequence set forth in SEQ ID NO:8, SEQ ID NO:10, or SEQ ID NO:12, e.g., due to either natural allelic variation or mutagenesis.

In some embodiments, the first nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:7, SEQ ID NO:9, or SEQ ID NO:11, or a biologically active portion of any one of them. For example, the first nucleotide sequence may encode the amino acid sequence set forth in SEQ ID NO:7, SEQ ID NO:9, or SEQ ID NO:11. In some embodiments, the first nucleotide sequence encodes an amino acid sequence that is substantially identical to the sequence set forth in SEQ ID NO:7, SEQ ID NO:9, or SEQ ID NO:11, and the first nucleotide sequence encodes a pyruvate decarboxylase protein that retains the activity of a protein encoded by SEQ ID NO:7, SEQ ID NO:9, or SEQ ID NO:11, yet the first nucleotide sequence encodes an amino acid sequence that differs from the sequence set forth in SEQ ID NO:7, SEQ ID NO:9, or SEQ ID NO:11, e.g., due to either natural allelic variation or mutagenesis.

b. Increasing the Activity of a Phosphate Acetyltransferase Protein

In some embodiments, the phosphate acetyltransferase protein is classified by Enzyme Commission number EC 2.2.1.8.

The phosphate acetyltransferase protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, or a biologically active portion of any one of them. For example, the phosphate acetyltransferase protein may be substantially identical to SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, and retain the functional activity of the protein of SEQ ID NO:1, SEQ ID NO:3, or SEQ ID NO:5, yet differ in amino acid sequence, e.g., due to either natural allelic variation or mutagenesis. In some embodiments, the phosphate acetyltransferase protein comprises the amino acid sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119.

The second genetic modification may be transformation with a second nucleic acid, and the second nucleic acid may encode a phosphate acetyltransferase protein, i.e., the second nucleic acid may comprise a second nucleotide sequence that encodes a phosphate acetyltransferase protein.

In some embodiments, the second nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, or SEQ ID NO:120. For example, the second nucleotide sequence may have the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, SEQ ID NO: 102, SEQ ID NO: 104, SEQ ID NO:106, SEQ ID NO:108, SEQ ID NO:110, SEQ ID NO:112, SEQ ID NO:114, SEQ ID NO: 116, SEQ ID NO: 118, or SEQ ID NO: 120. In some embodiments, the second nucleotide sequence is substantially identical to the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, SEQ ID NO: 102, SEQ ID NO: 104, SEQ ID NO:106, SEQ ID NO:108, SEQ ID NO:110, SEQ ID NO:112, SEQ ID NO:114, SEQ ID NO: 116, SEQ ID NO: 118, or SEQ ID NO: 120, and the second nucleotide sequence encodes a phosphate acetyltransferase protein that retains the activity of a protein encoded by SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, yet the second nucleotide sequence differs from the sequence set forth in SEQ ID NO:2, SEQ ID NO:4, SEQ ID NO:6, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, or SEQ ID NO:120, e.g., due to either natural allelic variation or mutagenesis.

In some embodiments, the second nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, or a biologically active portion of any one of them. For example, the second nucleotide sequence may encode the amino acid sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119. In some embodiments, the second nucleotide sequence encodes an amino acid sequence that is substantially identical to the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, and the second nucleotide sequence encodes a phosphate acetyltransferase protein that retains the activity of a protein encoded by SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, yet the second nucleotide sequence encodes an amino acid sequence that differs from the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119, e.g., due to either natural allelic variation or mutagenesis.

c. Increasing the Activity of an Acetate Kinase Protein

In some embodiments, the acetate kinase protein is classified by Enzyme Commission number EC 2.7.2.1.

The acetate kinase protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, or a biologically active portion of any one of them. For example, the acetate kinase protein may be substantially identical to SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, and retain the functional activity of the protein of SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, yet differ in amino acid sequence, e.g., due to either natural allelic variation or mutagenesis. In some embodiments, the acetate kinase protein comprises the amino acid sequence set forth in SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139.

The third genetic modification may be transformation with a third nucleic acid, and the third nucleic acid may encode an acetate kinase protein, i.e., the third nucleic acid may comprise a third nucleotide sequence that encodes an acetate kinase protein.

In some embodiments, the third nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:14, SEQ ID NO:16, SEQ ID NO:128, SEQ ID NO:130, SEQ ID NO:132, SEQ ID NO:134, SEQ ID NO:136, SEQ ID NO:138, or SEQ ID NO:140. For example, the third nucleotide sequence may have the sequence set forth in SEQ ID NO:14, SEQ ID NO:16, SEQ ID NO:128, SEQ ID NO:130, SEQ ID NO:132, SEQ ID NO:134, SEQ ID NO:136, SEQ ID NO:138, or SEQ ID NO:140. In some embodiments, the third nucleotide sequence is substantially identical to the sequence set forth in SEQ ID NO:14, SEQ ID NO:16, SEQ ID NO:128, SEQ ID NO:130, SEQ ID NO:132, SEQ ID NO:134, SEQ ID NO:136, SEQ ID NO:138, or SEQ ID NO:140 and the third nucleotide sequence encodes an acetate kinase protein that retains the activity of a protein encoded by SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, yet the third nucleotide sequence differs from the sequence set forth in SEQ ID NO:14, SEQ ID NO:16, SEQ ID NO:128, SEQ ID NO:130, SEQ ID NO:132, SEQ ID NO:134, SEQ ID NO:136, SEQ ID NO:138, or SEQ ID NO:140, e.g., due to either natural allelic variation or mutagenesis.

In some embodiments, the third nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, or a biologically active portion of any one of them. For example, the third nucleotide sequence may encode the amino acid sequence set forth in SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139. In some embodiments, the third nucleotide sequence encodes an amino acid sequence that is substantially identical to the sequence set forth in SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, and the third nucleotide sequence encodes an acetate kinase protein that retains the activity of a protein encoded by SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, yet the third nucleotide sequence encodes an amino acid sequence that differs from the sequence set forth in SEQ ID NO:13, SEQ ID NO:15, SEQ ID NO:127, SEQ ID NO:129, SEQ ID NO:131, SEQ ID NO:133, SEQ ID NO:135, SEQ ID NO:137, or SEQ ID NO:139, e.g., due to either natural allelic variation or mutagenesis.

d. Increasing the Activity of a Acetaldehyde Dehydrogenase Protein

In some embodiments, the transformed cell further comprises a genetic modification that increases the activity of a acetaldehyde dehydrogenase protein in the cell. For example, the genetic modification may be transformation with a nucleic acid that encodes a acetaldehyde dehydrogenase protein.

In some embodiments, the method further comprises transforming the cell with a nucleotide sequence that increases the activity of a acetaldehyde dehydrogenase protein in the cell. For example, the nucleotide sequence may encode a acetaldehyde dehydrogenase protein.

In some embodiments, the transformed cell further comprises a genetic modification that increases the activity of a NADP-acetaldehyde dehydrogenase protein in the cell. For example, the genetic modification may be transformation with a nucleic acid that encodes a NADP-acetaldehyde dehydrogenase protein.

In some embodiments, the method further comprises transforming the cell with a nucleotide sequence that increases the activity of a NADP-acetaldehyde dehydrogenase protein in the cell. For example, the nucleotide sequence may encode a NADP-acetaldehyde dehydrogenase protein.

In some embodiments, the acetaldehyde dehydrogenase protein is classified by Enzyme Commission number EC 1.2.1.4.

The acetaldehyde dehydrogenase protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:17, or a biologically active portion thereof. For example, the acetaldehyde dehydrogenase protein may be substantially identical to SEQ ID NO:17, and retain the functional activity of the protein of SEQ ID NO:17, yet differ in amino acid sequence, e.g., due to either natural allelic variation or mutagenesis. In some embodiments, the acetaldehyde dehydrogenase protein comprises the amino acid sequence set forth in SEQ ID NO:17.

The genetic modification may be transformation with a nucleic acid that encodes a acetaldehyde dehydrogenase protein, i.e., the nucleic acid may comprise a nucleotide sequence that encodes a acetaldehyde dehydrogenase protein.

In some embodiments, the nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:18. For example, the nucleotide sequence may have the sequence set forth in SEQ ID NO:18. In some embodiments, the nucleotide sequence is substantially identical to the sequence set forth in SEQ ID NO:18, and the nucleotide sequence encodes a acetaldehyde dehydrogenase protein that retains the activity of a protein encoded by SEQ ID NO:17, yet the nucleotide sequence differs from the sequence set forth in SEQ ID NO:18, e.g., due to either natural allelic variation or mutagenesis.

In some embodiments, the nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:17, or a biologically active portion thereof. For example, the nucleotide sequence may encode the amino acid sequence set forth in SEQ ID NO:17. In some embodiments, the nucleotide sequence encodes an amino acid sequence that is substantially identical to the sequence set forth in SEQ ID NO:17, and the nucleotide sequence encodes a acetaldehyde dehydrogenase protein that retains the activity of a protein encoded by SEQ ID NO:17, yet the nucleotide sequence encodes an amino acid sequence that differs from the sequence set forth in SEQ ID NO:17, e.g., due to either natural allelic variation or mutagenesis.

e. Decreasing the Activity of a Pyruvate Dehydrogenase Complex Protein

In some embodiments, the transformed cell further comprises a genetic modification that decreases the activity of a native pyruvate dehydrogenase complex protein in the cell, e.g., the cell may comprise a knockout mutation in a native pyruvate dehydrogenase complex gene.

In some embodiments, the method further comprises transforming the cell with a nucleotide sequence that decreases the activity of a native pyruvate dehydrogenase complex protein in the cell. For example, the nucleotide sequence may be capable of recombining with a nucleotide sequence in a native pyruvate dehydrogenase complex gene and/or a nucleotide sequence in the regulatory region of a native pyruvate dehydrogenase complex gene.

The pyruvate dehydrogenase complex protein may be classified by Enzyme Commission number EC 1.2.4.1, EC 2.3.1.12, or EC 1.8.1.4.

f. Decreasing the Activity of an ATP:Citrate Lyase Protein

In some embodiments, the transformed cell further comprises a genetic modification that decreases the activity of a native ATP:citrate lyase protein in the cell, e.g., the cell may comprise a knockout mutation in a native ATP:citrate lyase kinase gene.

In some embodiments, the method further comprises transforming the cell with a nucleotide sequence that decreases the activity of a native ATP:citrate lyase protein in the cell. For example, the nucleotide sequence may be capable of recombining with a nucleotide sequence in a native ATP:citrate lyase gene and/or a nucleotide sequence in the regulatory region of a native ATP:citrate lyase gene.

The ATP:citrate lyase protein may be classified by Enzyme Commission number EC 2.3.3.8.

Figure 5:
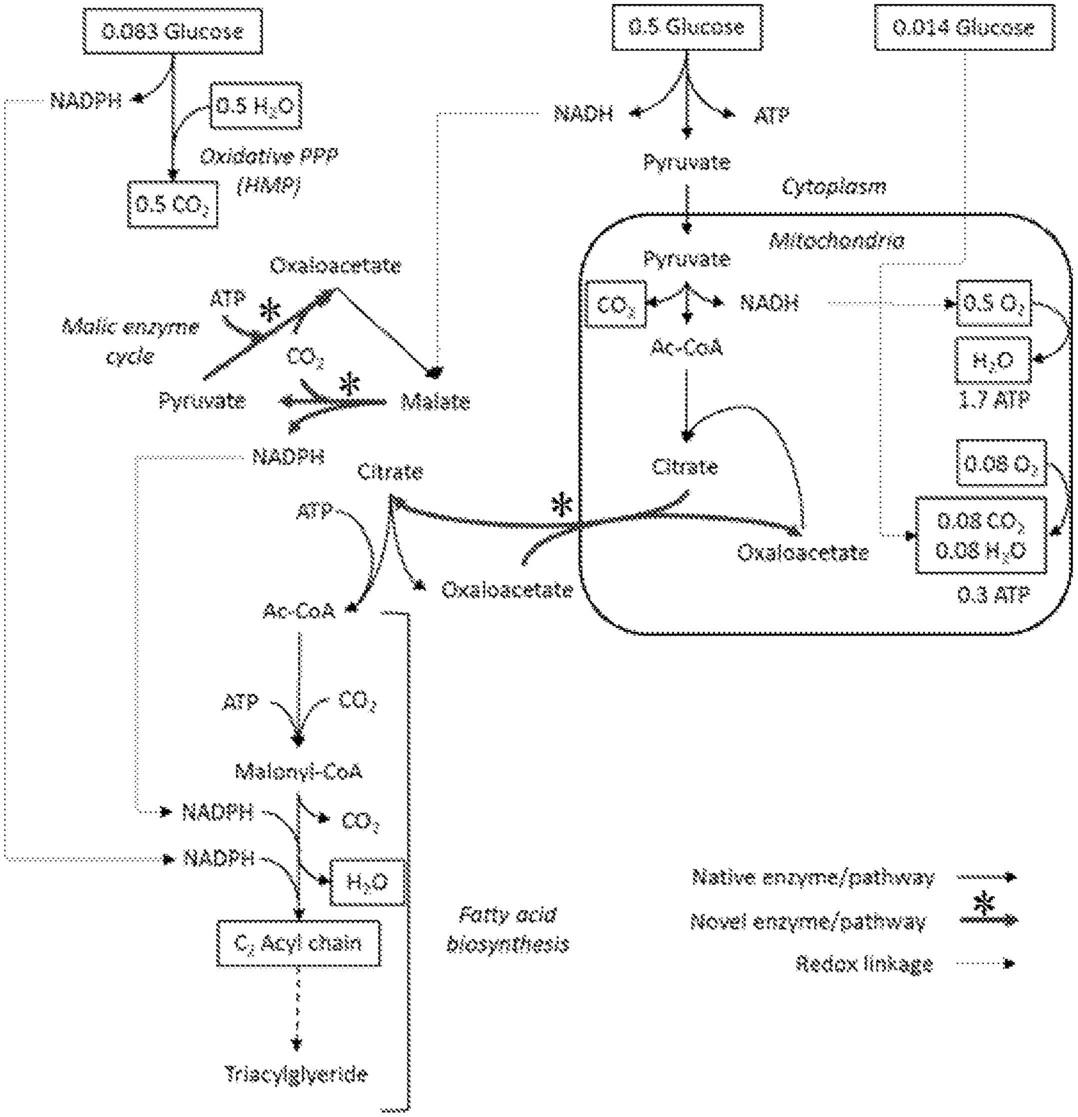
FIG. 5 depicts a novel citrate exporter pathway.

D. Cells Comprising Citrate/Oxaloacetate Mitochondrial Transporter Activity, Cytosolic Malic Enzyme Activity, and Cytosolic Pyruvate Carboxylase Activity Increasing the activity of a citrate/oxaloacetate mitochondrial transporter, cytosolic malic enzyme, and cytosolic pyruvate carboxylase in a cell allows the cell to more efficiently synthesize fatty acids from cytosolic citrate (FIG. 5).

In some embodiments, the invention relates to a transformed cell, comprising a first genetic modification, a second genetic modification, and a third genetic modification, wherein said first genetic modification increases the activity of a citrate/oxaloacetate mitochondrial transporter protein in the cell, said second genetic modification increases the activity of a cytosolic malic enzyme protein in the cell, and said third genetic modification increases the activity of a cytosolic pyruvate carboxylase protein in the cell. In some embodiments, the transformed cell synthesizes fatty acids from cytosolic citrate. In some embodiments, the transformed cell does not synthesize fatty acids from cytosolic citrate, e.g., the cell may increase its production of fatty acids from other substrates; or, e.g., the cell may serve as a host cell for molecular cloning.

In some embodiments, the invention relates to methods of increasing the lipid content of a cell, comprising transforming said cell with a first nucleotide sequence that encodes a citrate/oxaloacetate mitochondrial transporter protein, transforming said cell with a second nucleotide sequence that encodes a cytosolic malic enzyme protein, and transforming said cell with a third nucleotide sequence that encodes a cytosolic pyruvate carboxylase protein. In some embodiments, the method increases the lipid content of a cell by enabling the cell to more efficiently produce fatty acids from cytosolic citrate through production of cytosolic NADPH from cytosolic NADH generated during glycolysis. In the native pathway, glycolytic NADH is imported to the mitochondria during malate/citrate exchange across the mitochondrial membrane. In some embodiments, the method increases the lipid content of a cell through a molecular pathway other than the production of fatty acids from cytosolic citrate, e.g., increased cytosolic citrate may increase the production of lipids from a different substrate, or increased cytosolic citrate may decrease the degradation of lipids.

a. Increasing the Activity of a Citrate/Oxaloacetate Mitochondrial Transporter Protein The citrate/oxaloacetate mitochondrial transporter protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:19, or a biologically active portion thereof. For example, the citrate/oxaloacetate mitochondrial transporter protein may be substantially identical to SEQ ID NO:19, and retain the functional activity of the protein of SEQ ID NO:19, yet differ in amino acid sequence, e.g., due to either natural allelic variation or mutagenesis. In some embodiments, the citrate/oxaloacetate mitochondrial transporter protein comprises the amino acid sequence set forth in SEQ ID NO:19.

The first genetic modification may be transformation with a first nucleic acid, and the first nucleic acid may encode a citrate/oxaloacetate mitochondrial transporter protein, i.e., the first nucleic acid may comprise a first nucleotide sequence that encodes a citrate/oxaloacetate mitochondrial transporter protein.

In some embodiments, the first nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:20. For example, the first nucleotide sequence may have the sequence set forth in SEQ ID NO:20. In some embodiments, the first nucleotide sequence is substantially identical to the sequence set forth in SEQ ID NO:20, and the first nucleotide sequence encodes a citrate/oxaloacetate mitochondrial transporter protein that retains the activity of a protein encoded by SEQ ID NO:19, yet the first nucleotide sequence differs from the sequence set forth in SEQ ID NO:20, e.g., due to either natural allelic variation or mutagenesis.

In some embodiments, the first nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:19, or a biologically active portion thereof. For example, the first nucleotide sequence may encode the amino acid sequence set forth in SEQ ID NO:19. In some embodiments, the first nucleotide sequence encodes an amino acid sequence that is substantially identical to the sequence set forth in SEQ ID NO:19, and the first nucleotide sequence encodes a citrate/oxaloacetate mitochondrial transporter protein that retains the activity of a protein encoded by SEQ ID NO:19, yet the first nucleotide sequence encodes an amino acid sequence that differs from the sequence set forth in SEQ ID NO:19, e.g., due to either natural allelic variation or mutagenesis.

b. Increasing the Activity of a Cytosolic Malic Enzyme Protein

In some embodiments, the cytosolic malic enzyme protein is classified by Enzyme Commission number EC 1.1.1.39 or 1.1.1.40.

The second genetic modification may be transformation with a second nucleic acid, and the second nucleic acid may encode a cytosolic malic enzyme protein, i.e., the second nucleic acid may comprise a second nucleotide sequence that encodes a cytosolic malic enzyme protein.

c. Increasing the Activity of a Cytosolic Pyruvate Carboxylase Protein

The third genetic modification may be transformation with a third nucleic acid, and the third nucleic acid may encode a cytosolic pyruvate carboxylase protein, i.e., the third nucleic acid may comprise a third nucleotide sequence that encodes a cytosolic pyruvate carboxylase protein.

d. Decreasing the Activity of a Citrate/Malate Mitochondrial Transporter Protein In some embodiments, the transformed cell further comprises a genetic modification that decreases the activity of a native citrate/malate mitochondrial transporter protein in the cell, e.g., the cell may comprise a knockout mutation in a native citrate/malate mitochondrial transporter complex gene.

In some embodiments, the method further comprises transforming the cell with a nucleotide sequence that decreases the activity of a native citrate/malate mitochondrial transporter protein in the cell. For example, the nucleotide sequence may be capable of recombining with a nucleotide sequence in a native citrate/malate mitochondrial transporter gene and/or a nucleotide sequence in the regulatory region of a native citrate/malate mitochondrial transporter gene.

Figure 6:
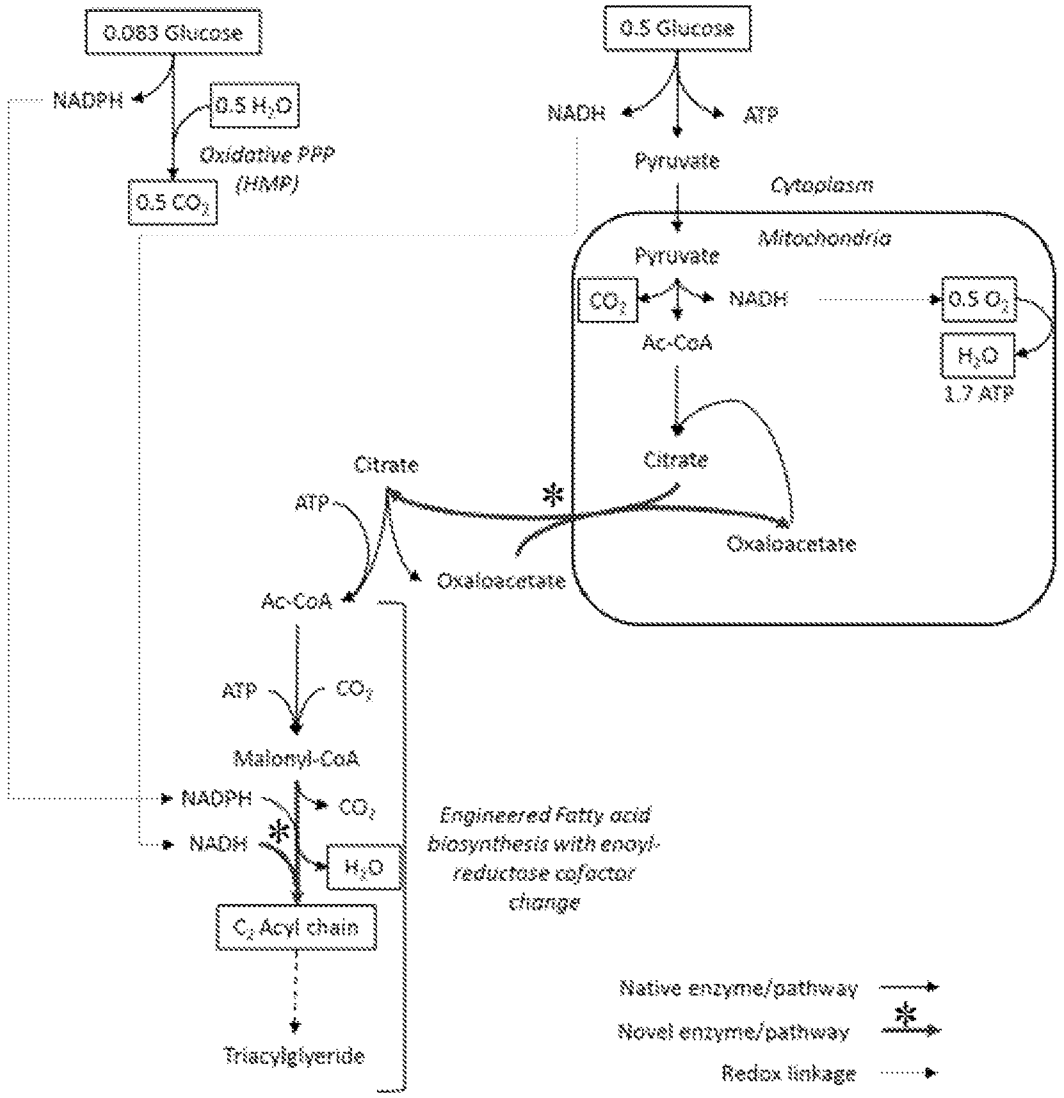
FIG. 6 depicts a novel citrate exporter pathway.

E. Cells Comprising Citrate/Oxaloacetate Mitochondrial Transporter Activity and Enoyl Acyl-Carrier Reductase Activity Increasing the activity of a citrate/oxaloacetate mitochondrial transporter and an enoyl acyl-carrier reductase in a cell allows the cell to more efficiently synthesize fatty acids from cytosolic citrate (FIG. 6).

In some embodiments, the invention relates to a transformed cell, comprising a first genetic modification, and a second genetic modification, wherein said first genetic modification increases the activity of a citrate/oxaloacetate mitochondrial transporter protein in the cell, and said second genetic modification increases the enoyl acyl-carrier reductase activity of the cell. In some embodiments, the transformed cell synthesizes fatty acids from cytosolic citrate. In some embodiments, the transformed cell does not synthesize fatty acids from cytosolic citrate, e.g., the cell may increase its production of fatty acids from other substrates; or, e.g., the cell may serve as a host cell for molecular cloning.

In some embodiments, the invention relates to methods of increasing the lipid content of a cell, comprising transforming said cell with a first nucleotide sequence that encodes a citrate/oxaloacetate mitochondrial transporter protein, and transforming said cell with a second nucleotide sequence. The second nucleotide sequence may either encode a enoyl acyl-carrier reductase protein, or the second nucleotide sequence may be capable of recombining with a nucleotide sequence in a native type I fatty acid synthase enoyl reductase gene; and transformation of the cell with the second nucleotide sequence may increase the enoyl acyl-carrier reductase activity of the cell. In some embodiments, the method increases the lipid content of a cell by enabling the cell to produce fatty acids more efficiently from cytosolic citrate. In some embodiments, the method increases the lipid content of a cell through a molecular pathway other than the production of fatty acids from cytosolic citrate, e.g., increased cytosolic citrate may increase the production of lipids from a different substrate, or increased cytosolic citrate may decrease the degradation of lipids.

In some embodiments, the invention relates to a transformed cell, comprising a first genetic modification, and a second genetic modification, wherein said first genetic modification increases the activity of a citrate/oxaloacetate mitochondrial transporter protein in the cell, and said second genetic modification increases the NADH-specific enoyl acyl-carrier reductase activity of the cell. In some embodiments, the transformed cell synthesizes fatty acids from cytosolic citrate. In some embodiments, the transformed cell does not synthesize fatty acids from cytosolic citrate, e.g., the cell may increase its production of fatty acids from other substrates; or, e.g., the cell may serve as a host cell for molecular cloning.

In some embodiments, the invention relates to methods of increasing the lipid content of a cell, comprising transforming said cell with a first nucleotide sequence that encodes a citrate/oxaloacetate mitochondrial transporter protein, and transforming said cell with a second nucleotide sequence. The second nucleotide sequence may either encode a NADH specific enoyl acyl-carrier reductase protein, or the second nucleotide sequence may be capable of recombining with a nucleotide sequence in a native type I fatty acid synthase enoyl reductase gene; and transformation of the cell with the second nucleotide sequence may increase the NADH specific enoyl acyl-carrier reductase activity of the cell. In some embodiments, the method increases the lipid content of a cell by enabling the cell to produce fatty acids more efficiently from cytosolic citrate. In some embodiments, the method increases the lipid content of a cell through a molecular pathway other than the production of fatty acids from cytosolic citrate, e.g., increased cytosolic citrate may increase the production of lipids from a different substrate, or increased cytosolic citrate may decrease the degradation of lipids.

a. Increasing the Activity of a Citrate/Oxaloacetate Mitochondrial Transporter Protein The citrate/oxaloacetate mitochondrial transporter protein may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:19, or a biologically active portion thereof. For example, the citrate/oxaloacetate mitochondrial transporter protein may be substantially identical to SEQ ID NO:19, and retain the functional activity of the protein of SEQ ID NO:19, yet differ in amino acid sequence, e.g., due to either natural allelic variation or mutagenesis. In some embodiments, the citrate/oxaloacetate mitochondrial transporter protein comprises the amino acid sequence set forth in SEQ ID NO:19.

The first genetic modification may be transformation with a first nucleic acid, and the first nucleic acid may encode a citrate/oxaloacetate mitochondrial transporter protein, i.e., the first nucleic acid may comprise a first nucleotide sequence that encodes a citrate/oxaloacetate mitochondrial transporter protein.

In some embodiments, the first nucleotide sequence has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:20. For example, the first nucleotide sequence may have the sequence set forth in SEQ ID NO:20. In some embodiments, the first nucleotide sequence is substantially identical to the sequence set forth in SEQ ID NO:20, and the first nucleotide sequence encodes a citrate/oxaloacetate mitochondrial transporter protein that retains the activity of a protein encoded by SEQ ID NO:19, yet the first nucleotide sequence differs from the sequence set forth in SEQ ID NO:20, e.g., due to either natural allelic variation or mutagenesis.

In some embodiments, the first nucleotide sequence encodes an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence homology with the sequence set forth in SEQ ID NO:19, or a biologically active portion thereof. For example, the first nucleotide sequence may encode the amino acid sequence set forth in SEQ ID NO:19. In some embodiments, the first nucleotide sequence encodes an amino acid sequence that is substantially identical to the sequence set forth in SEQ ID NO:19, and the first nucleotide sequence encodes a citrate/oxaloacetate mitochondrial transporter protein that retains the activity of a protein encoded by SEQ ID NO:19, yet the first nucleotide sequence encodes an amino acid sequence that differs from the sequence set forth in SEQ ID NO:19, e.g., due to either natural allelic variation or mutagenesis.

b. Increasing Enoyl Acyl-Carrier Reductase Activity

In some embodiments, the second genetic modification may be transformation with a second nucleic acid, and the second nucleic acid may encode an enoyl acyl-carrier reductase protein, i.e., the second nucleic acid may comprise a second nucleotide sequence that encodes an enoyl acyl-carrier reductase protein.

In some embodiments, the second genetic modification may be transformation with a second nucleic acid, and the second nucleic acid may encode a NADH-specific enoyl acyl-carrier reductase protein, i.e., the second nucleic acid may comprise a second nucleotide sequence that encodes a NADH-specific enoyl acyl-carrier reductase protein.

The NADH specific enoyl acyl-carrier reductase protein may be classified by Enzyme Commission number EC 1.3.1.9.

In some embodiments, the second genetic modification is a mutation to a native type I fatty acid synthase enoyl reductase protein, wherein the mutation increases the ability of the native type I fatty acid synthase enoyl reductase protein to accept NADH as an electron donor.

In some embodiments, the method comprises transforming the cell with a second nucleotide sequence that is capable of recombining with a nucleotide sequence in a native type I fatty acid synthase enoyl reductase gene to generate a mutation that increases the ability of the native type I fatty acid synthase enoyl reductase protein gene product to accept NADH as an electron donor.

c. Decreasing the Activity of a Citrate/Malate Mitochondrial Transporter Protein In some embodiments, the transformed cell further comprises a genetic modification that decreases the activity of a native citrate/malate mitochondrial transporter protein in the cell, e.g., the cell may comprise a knockout mutation in a native citrate/malate mitochondrial transporter complex gene.

In some embodiments, the method further comprises transforming the cell with a nucleotide sequence that decreases the activity of a native citrate/malate mitochondrial transporter protein in the cell. For example, the nucleotide sequence may be capable of recombining with a nucleotide sequence in a native citrate/malate mitochondrial transporter gene and/or a nucleotide sequence in the regulatory region of a native citrate/malate mitochondrial transporter gene.

F. Products

In some aspects, the invention relates to a method of producing a product, comprising providing a transformed cell, and culturing the cell for a period of time on a substrate, thereby producing the product.

The substrate may comprise depolymerized sugar beet pulp, glycerin, black liquor, corn, corn starch, corn dextrins, depolymerized cellulosic material, corn stover, sugar beet pulp, switchgrass, milk whey, molasses, potato, rice, sorghum, sugar cane, thick cane juice, sugar beet juice, and/or wheat. In certain embodiments, the transformed cells are grown in the presence of exogenous fatty acids, glucose, ethanol, xylose, sucrose, starch, starch dextrin, glycerol, cellulose, and/or acetic acid. These compounds may be added to the substrate during cultivation to increase lipid production. The exogenous fatty acids may include stearate, oleic acid, linoleic acid, γ-linolenic acid, dihomo-γ-linolenic acid, arachidonic acid, α-linolenic acid, stearidonic acid, eicosatetraenoic acid, eicosapenteaenoic acid, docosapentaenoic acid, eicosadienoic acid, and/or eicosatrienoic acid.

In certain embodiments, the present invention relates to a product produced by a modified host cell described herein. In certain embodiments, the product is an oil, lipid, fatty acid, fatty alcohol, triacylglyceride, isoprenoid, or farnesene. In some embodiments, the product is stearic acid, oleic acid, linoleic acid, capric acid, caprylic acid, caproic acid, lauric acid, myristic acid, palmitic acid, palmitoleic acid, or squalene. In certain embodiments, the product is a saturated fatty acid. Thus, the product may be caprylic acid, capric acid, lauric acid, myristic acid, palmitic acid, stearic acid, arachidic acid, behenic acid, lignoceric acid, or cerotic acid. In some embodiments, the product is an unsaturated fatty acid. Thus, the product may be myristoleic acid, palmitoleic acid, sapienic acid, oleic acid, elaidic acid, vaccenic acid, linoleic acid, linoelaidic acid, α-linolenic acid, arachidonic acid, eicosapenteaenoic acid, erucic acid, or docosahexaenoic acid.

In some embodiments, the product comprises an 18-carbon fatty acid. In some embodiments, the product comprises oleic acid, stearic acid, or linoleic acid. For example, the product may be oleic acid.

In some embodiments, the method comprises collecting the product. The method may comprise purifying the product, e.g., separating one or more lipid fractions from a culture of transformed cells from one or more aqueous fractions of the culture.

One skilled in the art will readily appreciate that the present invention is well adapted to carry out the objects and obtain the ends and advantages mentioned, as well as those inherent therein. The embodiments described herein are not intended as limitations on the scope of the invention.

EXEMPLIFICATION

Example 1—Expression of Phosphoketolase in Yeast

The phosphoketolase gene from *Trichoderma reesei* (NG306; SEQ ID NO:28) was cloned into *Saccharomyces cerevisiae* strain NS20. The phosphoketolase genes from *Trichoderma reesei* (NG306; SEQ ID NO:28) and *Aspergillus niger* (NG304; SEQ ID NO:24) were cloned, separately, into *Arxula adeninivorans* strain NS252.

Example 2—Expression of Phosphate Acetyltransferase in Yeast

Figure 7:
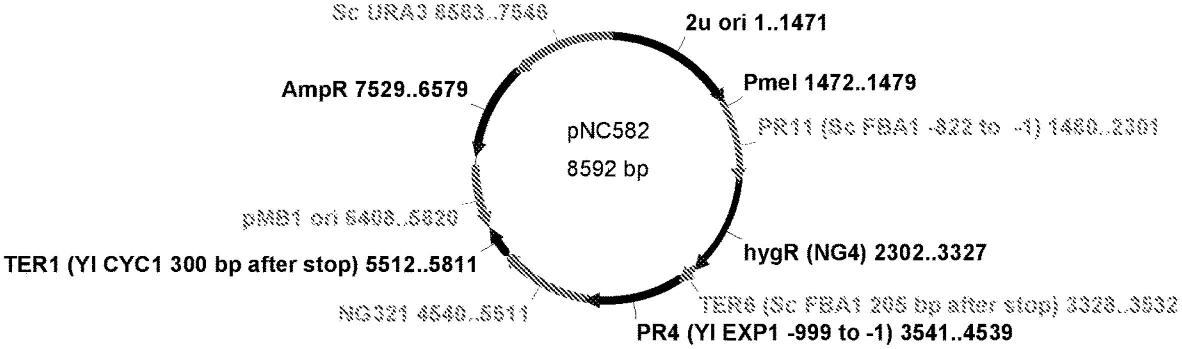
FIG. 7 is a map of the pNC582 construct, used to overexpress the phosphate acetyltransferase gene from *Bacillus subtilis* (SEQ ID NO:116) in yeast. "2μ ori" denotes a yeast origin of replication from the 2μ circle plasmid; "pMB1 ori" denotes the *E. coli* pMB1 origin of replication from the pBR322 plasmid; "AmpR" denotes the bla gene used as marker for selection with ampicillin; "PR11" denotes the *S. cerevisiae* FBA1 promoter −822 to −1; "NG4" denotes the *Escherichia coli* hph gene used as marker for selection with hygromycin; "TER6" denotes the *S. cerevisiae* FBA1 terminator 205 bp after stop; "PR4" denotes the *Y. lipolytica* EXP1 promoter −999 to −1; "NG321" denotes the native *Bacillus subtilis* subsp. *subtilis* 168 PTA cDNA synthetized by Life Technologies (SEQ ID NO:116); "TER1" denotes the *Y. lipolytica* CYC1 terminator 300 bp after stop; "Sc URA3" denotes the *S. cerevisiae* URA3 auxotrophic marker for selection in yeast.

A construct was engineered to overexpress the phosphate acetyltransferase gene from *Bacillus subtilis* (NG321; SEQ ID NO:116) in yeast (FIG. 7). Similar constructs were used to overexpress phosphate acetyltransferase genes from *Clostridium acetobutylicum* strain ATCC 824 (NG322; SEQ ID NO:118), *Thermoanaerobacterium saccharolyticum* (NG324; SEQ ID NO:120), *Methanosarcina thermophila* (NG309; SEQ ID NO:2), *Methanosarcina barkeri* strain Fusaro (NG310; SEQ ID NO:4), *Methanosarcina acetivorans* (NG311; SEQ ID NO:6), *Aphanomyces astaci* (NG350; SEQ ID NO:34), *Aphanomyces invadans* (NG351; SEQ ID NO:36), *Auxenochlorella protothecoides* (NG352; SEQ ID NO:38), *Beauveria bassiana* (NG353; SEQ ID NO:40), *Chlamydomonas reinhardtii* (NG354; SEQ ID NO:42), *Guillardia theta* (NG356; SEQ ID NO:46), *Helicosporidium* (NG357; SEQ ID NO:48), *Perkinsus marinus* (NG358; SEQ ID NO:50), *Phytophthora parasitica* (NG361; SEQ ID NO:56), *Phytophthora ramorum* (NG362; SEQ ID NO:58), *Phytophthora sojae* (NG363; SEQ ID NO:60), *Pythium ultimum* (NG364; SEQ ID NO:62), *Saprolegnia diclina* (NG365; SEQ ID NO:64), *Selaginella moellendorffii* (NG367; SEQ ID NO:68), *Volvox carteri* (NG369; SEQ ID NO:72), *Bacillus subtilis* subsp. *subtilis* strain 168 (NG370; SEQ ID NO:74), and *Thermoanaerobacterium saccharolyticum* (NG371; SEQ ID NO:76) in yeast.

The constructs were used to transform *Saccharomyces cerevisiae* strain NS20, *Yarrowia lipolytica* strain NS18, and *Arxula adeninivorans* strain NS252. Transformants were screened for phosphate acetyltransferase activity using an assay described by Bock et al. (J. Bacteriology 181(6):1861-67 (1999)). Briefly, cell-free extracts were prepared from 5 ml overnight YPD cultures using the Y-PER® Plus, Dialyzable Yeast Protein Extraction Reagent (Pierce Biotechnologies, catalog #78999). Cells were pelleted by centrifugation at 3000 rpm for 3 minutes and resuspended in 125-250 µl Y-PER Reagent per 50 mg cells by vortexing. 5 µl Thermo Scientific™ Pierce™ Protease Inhibitors (catalog # PI-36978) were added per 1 mL of the Y-PER Plus/cell mixture. The mixture was agitated and allowed to sit at room temperature for 20 minutes. Cell debris was pelleted by centrifugation at 14,000×g for 10 minutes, and the supernatant was stored at −80° C. until use.

10-80 µl of the cell-free extracts were added to acetyl-CoA reaction mixtures comprising a final concentration of 100 mM Tris-HCL (pH 7.2), 5 mM $MgCl_2$, 5 mM $KH_2PO_4$, and 0.1 mM DTNB in 1 mL water. An acetyl-CoA substrate was added to a final concentration of 0.1 mM, and absorbance was monitored at 412 nm for 5-thio-2-nitrobenzoic acid (6=14.5 $mM^{-1}$ $cm^{-1}$).

Figure 8:
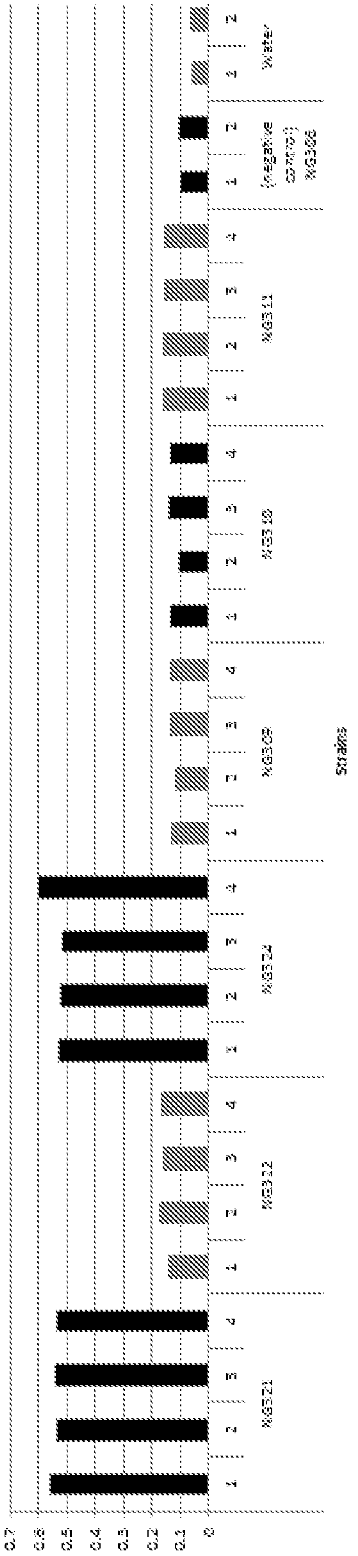
FIG. 8 is a graph that shows the absorbance at 412 nm for assays performed by incubating cell extracts with acetyl-CoA and DTNB. Cell extracts labeled NG321, NG322, NG324, NG309, NG310, and NG311 are cell extracts from *Saccharomyces cerevisiae* that each contain a gene for phosphate acetyltransferase, which can convert acetyl-CoA to CoA-SH, allowing CoA-SH to react with DTNB to produce the reporter molecule 5-thio-2-nitrobenzoate. The cell extract labeled NG306 is a cell extract from *Saccharomyces cerevisiae* comprising the phosphoketolase gene from *Trichoderma reesei* as a negative control.
Figure 9:
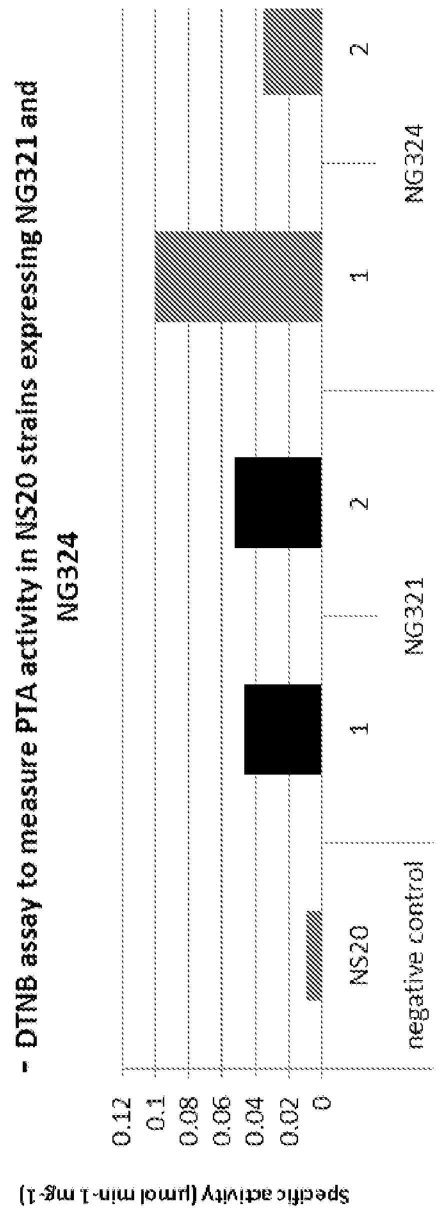
FIG. 9 is a graph that shows specific phosphate acetyltransferase activity for cell extracts from *Saccharomyces cerevisiae* that contain a gene for phosphate acetyltransferase, and for a negative control *Saccharomyces cerevisiae* strain NS20.

Each *S. cerevisiae* cell transformed with a phosphate acetyltransferase gene produced more 5-thio-2-nitrobenzoic acid than a control *S. cerevisiae* cell transformed with a phosphoketolase gene from *Trichoderma reesei* (FIG. 8). *S. cerevisiae* transformed with a phosphate acetyltransferase gene from either *Bacillus subtilis* (NG321; SEQ ID NO:116) or *Thermoanaerobacterium saccharolyticum* (NG324; SEQ ID NO:120) displayed superior performance in the phosphate acetyltransferase assay. The results were normalized by calculating specific activity, i.e., by dividing the rate of 5-thio-2-nitrobenzoic acid production by the amount of protein in each cell-free extract. Protein concentrations were measured using the Pierce™ Coomassie (Bradford) Protein Assay Kit. *S. cerevisiae* transformed with a phosphate acetyltransferase gene from either *Bacillus subtilis* (NG321; SEQ ID NO:116) or *Thermoanaerobacterium saccharolyticum* (NG324; SEQ ID NO:120) displayed more specific activity than a negative control (FIG. 9).

The phosphate acetyltransferase gene from *Bacillus subtilis* (NG321; SEQ ID NO:116) was codon optimized for yeast, resulting in SEQ ID NO:74 (NG370). The phosphate acetyltransferase gene from *Thermoanaerobacterium saccharolyticum* (NG324; SEQ ID NO:120) was codon optimized for yeast, resulting in SEQ ID NO:76 (NG371).

Figure 10:
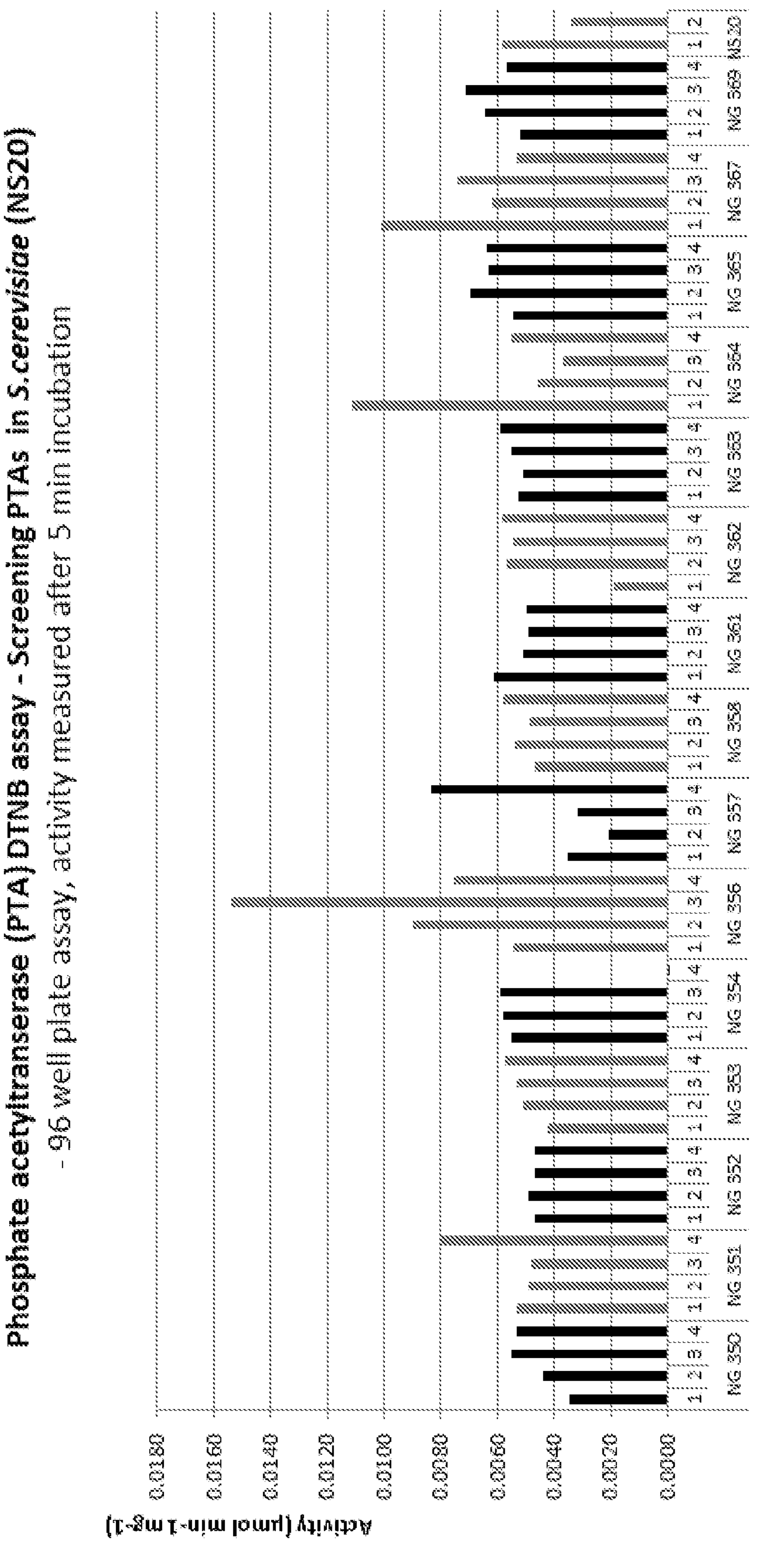
FIG. 10 is a graph that shows specific phosphate acetyltransferase activity for cell extracts from *Saccharomyces cerevisiae* that contain a gene for phosphate acetyltransferase, and for a negative control *Saccharomyces cerevisiae* strain NS20.

The specific activity for *S. cerevisiae* cell-extracts from cells transformed with phosphate acetyltransferase genes from either *Aphanomyces* astaci (NG350; SEQ ID NO:34), *Aphanomyces* invadans (NG351; SEQ ID NO:36), *Auxenochlorella protothecoides* (NG352; SEQ ID NO:38), *Beauveria bassiana* (NG353; SEQ ID NO:40), *Chlamydomonas reinhardtii* (NG354; SEQ ID NO:42), *Guillardia theta* (NG356; SEQ ID NO:46), *Helicosporidium* (NG357; SEQ ID NO:48), *Perkinsus marinus* (NG358; SEQ ID NO:50), *Phytophthora parasitica* (NG361; SEQ ID NO:56), *Phytophthora ramorum* (NG362; SEQ ID NO:58), *Phytophthora sojae* (NG363; SEQ ID NO:60), *Pythium ultimum* (NG364; SEQ ID NO:62), *Saprolegnia diclina* (NG365; SEQ ID NO:64), *Selaginella moellendorffii* (NG367; SEQ ID NO:68), or *Volvox* carteri (NG369; SEQ ID NO:72) are shown in FIG. 10.

Figure 11:
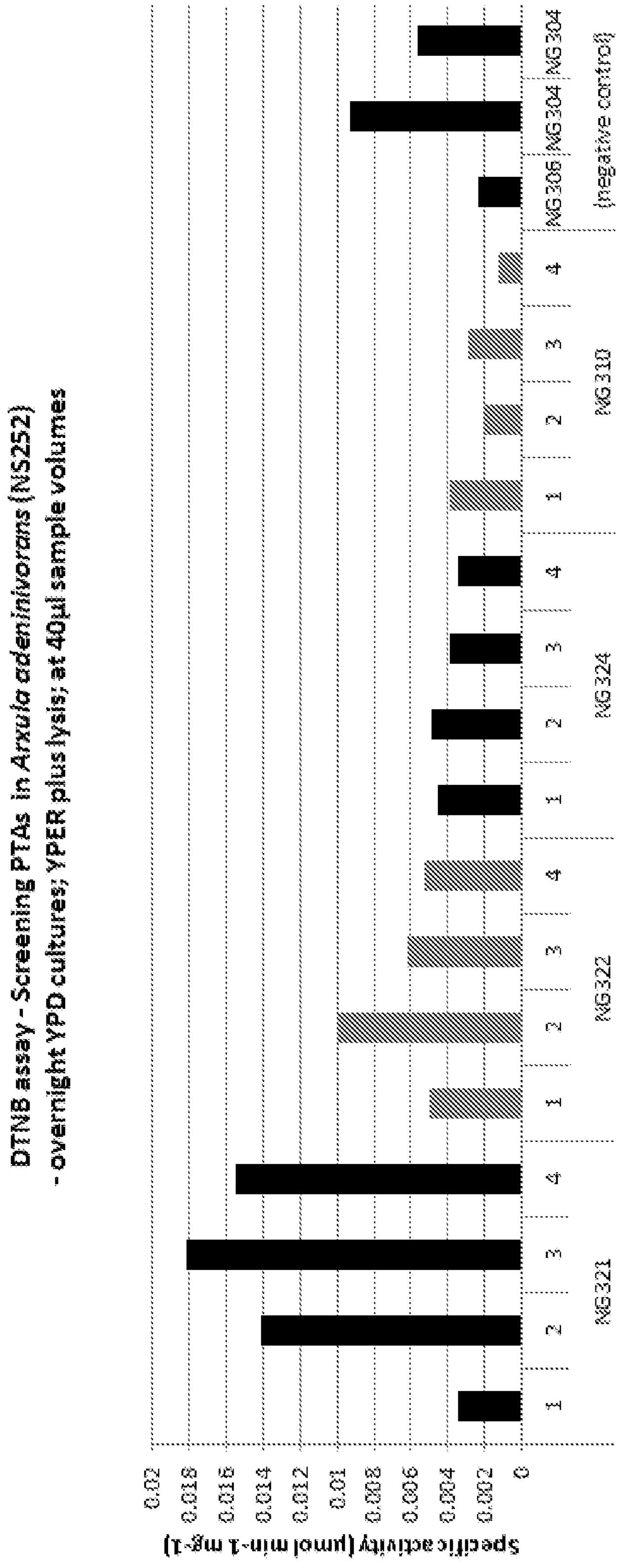
FIG. 11 is a graph that shows specific phosphate acetyltransferase activity for cell extracts from *Arxula adeninivorans* that contain a gene for phosphate acetyltransferase, and for negative control *Arxula adeninivorans* strains that each contain a gene for a phosphoketolase (NG304 and NG306).

*Arxula adeninivorans* strain NS252 was transformed with a phosphate acetyltransferase gene from either *Bacillus subtilis* (NG321; SEQ ID NO:116), *Clostridium acetobutylicum* strain ATCC 824 (NG322; SEQ ID NO:118), *Thermoanaerobacterium saccharolyticum* (NG324; SEQ ID NO:120), or *Methanosarcina barkeri* strain Fusaro (NG310; SEQ ID NO:4), and specific phosphate acetyltransferase activity was monitored (FIG. 11) as described above. Strain NS252, transformed with phosphoketolase genes from either *Trichoderma reesei* (NG306; SEQ ID NO:28) or *Aspergillus niger* (NG304; SEQ ID NO:24), was assayed as negative controls. The phosphate acetyltransferase from *Bacillus subtilis* (NG321; SEQ ID NO:116) displayed the highest activity.

Figure 12:
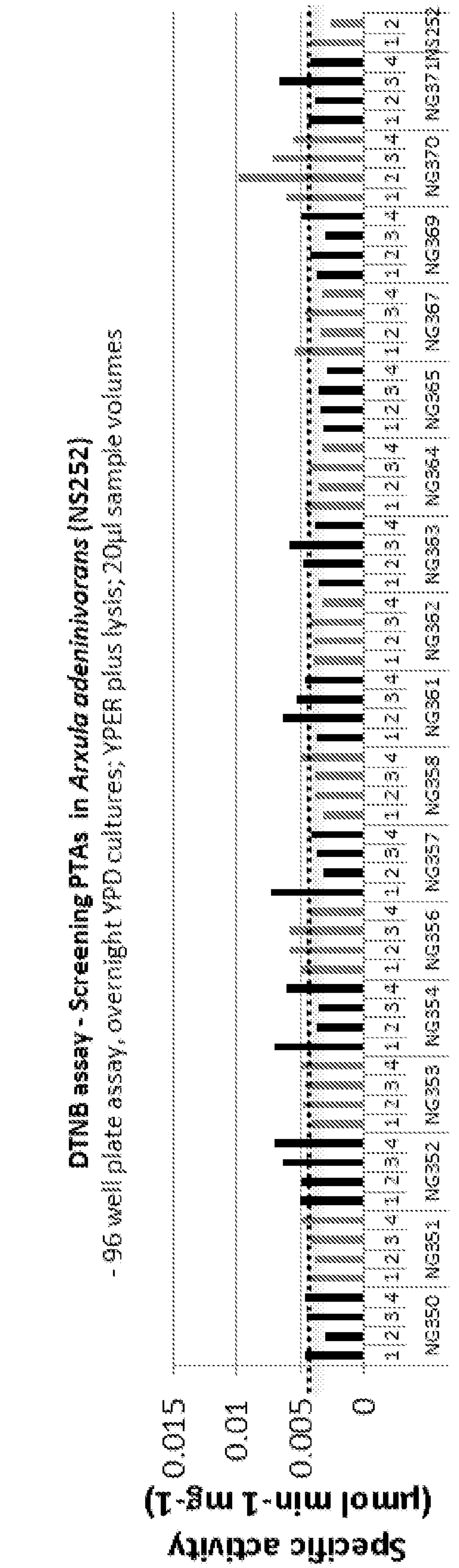
FIG. 12 is a graph that shows specific phosphate acetyltransferase activity for cell extracts from *Arxula adeninivorans* that contain a gene for phosphate acetyltransferase, and for a negative control *Arxula adeninivorans* strain NS252.

*Arxula adeninivorans* strain NS252 was transformed with a phosphate acetyltransferase gene from either *Aphanomyces* astaci (NG350; SEQ ID NO:34), *Aphanomyces invadans* (NG351; SEQ ID NO:36), *Auxenochlorella protothecoides* (NG352; SEQ ID NO:38), *Beauveria bassiana* (NG353; SEQ ID NO:40), *Chlamydomonas reinhardtii* (NG354; SEQ ID NO:42), *Guillardia* theta (NG356; SEQ ID NO:46), *Helicosporidium* (NG357; SEQ ID NO:48), *Perkinsus marinus* (NG358; SEQ ID NO:50), *Phytophthora parasitica* (NG361; SEQ ID NO:56), *Phytophthora ramorum* (NG362; SEQ ID NO:58), *Phytophthora sojae* (NG363; SEQ ID NO:60), *Pythium ultimum* (NG364; SEQ ID NO:62), *Saprolegnia diclina* (NG365; SEQ ID NO:64), *Selaginella moellendorffii* (NG367; SEQ ID NO:68), or *Volvox carteri* (NG369; SEQ ID NO:72), *Bacillus subtilis* subsp. *subtilis* strain 168 (NG370; SEQ ID NO:74), or *Thermoanaerobacterium saccharolyticum* (NG371; SEQ ID NO:76), and specific phosphate acetyltransferase activity was monitored (FIG. 12) as described above. Each gene was transformed into *A. adeninivorans* using a construct similar to pNC582 (FIG. 7) in which the NG321 gene is replaced with the phosphate acetyltransferase gene, under the control of the PR4 promoter from *Y. lipolytica*. Four transformants were analyzed for each construct. The phosphate acetyltransferase from *Bacillus subtilis* subsp. *subtilis* strain 168 (NG370; SEQ ID NO:74) displayed the highest activity.

Figure 13:
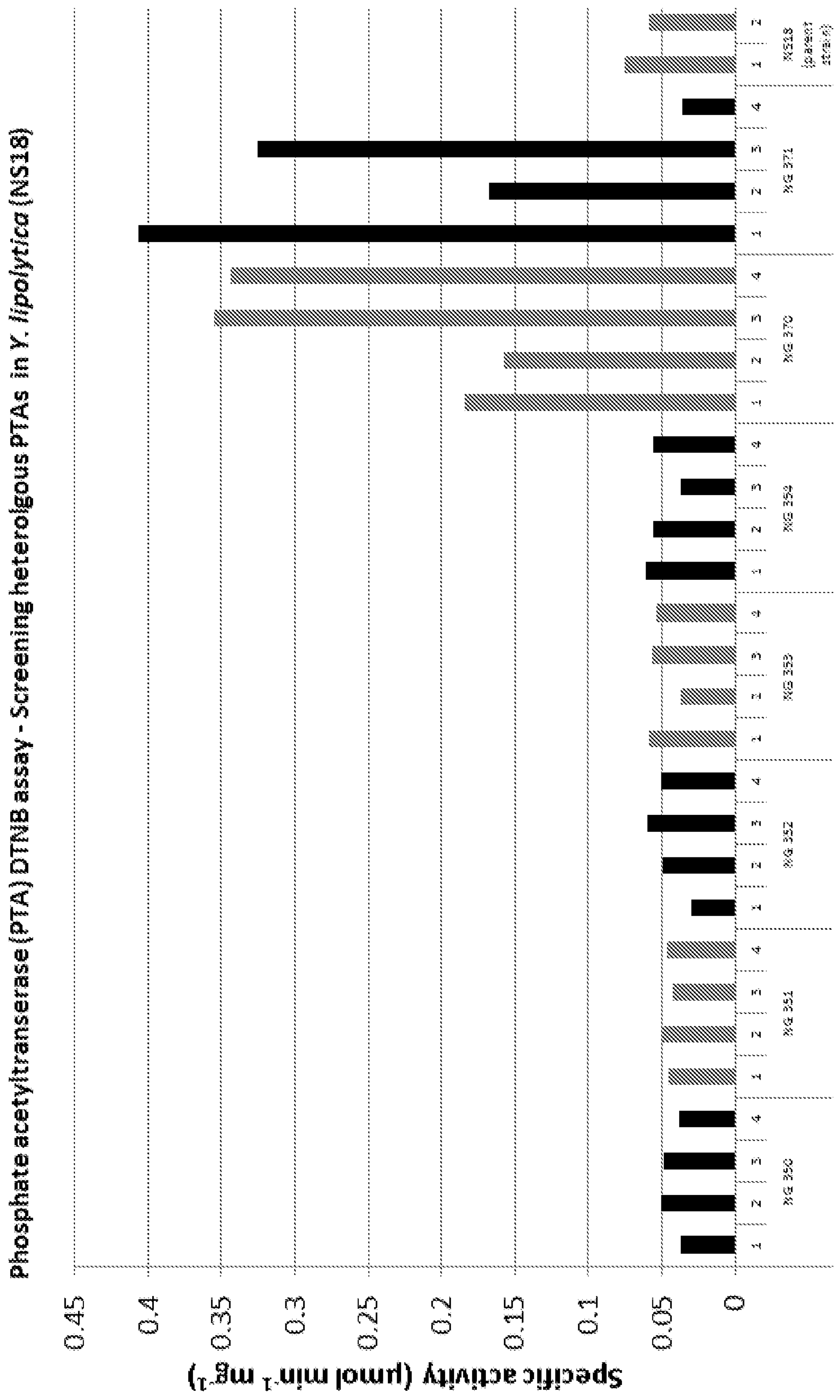
FIG. 13 is a graph that shows specific phosphate acetyltransferase activity for cell extracts from *Yarrowia lipolytica* that contain a gene for phosphate acetyltransferase, and for a negative control *Yarrowia lipolytica* strain NS18.

*Yarrowia lipolytica* strain NS18 was transformed with a phosphate acetyltransferase gene from either *Aphanomyces* astaci (NG350; SEQ ID NO:34), *Aphanomyces invadans* (NG351; SEQ ID NO:36), *Auxenochlorella protothecoides* (NG352; SEQ ID NO:38), *Beauveria bassiana* (NG353; SEQ ID NO:40), *Chlamydomonas reinhardtii* (NG354; SEQ ID NO:42), *Bacillus subtilis* subsp. *subtilis* strain 168 (NG370; SEQ ID NO:74), or *Thermoanaerobacterium saccharolyticum* (NG371; SEQ ID NO:76), and specific phosphate acetyltransferase activity was monitored (FIG. 13) as described above. The phosphate acetyltransferases from *Bacillus subtilis* subsp. *subtilis* strain 168 (NG370; SEQ ID NO:74) and *Thermoanaerobacterium saccharolyticum* (NG371; SEQ ID NO:76) displayed the highest activity.

Figure 14:
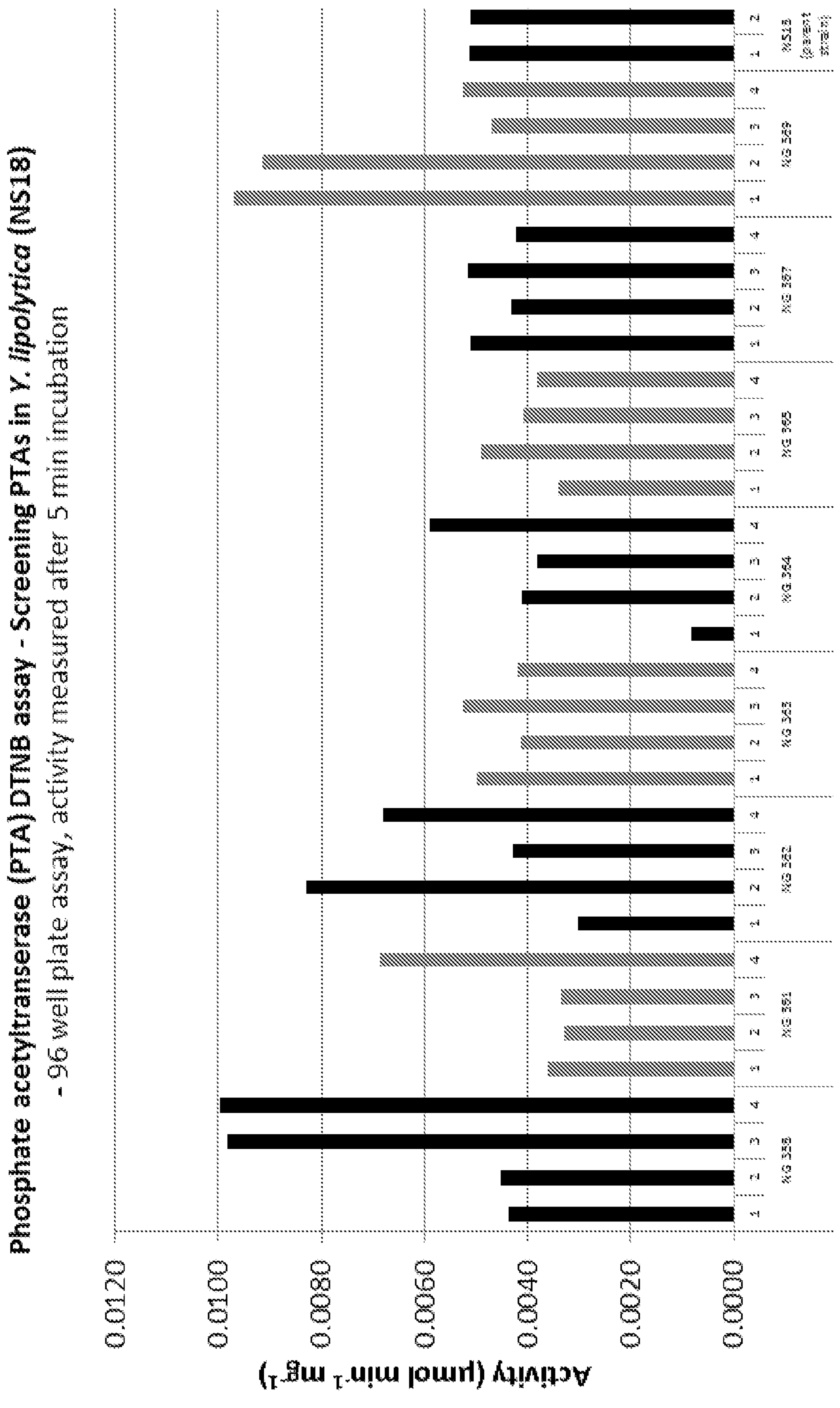
FIG. 14 is a graph that shows specific phosphate acetyltransferase activity for cell extracts from *Yarrowia lipolytica* that contain a gene for phosphate acetyltransferase, and for a negative control *Yarrowia lipolytica* strain NS18.

*Yarrowia lipolytica* strain NS18 was transformed with a phosphate acetyltransferase gene from either *Perkinsus marinus* (NG358; SEQ ID NO:50), *Phytophthora parasitica* (NG361; SEQ ID NO:56), *Phytophthora ramorum* (NG362; SEQ ID NO:58), *Phytophthora sojae* (NG363; SEQ ID NO:60), *Pythium ultimum* (NG364; SEQ ID NO:62), *Saprolegnia diclina* (NG365; SEQ ID NO:64), *Selaginella moellendorffii* (NG367; SEQ ID NO:68), or *Volvox* carteri (NG369; SEQ ID NO:72), and specific phosphate acetyltransferase activity was monitored (FIG. 14) as described above.

Example 3—Deletion of the 6-Phosphofructokinase Gene in Yeast

The PFK1 gene in *Y. lipolytica* encodes the 6-phosphofructokinase 1 protein PFK1 (SEQ ID NO:141). SEQ ID NO:142 contains the PFK1 nucleotide sequence, 100 upstream nucleotides, and 100 downstream nucleotides, and this sequence was used to design nucleic acids capable of recombining with the native *Y. lipolytica* 6-phosphofructokinase 1 gene to generate a PFK1 knockout.

Knockout cassettes comprising the nucleotide sequences set forth in SEQ ID NO:143 and SEQ ID NO:144 each comprise a portion of the nourseothricin resistance gene Nat as a marker. SEQ ID NO:144 also comprises a negative selection marker gene thymidine kinase (TDK), which confers sensitivity to 5-fluoro-2'-deoxyuridine (FUdR). Neither SEQ ID NO:143 nor SEQ ID NO:144 encodes a functional protein, but the two sequences are capable of encoding a functional protein that confers nourseothricin resistance upon successful recombination. Further, SEQ ID NO:143 does not contain a promoter and SEQ ID NO:144 does not contain a terminator, and thus, they rely on homologous recombination with the *Y. lipolytica* PFK1 gene in order for the Nat gene and the TDK gene to be transcribed and translated. In this way, successfully transformed cells may be selected by growing the cells on a medium containing nourseothricin. Additionally, transformed cells are unable to grow in FUdR-containing media due to the functional TDK gene. The TDK gene as a negative selection marker is added in order to facilitate the removal of the knockout cassette during a subsequent transformation, i.e., successful removal of the knockout cassette would mean the newly transformed cells would be able to grow on medium containing 5-fluoro-2'-deoxyuridine.

Figure 15:
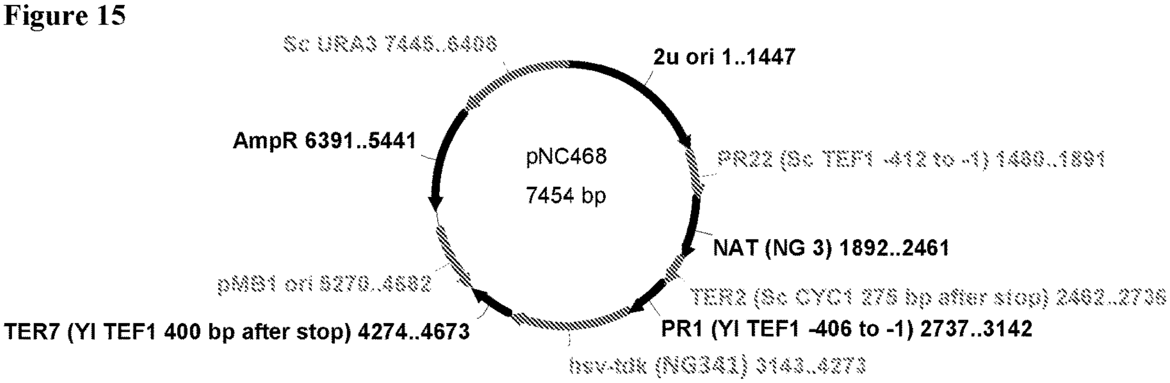
FIG. 15 is a map of the pNC468 construct, used to amplify knockout cassettes SEQ ID NO:143 and SEQ ID NO:144 to delete the PFK1 gene in *Yarrowia lipolytica* strain NS18. "2μ ori" denotes the *S. cerevisiae* origin of replication from the 2μ circle plasmid; "pMB1 ori" denotes the *E. coli* pMB1 origin of replication from the pBR322 plasmid; "AmpR" denotes the bla gene used as marker for selection with ampicillin; "PR22" denotes the *S. cerevisiae* TEF1 promoter −412 to −1; "NG3" denotes the *Streptomyces noursei* Nat gene used as marker for selection with Nourseothricin; "TER2" denotes the *S. cerevisiae* CYC1 terminator 275 bp after stop; "PR1" denotes the *Y. lipolytica* TEF1 promoter −406 to −1; "NG341" denotes the Herpes Simplex Virus TDK gene cDNA synthetized by Genscript; "TER7" denotes the *Y. lipolytica* TEF1 terminator 400 bp after stop; "Sc URA3" denotes the *S. cerevisiae* URA3 auxotrophic marker for selection in yeast.

A knockout cassette for SEQ ID NO:143 was prepared by amplifying a nourseothricin resistance gene Nat (SEQ ID NO:146) with primer NP2782 (SEQ ID NO:149) and primer NP356 (SEQ ID NO:152). A knockout cassette for SEQ ID NO:144 was prepared by amplifying the nourseothricin resistance gene Nat (SEQ ID NO:146) and FUdR sensitive gene TDK (SEQ ID NO:148) with primer NP355 (SEQ ID NO:151) and primer NP2783 (SEQ ID NO:150). The template vector used for these PCR reactions is the vector pNC468 (FIG. 15). Similar knockout cassettes may be designed to reduce the activity of the PFK1 gene of *Arxula adeninivorans* (SEQ ID NO:154), the PFK2 gene of *Arxula adeninivorans* (SEQ ID NO:156), or another known gene of *Arxula* or a different species.

Figure 16:
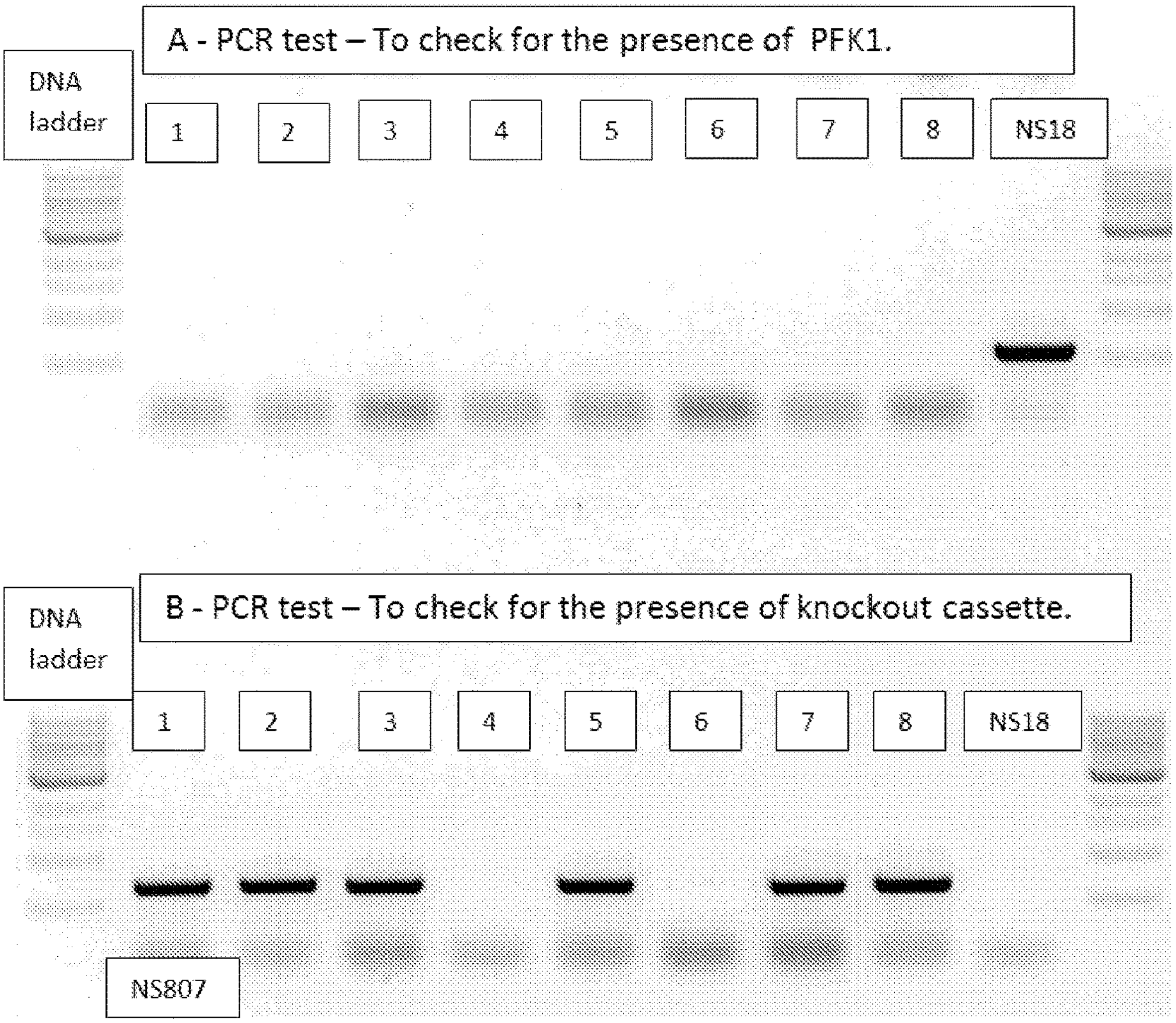
FIG. 16 consists of two panels, labeled panels (A) and (B). The two panels show imaged DNA gels comprising PCR products from PCR performed on *Y. lipolytica* strains transformed with knockout cassettes corresponding to SEQ ID NO:143 and SEQ ID NO:144. Additionally, PCR products from the parent *Y. lipolytica* strain NS18 were analyzed a control. Panel (A) (top) shows results obtained from PCR performed with primers NP2784 (SEQ ID NO:157) and NP2785 (SEQ ID NO:158), which were used to assess whether a *Y. lipolytica* colony possesses an intact PFK1 gene. Only the negative control NS18 shows a band corresponding to a NP2784/NP2785 PCR product. Panel (B) (bottom) shows results obtained from PCR performed with primers NP2784 (SEQ ID NO:157) and NP356 (SEQ ID NO:152), which were used to assess whether a *Y. lipolytica* colony comprised a knockout cassette integrated into the *Y. lipolytica* genome at the PFK1 gene locus. Colonies 1, 2, 3, 5, 7, and 8 each displayed bands corresponding to a NP2784/NP356 gene product. Colony 1 is named strain NS807.

Knockout cassettes for SEQ ID NO:143 and SEQ ID NO:144 were used to delete the PFK1 gene from *Yarrowia lipolytica* strain NS18. PCR was used to check for the presence of an intact PFK1 gene and to check for successful recombination of the SEQ ID NO:143 and SEQ ID NO:144 nucleotide sequences. Primer NP2784 (SEQ ID NO:157) binds to a region upstream of the *Y. lipolytica* PFK1 gene, primer NP2785 (SEQ ID NO:158) binds to an internal region of the PFK1 gene, and the two primers were used to determine whether transformed cells comprised an intact PFK1 gene. FIG. 16 panel A shows that none of eight transformed colonies comprised an intact PFK1 gene, whereas the untransformed negative control NG18 comprised an intact PFK1 gene. Thus, the two knockout cassettes successfully deleted the PFK1 gene in each transformant. Primer NP2784 (SEQ ID NO:157) binds to a region upstream of the PFK1 gene, primer NP356 (SEQ ID NO:152) binds to the Nat gene, and the two primers were used to determine whether transformed cells comprised the knockout cassette. FIG. 16 panel B shows that six of eight transformants contained a knockout cassette integrated into the PFK1 gene locus. Colony 1, which comprises a PFK1 deletion and integrated knockout cassette, was named strain NS807.

Figure 17:
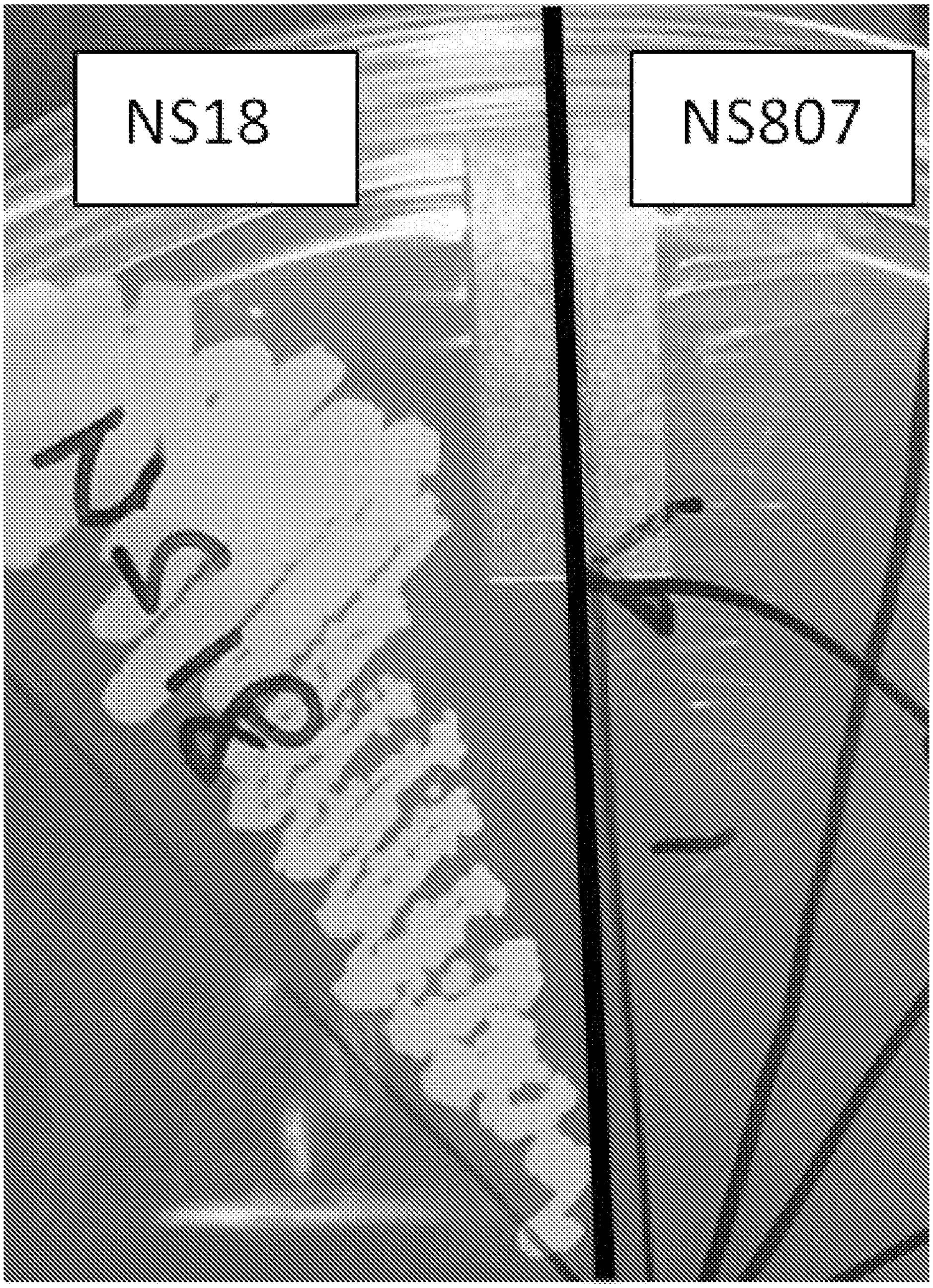
FIG. 17 is an image of *Yarrowia lipolytica* strain NS18, a wild type strain, and NS807, a strain transformed with knockout cassettes corresponding to SEQ ID NO:143 and SEQ ID NO:144. The strains were grown on plates comprising minimal media with glucose as the only carbon source. Strain NS18 was able to grow on glucose whereas strain NS807, which was engineered to delete phosphofructokinase 1, did not grow on glucose.

Wild type *Yarrowia lipolytica* strain NS18 and PFK1 knockout strain NS807 were plated on minimal media containing glucose as the sole carbon source. Strain NS18 was able to grow on glucose whereas strain NS807 was not, thereby confirming the PFK1 deletion in strain NS807 (FIG. 17).

Figure 18:
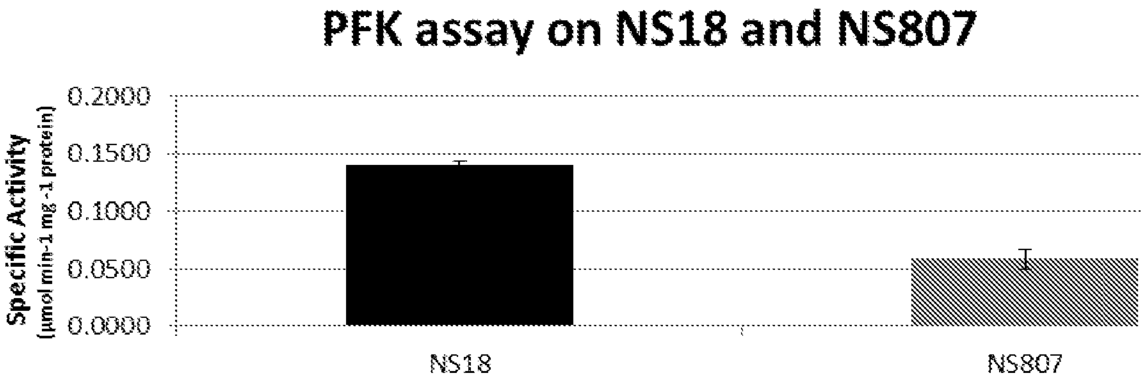
FIG. 18 is a graph showing the specific phosphofructokinase activity of wild type *Yarrowia lipolytica* strain NS18 and knockout strain NS807.

The phosphofructokinase activity of wild type *Yarrowia lipolytica* strain NS18 and PFK1 knockout strain NS807 was assessed using a phosphofructokinase assay described by Flores et al. (Microbiology, 151:1465-74 (2005)). Protein was extracted from 2 L overnight cultures of each strain grown to an $OD_{600}$ of 0.5-0.6. Cells were pelleted at 5000 rpm at 4° C. and washed twice in 20 mM HEPES, pH 7.6, containing 1M sorbitol. Cell pellets were washed in lysis buffer containing 100 mM HEPES, pH 7.6, containing 0.8M sorbitol, 10 mM magnesium acetate, 2 mM EDTA, and 300 mM potassium glutamate, and then suspended in a minimal volume of lysis buffer (approximately ⅓rd of the pellet volume). The cells were frozen in liquid nitrogen and stored at −80° C. The cells were lysed in a coffee grinder with dry ice by grinding 15-20 times using 20-second pulses. The ground dry ice/cell mix was transferred into a centrifuge tube, and the dry ice was allowed to sublimate at room temperature. The cell debris was pelleted at 22,000 rpm for 30 minutes at 4° C., and the supernatant was stored at −80° C. until use. The supernatant was used to assess phosphofructokinase activity as described by Flores et al. (Microbiology, 151:1465-74 (2005)). Activity was normalized using total protein concentration, which was calculated using the Pierce™ Coomassie (Bradford) Protein Assay Kit. Deletion of the PFK1 gene from *Y. lipolytica* reduced PFK activity in strain NS807 relative to wild type strain NS18 (FIG. 18).

INCORPORATION BY REFERENCE

All of the patents, published patent applications, and non-patent literature cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant yeast cell, comprising:

a first exogenous nucleic acid sequence encoding a phosphoketolase protein; and a second exogenous nucleic acid sequence encoding a phosphate acetyltransferase protein from *Thermoanaerobacterium saccharolyticum;* wherein the recombinant yeast cell does not express an endogenous functional phosphofructokinase protein.

2. The recombinant yeast cell of claim 1, wherein the first nucleic acid sequence comprises SEQ ID NO:22, SEQ ID NO:24, SEQ ID NO:26, SEQ ID NO:28, SEQ ID NO:30, SEQ ID NO:32, SEQ ID NO:122, SEQ ID NO:124, or SEQ ID NO:126.

3. The recombinant yeast cell of claim 1, wherein the first nucleic acid sequence encodes an amino acid sequence having at least 95% sequence identity to SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125.

4. The recombinant yeast cell of claim 1, wherein the second nucleic acid sequence comprises SEQ ID NO:120 or SEQ ID NO:76.

5. The recombinant yeast cell of claim 1, wherein the second nucleic acid sequence encodes an amino acid sequence having at least 95% sequence identity with SEQ ID NO:75.

6. The recombinant yeast cell of claim 1, wherein the phosphofructokinase protein is encoded by a nucleic acid sequence comprising SEQ ID NO:142, SEQ ID NO:154, or SEQ ID NO:156.

7. The recombinant yeast cell of claim 1, further comprising a deletion of a nucleic acid sequence encoding a native transaldolase protein.

8. The recombinant yeast cell of claim 7, wherein the recombinant cell comprises a deletion of a transaldolase protein classified by Enzyme Commission number EC 2.2.1.2.

9. The recombinant yeast cell of claim 7 further comprising a nucleic acid that encodes a soluble transhydrogenase protein or an external oxidoreductase protein.

10. The recombinant yeast cell of claim 1, wherein the cell is selected from the group consisting of *Arxula, Aspegillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, and *Yarrowia.*

11. The recombinant yeast cell of claim 10, wherein the cell is selected from the group consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, and *Yarrowia lipolytica.*

12. The recombinant yeast cell of claim 11, wherein the cell is selected from the group consisting of *Arxula adeninivorans, Saccharomyces cerevisiae*, and *Yarrowia lipolytica.*

13. The recombinant yeast cell of claim 1, wherein the cell is not *Saccharomyces cerevisiae.*

14. The recombinant yeast cell of claim 1, wherein the cell does not comprise a deletion, mutation, or substitution in a native pyruvate decarboxylase gene.

15. The recombinant yeast cell of claim 1, wherein the cell produces a product selected from the group consisting of an oil, a lipid, a fatty acid, a fatty alcohol, and a triacylglyceride.

16. The recombinant yeast cell of claim 1, wherein the cell produces a higher lipid yield relative to an unmodified cell of the same type under the same conditions.

17. A method of collecting a product from a yeast cell, comprising:

transforming the yeast cell with a first nucleic acid sequence that encodes a phosphoketolase protein;

transforming the yeast cell with a second nucleic acid sequence that encodes a phosphate acetyltransferase protein;

eliminating expression of a functional native phosphofructokinase protein in the yeast cell; and collecting the product from the yeast cell, wherein the product is an oil, a lipid, a fatty acid, a fatty alcohol, or a triacylglyceride.

18. The method of claim 17, wherein the first nucleic acid sequence encodes an amino acid sequence having at least 95% sequence identity with the sequence set forth in SEQ ID NO:21, SEQ ID NO:23, SEQ ID NO:25, SEQ ID NO:27, SEQ ID NO:29, SEQ ID NO:31, SEQ ID NO:121, SEQ ID NO:123, or SEQ ID NO:125.

19. The method of claim 17, wherein the second nucleic acid sequence encodes an amino acid sequence having at least 95% sequence identity with the sequence set forth in SEQ ID NO:1, SEQ ID NO:3, SEQ ID NO:5, SEQ ID NO:33, SEQ ID NO:35, SEQ ID NO:37 SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, or SEQ ID NO:119.

20. The method of claim 17 wherein the phosphofructokinase protein is encoded by a nucleic acid sequence comprising SEQ ID NO:142, SEQ ID NO:154, or SEQ ID NO:156.

21. The method of claim 17, wherein the product is stearic acid, oleic acid, linoleic acid, capric acid, caprylic acid, caproic acid, lauric acid, myristic acid, palmitic acid, palmitoleic acid, or squalene.

* * * * *

SEQUENCE LISTING

```
<160> NUMBER OF SEQ ID NOS: 166

<210> SEQ ID NO 1
<211> LENGTH: 333
<212> TYPE: PRT
<213> ORGANISM: Methanosarcina thermophila

<400> SEQUENCE: 1

Leu Val Thr Phe Leu Glu Lys Ile Ser Glu Arg Ala Lys Lys Leu Asn
1               5                   10                  15

Lys Thr Ile Ala Leu Pro Glu Thr Glu Asp Ile Arg Thr Leu Gln Ala
            20                  25                  30

Ala Ala Lys Ile Leu Glu Arg Gly Ile Ala Asp Ile Val Leu Val Gly
        35                  40                  45

Asn Glu Ala Asp Ile Lys Ala Leu Ala Gly Asp Leu Asp Leu Ser Lys
    50                  55                  60

Ala Lys Ile Val Asp Pro Lys Thr Tyr Glu Lys Lys Asp Glu Tyr Ile
65                  70                  75                  80

Asn Ala Phe Tyr Glu Leu Arg Lys His Lys Gly Ile Thr Leu Glu Asn
                85                  90                  95

Ala Ala Glu Ile Met Ser Asp Tyr Val Tyr Phe Ala Val Met Met Ala
            100                 105                 110

Lys Leu Gly Glu Val Asp Gly Val Val Ser Gly Ala Ala His Ser Ser
        115                 120                 125

Ser Asp Thr Leu Arg Pro Ala Val Gln Ile Val Lys Thr Ala Lys Gly
    130                 135                 140

Ala Ala Leu Ala Ser Ala Phe Phe Ile Ile Ser Val Pro Asp Cys Glu
145                 150                 155                 160

Tyr Gly Ser Asp Gly Thr Phe Leu Phe Ala Asp Ser Gly Met Val Glu
                165                 170                 175

Met Pro Ser Val Glu Asp Val Ala Asn Ile Ala Val Ile Ser Ala Lys
            180                 185                 190

Thr Phe Glu Leu Leu Val Gln Asp Val Pro Lys Val Ala Met Leu Ser
        195                 200                 205

Tyr Ser Thr Lys Gly Ser Ala Lys Ser Lys Leu Thr Glu Ala Thr Ile
    210                 215                 220

Ala Ser Thr Lys Leu Ala Gln Glu Leu Ala Pro Asp Ile Ala Ile Asp
225                 230                 235                 240

Gly Glu Leu Gln Val Asp Ala Ala Ile Val Pro Lys Val Ala Ala Ser
                245                 250                 255
```

-continued

```
Lys Ala Pro Gly Ser Pro Val Ala Gly Lys Ala Asn Val Phe Ile Phe
            260                 265                 270

Pro Asp Leu Asn Cys Gly Asn Ile Ala Tyr Lys Ile Ala Gln Arg Leu
        275                 280                 285

Ala Lys Ala Glu Ala Tyr Gly Pro Ile Thr Gln Gly Leu Ala Lys Pro
    290                 295                 300

Ile Asn Asp Leu Ser Arg Gly Cys Ser Asp Glu Asp Ile Val Gly Ala
305                 310                 315                 320

Val Ala Ile Thr Cys Val Gln Ala Ala Ala Gln Asp Lys
                325                 330


<210> SEQ ID NO 2
<211> LENGTH: 1002
<212> TYPE: DNA
<213> ORGANISM: Methanosarcina thermophila

<400> SEQUENCE: 2

ttggtaacat ttttagagaa gatcagtgaa agagcaaaga aacttaacaa aacaatcgct      60

ttacccgaaa ctgaagatat aagaaccctc caggcagctg ccaagatcct tgaaagaggt     120

attgcagaca ttgtccttgt cggtaatgag gcagatatta aggcgctcgc aggagatctg     180

gatctctcaa aagcaaaaat tgtagatcct aaaacctatg agaaaaaaga tgaatacatt     240

aacgctttct acgagttgag aaagcacaaa ggcatcacac tcgaaaatgc agctgaaatc     300

atgagcgatt acgtttactt cgctgttatg atggccaaac tcggggaagt agacggtgta     360

gtatcaggcg ctgcccactc ttcttcagac accctgaggc ctgctgtcca gatcgtgaaa     420

acagccaagg gcgcagctct tgcatccgct ttcttcataa tctctgtgcc tgactgtgaa     480

tatgggtcag atggcacatt ccttttcgct gactctggca tggttgaaat gccgagcgta     540

gaagacgttg caaacattgc agttatttcc gcaaagacct tcgaattgct ggtccaggac     600

gtgccaaagg ttgcaatgct ctcctactcc accaagggaa gcgccaagag caaactgacc     660

gaagcaacaa ttgcttctac aaaacttgca caggaacttg ctcctgatat cgcaattgac     720

ggtgaactcc aggttgacgc cgcgattgtc cccaaagttg cagcttcaaa agcccccgga     780

agccctgttg caggcaaagc caatgtcttc attttccctg acctgaactg tggaaacatc     840

gcatacaaga tcgcccagag gcttgctaaa gctgaagctt atggtcctat cacccaggga     900

ctggcaaagc caattaacga cctgtccaga ggctgcagcg acgaagatat tgtcggtgcc     960

gttgccatta cctgtgtaca ggccgcagca caggacaaat aa                       1002


<210> SEQ ID NO 3
<211> LENGTH: 333
<212> TYPE: PRT
<213> ORGANISM: Methanosarcina barkeri

<400> SEQUENCE: 3

Met Val Thr Phe Leu Glu Lys Ile Ser Glu Arg Ala Lys Lys Leu Asn
1               5                   10                  15

Lys Thr Ile Ala Leu Pro Glu Thr Thr Asp Ile Arg Thr Leu Gln Ala
            20                  25                  30

Ala Ala Lys Ala Leu Glu Arg Gly Val Ala Asn Ile Val Leu Ile Gly
        35                  40                  45

Asp Glu Ala Asn Ile Lys Glu Leu Ala Gly Asp Leu Asp Leu Ser Lys
    50                  55                  60

Ala Lys Ile Val Asn Pro Glu Thr Tyr Glu Lys Lys Asp Glu Tyr Ile
65                  70                  75                  80
```

```
Gln Ala Phe Tyr Glu Leu Arg Lys His Lys Gly Ile Thr Leu Glu Ser
                85                  90                  95

Ala Ala Glu Ile Met Lys Asp Tyr Val Tyr Phe Ala Val Met Ala Ala
            100                 105                 110

Lys Leu Asn Glu Val Asp Gly Val Val Ser Gly Ala Val His Ser Ser
        115                 120                 125

Ser Asp Thr Leu Arg Pro Ala Val Gln Ile Val Lys Thr Ala Pro Asp
    130                 135                 140

Ala Ala Leu Ala Ser Ala Phe Phe Ile Ile Ala Val Pro Asp Cys Glu
145                 150                 155                 160

Tyr Gly Ser Glu Gly Thr Phe Leu Phe Ala Asp Ser Gly Met Val Glu
                165                 170                 175

Met Pro Ser Pro Glu Asp Val Ala Asn Ile Ala Ile Ile Ser Ala Lys
            180                 185                 190

Thr Phe Glu Leu Leu Val Gln Asp Asp Pro Tyr Val Ala Met Leu Ser
        195                 200                 205

Tyr Ser Thr Lys Gly Ser Ala His Ser Lys Leu Thr Glu Ala Thr Ile
    210                 215                 220

Ala Ala Thr Lys Leu Ala Gln Glu Leu Ala Pro Asp Ile Pro Ile Asp
225                 230                 235                 240

Gly Glu Leu Gln Val Asp Ala Ala Ile Val Pro Lys Val Ala Ala Ser
                245                 250                 255

Lys Ala Pro Gly Ser Pro Val Ala Gly Lys Ala Asn Val Phe Ile Phe
            260                 265                 270

Pro Asp Leu Asn Ala Gly Asn Ile Ala Tyr Lys Ile Ala Gln Arg Leu
        275                 280                 285

Ala Lys Ala Glu Ala Tyr Gly Pro Ile Thr Gln Gly Leu Ala Lys Pro
    290                 295                 300

Ile Asn Asp Leu Ser Arg Gly Cys Ser Asp Glu Asp Ile Val Gly Ala
305                 310                 315                 320

Ile Ala Ile Thr Cys Val Gln Ala Ala Ala Gln Asp Lys
                325                 330
```

<210> SEQ ID NO 4
<211> LENGTH: 1002
<212> TYPE: DNA
<213> ORGANISM: Methanosarcina barkeri

<400> SEQUENCE: 4

```
ttggtaacat ttttagaaaa aatcagtgaa agagcaaaga aactcaacaa aacaattgct      60

ttacctgaaa ctaccgatat aagaactctt caggcagctg ccaaggccct cgaaagaggg     120

gttgcaaata tcgttctcat cggcgatgaa gcaaatatta aggagcttgc aggagatctt     180

gacctctcaa aagcaaaaat tgtaaatcct gagacttacg agaaaaagga tgaatacatt     240

caggctttct acgagctgag aaagcataag ggtattacac tcgaaagtgc agccgaaatt     300

atgaaggatt acgtttactt cgctgttatg gcggctaaac tcaatgaagt agacggtgta     360

gtttcaggtg ctgttcactc ttcctctgat acacttagac ctgctgtcca gattgttaaa     420

actgcccctg atgcagctct cgcatctgct tttttcatta ttgccgtgcc ggactgtgaa     480

tatgggtcag aagggacatt cctctttgct gactcaggta tggttgaaat gcccagtcct     540

gaagacgttg caaacattgc tatcatttct gcaaaaacct ttgaactgct ggttcaggat     600

gatccatatg ttgcaatgct ttcttattcc actaagggaa gtgcacacag caaactgact     660
```

-continued

```
gaggcaacaa ttgctgccac aaagcttgca caggaactcg ctccagatat tccaattgat    720

ggtgaactcc aggtagatgc agcaattgtt ccaaaagttg cagcttcaaa ggctccagga    780

agccctgttg caggcaaagc taatgtcttt atcttccctg accttaacgc tggaaacata    840

gcatacaaga ttgcccagag gctcgccaag gccgaagctt atggccctat tactcaggga    900

cttgccaagc caattaatga cttatccaga ggctgcagcg acgaagacat tgtcggtgct    960

attgcaatta cgtgcgttca ggccgcagca caggacaaat aa                      1002
```

```
<210> SEQ ID NO 5
<211> LENGTH: 333
<212> TYPE: PRT
<213> ORGANISM: Methanosarcina acetivorans

<400> SEQUENCE: 5

Leu Val Thr Phe Leu Glu Lys Ile Ser Glu Arg Ala Lys Lys Leu Asn
1               5                   10                  15

Lys Thr Ile Ala Leu Pro Glu Thr Glu Asp Ile Arg Thr Leu Gln Ala
            20                  25                  30

Ala Ala Lys Ile Leu Glu Arg Gly Ile Ala Asn Val Val Leu Val Gly
        35                  40                  45

Asp Glu Ala Asp Ile Lys Ala Leu Ala Gly Asp Leu Asp Leu Ser Lys
    50                  55                  60

Ala Lys Ile Val Asn Pro Lys Thr Tyr Glu Lys Lys Asp Glu Tyr Ile
65                  70                  75                  80

Asn Thr Phe Tyr Glu Leu Arg Lys His Lys Gly Ile Thr Pro Glu Thr
                85                  90                  95

Ala Ala Glu Val Met Ser Asp Tyr Val Tyr Phe Ala Val Met Met Ala
            100                 105                 110

Lys Leu Gly Glu Val Asp Gly Val Val Ser Gly Ala Ala His Ser Ser
        115                 120                 125

Ser Asp Thr Leu Arg Pro Ala Val Gln Ile Val Lys Thr Ala Pro Gly
    130                 135                 140

Ala Ala Leu Ala Ser Ala Phe Phe Ile Ile Ala Val Pro Asp Cys Glu
145                 150                 155                 160

Tyr Gly Ser Asp Gly Thr Phe Leu Phe Ala Asp Ser Gly Met Val Glu
                165                 170                 175

Ile Pro Ser Val Glu Asp Val Ala Asn Ile Ala Val Ile Ser Ala Lys
            180                 185                 190

Thr Phe Glu Leu Leu Val Gln Asp Thr Pro Tyr Val Ala Met Leu Ser
        195                 200                 205

Tyr Ser Thr Lys Gly Ser Ala His Ser Lys Leu Thr Glu Ala Thr Val
    210                 215                 220

Ala Ala Thr Lys Leu Ala Gln Glu Leu Ala Pro Asp Val Ala Ile Asp
225                 230                 235                 240

Gly Glu Leu Gln Val Asp Ala Ala Val Val Pro Lys Val Ala Ala Ser
                245                 250                 255

Lys Ala Pro Gly Ser Pro Val Ala Gly Lys Ala Asn Val Phe Ile Phe
            260                 265                 270

Pro Asp Leu Asn Ala Gly Asn Ile Ala Tyr Lys Ile Ala Gln Arg Leu
        275                 280                 285

Ala Lys Ala Glu Ala Tyr Gly Pro Ile Thr Gln Gly Leu Ala Lys Pro
    290                 295                 300

Ile Asn Asp Leu Ser Arg Gly Cys Ser Asp Glu Asp Ile Val Gly Ala
305                 310                 315                 320
```

```
Val Ala Ile Thr Cys Val Gln Ala Ala Ala Gln Asp Lys
                325                 330


<210> SEQ ID NO 6
<211> LENGTH: 1002
<212> TYPE: DNA
<213> ORGANISM: Methanosarcina acetivorans

<400> SEQUENCE: 6

ttggtaacat ttttagagaa gatcagtgaa agagcaaaga aactcaacaa gacaatcgct     60

ttacctgaaa ctgaagatat aaggaccctc caggcagctg ccaagatcct tgaaagaggt    120

attgcaaacg ttgtccttgt cggtgatgaa gccgacatta aggcgctcgc aggagatctt    180

gatctctcaa aagcaaaaat tgtaaatccg aaaacctatg agaaaaaaga cgaatacatt    240

aacactttct atgagctgag aaagcacaaa ggtataaccc ccgaaactgc agctgaagtt    300

atgagcgatt acgtttactt cgccgttatg atggcaaaac tcggagaagt agacggagta    360

gtatcaggag ctgctcactc ttcttcagac accctgagac ctgctgtcca gatagttaag    420

actgctccag gcgcagcact tgcatccgct ttcttcatca ttgccgtacc tgactgtgaa    480

tacggatcag atgggacctt cctctttgcc gactcgggta tggttgaaat tccaagtgta    540

gaggatgttg caaacattgc agttatttct gcaaagacct tcgaactgct ggttcaggac    600

actccgtatg ttgcaatgct ttcctattcc accaaaggaa gtgcacacag caaactgacc    660

gaggcaacag tcgctgccac aaagcttgca caggaacttg ctcctgacgt tgcaatcgac    720

ggtgaactgc aggttgatgc agcagttgtc cccaaagttg cagcttcaaa ggctcccgga    780

agccctgtcg caggtaaagc caatgtcttt atcttccccg atctgaacgc tggaaacatc    840

gcatacaaga tcgcccagag gcttgccaag gctgaagcat atggtcctat cacccaggga    900

cttgcaaagc cgattaacga cctgtccaga ggatgcagtg acgaagatat tgtcggtgct    960

gttgcgatta cctgtgtcca ggccgcagcc caggacaaat aa                      1002


<210> SEQ ID NO 7
<211> LENGTH: 549
<212> TYPE: PRT
<213> ORGANISM: Saccharomyces cerevisiae

<400> SEQUENCE: 7

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His Thr Leu Gly Asn Gly Asp Phe Thr Val Phe His Arg Met Ser
        115                 120                 125

Ala Asn Ile Ser Glu Thr Thr Ala Met Ile Thr Asp Ile Cys Thr Pro
```

-continued

```
    130                 135                 140

Gln Ala Glu Ile Asp Arg Cys Ile Arg Thr Thr Tyr Val Thr Gln Arg
145                 150                 155                 160

Pro Val Tyr Leu Gly Leu Pro Ala Asn Leu Val Asp Leu Asn Val Pro
                165                 170                 175

Ala Lys Leu Leu Gln Thr Pro Ile Asp Met Ser Leu Lys Pro Asn Asp
            180                 185                 190

Ala Glu Ser Glu Lys Glu Val Ile Asp Thr Ile Leu Val Leu Val Lys
        195                 200                 205

Asp Ala Lys Asn Pro Val Ile Leu Ala Asp Ala Cys Cys Ser Arg His
    210                 215                 220

Asp Val Lys Ala Glu Thr Lys Lys Leu Ile Asp Leu Thr Gln Phe Pro
225                 230                 235                 240

Ala Phe Val Thr Pro Met Gly Lys Gly Ser Ile Ser Glu Gln His Pro
                245                 250                 255

Arg Tyr Gly Gly Val Tyr Val Gly Thr Leu Ser Lys Pro Glu Val Lys
            260                 265                 270

Glu Ala Val Glu Ser Ala Asp Leu Ile Leu Ser Val Gly Ala Leu Leu
        275                 280                 285

Ser Asp Phe Asn Thr Gly Ser Phe Ser Tyr Ser Tyr Lys Thr Lys Asn
    290                 295                 300

Ile Val Glu Phe His Ser Asp His Met Lys Ile Arg Asn Ala Thr Phe
305                 310                 315                 320

Pro Gly Val Gln Met Lys Phe Val Leu Gln Lys Leu Leu Thr Asn Ile
                325                 330                 335

Ala Asp Ala Ala Lys Gly Tyr Lys Pro Val Ala Val Pro Ala Arg Thr
            340                 345                 350

Pro Ala Asn Ala Ala Val Pro Ala Ser Thr Pro Leu Lys Gln Glu Trp
        355                 360                 365

Met Trp Asn Gln Leu Gly Asn Phe Leu Gln Glu Gly Asp Val Val Ile
    370                 375                 380

Ala Glu Thr Gly Thr Ser Ala Phe Gly Ile Asn Gln Thr Thr Phe Pro
385                 390                 395                 400

Asn Asn Thr Tyr Gly Ile Ser Gln Val Leu Trp Gly Ser Ile Gly Phe
                405                 410                 415

Thr Thr Gly Ala Thr Leu Gly Ala Ala Phe Ala Ala Glu Glu Ile Asp
            420                 425                 430

Pro Lys Lys Arg Val Ile Leu Phe Ile Gly Asp Gly Ser Leu Gln Leu
        435                 440                 445

Thr Val Gln Glu Ile Ser Thr Met Ile Arg Trp Gly Leu Lys Pro Tyr
    450                 455                 460

Leu Phe Val Leu Asn Asn Asp Gly Tyr Thr Ile Glu Lys Leu Ile His
465                 470                 475                 480

Gly Pro Lys Ala Gln Tyr Asn Glu Ile Gln Gly Trp Asp His Leu Ser
                485                 490                 495

Leu Leu Pro Thr Phe Gly Ala Lys Asp Tyr Glu Thr His Arg Val Ala
            500                 505                 510

Thr Thr Gly Glu Trp Asp Lys Leu Thr Gln Asp Lys Ser Phe Asn Asp
        515                 520                 525

Asn Ser Lys Ile Arg Met Ile Glu Val Met Leu Pro Val Phe Asp Cys
    530                 535                 540

Ser Thr Lys Leu Gly
545
```

<210> SEQ ID NO 8
<211> LENGTH: 1650
<212> TYPE: DNA
<213> ORGANISM: Saccharomyces cerevisiae

<400> SEQUENCE: 8
atgtctgaaa ttactttggg taaatatttg ttcgaaagat taaagcaagt caacgttaac 60
accgttttcg gtttgccagg tgacttcaac ttgtccttgt tggacaagat ctacgaagtt 120
gaaggtatga gatgggctgg taacgccaac gaattgaacg ctgcttacgc cgctgatggt 180
tacgctcgta tcaagggtat gtcttgtatc atcaccacct tcggtgtcgg tgaattgtct 240
gctttgaacg gtattgccgg ttcttacgct gaacacgtcg gtgttttgca cgttgttggt 300
gtcccatcca tctcttctca agctaagcaa ttgttgttgc acaccttggg taacggtgac 360
ttcactgttt tccacagaat gtctgccaac atttctgaaa ccactgctat gatcactgac 420
atctgtacgc ccaggctgga aattgacaga tgtatcagaa ccacttacgt cacccaaaga 480
ccagtctact taggtttgcc agctaacttg gtcgacttga acgtcccagc taagttgttg 540
caaactccaa ttgacatgtc tttgaagcca aacgatgctg aatccgaaaa ggaagtcatt 600
gacaccatct tggtcttggt caaggatgct aagaacccag ttattctggc tgatgcttgt 660
tgttccagac acgacgtcaa ggctgaaact aagaagttga ttgacttgac tcaattccca 720
gctttcgtca ccccaatggg taagggttcc attagcgaac aacacccaag atacggtggt 780
gtttacgtcg gtaccttgtc caagccagaa gttaaggaag ccgttgaatc tgctgacttg 840
attttgtctg tcggtgcttt gttgtctgat ttcaacaccg gttctttctc ttactcttac 900
aagaccaaga acattgtcga attccactcc gaccacatga agatcagaaa cgccactttc 960
ccaggtgtcc aaatgaaatt cgttttgcaa aagttgttga ccaatattgc tgacgccgct 1020
aagggttaca agccagttgc tgtcccagct agaactccag ctaacgctgc tgtcccagct 1080
tctaccccat tgaagcaaga atggatgtgg aaccaattgg gtaacttctt gcaagaaggt 1140
gatgttgtca ttgctgaaac cggtacctcc gctttcggta tcaaccaaac cactttccca 1200
aacaacacct acggtatctc tcaagtctta tggggttcca ttggtttcac cactggtgct 1260
accttgggtg ctgctttcgc tgctgaagaa attgatccaa agaagagagt tatcttattc 1320
attggtgacg gttctttgca attgactgtt caagaaatct ccaccatgat cagatggggc 1380
ttgaagccat acttgttcgt cttgaacaac gatggttaca ccattgaaaa gttgattcac 1440
ggtccaaagg ctcaatacaa cgaaattcaa ggttgggacc acctatcctt gttgccaact 1500
ttcggtgcta aggactacga aacccacaga gtcgctacca ccggtgaatg ggacaagttg 1560
acccaagaca agtctttcaa cgacaactct aagatcagaa tgattgaggt tatgttgcca 1620
gtcttcgatt gctccacaaa acttggttga 1650

<210> SEQ ID NO 9
<211> LENGTH: 563
<212> TYPE: PRT
<213> ORGANISM: Saccharomyces cerevisiae

<400> SEQUENCE: 9

Met Ser Glu Ile Thr Leu Gly Lys Tyr Leu Phe Glu Arg Leu Ser Gln
1 5 10 15

Val Asn Cys Asn Thr Val Phe Gly Leu Pro Gly Asp Phe Asn Leu Ser
20 25 30

```
Leu Leu Asn Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Arg Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Glu Val Val Arg Thr Val Val Glu Phe Ile
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Ala Lys Asp Tyr Lys Pro Val Ala Val Pro Ala Arg
            340                 345                 350

Val Pro Ile Thr Lys Ser Thr Pro Ala Asn Thr Pro Met Lys Gln Glu
        355                 360                 365

Trp Met Trp Asn Gln Leu Gly Asn Phe Leu Arg Glu Gly Asp Ile Val
    370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
```

-continued

```
    450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
        515                 520                 525

Asp Asn Ser Lys Ile Arg Met Ile Glu Val Met Leu Pro Val Phe Asp
    530                 535                 540

Ala Pro Gln Asn Leu Val Lys Gln Ala Gln Leu Thr Ala Ala Thr Asn
545                 550                 555                 560

Ala Lys Gln


<210> SEQ ID NO 10
<211> LENGTH: 1692
<212> TYPE: DNA
<213> ORGANISM: Saccharomyces cerevisiae

<400> SEQUENCE: 10

atgtctgaaa taaccttagg taaatattta tttgaaagat tgagccaagt caactgtaac      60

accgtcttcg gtttgccagg tgactttaac ttgtctcttt tgaataagct ttatgaagtc     120

aaaggtatga gatgggctgg taacgctaac gaattgaacg ctgcctatgc tgctgatggt     180

tacgctcgta tcaagggtat gtcctgtatt attaccacct tcggtgtcgg tgaattgtct     240

gctttgaatg gtattgccgg ttcttacgct gaacatgtcg gtgttttgca cgttgttggt     300

gttccatcca tctcttctca agctaagcaa ttgttgttgc atcatacctt gggtaacggt     360

gacttcactg ttttccacag aatgtctgcc aacatttctg aaaccactgc catgatcact     420

gatattcgta acgctccagc tgaaattgac agatgtatca gaaccaccta cactacccaa     480

agaccagtct acttgggttt gccagctaac ttggttgact tgaacgtccc agccaagtta     540

ttggaaactc caattgactt gtctttgaag ccaaacgacg ctgaagctga agctgaagtt     600

gttagaactg ttgttgaatt catcaaggat gctaagaacc cagttatctt ggctgatgct     660

tgttgctcta gacatgatgt caaggctgaa actaagaagt tgatggactt gactcaattc     720

ccagtttacg tcaccccaat gggtaagggt gctattgacg aacaacaccc aagatacggt     780

ggtgtttacg ttggtacctt gtctagacca gaagttaaga aggctgtaga atctgctgat     840

ttgatattgt ctatcggtgc tttgttgtct gatttcaaca ccggttcttt ctcttactcc     900

tacaagacca agaacattgt cgaattccac tctgaccaca tcaagatcag aaacgccacc     960

ttcccaggtg ttcaaatgaa atttgccttg caaaaattgt tggatgctat tccagaagtc    1020

gctaaggact acaaaccagt tgctgtccca gctagagttc caattaccaa gtctactcca    1080

gctaacactc caatgaagca agaatggatg tggaaccaat tgggtaactt cttgagagaa    1140

ggtgatattg ttattgctga aaccggtact tccgccttcg gtattaacca aactactttc    1200

ccaacagatg tatacgctat cgtccaagtc ttgtggggtt ccattggttt cacagtcggt    1260

gctctattgg gtgctactat ggccgctgaa gaacttgatc caaagaagag agttatttta    1320

ttcattggtg acggttctct acaattgact gttcaagaaa tctctaccat gattagatgg    1380

ggtttgaagc catacatttt tgtcttgaat aacaacggtt acaccattga aaaattgatt    1440

cacggtcctc atgccgaata taatgaaatt caaggttggg accacttggc cttattgcca    1500
```

actttcggtg ctagaaacta cgaaacccac agagttgcta ccactggtga atgggaaaag 1560
ttgactcaag acaaggactt ccaagacaac tctaagatta gaatgattga agttatgttg 1620
ccagtctttg atgctccaca aaacttggtt aaacaagctc aattgactgc cgctactaac 1680
gctaaacaat aa 1692

<210> SEQ ID NO 11
<211> LENGTH: 563
<212> TYPE: PRT
<213> ORGANISM: Saccharomyces cerevisiae

<400> SEQUENCE: 11

Met Ser Glu Ile Thr Leu Gly Lys Tyr Leu Phe Glu Arg Leu Lys Gln
1 5 10 15

Val Asn Val Asn Thr Ile Phe Gly Leu Pro Gly Asp Phe Asn Leu Ser
20 25 30

Leu Leu Asp Lys Ile Tyr Glu Val Asp Gly Leu Arg Trp Ala Gly Asn
35 40 45

Ala Asn Glu Leu Asn Ala Ala Tyr Ala Ala Asp Gly Tyr Ala Arg Ile
50 55 60

Lys Gly Leu Ser Val Leu Val Thr Thr Phe Gly Val Gly Glu Leu Ser
65 70 75 80

Ala Leu Asn Gly Ile Ala Gly Ser Tyr Ala Glu His Val Gly Val Leu
85 90 95

His Val Val Gly Val Pro Ser Ile Ser Ala Gln Ala Lys Gln Leu Leu
100 105 110

Leu His His Thr Leu Gly Asn Gly Asp Phe Thr Val Phe His Arg Met
115 120 125

Ser Ala Asn Ile Ser Glu Thr Thr Ser Met Ile Thr Asp Ile Ala Thr
130 135 140

Ala Pro Ser Glu Ile Asp Arg Leu Ile Arg Thr Thr Phe Ile Thr Gln
145 150 155 160

Arg Pro Ser Tyr Leu Gly Leu Pro Ala Asn Leu Val Asp Leu Lys Val
165 170 175

Pro Gly Ser Leu Leu Glu Lys Pro Ile Asp Leu Ser Leu Lys Pro Asn
180 185 190

Asp Pro Glu Ala Glu Lys Glu Val Ile Asp Thr Val Leu Glu Leu Ile
195 200 205

Gln Asn Ser Lys Asn Pro Val Ile Leu Ser Asp Ala Cys Ala Ser Arg
210 215 220

His Asn Val Lys Lys Glu Thr Gln Lys Leu Ile Asp Leu Thr Gln Phe
225 230 235 240

Pro Ala Phe Val Thr Pro Leu Gly Lys Gly Ser Ile Asp Glu Gln His
245 250 255

Pro Arg Tyr Gly Gly Val Tyr Val Gly Thr Leu Ser Lys Gln Asp Val
260 265 270

Lys Gln Ala Val Glu Ser Ala Asp Leu Ile Leu Ser Val Gly Ala Leu
275 280 285

Leu Ser Asp Phe Asn Thr Gly Ser Phe Ser Tyr Ser Tyr Lys Thr Lys
290 295 300

Asn Val Val Glu Phe His Ser Asp Tyr Val Lys Val Lys Asn Ala Thr
305 310 315 320

Phe Leu Gly Val Gln Met Lys Phe Ala Leu Gln Asn Leu Leu Lys Val
325 330 335

```
Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln
```

<210> SEQ ID NO 12
<211> LENGTH: 1692
<212> TYPE: DNA
<213> ORGANISM: Saccharomyces cerevisiae

<400> SEQUENCE: 12

```
atgtctgaaa ttactcttgg aaaatactta tttgaaagat tgaagcaagt taatgttaac      60

accatttttg ggctaccagg cgacttcaac ttgtccctat tggacaagat ttacgaggta     120

gatggattga gatgggctgg taatgcaaat gagctgaacg ccgcctatgc cgccgatggt     180

tacgcacgca tcaagggttt atctgtgctg gtaactactt ttggcgtagg tgaattatcc     240

gccttgaatg gtattgcagg atcgtatgca gaacacgtcg gtgtactgca tgttgttggt     300

gtcccctcta tctccgctca ggctaagcaa ttgttgttgc atcatacctt gggtaacggt     360

gattttaccg tttttcacag aatgtccgcc aatatctcag aaactacatc aatgattaca     420

gacattgcta cagccccttc agaaatcgat aggttgatca ggacaacatt tataacacaa     480

aggcctagct acttggggtt gccagcgaat ttggtagatc taaaggttcc tggttctctt     540

ttggaaaaac cgattgatct atcattaaaa cctaacgatc ccgaagctga aaaggaagtt     600

attgataccg tactagaatt gatccagaat tcgaaaaacc ctgttatact atcggatgcc     660

tgtgcttcta ggcacaacgt taaaaaagaa acccagaagt taattgattt gacgcaattc     720

ccagcttttg tgacacctct aggtaaaggg tcaatagatg aacagcatcc cagatatggc     780
```

-continued

```
ggtgtttatg tgggaacgct gtccaaacaa gacgtgaaac aggccgttga gtcggctgat    840

ttgatccttt cggtcggtgc tttgctctct gattttaaca caggttcgtt ttcctactcc    900

tacaagacta aaaatgtagt ggagtttcat tccgattacg taaaggtgaa gaacgctacg    960

ttcctcggtg tacaaatgaa atttgcacta caaaacttac tgaaggttat tcccgatgtt   1020

gttaagggct acaagagcgt tcccgtacca accaaaactc ccgcaaacaa aggtgtacct   1080

gctagcacgc ccttgaaaca agagtggttg tggaacgaat tgtccaaatt cttgcaagaa   1140

ggtgatgtta tcatttccga gaccggcacg tctgccttcg gtatcaatca aactatcttt   1200

cctaaggacg cctacggtat ctcgcaggtg ttgtgggggt ccatcggttt tacaacagga   1260

gcaactttag gtgctgcctt tgccgctgag gagattgacc ccaacaagag agtcatctta   1320

ttcataggtg acgggtcttt gcagttaacc gtccaagaaa tctccaccat gatcagatgg   1380

gggttaaagc cgtatctttt tgtccttaac aacgacggct acactatcga aaagctgatt   1440

catgggcctc acgcagagta caacgaaatc cagacctggg atcacctcgc cctgttgccc   1500

gcatttggtg cgaaaaagta cgaaaatcac aagatcgcca ctacgggtga gtgggatgcc   1560

ttaaccactg attcagagtt ccagaaaaac tcggtgatca gactaattga actgaaactg   1620

cccgtctttg atgctccgga aagtttgatc aaacaagcgc aattgactgc cgctacaaat   1680

gccaaacaat aa                                                       1692
```

```
<210> SEQ ID NO 13
<211> LENGTH: 408
<212> TYPE: PRT
<213> ORGANISM: Methanosarcina thermophila

<400> SEQUENCE: 13

Met Lys Val Leu Val Ile Asn Ala Gly Ser Ser Ser Leu Lys Tyr Gln
1               5                   10                  15

Leu Ile Asp Met Thr Asn Glu Ser Ala Leu Ala Val Gly Leu Cys Glu
            20                  25                  30

Arg Ile Gly Ile Asp Asn Ser Ile Ile Thr Gln Lys Lys Phe Asp Gly
        35                  40                  45

Lys Lys Leu Glu Lys Leu Thr Asp Leu Pro Thr His Lys Asp Ala Leu
    50                  55                  60

Glu Glu Val Val Lys Ala Leu Thr Asp Asp Glu Phe Gly Val Ile Lys
65                  70                  75                  80

Asp Met Gly Glu Ile Asn Ala Val Gly His Arg Val Val His Gly Gly
                85                  90                  95

Glu Lys Phe Thr Thr Ser Ala Leu Tyr Asp Glu Gly Val Glu Lys Ala
            100                 105                 110

Ile Lys Asp Cys Phe Glu Leu Ala Pro Leu His Asn Pro Pro Asn Met
        115                 120                 125

Met Gly Ile Ser Ala Cys Ala Glu Ile Met Pro Gly Thr Pro Met Val
    130                 135                 140

Ile Val Phe Asp Thr Ala Phe His Gln Thr Met Pro Pro Tyr Ala Tyr
145                 150                 155                 160

Met Tyr Ala Leu Pro Tyr Asp Leu Tyr Glu Lys His Gly Val Arg Lys
                165                 170                 175

Tyr Gly Phe His Gly Thr Ser His Lys Tyr Val Ala Glu Arg Ala Ala
            180                 185                 190

Leu Met Leu Gly Lys Pro Ala Glu Glu Thr Lys Ile Ile Thr Cys His
        195                 200                 205
```

-continued

```
Leu Gly Asn Gly Ser Ser Ile Thr Ala Val Glu Gly Gly Lys Ser Val
    210                 215                 220

Glu Thr Ser Met Gly Phe Thr Pro Leu Glu Gly Leu Ala Met Gly Thr
225                 230                 235                 240

Arg Cys Gly Ser Ile Asp Pro Ala Ile Val Pro Phe Leu Met Glu Lys
                245                 250                 255

Glu Gly Leu Thr Thr Arg Glu Ile Asp Thr Leu Met Asn Lys Lys Ser
            260                 265                 270

Gly Val Leu Gly Val Ser Gly Leu Ser Asn Asp Phe Arg Asp Leu Asp
        275                 280                 285

Glu Ala Ala Ser Lys Gly Asn Arg Lys Ala Glu Leu Ala Leu Glu Ile
    290                 295                 300

Phe Ala Tyr Lys Val Lys Lys Phe Ile Gly Glu Tyr Ser Ala Val Leu
305                 310                 315                 320

Asn Gly Ala Asp Ala Val Val Phe Thr Ala Gly Ile Gly Glu Asn Ser
                325                 330                 335

Ala Ser Ile Arg Lys Arg Ile Leu Thr Gly Leu Asp Gly Ile Gly Ile
            340                 345                 350

Lys Ile Asp Asp Glu Lys Asn Lys Ile Arg Gly Gln Glu Ile Asp Ile
        355                 360                 365

Ser Thr Pro Asp Ala Lys Val Arg Val Phe Val Ile Pro Thr Asn Glu
    370                 375                 380

Glu Leu Ala Ile Ala Arg Glu Thr Lys Glu Ile Val Glu Thr Glu Val
385                 390                 395                 400

Lys Leu Arg Ser Ser Ile Pro Val
                405


<210> SEQ ID NO 14
<211> LENGTH: 1227
<212> TYPE: DNA
<213> ORGANISM: Methanosarcina thermophila

<400> SEQUENCE: 14

atgaaagtac tggttataaa cgcagggagt tcatctctca aatatcaatt aattgatatg      60

acaaatgagt cagctcttgc agtaggtctt tgcgagagga taggtattga caactcgatc     120

atcactcaga agaagtttga cggcaagaag ctggaaaagc tgactgacct ccccactcac     180

aaggacgcac ttgaggaagt cgtaaaagct cttaccgatg atgaattcgg tgtcatcaaa     240

gacatgggtg agatcaatgc agtcggacac agagttgtgc atggtggaga gaaattcacg     300

acgtctgctt tatatgatga gggcgtagaa aaggctatca aggactgctt tgaactggca     360

ccccttcaca accctccaaa catgatggga atttcagctt gtgcagagat catgcctggg     420

acgccaatgg ttattgtttt tgatactgca ttccaccaga caatgccgcc atatgcctac     480

atgtatgctc tcccgtacga cctgtacgag aagcatgggg tcaggaaata cggtttccac     540

ggcacatccc acaagtacgt tgccgaaagg gctgctctta tgctcggaaa gcccgcagaa     600

gaaaccaaaa ttatcacctg tcaccttgga aatggttcaa gcattacagc tgtagaaggc     660

ggaaaatccg ttgaaaccag catgggcttc acacctcttg aagggcttgc aatgggcaca     720

agatgcggtt cgattgaccc tgcaatagtc cccttcctta tggaaaaaga aggcttgaca     780

acaagagaaa ttgacaccct tatgaacaag aagtcaggtg tgcttggtgt ttccgggctc     840

agcaatgact tcagagacct cgatgaagca gcttccaagg gcaacaggaa agccgaactt     900

gctcttgaaa ttttcgcata caaggtcaag aagttcatag gtgaatattc agctgtcctc     960
```

```
aatggtgcag atgcagtggt ctttactgca ggcattggag aaaacagcgc aagcatcagg   1020

aagagaatcc tcaccggtct tgatggcatc ggcataaaaa tcgatgacga aaagaacaag   1080

atcagaggtc aggaaatcga tatcagcaca ccggatgcaa aagtaagagt ttttgtcatc   1140

ccaaccaatg aggaacttgc cattgcaagg gaaacaaagg aaattgttga gaccgaagtg   1200

aagttacgca gttctatacc tgtataa                                       1227


<210> SEQ ID NO 15
<211> LENGTH: 400
<212> TYPE: PRT
<213> ORGANISM: Escherichia coli

<400> SEQUENCE: 15

Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
    130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
    210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285

Val Glu Asp Asn Tyr Ala Thr Lys Glu Asp Ala Lys Arg Ala Met Asp
    290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
```

325 330 335

Asn Ala Ala Met Val Arg Glu Leu Ser Leu Gly Lys Leu Gly Val Leu
340 345 350

Gly Phe Glu Val Asp His Glu Arg Asn Leu Ala Ala Arg Phe Gly Lys
355 360 365

Ser Gly Phe Ile Asn Lys Glu Gly Thr Arg Pro Ala Val Val Ile Pro
370 375 380

Thr Asn Glu Glu Leu Val Ile Ala Gln Asp Ala Ser Arg Leu Thr Ala
385 390 395 400

<210> SEQ ID NO 16
<211> LENGTH: 1203
<212> TYPE: DNA
<213> ORGANISM: Escherichia coli

<400> SEQUENCE: 16
atgtcgagta agttagtact ggttctgaac tgcggtagtt cttcactgaa atttgccatc 60
atcgatgcag taaatggtga agagtacctt tctggtttag ccgaatgttt ccacctgccc 120
gaagcacgta tcaaatggaa aatggacggc aataaacagg aagcggcttt aggtgcaggc 180
gccgctcaca gcgaagcgct caactttatc gttaatacta ttctggcaca aaaaccagaa 240
ctgtctgcgc agctgactgc tatcggtcac cgtatcgtac acggcggcga aaagtatacc 300
agctccgtag tgatcgatga gtctgttatt cagggtatca aagatgcagc ttcttttgca 360
ccgctgcaca acccggctca cctgatcggt atcgaagaag ctctgaaatc tttcccacag 420
ctgaaagaca aaaacgttgc tgtatttgac accgcgttcc accagactat gccggaagag 480
tcttacctct acgccctgcc ttacaacctg tacaaagagc acggcatccg tcgttacggc 540
gcgcacggca ccagccactt ctatgtaacc caggaagcgg caaaaatgct gaacaaaccg 600
gtagaagaac tgaacatcat cacctgccac ctgggcaacg gtggttccgt ttctgctatc 660
cgcaacggta aatgcgttga cacctctatg ggcctgaccc cgctggaagg tctggtcatg 720
ggtacccgtt ctggtgatat cgatccggcg atcatcttcc acctgcacga caccctgggc 780
atgagcgttg acgcaatcaa caaactgctg accaaagagt ctggcctgct gggtctgacc 840
gaagtgacca gcgactgccg ctatgttgaa gacaactacg cgacgaaaga agacgcgaag 900
cgcgcaatgg acgtttactg ccaccgcctg gcgaaataca tcggtgccta cactgcgctg 960
atggatggtc gtctggacgc tgttgtattc actggtggta tcggtgaaaa tgccgcaatg 1020
gttcgtgaac tgtctctggg caaactgggc gtgctgggct ttgaagttga tcatgaacgc 1080
aacctggctg cacgtttcgg caaatctggt ttcatcaaca aagaaggtac ccgtcctgcg 1140
gtggttatcc caaccaacga agaactggtt atcgcgcaag acgcgagccg cctgactgcc 1200
taa 1203

<210> SEQ ID NO 17
<211> LENGTH: 501
<212> TYPE: PRT
<213> ORGANISM: Saccharomyces cerevisiae

<400> SEQUENCE: 17

Met Thr Lys Leu His Phe Asp Thr Ala Glu Pro Val Lys Ile Thr Leu
1 5 10 15

Pro Asn Gly Leu Thr Tyr Glu Gln Pro Thr Gly Leu Phe Ile Asn Asn
20 25 30

Lys Phe Met Lys Ala Gln Asp Gly Lys Thr Tyr Pro Val Glu Asp Pro

```
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Phe Lys Ala Arg Gly Asp Val Thr
        115                 120                 125

Ile Ala Ile Asn Cys Leu Arg Asp Ala Ala Ala Tyr Ala Asp Lys Val
    130                 135                 140

Asn Gly Arg Thr Ile Asn Thr Gly Asp Gly Tyr Met Asn Phe Thr Thr
145                 150                 155                 160

Leu Glu Pro Ile Gly Val Cys Gly Gln Ile Ile Pro Trp Asn Phe Pro
                165                 170                 175

Ile Met Met Leu Ala Trp Lys Ile Ala Pro Ala Leu Ala Met Gly Asn
            180                 185                 190

Val Cys Ile Leu Lys Pro Ala Ala Val Thr Pro Leu Asn Ala Leu Tyr
        195                 200                 205

Phe Ala Ser Leu Cys Lys Lys Val Gly Ile Pro Ala Gly Val Val Asn
    210                 215                 220

Ile Val Pro Gly Pro Gly Arg Thr Val Gly Ala Ala Leu Thr Asn Asp
225                 230                 235                 240

Pro Arg Ile Arg Lys Leu Ala Phe Thr Gly Ser Thr Glu Val Gly Lys
                245                 250                 255

Ser Val Ala Val Asp Ser Ser Glu Ser Asn Leu Lys Lys Ile Thr Leu
            260                 265                 270

Glu Leu Gly Gly Lys Ser Ala His Leu Val Phe Asp Asp Ala Asn Ile
        275                 280                 285

Lys Lys Thr Leu Pro Asn Leu Val Asn Gly Ile Phe Lys Asn Ala Gly
    290                 295                 300

Gln Ile Cys Ser Ser Gly Ser Arg Ile Tyr Val Gln Glu Gly Ile Tyr
305                 310                 315                 320

Asp Glu Leu Leu Ala Ala Phe Lys Ala Tyr Leu Glu Thr Glu Ile Lys
                325                 330                 335

Val Gly Asn Pro Phe Asp Lys Ala Asn Phe Gln Gly Ala Ile Thr Asn
            340                 345                 350

Arg Gln Gln Phe Asp Thr Ile Met Asn Tyr Ile Asp Ile Gly Lys Lys
        355                 360                 365

Glu Gly Ala Lys Ile Leu Thr Gly Gly Glu Lys Val Gly Asp Lys Gly
    370                 375                 380

Tyr Phe Ile Arg Pro Thr Val Phe Tyr Asp Val Asn Glu Asp Met Arg
385                 390                 395                 400

Ile Val Lys Glu Glu Ile Phe Gly Pro Val Val Thr Val Ala Lys Phe
                405                 410                 415

Lys Thr Leu Glu Glu Gly Val Glu Met Ala Asn Ser Ser Glu Phe Gly
            420                 425                 430

Leu Gly Ser Gly Ile Glu Thr Glu Ser Leu Ser Thr Gly Leu Lys Val
        435                 440                 445

Ala Lys Met Leu Lys Ala Gly Thr Val Trp Ile Asn Thr Tyr Asn Asp
    450                 455                 460
```

```
Phe Asp Ser Arg Val Pro Phe Gly Gly Val Lys Gln Ser Gly Tyr Gly
465                 470                 475                 480

Arg Glu Met Gly Glu Glu Val Tyr His Ala Tyr Thr Glu Val Lys Ala
                485                 490                 495

Val Arg Ile Lys Leu
            500


<210> SEQ ID NO 18
<211> LENGTH: 1506
<212> TYPE: DNA
<213> ORGANISM: Saccharomyces cerevisiae

<400> SEQUENCE: 18

atgactaagc tacactttga cactgctgaa ccagtcaaga tcacacttcc aaatggtttg     60

acatacgagc aaccaaccgg tctattcatt aacaacaagt ttatgaaagc tcaagacggt    120

aagacctatc ccgtcgaaga tccttccact gaaaacaccg tttgtgaggt ctcttctgcc    180

accactgaag atgttgaata tgctatcgaa tgtgccgacc gtgctttcca cgacactgaa    240

tgggctaccc aagacccaag agaaagaggc cgtctactaa gtaagttggc tgacgaattg    300

gaaagccaaa ttgacttggt ttcttccatt gaagctttgg acaatggtaa aactttggcc    360

tttaaggccc gtggggatgt taccattgca atcaactgtc taagagatgc tgctgcctat    420

gccgacaaag tcaacggtag aacaatcaac accggtgacg gctacatgaa cttcaccacc    480

ttagagccaa tcggtgtctg tggtcaaatt attccatgga actttccaat aatgatgttg    540

gcttggaaga tcgccccagc attggccatg ggtaacgtct gtatcttgaa acccgctgct    600

gtcacacctt taaatgccct atactttgct tctttatgta agaaggttgg tattccagct    660

ggtgtcgtca acatcgttcc aggtcctggt agaactgttg gtgctgcttt gaccaacgac    720

ccaagaatca gaaagctggc ttttaccggt tctacagaag tcggtaagag tgttgctgtc    780

gactcttctg aatctaactt gaagaaaatc actttggaac taggtggtaa gtccgcccat    840

ttggtctttg acgatgctaa cattaagaag actttaccaa atctagtaaa cggtattttc    900

aagaacgctg gtcaaatttg ttcctctggt tctagaattt acgttcaaga aggtatttac    960

gacgaactat tggctgcttt caaggcttac ttggaaaccg aaatcaaagt tggtaatcca   1020

tttgacaagg ctaacttcca aggtgctatc actaaccgtc aacaattcga cacaattatg   1080

aactacatcg atatcggtaa gaaagaaggc gccaagatct taactggtgg cgaaaaagtt   1140

ggtgacaagg gttacttcat cagaccaacc gttttctacg atgttaatga agacatgaga   1200

attgttaagg aagaaatttt tggaccagtt gtcactgtcg caaagttcaa gactttagaa   1260

gaaggtgtcg aaatggctaa cagctctgaa ttcggtctag gttctggtat cgaaacagaa   1320

tctttgagca caggtttgaa ggtggccaag atgttgaagg ccggtaccgt ctggatcaac   1380

acatacaacg attttgactc cagagttcca ttcggtggtg ttaagcaatc tggttacggt   1440

agagaaatgg gtgaagaagt ctaccatgca tacactgaag taaaagctgt cagaattaag   1500

ttgtaa                                                               1506


<210> SEQ ID NO 19
<211> LENGTH: 314
<212> TYPE: PRT
<213> ORGANISM: Saccharomyces cerevisiae

<400> SEQUENCE: 19

Met Pro Ser Thr Thr Asn Thr Ala Ala Ala Asn Val Ile Glu Lys Lys
```

```
1               5                   10                  15

Pro Val Ser Phe Ser Asn Ile Leu Leu Gly Ala Cys Leu Asn Leu Ser
            20                  25                  30

Glu Val Thr Thr Leu Gly Gln Pro Leu Glu Val Val Lys Thr Thr Met
        35                  40                  45

Ala Ala Asn Arg Asn Phe Thr Phe Leu Glu Ser Val Lys His Val Trp
    50                  55                  60

Ser Arg Gly Gly Ile Leu Gly Tyr Tyr Gln Gly Leu Ile Pro Trp Ala
65                  70                  75                  80

Trp Ile Glu Ala Ser Thr Lys Gly Ala Val Leu Leu Phe Val Ser Ala
                85                  90                  95

Glu Ala Glu Tyr Arg Phe Lys Ser Leu Gly Leu Asn Asn Phe Ala Ser
            100                 105                 110

Gly Ile Leu Gly Gly Val Thr Gly Gly Val Thr Gln Ala Tyr Leu Thr
        115                 120                 125

Met Gly Phe Cys Thr Cys Met Lys Thr Val Glu Ile Thr Arg His Lys
    130                 135                 140

Ser Ala Ser Ala Gly Gly Val Pro Gln Ser Ser Trp Ser Val Phe Lys
145                 150                 155                 160

Asn Ile Tyr Lys Lys Glu Gly Ile Arg Gly Ile Asn Lys Gly Val Asn
                165                 170                 175

Ala Val Ala Ile Arg Gln Met Thr Asn Trp Gly Ser Arg Phe Gly Leu
            180                 185                 190

Ser Arg Leu Val Glu Asp Gly Ile Arg Lys Ile Thr Gly Lys Thr Asn
        195                 200                 205

Lys Asp Asp Lys Leu Asn Pro Phe Glu Lys Ile Gly Ala Ser Ala Leu
    210                 215                 220

Gly Gly Gly Leu Ser Ala Trp Asn Gln Pro Ile Glu Val Ile Arg Val
225                 230                 235                 240

Glu Met Gln Ser Lys Lys Glu Asp Pro Asn Arg Pro Lys Asn Leu Thr
                245                 250                 255

Val Gly Lys Thr Phe Lys Tyr Ile Tyr Gln Ser Asn Gly Leu Lys Gly
            260                 265                 270

Leu Tyr Arg Gly Val Thr Pro Arg Ile Gly Leu Gly Ile Trp Gln Thr
        275                 280                 285

Val Phe Met Val Gly Phe Gly Asp Met Ala Lys Glu Phe Val Ala Arg
    290                 295                 300

Met Thr Gly Glu Thr Pro Val Ala Lys His
305                 310
```

<210> SEQ ID NO 20
<211> LENGTH: 945
<212> TYPE: DNA
<213> ORGANISM: Saccharomyces cerevisiae

<400> SEQUENCE: 20

```
atgccatcta ccactaatac tgctgcagca aacgtaatag aaaaaaagcc agtctcgttt      60

tctaatatcc tattgggtgc ctgtttaaac ttgtcagagg tgactacatt agggcaacct     120

ttggaggttg ttaagaccac aatggctgca aacagaaact tcacattttt agaatctgtt     180

aagcatgtct ggtcaagagg tggtatcttg ggttactacc aaggtttgat tccatgggca     240

tggatcgaag cctccactaa aggtgctgtg ttgctgttcg tgtcagctga ggctgagtat     300

cgtttcaaaa gtttggggtt gaacaacttt gcctcaggta tattaggtgg tgtcacgggt     360
```

```
ggtgtcactc aagcctactt aaccatgggg ttctgtacct gtatgaaaac ggtggaaatt    420

acaagacata aatctgcctc cgcaggtggt gtcccacaat cttcttggag tgtgttcaag    480

aatatttata aaaaggaagg tattagaggt attaataagg gtgttaatgc tgttgctatt    540

agacaaatga ccaactgggg ttctcgtttt ggtttgtcca gactagtgga agatggtatc    600

agaaagatca ccgggaaaac caataaagac gacaagttga atccgttcga gaaaattggt    660

gccagtgctt taggtggtgg tttaagtgct tggaatcaac caatcgaagt cattagagtt    720

gaaatgcaat ctaagaagga agatccaaac agaccaaaaa atttgactgt tggtaagaca    780

tttaaataca tctatcaatc aaatggtcta aagggtcttt accgtggtgt caccccaaga    840

attggtttag gtatctggca aactgtcttc atggttggtt ttggtgatat ggcgaaggaa    900

tttgtcgcca gaatgactgg tgaaacccca gttgccaaac attag                    945
```

<210> SEQ ID NO 21
<211> LENGTH: 865
<212> TYPE: PRT
<213> ORGANISM: Rhodosporidium toruloides

<400> SEQUENCE: 21

```
Met Ala Asp Asn Ala Asp Ala Pro Pro Pro Pro Ile Val Pro Ser Gln
1               5                   10                  15

Tyr Ala Gln His Pro Asp Ala Pro Leu Ser Ser Leu Pro Val Gln Leu
            20                  25                  30

Asp Pro Ser Gln Tyr Thr Ala Lys Tyr Pro Ala Lys His Leu Asp Ala
        35                  40                  45

Ile Val Ala Asn Trp Arg Leu Ser Cys Tyr Leu Gly Ala Ser Gln Ile
    50                  55                  60

Phe Leu Gln Ser Asn Ala Ile Leu Ser Arg Lys Leu Thr Lys Asp Asp
65                  70                  75                  80

Val Lys Pro Arg Arg Ala His Thr Asn Leu Ala Gly Asp Ile Gln Gly
                85                  90                  95

Gly Leu Ser Leu Ala Tyr Val His Thr Gln Ala Leu Ile Arg Arg Lys
            100                 105                 110

Gly Asp Glu Glu Gly Ala Glu Pro Lys Met Ile Phe Val Thr Gly Pro
        115                 120                 125

Gly His Gly Ala Pro Ala Ile Leu Ser Pro Leu Tyr Ile Glu Gly Ala
    130                 135                 140

Ile Ser Lys Phe Tyr Pro Gln Tyr Pro Leu Asn Glu Gln Gly Leu Glu
145                 150                 155                 160

Lys Phe Val Lys Tyr Phe Ser Trp Pro Gly Gly Phe Pro Ser His Val
                165                 170                 175

Asn Ala Glu Thr Pro Gly Cys Ile His Glu Gly Gly Glu Leu Gly Tyr
            180                 185                 190

Ala Leu Gly Val Ala Tyr Gly Ser Val Met Asp Arg Pro Glu Gln Ile
        195                 200                 205

Ser Val Val Val Val Gly Asp Gly Glu Ser Glu Thr Gly Pro Thr Ala
    210                 215                 220

Thr Ala Trp His Ser His Lys Trp Leu Asp Pro Ala Glu Ser Gly Ala
225                 230                 235                 240

Val Leu Pro Ile Leu His Val Asn Gly Phe Lys Ile Ser Glu Arg Thr
                245                 250                 255

Ile Pro Gly Thr Met Asp Asn Val Glu Leu Ser Leu Leu Tyr Ser Gly
            260                 265                 270
```

```
Tyr Gly Tyr Gln Val Arg Phe Val Glu Tyr Lys Ala Gln Gly Glu Ala
        275                 280                 285

His Met Gly Gly Asn Asp Pro Ala Asp Arg Val Leu His Glu Asp Met
    290                 295                 300

Ala Ala Ser Leu Asp Trp Ala Tyr Gly Glu Ile Arg Lys Ile Gln Lys
305                 310                 315                 320

Ala Ala Arg Ser Gly Gly Lys Pro Ile Asp Lys Pro Arg Trp Pro Met
                325                 330                 335

Ile Ile Leu Arg Ser Pro Lys Gly Trp Thr Gly Pro Ser Ser Glu His
            340                 345                 350

Gly Lys Gln Leu Leu Asn Asn Phe Ala Ser His Gln Val Pro Leu Pro
        355                 360                 365

Asp Ala Lys Thr Asp Asp Glu Ala Asn Ala Tyr Leu Glu Arg Trp Leu
    370                 375                 380

Lys Ser Tyr Glu Ala Asp Lys Leu Phe Asp Phe Ser Glu Asp Asn Leu
385                 390                 395                 400

Lys Arg Gly Thr Ile Phe Asp Gln Leu Leu Tyr Glu Ala Leu Pro Lys
                405                 410                 415

Asp Met Glu Arg Arg Leu Gly Phe Val Lys Glu Thr Tyr Asn Gly Tyr
            420                 425                 430

Lys Pro Leu Glu Leu Asp Asp Trp Lys Lys Tyr Gly Phe Lys Lys Gly
        435                 440                 445

Glu Asp Val Ser Cys Met Lys Ala Ile Ala Gly Tyr Leu Thr Asp Val
    450                 455                 460

Ile Lys Arg Asn Pro Lys Glu Phe Arg Ile Phe Ser Pro Asp Glu Leu
465                 470                 475                 480

Ala Leu Asn Lys Leu Asp Gly Val Phe Ser Val Thr Glu Arg Asn Met
                485                 490                 495

Gln Trp Asp Pro Glu Thr Ala His Lys Gly Gly Arg Val Thr Glu Met
            500                 505                 510

Leu Ser Glu His Ser Leu Gln Ala Trp Leu Gln Gly Tyr Thr Leu Thr
        515                 520                 525

Gly Arg His Gly Val Phe Pro Ser Tyr Glu Ala Phe Leu Gly Ile Val
    530                 535                 540

Ala Thr Met Thr Val Gln Tyr Thr Lys Phe Met Lys Met Ala Leu Glu
545                 550                 555                 560

Thr Asn Trp Arg Gly Pro Thr Ala Ser Leu Thr Tyr Ile Glu Thr Ser
                565                 570                 575

Thr Trp Thr Arg Gln Glu His Asn Gly Tyr Ser His Gln Asn Pro Gly
            580                 585                 590

Phe Val Ser Thr Val Leu Ser Leu Pro Ser Gln Leu Ala Arg Val Tyr
        595                 600                 605

Phe Pro Ser Asp Ala Asn Thr Ser Val Ser Val Ile Ala His Cys Leu
    610                 615                 620

Arg Ser Lys Asn Tyr Ile Asn Leu Ile Val Gly Thr Lys Ala Pro Thr
625                 630                 635                 640

Pro Val Tyr Leu Ser Val Glu Glu Ala Glu Arg His Cys Ile Ala Gly
                645                 650                 655

Ala Ser Val Trp Glu Asn Tyr Ser Val Asp Lys Gly Val Asp Pro Asp
            660                 665                 670

Val Val Leu Val Gly Ile Gly Tyr Glu Leu Thr Glu Glu Val Ile His
        675                 680                 685

Ala Ala Ala Leu Leu Arg Lys Asp Phe Gly Thr Glu Leu Arg Val Arg
```

```
    690                 695                 700

Val Val Asn Val Val Asp Leu Leu Val Leu Ala Pro Lys Gly Asp His
705                 710                 715                 720

Pro His Ala Leu Asp Glu Ala Gly Phe Asn Ser Leu Phe Pro Pro Gly
                725                 730                 735

Val Pro Ile Ile Phe Asn Tyr His Gly Tyr Ala Gly Gln Leu Ala Ser
            740                 745                 750

Leu Leu Phe Asp Arg Lys His Ser Val Gly Arg Ser Arg Met Arg Ile
        755                 760                 765

Phe Ala Tyr Ser Glu Gln Gly Thr Thr Thr Thr Pro Phe Ala Met Met
    770                 775                 780

Cys Cys Asn Asn Thr Asp Arg Phe Asn Leu Ala Ala Glu Ala Leu Glu
785                 790                 795                 800

Met Val Thr Leu Asn Leu Thr Thr Gln His Asn Ile Thr Gly Glu Glu
                805                 810                 815

Lys Arg His Arg Val Gly Ser Val Val Ala Arg Ala His Glu Arg Met
            820                 825                 830

Ser Phe Tyr Lys His Lys Lys Val Val Met Met Arg Tyr Ala Ala Glu
        835                 840                 845

Thr Gln Lys Asp His Pro Glu Ile Gly Glu Val Ala Thr Leu Ala Glu
    850                 855                 860

Gln
865


<210> SEQ ID NO 22
<211> LENGTH: 2598
<212> TYPE: DNA
<213> ORGANISM: Rhodosporidium toruloides

<400> SEQUENCE: 22

atggcagaca acgcagacgc ccctcccccg cccatcgtgc cctcgcagta cgcccagcac     60

ccggacgcac ctctctcgag tctccccgtc cagctcgacc cgagccagta caccgccaag    120

taccccgcca agcacctcga tgccattgtc gcaaactggc gcttgtcgtg ctacttggga    180

gcgtcgcaaa tcttcctcca gtcgaacgcg atcctctcga ggaagttgac caaggacgac    240

gtcaagcctc ggagggccca cactaacctt gctggcgaca tacagggagg tctttcgctc    300

gcctacgtcc acactcaagc gctcatccgc cgcaagggcg acgaggaagg cgccgaaccc    360

aagatgatct tcgtcaccgg tccgggccac ggcgcacccg ccatcctctc gcctctctac    420

atcgaaggcg ccatctccaa gttttacccc cagtaccctc tcaacgagca aggactcgag    480

aagtttgtca agtacttctc gtggccggga ggattccctt cgcatgttaa cgctgagacg    540

ccgggatgta tccacgaggg cggagagctc gggtatgcgc ttggagtcgc gtacggatcg    600

gtcatggacc gcccggagca gatctcggtc gttgttgtcg gtgacggcga gagcgagacg    660

ggaccgaccg cgacggcgtg gcactcgcac aagtggctcg accccgccga gtcaggcgcc    720

gtcctcccca tccttcacgt caacggcttc aagatctcgg agcgcaccat ccccggcacg    780

atggacaacg tcgagctttc ccttctctac tccggctacg ggtaccaggt ccgcttcgtc    840

gaatacaagg cgcagggcga ggcgcacatg ggtggcaacg atccggccga ccgcgtcctc    900

cacgaggata tggctgcctc gctcgactgg gcctacggcg agatccgcaa gatccagaag    960

gctgctcgct ccggcggcaa gcccatcgac aagcctcgct ggccgatgat catcctccgc   1020

tcgcccaagg gatggaccgg cccgtcgagt gagcacggca agcagctcct caacaacttc   1080
```

```
gcctcgcacc aggtccccct ccccgacgcc aagacggacg acgaagcgaa cgcctacctc   1140
gagcgctggc tcaagtcgta cgaagccgac aaactcttcg acttttccga agacaacctc   1200
aagcgcggta ccatctttga ccagctcttg tacgaggcgc tcccgaagga tatggaaagg   1260
cgccttgggt ttgtcaagga gacctacaac ggttacaagc cccttgagct ggacgactgg   1320
aagaagtacg gcttcaagaa gggcgaggat gtctcgtgca tgaaggcgat cgctggctac   1380
ctcaccgacg tgatcaagcg caacccgaaa gagttccgca tcttctcgcc cgacgagctc   1440
gccttgaaca agctcgatgg cgtcttctcc gtcaccgagc gcaacatgca gtgggacccg   1500
gagacggcgc acaagggcgg cagggtcacc gagatgcttt ctgagcactc gttgcaggcc   1560
tggttgcagg ggtacaccct cacgggcagg catggcgtct tcccctcgta cgaggccttc   1620
ctcggcatcg tcgcgaccat gaccgtccaa tacaccaagt tcatgaagat ggcgctcgag   1680
accaactggc gcggaccgac cgcctcgctg acctacatcg agacctcgac ctggacccgc   1740
caggagcaca acggctactc gcaccagaac cctggcttcg tctcgaccgt cctctcgctc   1800
ccctcccagc tcgcccgcgt ctacttcccc tcggacgcta acacgagcgt cagcgtcatc   1860
gcacactgct tgcgcagcaa gaactacatc aacctcatcg tcggcaccaa ggctcctacg   1920
cctgtctacc tcagcgtcga ggaggccgag cgtcactgca ttgccggcgc ttcggtctgg   1980
gagaactact cggtcgacaa gggtgtcgac ccggatgtcg tcctcgtcgg tatcggctac   2040
gagctgacgg aggaggtcat ccatgccgcg gcgctcctcc gcaaggactt tggcaccgaa   2100
ttgagggtca gggtcgtcaa tgtcgtcgac ttgctcgtcc tcgcgcccaa gggcgaccac   2160
ccgcatgctc tcgacgaagc cggcttcaac tcactcttcc cgcccggcgt tcctatcatc   2220
ttcaactacc acggctacgc tggccagctc gcgtcgctcc tcttcgaccg caagcactcg   2280
gtcggccgtt cgcgcatgcg catctttgcc tactcggagc agggcacgac gacgactccg   2340
ttcgccatga tgtgctgcaa caacaccgac aggttcaacc tcgcggccga ggcgctcgag   2400
atggtcaccc tcaacctaac gacgcagcac aacatcaccg gcgaggagaa gcgccaccgc   2460
gtcggctcgg tcgtcgcgcg cgcgcacgag cgcatgtcgt tctacaagca caagaaggtc   2520
gtcatgatgc gctacgctgc cgagactcag aaggaccacc cggagattgg cgaggttgcc   2580
acgcttgccg agcagtaa                                                 2598
```

```
<210> SEQ ID NO 23
<211> LENGTH: 806
<212> TYPE: PRT
<213> ORGANISM: Aspergillus niger

<400> SEQUENCE: 23

Met Pro Gly Glu Val Ile Asp Arg Pro Asn Pro Lys Ala Glu Pro Ser
1               5                   10                  15

His Ile Pro Asp Leu Val Asn Gln Leu Gln Val Lys Leu Gln Glu Thr
            20                  25                  30

Arg Leu Glu Glu Thr Asp Tyr Asn Ala Leu Leu Lys Phe Arg Arg Ala
        35                  40                  45

Ala Ala Tyr Ile Ala Ala Ala Met Ile Phe Leu Gln Asp Asn Val Leu
    50                  55                  60

Leu Lys Gln Asn Leu Arg His Glu Asp Ile Lys Pro Arg Leu Leu Gly
65                  70                  75                  80

His Trp Gly Thr Cys Pro Gly Leu Ile Leu Val Tyr Ser His Leu Asn
                85                  90                  95

Tyr Ile Ile Arg Lys Gln Asn Leu Asp Met Leu Tyr Val Val Gly Pro
```

-continued

```
            100                 105                 110

Gly His Gly Ala Pro Ala Ile Leu Ala Ser Leu Trp Leu Glu Gly Ser
        115                 120                 125

Leu Glu Lys Phe Tyr Pro His Tyr Ser Arg Asp Met Asp Gly Leu His
    130                 135                 140

Glu Leu Ile Ser Thr Phe Ser Thr Ser Ala Gly Leu Pro Ser His Ile
145                 150                 155                 160

Asn Ala Glu Thr Pro Gly Ala Ile His Glu Gly Gly Glu Leu Gly Tyr
                165                 170                 175

Ala Leu Ala Val Ser Phe Gly Ala Val Met Asp Asn Pro Asp Met Ile
            180                 185                 190

Val Thr Cys Val Val Gly Asp Gly Glu Ala Glu Thr Gly Pro Thr Ala
        195                 200                 205

Thr Ser Trp His Ala Ile Lys Tyr Ile Asp Pro Ala Glu Ser Gly Ala
    210                 215                 220

Val Leu Pro Ile Leu His Val Asn Gly Phe Lys Ile Ser Glu Arg Thr
225                 230                 235                 240

Ile Tyr Gly Cys Met Asp Asn Lys Glu Leu Val Ser Leu Phe Thr Gly
                245                 250                 255

Tyr Gly Tyr Gln Val Arg Ile Val Glu Asn Leu Asp Asp Ile Asp Ala
            260                 265                 270

Asp Leu His Ser Ser Met Met Trp Ala Val Glu Glu Ile His Lys Ile
        275                 280                 285

Gln Lys Ala Ala Arg Ser Gly Lys Pro Ile Met Lys Pro Arg Trp Pro
    290                 295                 300

Met Ile Val Leu Arg Thr Pro Lys Gly Trp Ser Gly Pro Lys Glu Leu
305                 310                 315                 320

His Gly Ser Phe Ile Glu Gly Ser Phe His Ser His Gln Val Pro Leu
                325                 330                 335

Pro Asn Ala Lys Lys Asp Lys Glu Glu Leu Gln Ala Leu Gln Lys Trp
            340                 345                 350

Leu Ser Ser Tyr Asn Pro His Glu Leu Phe Thr Glu Thr Gly Asp Ile
        355                 360                 365

Ile Asp Asp Ile Lys Ser Val Ile Pro Leu Glu Asp Thr Lys Lys Leu
    370                 375                 380

Gly Gln Arg Ala Glu Ala Tyr Lys Gly Tyr Arg Ala Pro Asp Leu Pro
385                 390                 395                 400

Asp Trp Arg Lys Phe Gly Val Glu Lys Gly Ser Gln Gln Ser Ala Met
                405                 410                 415

Lys Thr Ile Gly Lys Phe Ile Asp Gln Val Phe Thr Gln Asn Pro His
            420                 425                 430

Gly Val Arg Val Phe Ser Pro Asp Glu Leu Glu Ser Asn Lys Leu Asp
        435                 440                 445

Ala Ala Leu Ala His Thr Gly Arg Asn Phe Gln Trp Asp Gln Phe Ser
    450                 455                 460

Asn Ala Lys Gly Gly Arg Val Ile Glu Val Leu Ser Glu His Leu Cys
465                 470                 475                 480

Gln Gly Phe Met Gln Gly Tyr Thr Leu Thr Gly Arg Val Gly Ile Phe
                485                 490                 495

Pro Ser Tyr Glu Ser Phe Leu Gly Ile Ile His Thr Met Met Val Gln
            500                 505                 510

Tyr Ala Lys Phe Asn Lys Met Ala Gln Glu Thr Thr Trp His Lys Pro
        515                 520                 525
```

```
Val Ser Ser Ile Asn Tyr Ile Glu Thr Ser Thr Trp Ala Arg Gln Glu
    530                 535                 540

His Asn Gly Phe Ser His Gln Asn Pro Ser Phe Ile Gly Ala Val Leu
545                 550                 555                 560

Arg Leu Lys Pro Thr Ala Ala Arg Val Tyr Leu Pro Pro Asp Ala Asn
                565                 570                 575

Thr Phe Leu Thr Thr Leu His His Cys Leu Lys Ser Lys Asn Tyr Val
            580                 585                 590

Asn Leu Met Val Gly Ser Lys Gln Pro Thr Pro Val Tyr Leu Ser Pro
        595                 600                 605

Glu Glu Ala Glu Ser His Cys Arg Ala Gly Ala Ser Ile Trp Arg Phe
    610                 615                 620

Cys Ser Thr Asp Asn Gly Leu Asn Pro Asp Val Val Leu Val Gly Ile
625                 630                 635                 640

Gly Val Glu Val Met Phe Glu Val Ile Tyr Ala Ala Ala Ile Leu Arg
                645                 650                 655

Lys Arg Cys Pro Glu Leu Arg Val Arg Val Val Asn Val Thr Asp Leu
            660                 665                 670

Met Ile Leu Glu Lys Glu Gly Leu His Pro His Ala Leu Thr Thr Glu
        675                 680                 685

Ala Phe Asp Ser Leu Phe Gly Ser Asp Arg Pro Ile His Phe Asn Tyr
    690                 695                 700

His Gly Tyr Pro Gly Glu Leu Lys Gly Leu Leu Phe Gly Arg Pro Arg
705                 710                 715                 720

Leu Asp Arg Val Ser Val Glu Gly Tyr Met Glu Glu Gly Ser Thr Thr
                725                 730                 735

Thr Pro Phe Asp Met Met Leu Leu Asn Arg Val Ser Arg Tyr His Val
            740                 745                 750

Ala Gln Ala Ala Val Ile Gly Ala Ser Arg Arg Asn Glu Lys Val Gln
        755                 760                 765

Val Arg Gln His Glu Leu Val Ser Glu Phe Gly His Asn Ile Val Glu
    770                 775                 780

Thr Arg Lys Tyr Ile Leu Ala Asn Arg Lys Asp Pro Asp Asp Thr Tyr
785                 790                 795                 800

Asp Met Pro Ser Phe Glu
                805


<210> SEQ ID NO 24
<211> LENGTH: 2421
<212> TYPE: DNA
<213> ORGANISM: Aspergillus niger

<400> SEQUENCE: 24

atgcctggag aggtcatcga caggccaaat cccaaggctg agccttcaca catccccgat      60

cttgtcaatc aattgcaggt caaacttcaa gagacgcgtt tggaggaaac tgattacaat     120

gcccttctga aattccgccg tgcagcggcc tacattgctg ctgcaatgat ctttctccaa     180

gacaatgtgc tgctgaagca gaatctaagg cacgaggaca tcaagcccag gcttcttggc     240

cactggggaa catgtcccgg gttgattctt gtatactctc acttgaacta catcatcaga     300

aagcagaacc tggatatgtt gtatgtcgtc gggcctggcc acggcgcgcc agctattttg     360

gcctcactgt ggcttgaggg ctctttagag aaattctacc cccactactc acgagacatg     420

gatggtctcc atgagctcat ctcgaccttc agcacaagtg ctggattacc aagccatatc     480
```

```
aatgcggaaa ctcccggtgc aatccatgaa ggtggtgaat tgggttatgc gttagctgtc    540
tcttttggtg ctgttatgga caatcccgac atgatcgtca cctgcgtggt tggtgacggg    600
gaagcagaaa ctggtcctac cgcgacgtcc tggcatgcaa tcaagtacat tgaccccgca    660
gaatcaggtg ccgtcctgcc gattctccac gttaatggct ttaagatcag cgagcgcacc    720
atttatggct gcatggacaa caaagagctg gtctccctct tcacgggtta tggataccag    780
gtgcgcattg ttgagaacct ggatgacatc gacgcagatc tccatagctc tatgatgtgg    840
gcagttgagg agatccacaa gatccaaaaa gcggcgcgtt ccggcaagcc aattatgaag    900
cctagatggc caatgattgt tttgcgcaca ccgaagggtt ggtcaggacc taaagagctc    960
cacgggtcat tcatagaggg atctttccac tcacatcagg ttcctctacc taatgcaaag   1020
aaggataaag aggagcttca ggctctgcag aaatggctgt cctcgtataa tccgcacgaa   1080
cttttcactg agacgggaga catcattgac gacatcaagt cagtgatccc tctggaagac   1140
accaagaagc ttgggcagcg agcagaagcc tacaagggct atagggcacc cgatctccca   1200
gactggcgca agtttggcgt agaaaagggc tcccagcaga gcgctatgaa aacaattgga   1260
aagttcattg accaagtgtt tacccaaaat cctcatggcg tccgtgtatt ttcgccagac   1320
gagctagaga gcaacaagct ggatgcagca ctggcgcaca cgggaaggaa ctttcagtgg   1380
gatcaattct cgaatgccaa aggcggccgc gtcatcgagg tgctcagtga gcacctgtgc   1440
cagggcttta tgcagggata cacgttgacg ggccgggtgg gcattttccc atcgtacgaa   1500
agcttcttgg gaatcatcca taccatgatg gtgcaatatg ccaaatttaa caaaatggct   1560
caagagacga cctggcataa gccggttagt agcatcaact atatcgaaac gagtacgtgg   1620
gctcgtcagg agcacaatgg attctctcac cagaacccct cctttatcgg agctgtgctc   1680
aggctgaagc ccaccgccgc gcgagtttat ctgccacctg atgctaacac atttttgacc   1740
acccttcacc actgtctcaa gtccaagaat tatgtcaacc tcatggtagg ttcaaaacag   1800
ccaactcccg tgtacttgag ccccgaggaa gcagagagcc actgccgagc cggcgcatcg   1860
atctggagat tctgtagtac cgacaatggg ctgaacccgg atgtcgtgct ggttggcatt   1920
ggagtagagg tgatgttcga ggtcatctac gcggcggcca tcctccgcaa gcgttgtcca   1980
gaactccggg tgcgtgtggt caatgtgacc gacttgatga ttctggagaa ggaaggtcta   2040
catccacatg cattgacgac cgaagctttc gacagtctgt ttggctcgga ccggccgata   2100
cacttcaact accacggata cccgggcgag ctcaaaggtc tgctctttgg gcggccccgc   2160
ctggaccgag tttcagtaga aggatacatg gaggaaggaa gcacgacgac gccgttcgat   2220
atgatgttgc tgaaccgcgt ctcacgatac cacgtggcgc aggcagccgt gatcggggcg   2280
tccagacgga atgagaaggt tcaagttcgg cagcacgaac tggtcagcga attcggccac   2340
aacatcgtgg agacacgcaa atacattctg gccaaccgca aagacccgga tgatacgtat   2400
gatatgccct cctttgaata a                                             2421
```

<210> SEQ ID NO 25
<211> LENGTH: 822
<212> TYPE: PRT
<213> ORGANISM: Penicillium chrysogenum

<400> SEQUENCE: 25

```
Met Pro Ala Glu Val Ile Ser Glu Pro Asn Pro Gln Ala Leu Pro Ser
1               5                   10                  15

His Leu Pro Asp Tyr Leu Glu Lys Leu Ser Val Ser Leu Glu Arg Glu
            20                  25                  30
```

-continued

```
Lys Leu Asp Glu Lys Thr Tyr Asp Ala Leu Ile Lys Phe Arg Arg Ala
        35                  40                  45

Ala Cys Tyr Ile Ala Ala Ala Met Ile Phe Leu Gln Glu Asn Thr Leu
    50                  55                  60

Leu Lys Ser Glu Leu Thr Phe Gln His Val Lys Pro Arg Leu Leu Gly
65                  70                  75                  80

His Trp Gly Thr Cys Pro Gly Leu Ile Phe Val Tyr Ser His Leu Asn
                85                  90                  95

Tyr Leu Ile Arg Thr Met Asn Leu Asp Met Leu Tyr Val Val Gly Pro
            100                 105                 110

Gly His Gly Ala Pro Ala Ile Leu Ala Ala Leu Trp Leu Glu Gly Ser
        115                 120                 125

Leu Glu Lys Phe Tyr Pro His Tyr Ser Arg Asp Glu Lys Gly Leu His
    130                 135                 140

Arg Leu Ile Ser Thr Phe Ser Thr Thr Gly Gly Phe Pro Ser His Ile
145                 150                 155                 160

Asn Ser Glu Thr Pro Gly Ala Ile His Glu Gly Gly Glu Leu Gly Tyr
                165                 170                 175

Ala Leu Ala Val Ser Phe Gly Ala Val Met Asp Asn Pro Asp Leu Ile
            180                 185                 190

Val Thr Cys Ile Val Gly Asp Gly Glu Ala Glu Ser Gly Pro Thr Ala
        195                 200                 205

Thr Ser Trp His Ala Ile Lys Tyr Ile Asp Pro Lys Glu Ser Gly Ala
    210                 215                 220

Val Leu Pro Ile Leu His Leu Asn Gly Phe Lys Ile Ser Glu Arg Thr
225                 230                 235                 240

Ile Phe Gly Cys Met Asp His Lys Glu Leu Leu Thr Leu Phe Ser Gly
                245                 250                 255

Tyr Gly Tyr Gln Val Arg Phe Val Glu Asp Asn Asn Asp Ile Asp Ala
            260                 265                 270

Asp Leu His Thr Ser Met Ile Trp Ala Val Asn Glu Ile Gln Lys Ile
        275                 280                 285

Gln Lys Ala Ala Arg Ser Gly Lys Pro Ile Met Lys Pro Arg Trp Pro
    290                 295                 300

Met Leu Ile Leu Arg Thr Ser Lys Gly Trp Thr Gly Pro Lys Gln Leu
305                 310                 315                 320

His Gly Lys Phe Leu Glu Gly Ser Tyr His Ser His Gln Val Pro Leu
                325                 330                 335

Pro Lys Ala Lys Thr Asp Lys Glu Gln Leu Asp Leu Leu Gln Asn Trp
            340                 345                 350

Leu Ser Ser Tyr Lys Pro Glu Glu Leu Phe Thr Ser Asn Gly Asp Val
        355                 360                 365

Ile Asp Glu Ile Lys Ser Val Ile Pro Thr Glu Asp Lys Lys Lys Leu
    370                 375                 380

Gly Gln Arg Ile Glu Val Tyr Asn Ser Tyr Thr Pro Pro Asn Leu Pro
385                 390                 395                 400

Asp Trp Lys Pro Phe Cys Ala Asp Lys Gly Ser Gln Glu Ser Ala Met
                405                 410                 415

Lys Ala Ala Gly Thr Phe Ile Asn Gln Thr Phe Lys Asp Asn Pro Asn
            420                 425                 430

Ser Val Arg Leu Phe Ser Pro Asp Glu Leu Glu Ser Asn Lys Leu Asp
        435                 440                 445
```

```
Ala Val Phe Glu Tyr Thr Asn Arg Asn Phe Gln Trp Asp Glu Phe Ala
    450                 455                 460

Asn Ala Arg Gly Gly Arg Val Ile Glu Val Leu Ser Glu His Met Cys
465                 470                 475                 480

Gln Gly Phe Met Gln Gly Tyr Thr Leu Thr Gly Arg Ile Gly Ile Phe
                485                 490                 495

Pro Ser Tyr Glu Ser Phe Leu Gly Ile Ile His Thr Met Met Val Gln
            500                 505                 510

Tyr Ala Lys Phe Ile Lys Met Gly Leu Glu Thr Thr Trp His Ser Gly
        515                 520                 525

Val Ser Ser Val Asn Tyr Ile Glu Ser Ser Thr Trp Ala Arg Gln Glu
    530                 535                 540

His Asn Gly Phe Ser His Gln Asn Pro Ser Phe Ile Gly Ala Val Leu
545                 550                 555                 560

Lys Leu Lys Pro Ser Ala Ala Arg Val Tyr Leu Pro Pro Asp Ala Asn
                565                 570                 575

Thr Phe Leu Thr Thr Ile His His Cys Leu Lys Ser Lys Asn Tyr Ile
            580                 585                 590

Asn Leu Met Val Gly Ser Lys Gln Pro Thr Pro Val Tyr Leu Thr Pro
        595                 600                 605

Lys Glu Ala Glu Ser His Cys Arg Ala Gly Ala Ser Ile Trp Lys Phe
    610                 615                 620

Cys Ser Thr Asp Asp Gly Ile Asn Pro Asp Val Val Leu Val Gly Ile
625                 630                 635                 640

Gly Val Glu Val Met Phe Glu Val Ile Ala Ala Ala Ala Leu Leu Arg
                645                 650                 655

Lys Leu Ile Pro Glu Leu Arg Val Cys Val Ile Asn Val Thr Asp Leu
            660                 665                 670

Met Ile Leu Asp Asn Glu Gly Ala His Pro His Ala Leu Ser Thr Glu
        675                 680                 685

Ala Phe Asp Gly Leu Phe Thr Ser Asp Arg Pro Ile His Phe Asn Tyr
    690                 695                 700

His Gly Tyr Pro Thr Glu Leu Gln Gly Leu Leu Phe Gly Arg Pro Arg
705                 710                 715                 720

Leu Asp Arg Val Ser Val Ala Gly Tyr Ile Glu Glu Gly Ser Thr Thr
                725                 730                 735

Thr Pro Phe Asp Met Met Leu Val Asn Arg Val Ser Arg Phe His Val
            740                 745                 750

Ala Gln His Ala Ile Arg Gly Ala Ala Lys Val Asn Glu Lys Val Arg
        755                 760                 765

Val Tyr Gln Gln Glu Leu Asn Ala Gln Leu Glu Ala Ser Met Val Ser
    770                 775                 780

Thr Arg Lys Tyr Ile Val Glu Asn Arg Asp Asp Pro Asp Gly Ile Tyr
785                 790                 795                 800

Asp Met Pro Gln Phe His Ser Phe His Lys Pro Ala Glu Ser Glu Thr
                805                 810                 815

Phe Trp Asn Ile Ala Gln
            820
```

<210> SEQ ID NO 26
<211> LENGTH: 2469
<212> TYPE: DNA
<213> ORGANISM: Penicillium chrysogenum

<400> SEQUENCE: 26
atgcctgcag aagttataag cgaaccaaat ccacaagctc tgccgtcgca tctgccagac 60
tatcttgaga aattgagcgt cagcttggaa cgtgagaaac tagatgaaaa gacctacgat 120
gccttgatca agttccgccg agcggcttgt tacattgcgg cagctatgat atttctgcaa 180
gaaaatactc ttttgaagtc agaactcaca tttcaacatg tcaagcctag actactcggt 240
cactggggaa catgcccggg cctaatcttt gtctactctc atttgaacta cctgatccgg 300
acaatgaatc tggacatgtt gtacgttgtc ggtccaggac atggcgcacc ggcaatacta 360
gccgcgctat ggttggaggg ttcgctggag aaattctatc cccactattc gcgagacgaa 420
aagggcctac acagattgat ctcgaccttt agtaccacag gtggttttcc cagccacatc 480
aattccgaga cccccggtgc aatccatgaa ggtggagaac tgggttacgc tctggcagtg 540
tcctttggcg ctgtcatgga taaccccgat ctgattgtga cttgtattgt gggggacggg 600
gaggctgaaa gcggtcccac tgctacgtcc tggcatgcga tcaagtacat tgatccaaag 660
gagtccggtg cagttttacc aattctgcat ttgaatggat tcaagatcag cgagcgcact 720
atcttcgggt gcatggacca caaagagctt ttgactctct tcagtggata cgggtaccag 780
gttcgctttg tcgaggataa caacgatatt gatgcggatt tacacacctc tatgatctgg 840
gccgtcaatg aaatccagaa gatccagaag gctgcccgtt cagggaagcc gattatgaag 900
ccaaggtggc cgatgctgat tctgcgtact tccaagggct ggactgggcc caagcagctt 960
catggcaagt ttcttgaggg ctcataccat tctcaccagg tgccattgcc caaagcaaag 1020
accgacaagg aacaactaga tctgctgcag aattggctgt ctagttataa gccagaagag 1080
ctgttcactt cgaacggtga tgtaattgat gagatcaagt ctgtgatacc cacagaagac 1140
aaaaagaagc ttggccagcg catcgaagtc tacaatagtt atacaccacc gaatctgccg 1200
gattggaagc ccttctgcgc ggataaaggc tctcaagaaa gcgctatgaa agcggctggc 1260
accttcatta atcagacatt caaggacaac ccgaacagcg tgcgactctt ctcgccggac 1320
gagttggaaa gcaacaaact cgatgcggta tttgaataca caaaccgcaa tttccaatgg 1380
gacgagttcg ccaatgcccg cggcggccgt gtaattgaag tccttagcga acatatgtgt 1440
caaggattca tgcagggcta taccttgacc gggcgcattg gtattttccc gtcctatgag 1500
agcttcctcg gcatcattca tacgatgatg gtgcagtatg ccaagttcat caagatggga 1560
ctggaaacaa cttggcactc cggcgtcagt agtgtgaact acatcgaatc gagcacctgg 1620
gcacgccaag aacacaacgg cttctctcac cagaacccat ccttcatcgg cgctgtgcta 1680
aagctgaagc ctagtgcagc tcgggtatac ttaccaccag atgcgaatac tttcctgaca 1740
accatccacc attgtttaaa atcaaagaat tacatcaacc taatggtagg ctcaaagcag 1800
ccaactccag tgtacctgac tcccaaagag gcggaaagcc actgtcgcgc aggagcatcc 1860
atttggaagt tctgcagcac ggacgatgga attaatccgg atgtcgtgct ggtcggtatt 1920
ggtgttgagg tgatgttcga agtaattgcg gcagcggcgc ttctgcgtaa gctcatccca 1980
gagcttcgtg tttgtgtcat taacgtgacg gacctgatga ttcttgataa cgagggtgcg 2040
catccgcatg ccctgtccac tgaggcattc gatggtctct ttacttccga caggcccatt 2100
cacttcaatt accacggcta tccaactgag ctgcagggtt tgctctttgg acgtccccgc 2160
cttgatcgcg tcagtgtcgc cggctatatc gaagagggta gcaccaccac gcctttcgac 2220
atgatgcttg tcaaccgtgt ctcgcgtttc catgtcgccc agcatgctat tcgtggtgct 2280
gccaaagtaa atgagaaggt cagggtgtat cagcaggagc tgaatgctca gcttgaggcg 2340

-continued agtatggtca gcacgaggaa gtatattgtg gaaaaccggg atgaccccga cggcatttat 2400
gacatgccac aattccacag cttccacaaa ccggctgagt ctgagacatt ctggaatatt 2460
gcccagtag 2469

<210> SEQ ID NO 27
<211> LENGTH: 808
<212> TYPE: PRT
<213> ORGANISM: Trichoderma reesei

<400> SEQUENCE: 27

Met Pro Gly Glu Val Ile Asp Gln Pro Asn Pro Pro Pro Leu Thr Ser
1 5 10 15

His Leu Pro Asp Thr Ile Glu Glu Leu Ala Val Lys Pro Ser Lys Ala
20 25 30

Pro Leu Ser Asn Leu Asp Leu Val Ser Leu Arg Glu Phe Gln Arg Ala
35 40 45

Ala Cys Tyr Ile Ala Ser Ala Met Ile Phe Leu Lys Asp Asn Val Leu
50 55 60

Leu Asp Arg Glu Leu Arg Phe Glu Asp Val Lys Pro Arg Leu Leu Gly
65 70 75 80

His Trp Gly Thr Cys Pro Gly Leu Ile Leu Ile Trp Ser His Leu Asn
85 90 95

Leu Leu Ile Arg Asp Ser Ser Gln Asp Met Leu Phe Val Ile Gly Pro
100 105 110

Gly His Gly Ala Pro Ala Ala Leu Ala Cys Leu Trp Leu Glu Gly Ser
115 120 125

Leu Glu Arg Phe Tyr Pro Asp Lys Tyr Arg Thr Asp Lys Glu Gly Leu
130 135 140

His Asn Leu Ile Thr Lys Phe Ser Val Pro Thr Gly Phe Pro Ser His
145 150 155 160

Ile Asn Pro Glu Thr Pro Gly Cys Ile His Glu Gly Gly Glu Leu Gly
165 170 175

Tyr Ala Leu Ala Val Ser Phe Gly Ala Val Met Asp Lys Pro Asp Leu
180 185 190

Ile Val Pro Cys Val Val Gly Asp Gly Glu Ala Glu Thr Gly Pro Thr
195 200 205

Ala Ala Ala Trp His Ser Ile Lys Tyr Leu Asp Pro Ala Glu Ser Gly
210 215 220

Ala Val Ile Pro Ile Leu His Val Asn Gly Phe Lys Ile Ser Glu Arg
225 230 235 240

Thr Ile Phe Gly Cys Met Asp Asn Thr Glu Leu Val Leu Leu Phe Ser
245 250 255

Gly Tyr Gly Tyr Glu Val Cys Ile Val Glu Asn Leu Asp Ala Ile Asp
260 265 270

Thr Glu Leu His Thr Ala Leu Phe Trp Ala Leu Ser Glu Ile Lys Arg
275 280 285

Ile Gln Gly Ala Ala Arg Ser Gly Asn Pro Ile Thr Lys Pro Arg Trp
290 295 300

Pro Met Ile Ile Leu Arg Thr Pro Lys Gly Trp Thr Gly Pro Arg Thr
305 310 315 320

Val Asp Asp Lys Ile Ile Glu Gly Ser Phe His Ala His Gln Val Pro
325 330 335

Val Thr Lys Ala Asn Lys Asp Glu Gly His Leu Arg Ile Leu Gln Asp
340 345 350

```
Trp Leu Lys Ser Tyr Asp Val Arg Gly Leu Leu Pro Asp Gly Lys Pro
        355                 360                 365

Ser Gly Asp Phe Leu Asp Ile Leu Pro Pro Asp Pro His Lys Arg Leu
    370                 375                 380

Gly Gln Ser Lys Leu Ala Tyr Asp Cys His Gln Pro Leu Asp Leu Pro
385                 390                 395                 400

Asp Trp Arg Pro His Ser Val Asp Lys Phe Glu Glu Ala Ser Ser Met
                405                 410                 415

Gln Gln Ser Gly Lys Phe Leu Asp Val Val Ala Arg Gln Asn Met Lys
            420                 425                 430

Thr Phe Arg Ile Phe Ser Pro Asp Glu Leu Glu Ser Asn Lys Leu Ser
        435                 440                 445

Ala Val Leu Asp His Ser Ser Arg Asn Phe Gln Trp Asp Gln Tyr Ser
    450                 455                 460

Arg Ala Gln Gly Gly Arg Val Ile Glu Ile Leu Ser Glu His Cys Cys
465                 470                 475                 480

Gln Gly Phe Leu Gln Gly Tyr Thr Leu Thr Gly Arg Thr Ala Ile Phe
                485                 490                 495

Pro Ser Tyr Glu Ser Phe Leu Gly Ile Ile His Thr Met Met Ile Gln
            500                 505                 510

Tyr Ser Lys Phe Ser Lys Ile Ser Arg Lys Leu Pro Trp Arg Gly Asp
        515                 520                 525

Leu Ser Ser Ile Asn Tyr Ile Glu Thr Ser Thr Trp Ala Arg Gln Glu
    530                 535                 540

His Asn Gly Phe Ser His Gln Asn Pro Ser Phe Ile Gly Ala Val Leu
545                 550                 555                 560

Asn Leu Lys Ala Glu Ile Ala Arg Val Tyr Leu Pro Pro Asp Ala Asn
                565                 570                 575

Cys Phe Leu Ser Thr Leu His His Cys Leu Gln Ser Lys Asn Tyr Val
            580                 585                 590

Asn Leu Met Ile Gly Ser Lys Gln Pro Thr Pro Val Tyr Leu Ser Ala
        595                 600                 605

Glu Asp Ala Gln Arg His Cys Glu Asp Gly Ala Ser Ile Trp Arg Trp
    610                 615                 620

Ala Ser Thr His Asp Gly Glu His Pro Asp Val Val Leu Val Gly Ile
625                 630                 635                 640

Gly Val Glu Val Thr Phe Glu Val Ile Lys Ala Ala Gln Leu Leu Ser
                645                 650                 655

Arg Leu Ala Pro Asn Leu Arg Val Arg Val Val Asn Val Thr Asp Leu
            660                 665                 670

Leu Val Leu Pro His Glu Ser His His Pro His Ala Leu Asp Ser Lys
        675                 680                 685

Ala Phe Glu Asp Met Phe Thr Leu Asp Lys Pro Val Cys Phe Asn Tyr
    690                 695                 700

His Ser Tyr Ala Thr Glu Leu Gln Gly Leu Leu Phe Gly Arg Pro Ala
705                 710                 715                 720

Leu His Arg Met Ser Val Glu Gly Tyr Lys Glu Glu Gly Ser Thr Thr
                725                 730                 735

Thr Pro Phe Asp Met Met Leu Val Asn Thr Val Ser Arg Phe His Val
            740                 745                 750

Ala Ser Arg Ala Leu Lys Ala Ala Ala Ala Gln Asn Asp Glu Val Lys
        755                 760                 765
```

```
Glu Asn Leu Ser Ala Leu Leu Ala Lys Val Asp Asp Glu Met Lys Ser
    770                 775                 780

Val Lys Asp Tyr Ile Glu Gln Trp Gly Lys Asp Pro Asp Asp Ile Tyr
785                 790                 795                 800

Glu Leu Asp Phe Leu Lys Lys Asp
                805


<210> SEQ ID NO 28
<211> LENGTH: 2427
<212> TYPE: DNA
<213> ORGANISM: Trichoderma reesei

<400> SEQUENCE: 28

atgcctggag aagtcattga tcaaccgaac cccccgccgc tcacgagcca tctcccggat     60

acgatagagg agctggctgt caagccctca aaggcaccgc tgagcaacct cgacttggtc    120

tcgctcagag agttccaacg ggcagcatgt tacattgcga gcgccatgat attcctcaag    180

gacaatgtcc ttttggaccg cgagctacgg tttgaagatg tgaaacccag gcttctaggc    240

cactggggta cctgccctgg tctcatcctc atctggtcac atttgaatct ccttatccgc    300

gacagttccc aggacatgct ctttgtcatt ggacctggtc atggagcccc agctgccttg    360

gcctgcctct ggctcgaagg ttcacttgaa cgattctatc cagacaaata cagaaccgat    420

aaagagggac tgcataacct cattacgaaa ttctctgttc ctacagggtt tccaagccac    480

atcaacccgg agactccagg ttgcatccac gagggcggag agctgggata tgcgttggca    540

gtgtcctttg gagcagtcat ggataagcca gacctcattg ttccatgtgt tgtcggcgat    600

ggcgaggccg agactggccc tacggcagcc gcatggcatt ccatcaagta cttggatccc    660

gcagagtctg gagcagtcat ccccatcctg cacgtcaacg gcttcaagat cagcgagcgg    720

accatcttcg gctgcatgga caacacagag ctcgtcctgc tcttctcggg ctacggctac    780

gaggtgtgca tcgtcgagaa cctggatgcc atagacaccg aactgcatac ggcactattc    840

tgggccctat cagaaatcaa gaggatccaa ggagccgcgc gatcaggaaa ccccatcacc    900

aagccccggt ggcccatgat catcctccga acgccaaagg gatggacagg accccgaacg    960

gtcgacgaca agatcatcga gggctcattc cacgcgcacc aggtgccggt gacaaaggcc   1020

aacaaagacg agggccatct tcgcatcctg caagactggc tcaagagcta cgacgtgcgc   1080

ggactgctcc ccgacggcaa gccttcaggc gacttcctcg acattctgcc gccagaccct   1140

cacaagaggc tgggtcagtc caagcttgcg tacgactgcc atcagcccct cgatctgccg   1200

gactggaggc cgcattcggt ggacaagttt gaagaagcca gcagcatgca gcagtcgggc   1260

aagttcctcg acgtcgtggc gaggcagaac atgaagacgt tccgcatctt ctcccccgac   1320

gagctggaga gcaacaagct gagcgcagtc ctggaccact cgagccgaaa cttccaatgg   1380

gaccagtact cccgcgcgca gggcggccgc gtcattgaga tcctgtccga gcactgctgt   1440

caggggttcc tccagggata caccctgacg ggcgaacgg ccatcttccc cagctacgag   1500

tcgttcctgg gcatcatcca caccatgatg attcagtact ccaaattctc caagatcagc   1560

cgcaagctgc cctggcgagg cgacctgagc tccatcaact acatcgagac gagcacctgg   1620

gcgcgacagg agcacaacgg cttctcgcac cagaaccctt ccttcatcgg cgccgtcctg   1680

aacctcaagg ccgaaatcgc acgggtctac ctgccccctg acgcaaactg cttcctcagc   1740

acccttcacc actgcctcca gtccaagaac tacgtcaacc tgatgattgg ctccaagcag   1800

cccacgcccg tctacctctc tgccgaagac gcccagaggc attgtgaaga cggcgcctcc   1860
```

-continued

```
atctggagat gggcaagcac ccacgacggc gagcacccag acgtggtgct cgtcggaatc   1920

ggcgtcgagg tgacctttga agtcatcaaa gccgcccaac tcctctccag gctcgcaccg   1980

aatctgcgcg tccgcgtcgt caacgtgacc gatctcctgg tcctccccca cgaatcgcac   2040

caccctcacg ccctcgactc caaggccttt gaagacatgt tcacgctcga caagcccgtg   2100

tgcttcaact accacagcta cgcgacggag ctgcaggggc ttctgtttgg ccgcccggcg   2160

ctgcatcgca tgagcgtgga gggctacaag gaggagggca gcacgacgac gccgtttgac   2220

atgatgcttg tgaataccgt cagccgcttc catgtggcgt cgagggcatt gaaagctgcg   2280

gctgcgcaaa acgacgaggt caaggagaat ctgtctgcct tgttggccaa ggttgacgac   2340

gagatgaaga gcgtaaagga ctatatcgag cagtggggga aagacccaga tgatatttac   2400

gaattggatt tcttgaagaa ggattag                                      2427
```

<210> SEQ ID NO 29
<211> LENGTH: 787
<212> TYPE: PRT
<213> ORGANISM: Lactobacillus curvatus

<400> SEQUENCE: 29

```
Met Thr Asp Tyr Ser Ser Lys Glu Tyr Leu Ala Lys Val Asp Ala Phe
1               5                   10                  15

Trp Arg Ala Ala Asn Tyr Ile Ser Val Gly Gln Leu Tyr Leu Lys Asp
            20                  25                  30

Asn Pro Leu Leu Lys Cys Pro Leu Glu Ala Lys Asp Val Lys Ala Lys
        35                  40                  45

Pro Ile Gly His Trp Gly Thr Ile Ser Gly Gln Asn Phe Leu Tyr Ala
    50                  55                  60

His Leu Asn Arg Ala Ile Asn Lys Tyr Asn Leu Asn Met Phe Tyr Val
65                  70                  75                  80

Glu Gly Pro Gly His Gly Gly Gln Val Met Val Ser Asn Ser Tyr Leu
                85                  90                  95

Asp Gly Ser Tyr Ser Glu Ile Tyr Pro Glu Ile Ser Gln Asp Val Glu
            100                 105                 110

Gly Met Lys Lys Leu Phe Lys Gln Phe Ser Phe Pro Gly Gly Val Ala
        115                 120                 125

Ser His Ala Ala Pro Glu Thr Pro Gly Ser Ile His Glu Gly Gly Glu
    130                 135                 140

Leu Gly Tyr Ser Leu Ser His Gly Val Gly Ala Ile Leu Asp Asn Pro
145                 150                 155                 160

Asp Val Ile Ala Ala Val Val Val Gly Asp Gly Glu Ala Glu Thr Gly
                165                 170                 175

Pro Leu Ala Ala Ser Trp Leu Ser Ser Thr Phe Ile Asn Pro Lys Asn
            180                 185                 190

Asp Gly Ala Val Leu Pro Ile Leu Asn Leu Asn Gly Phe Lys Ile Ser
        195                 200                 205

Asn Pro Thr Ile Leu Ser Arg Lys Ser Asp Glu Glu Leu Thr Lys Tyr
    210                 215                 220

Phe Glu Gly Asn Gly Trp Glu Pro Ile Phe Val Glu Gly Asp Asp Pro
225                 230                 235                 240

Glu Lys Met His Pro Ala Thr Ala Ala Ala Met Asp Glu Ala Ile Glu
                245                 250                 255

Lys Ile Gln Ala Ile Gln Lys Asn Ala Arg Glu Asn Gly Asp Ser Ser
            260                 265                 270
```

-continued

```
Arg Pro Val Trp Pro Met Ile Val Phe Arg Ala Pro Lys Gly Trp Thr
        275                 280                 285

Gly Pro Lys Thr Trp Asp Gly Ala Pro Ile Glu Asn Ser Phe Arg Ala
    290                 295                 300

His Gln Ile Pro Val Pro Ile Asp Ser Ala Asp Met Gln His Val Asp
305                 310                 315                 320

Ala Leu Val Asp Trp Met Lys Ser Tyr Arg Pro Glu Glu Leu Phe Thr
                325                 330                 335

Glu Glu Gly Gln Leu Lys Pro Glu Ile Ala Ala Ile Ala Pro Lys Gly
            340                 345                 350

Asp Gln Arg Met Ala Ala Asn Pro Ile Thr Asn Gly Gly Ile Asp Pro
        355                 360                 365

Lys Pro Leu Arg Leu Pro Asp Tyr Arg Asp Tyr Ala Val Asp Asn Ser
    370                 375                 380

Glu His Gly Lys Val Val Ala Gln Asp Met Ile Val Leu Gly Glu Tyr
385                 390                 395                 400

Val Arg Asp Ile Ile Lys Asp Asn Asp Gln Asn Lys Asn Phe Arg Ile
                405                 410                 415

Phe Gly Pro Asp Glu Thr Met Ser Asn Arg Leu Asn His Ile Phe Glu
            420                 425                 430

Ala Thr Asn Arg Gln Trp Met Glu Pro Ile Lys Glu Pro Asn Asp Gln
        435                 440                 445

Tyr Met Ala Thr Glu Gly Arg Val Leu Asp Ser Gln Leu Ser Glu His
    450                 455                 460

Gln Ala Glu Gly Trp Leu Glu Gly Tyr Val Leu Thr Gly Arg His Gly
465                 470                 475                 480

Phe Phe Ala Ser Tyr Glu Ser Phe Leu Arg Val Val Asp Ser Met Leu
                485                 490                 495

Thr Gln His Phe Lys Trp Leu Arg Lys Ala Asp Glu Gln Ala Trp Arg
            500                 505                 510

Asn Lys Tyr Pro Ser Leu Asn Val Ile Ala Thr Ser Thr Val Phe Gln
        515                 520                 525

Gln Asp His Asn Gly Tyr Thr His Gln Asp Pro Gly Ile Leu Thr His
    530                 535                 540

Leu Ala Glu Lys Lys Pro Glu Phe Ile Arg Glu Tyr Leu Pro Ala Asp
545                 550                 555                 560

Ala Asn Thr Leu Leu Ala Thr Met Asp Thr Val Phe Lys Ser Gln Glu
                565                 570                 575

Lys Ile Asn Leu Val Val Ala Ser Lys His Pro Arg Gln Gln Trp Phe
            580                 585                 590

Ser Ile Asp Glu Ala Thr Val Leu Val Lys Asn Gly Leu Lys Ile Ile
        595                 600                 605

Asp Trp Ala Ser Thr Asp Gln Asp Ala Glu Pro Asp Val Val Ile Ala
    610                 615                 620

Ala Ala Gly Thr Glu Pro Thr Leu Glu Ser Leu Ala Ala Ile Ser Ile
625                 630                 635                 640

Leu His Lys Gln Tyr Pro Asp Met Lys Ile Arg Phe Ile Asn Val Val
                645                 650                 655

Asp Leu Leu Lys Leu Arg Ser Pro Lys Val Asp Pro Arg Gly Leu Thr
            660                 665                 670

Asp Glu Glu Phe Asp Met Tyr Phe Thr Lys Asp Lys Pro Val Val Phe
        675                 680                 685

Ala Phe His Gly Phe Glu Gly Leu Val Arg Asp Ile Phe Phe Asp Arg
```

```
    690                 695                 700

His Asn His Asn Leu His Val His Gly Tyr Arg Glu Asn Gly Asp Ile
705                 710                 715                 720

Thr Thr Pro Phe Asp Met Arg Val Leu Asn Gln Met Asp Arg Phe Ser
                725                 730                 735

Leu Ser Lys Glu Val Ala Val Asp Val Leu Gly Asp Gln Ala Gly Gln
            740                 745                 750

Phe Ala Gln Ser Met Asp Asp Met Val Ala Lys His Asn Gln Tyr Ile
        755                 760                 765

Arg Asp Glu Gly Thr Asp Leu Pro Glu Val Glu Glu Trp Gln Trp Glu
    770                 775                 780

Pro Leu Arg
785


<210> SEQ ID NO 30
<211> LENGTH: 2364
<212> TYPE: DNA
<213> ORGANISM: Lactobacillus curvatus

<400> SEQUENCE: 30

atgacagatt attcaagcaa agaatacctt gctaaagttg acgcattttg gcgggctgca      60

aattatatct cagttggtca attatactta aaagataacc cactattgaa atgtcctttg     120

gaagcaaaag atgttaaggc aaaaccaatt ggtcactggg ggacaatctc aggccaaaac     180

ttcctatatg ctcatttaaa ccgtgcaatt aataaatata acttaaacat gttctacgtt     240

gaaggcccag gtcacggtgg tcaagtgatg gtctcaaact catatttaga tggtagctat     300

tcagaaatct atccagaaat ttctcaagat gttgaaggga tgaagaaatt attcaaacaa     360

ttctcattcc caggcggcgt tgcttctcat gcggctcctg aaacacctgg ttcaatccat     420

gaaggtggcg aacttggtta ttcattatca cacggtgttg gtgcgatctt agataaccca     480

gacgtgattg ctgctgttgt tgtgggtgat ggggaagctg aaactggccc attagctgca     540

tcatggttat caagcacatt catcaatcct aagaatgatg gtgctgtctt accaatcttg     600

aacttaaacg gtttcaagat ttctaaccca acaattcttt cacgcaagag tgatgaagaa     660

ttaacgaaat acttcgaagg caatggttgg gaaccaatct ttgttgaagg cgacgaccct     720

gaaaagatgc acccagcaac tgctgctgca atggatgaag ccatcgaaaa aatccaagca     780

attcaaaaga atgcgcgtga aaatggcgat tcatctcgtc cagtatggcc aatgatcgtc     840

ttccgcgcac ctaagggttg gactggtcct aagacatggg atggcgcacc aatcgaaaat     900

tcattccgcg cgcaccaaat tccagtgcca atcgacagtg ctgacatgca acacgttgat     960

gcattagtag actggatgaa gtcataccgt ccagaagaat tgtttacaga agaaggccaa    1020

ttaaaacctg aaatcgcagc aattgcacct aaaggcgatc aacggatggc tgctaaccca    1080

attaccaatg gtgggattga tcctaaacca ttacgcttac cagattaccg tgattatgct    1140

gtggataatt cagaacacgg taaagtcgta gcgcaagaca tgattgtttt aggcgaatat    1200

gttcgtgata tcatcaaaga caacgatcaa aataaaaact tcagaatctt cggccctgac    1260

gaaacaatgt caaaccgttt gaaccatatt tttgaagcaa caaaccgtca atggatggaa    1320

ccaatcaaag aaccaaacga tcaatacatg gcaacagaag gccgtgttct tgattcacaa    1380

ttatcagaac atcaagctga aggttggtta gaaggttatg tcctaactgg tcgtcatggt    1440

ttctttgcaa gttacgaatc attcttgcgc gttgtggatt caatgttaac acaacacttc    1500

aagtggttac gtaaggctga tgaacaagca tggcgtaaca agtatccttc attgaacgtg    1560
```

attgccacat caactgtttt ccaacaagat cacaatggtt acacacatca agatccaggt 1620
atcttaacac acttagctga aaagaaacct gaatttattc gtgaatactt acctgctgat 1680
gctaacacgt tgttagcaac aatggatact gtcttcaaga gtcaagaaaa gatcaattta 1740
gtggttgctt caaaacaccc acgtcaacaa tggttctcaa ttgacgaagc aacagtctta 1800
gttaaaaatg gtttgaagat tattgactgg gcaagtacag accaagatgc tgaaccagat 1860
gttgtgattg cagctgctgg gacagaacca acacttgaaa gtttggctgc aatctcaatc 1920
ttgcacaaac aatatcctga catgaagatt cgtttcatta acgttgttga tttattgaaa 1980
cttcgttcac ctaaagtgga ccctcgtggt ttaacagatg aagaattcga catgtacttt 2040
acaaaagaca aaccagtggt tttcgcattc cacggtttcg aaggcttagt acgtgatatc 2100
ttctttgacc gtcacaacca taaccttcat gttcatggct accgtgaaaa tggtgacatt 2160
acaacaccat ttgacatgcg tgtcttgaat caaatggatc gtttcagtct atctaaagaa 2220
gttgcagttg acgtacttgg cgatcaagct ggtcaattcg cacaatcaat ggatgacatg 2280
gttgctaaac acaatcaata cattcgcgat gaaggtactg acttaccaga agttgaagaa 2340
tggcaatggg aaccactccg ttaa 2364

<210> SEQ ID NO 31
<211> LENGTH: 825
<212> TYPE: PRT
<213> ORGANISM: Bifidobacterium adolescentis

<400> SEQUENCE: 31

Met Thr Ser Pro Val Ile Gly Thr Pro Trp Lys Lys Leu Asn Ala Pro
1 5 10 15

Val Ser Glu Glu Ala Ile Glu Gly Val Asp Lys Tyr Trp Arg Ala Ala
20 25 30

Asn Tyr Leu Ser Ile Gly Gln Ile Tyr Leu Arg Ser Asn Pro Leu Met
35 40 45

Lys Glu Pro Phe Thr Arg Glu Asp Val Lys His Arg Leu Val Gly His
50 55 60

Trp Gly Thr Thr Pro Gly Leu Asn Phe Leu Ile Gly His Ile Asn Arg
65 70 75 80

Leu Ile Ala Asp His Gln Gln Asn Thr Val Ile Ile Met Gly Pro Gly
85 90 95

His Gly Gly Pro Ala Gly Thr Ala Gln Ser Tyr Leu Asp Gly Thr Tyr
100 105 110

Thr Glu Tyr Phe Pro Asn Ile Thr Lys Asp Glu Ala Gly Leu Gln Lys
115 120 125

Phe Phe Arg Gln Phe Ser Tyr Pro Gly Gly Ile Pro Ser His Tyr Ala
130 135 140

Pro Glu Thr Pro Gly Ser Ile His Glu Gly Gly Glu Leu Gly Tyr Ala
145 150 155 160

Leu Ser His Ala Tyr Gly Ala Val Met Asn Asn Pro Ser Leu Phe Val
165 170 175

Pro Ala Ile Val Gly Asp Gly Glu Ala Glu Thr Gly Pro Leu Ala Thr
180 185 190

Gly Trp Gln Ser Asn Lys Leu Ile Asn Pro Arg Thr Asp Gly Ile Val
195 200 205

Leu Pro Ile Leu His Leu Asn Gly Tyr Lys Ile Ala Asn Pro Thr Ile
210 215 220

-continued

```
Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
            260                 265                 270

Glu Ile Cys Asp Ile Lys Ala Ala Ala Gln Thr Asp Asp Met Thr Arg
        275                 280                 285

Pro Phe Tyr Pro Met Ile Ile Phe Arg Thr Pro Lys Gly Trp Thr Cys
    290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Glu
            340                 345                 350

Asn Gly Ala Val Lys Pro Glu Val Thr Ala Phe Met Pro Thr Gly Glu
        355                 360                 365

Leu Arg Ile Gly Glu Asn Pro Asn Ala Asn Gly Gly Arg Ile Arg Glu
    370                 375                 380

Glu Leu Lys Leu Pro Lys Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ala Tyr Asp
        435                 440                 445

Val Thr Asn Lys Gln Trp Asp Ala Gly Tyr Leu Ser Ala Gln Val Asp
    450                 455                 460

Glu His Met Ala Val Thr Gly Gln Val Thr Glu Gln Leu Ser Glu His
465                 470                 475                 480

Gln Met Glu Gly Phe Leu Glu Gly Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
                565                 570                 575

Phe Pro Val Asp Ser Asn Met Leu Leu Ala Val Ala Glu Lys Cys Tyr
            580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
    610                 615                 620

Ala Ala Glu Trp Lys Trp Ala Ser Asn Val Lys Ser Asn Asp Glu Ala
625                 630                 635                 640

Gln Ile Val Leu Ala Ala Thr Gly Asp Val Pro Thr Gln Glu Ile Met
```

```
                645                 650                 655

Ala Ala Ala Asp Lys Leu Gly Ala Met Gly Ile Lys Phe Lys Val Val
            660                 665                 670

Asn Val Val Asp Leu Val Lys Leu Gln Ser Ala Lys Glu Asn Asn Glu
        675                 680                 685

Ala Leu Ser Asp Glu Glu Phe Ala Glu Leu Phe Thr Glu Asp Lys Pro
    690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Thr Pro Tyr Asp Met Val Arg Val Asn Asn Ile
            740                 745                 750

Asp Arg Tyr Glu Leu Gln Ala Glu Ala Leu Arg Met Ile Asp Ala Asp
        755                 760                 765

Lys Tyr Ala Asp Lys Ile Asn Glu Leu Glu Ala Phe Arg Gln Glu Ala
    770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
                805                 810                 815

Thr Ala Ala Thr Ala Gly Asp Asn Glu
            820                 825


<210> SEQ ID NO 32
<211> LENGTH: 2478
<212> TYPE: DNA
<213> ORGANISM: Bifidobacterium adolescentis

<400> SEQUENCE: 32

atgacgagtc ctgttattgg cacccccttgg aagaagctga acgctccggt ttccgaggaa      60

gctatcgaag gcgtggataa gtactggcgc gcagccaact acctctccat cggccagatc     120

tatctgcgta gcaacccgct gatgaaggag cctttcaccc gcgaagacgt caagcaccgt     180

ctggtcggtc actggggcac caccccgggc ctgaacttcc tcatcggcca catcaaccgt     240

ctcattgctg atcaccagca gaacactgtg atcatcatgg gcccgggcca cggcggcccg     300

gctggtaccg ctcagtccta cctggacggc acctacaccg agtacttccc gaacatcacc     360

aaggatgagg ctggcctgca gaagttcttc cgccagttct cctacccggg tggcatcccg     420

tcccactacg ctccggagac cccgggctcc atccacgaag gcggcgagct gggttacgcc     480

ctgtcccacg cctacggcgc tgtgatgaac aacccgagcc tgttcgtccc ggccatcgtc     540

ggcgacggtg aagctgagac cggcccgctg gccaccggct ggcagtccaa caagctcatc     600

aacccgcgca ccgacggtat cgtgctgccg atcctgcacc tcaacggcta caagatcgcc     660

aacccgacca tcctgtcccg catctccgac gaagagctcc acgagttctt ccacggcatg     720

ggctatgagc cgtacgagtt cgtcgctggc ttcgacaacg aggatcacct gtcgatccac     780

cgtcgtttcg ccgagctgtt cgagaccgtc ttcgacgaga tctgcgacat caaggccgcc     840

gctcagaccg acgacatgac tcgtccgttc tacccgatga tcatcttccg taccccgaag     900

ggctggacct gcccgaagtt catcgacggc aagaagaccg agggctcctg gcgttcccac     960

caggtgccgc tggcttccgc ccgcgatacc gaggcccact tcgaggtcct caagaactgg    1020

ctcgagtcct acaagccgga agagctgttc gacgagaacg gcgccgtgaa gccggaagtc    1080
```

-continued

```
accgccttca tgccgaccgg cgaactgcgc atcggtgaga acccgaacgc caacggtggc   1140

cgcatccgcg aagagctgaa gctgccgaag ctggaagact acgaggtcaa ggaagtcgcc   1200

gagtacggcc acggctgggg ccagctcgag gccacccgtc gtctgggcgt ctacacccgc   1260

gacatcatca agaacaaccc ggactccttc cgtatcttcg gaccggatga gaccgcttcc   1320

aaccgtctgc aggccgctta cgacgtcacc aacaagcagt gggacgccgg ctacctgtcc   1380

gctcaggtcg acgagcacat ggctgtcacc ggccaggtca ccgagcagct ttccgagcac   1440

cagatggaag gcttcctcga gggctacctg ctgaccggcc gtcacggcat ctggagctcc   1500

tatgagtcct tcgtgcacgt gatcgactcc atgctgaacc agcacgccaa gtggctcgag   1560

gctaccgtcc gcgagattcc gtggcgcaag ccgatctcct ccatgaacct gctcgtctcc   1620

tcccacgtgt ggcgtcagga tcacaacggc ttctcccacc aggatccggg tgtcacctcc   1680

gtcctgctga acaagtgctt caacaacgat cacgtgatcg gcatctactt cccggtggat   1740

tccaacatgc tgctcgctgt ggctgagaag tgctacaagt ccaccaacaa gatcaacgcc   1800

atcatcgccg gcaagcagcc ggccgccacc tggctgaccc tggacgaagc tcgcgccgag   1860

ctcgagaagg gtgctgccga gtggaagtgg gcttccaacg tgaagtccaa cgatgaggct   1920

cagatcgtgc tcgccgccac cggtgatgtt ccgactcagg aaatcatggc cgctgccgac   1980

aagctgggcg ccatgggcat caagttcaag gtcgtcaacg tggttgacct ggtcaagctg   2040

cagtccgcca aggagaacaa cgaggccctc tccgatgagg agttcgctga gctgttcacc   2100

gaggacaagc cggtcctgtt cgcttaccac tcctatgccc gcgatgtgcg tggtctgatc   2160

tacgatcgcc cgaaccacga caacttcaac gttcacggct acgaggagca gggctccacc   2220

accaccccgt acgacatggt tcgcgtgaac aacatcgatc gctacgagct ccaggctgaa   2280

gctctgcgca tgattgacgc tgacaagtac gccgacaaga tcaacgagct cgaggccttc   2340

cgtcaggaag ccttccagtt cgctgtcgac aacggctacg atcacccgga ttacaccgac   2400

tgggtctact ccggtgtcaa caccaacaag cagggtgcta tctccgctac cgccgcaacc   2460

gctggcgaca acgagtga                                                  2478


<210> SEQ ID NO 33
<211> LENGTH: 733
<212> TYPE: PRT
<213> ORGANISM: Aphanomyces astaci

<400> SEQUENCE: 33

Met Ser His Gln Phe Thr Thr Lys Ser Val Ala Ser Gln Ser Thr Met
1               5                   10                  15

Leu Arg Val Arg Pro Phe Leu Ser Ser Arg Lys Ala Ala Ile Thr Leu
            20                  25                  30

Leu Pro Arg Ala Thr Thr Ser Arg Phe Phe Thr Asp Asp Ala Thr Lys
        35                  40                  45

Lys Asn Asp Arg Leu Leu Val Met Thr Asn Gly Gly Val Ala Lys His
    50                  55                  60

Ser His Leu Leu Leu Gly Leu Met Asn Lys Leu Ser Tyr Thr Phe Pro
65                  70                  75                  80

Ser Val Gly Tyr Phe Arg Pro Val Ala Pro Asn Phe His Ser Thr His
                85                  90                  95

Gly Asp His His Val Asp Leu Ile Arg Ser Glu Phe Lys Ile Lys Asp
            100                 105                 110

Glu Pro Tyr Gln Leu Val Gly Met Thr Gln Ala Asp Ile Thr His Ala
        115                 120                 125
```

-continued

```
His Leu Glu Gly Asp Thr Asp Ser Val Ile Asp Thr Met Leu Ser Lys
    130                 135                 140

Phe Glu Tyr Leu Arg Glu Lys His Asp Phe Val Val Met Glu Gly Ala
145                 150                 155                 160

Val Leu Asp Thr Ser Pro Glu Leu Ser Trp Glu Leu Asn Val Asp Ile
                165                 170                 175

Ala Lys Ser Leu Asn Ala Pro Val Leu Leu Thr Val Asp Ala Asp Asp
            180                 185                 190

Leu Thr Val Asp Pro Ala Leu His Trp Thr Ala Ala Glu Ser Val Ala
        195                 200                 205

Trp Leu Ala Asp Gln Ile Thr Thr Arg Val Leu Leu Ala Lys Asp Met
    210                 215                 220

Ala His Ala Glu Gly Leu Thr His Val Gly Thr Ile Val Asn Arg Val
225                 230                 235                 240

Lys Thr Asp Asp Ala Leu Glu Leu Arg Asp Leu Val His Ala Gln Ile
                245                 250                 255

Lys Ala Arg Gly Phe Asp Pro Thr Lys Leu Leu Gly Ile Leu Pro Leu
            260                 265                 270

Asp Pro Val Leu Asn Ser Lys Arg Leu Asn Glu Val Val Ala Gln Leu
        275                 280                 285

His Ala Lys Gln Leu Tyr Gly Asn Pro Met Ser Asn Ser Val Val Val
    290                 295                 300

Thr Asp Gly Leu Met Ala Thr Thr Glu Leu Lys Asp Leu Phe Lys His
305                 310                 315                 320

Ile Asn Lys His Asp Asp Gly Leu Leu Val Ile Val Ser Ser Glu Arg
                325                 330                 335

Thr Asp Val Ile Leu Gly Leu Leu Ala Ser Arg Leu Ser Gly Ala Leu
            340                 345                 350

Pro Gln Ile Ser Gly Ile Ile Leu Thr Asn Gly Gly Ile Pro Gln Asn
        355                 360                 365

Glu Cys Gln Asp Ile Leu Ile Gly Leu Ala Gln Ile Asp Lys Ala Ser
    370                 375                 380

Val Pro Ile Tyr Ser Val Glu Leu Asp Ser Tyr Arg Thr Ala Ile Ala
385                 390                 395                 400

Leu Ser Lys Val Thr Cys Asp Ile Leu Pro Thr Ser Gln Asn Lys Ile
                405                 410                 415

Gln Gln Ala Tyr Ile Leu Phe Asp Thr Asn Val Glu Ser Asp Glu Leu
            420                 425                 430

Leu Ser His Leu Ile Glu Arg Thr Gly Gly His Gly Arg Thr Pro Lys
        435                 440                 445

Gln Phe Lys His Phe Leu Phe Glu Ala Ser Arg Lys Ala Asp Gln His
    450                 455                 460

Ile Val Leu Thr Glu Gly Glu Asp Asp Arg Ile Leu Gln Ala Ala Asp
465                 470                 475                 480

Glu Val Leu Arg Arg Gly Ile Ala Arg Leu Thr Ile Leu Gly Asp Val
                485                 490                 495

Glu Ser Ile Asn Ala Arg Ala Lys Thr Leu Arg Leu Asp Leu Ser Gln
            500                 505                 510

Ala Thr Leu Leu Asp Pro Ser Lys Ala Asp Lys Leu Ala Thr Tyr Ala
        515                 520                 525

Asp His Tyr Phe Glu Lys Arg Lys Ser Lys Gly Ile Thr Pro Glu Leu
    530                 535                 540
```

-continued

```
Ala Lys Glu Thr Val Gly Glu Ala Thr Tyr Phe Gly Thr Val Met Val
545                 550                 555                 560

Asp Leu Asp Asp Ala Asp Gly Met Val Ser Gly Val Cys His Thr Thr
                565                 570                 575

Ala Asn Thr Ile Arg Pro Ala Leu Gln Leu Ile Lys Thr Arg Pro Asp
            580                 585                 590

Ile Pro Leu Val Ser Ser Val Phe Phe Met Cys Leu Glu His Asp Val
        595                 600                 605

Val Leu Tyr Gly Asp Cys Ala Val Asn Thr Asp Pro Thr Ala Gln Gln
    610                 615                 620

Leu Ala Gln Ile Ala Val Gln Ser Ala Glu Ser Ala Val Ala Phe Gly
625                 630                 635                 640

Ile Glu Pro Arg Val Ala Leu Leu Ser Tyr Ala Thr Gly Asp Ser Asn
                645                 650                 655

Lys Gly Pro Ile Ile Asp Lys Val Arg Glu Ala Thr Lys Leu Ala Gln
            660                 665                 670

Ser Met Ala Pro Gly Val Ser Ile Tyr Gly Pro Ile Gln Tyr Asp Ala
        675                 680                 685

Ala Thr Asn Pro Ser Ile Ala Lys Gln Lys Val Lys Gly Leu Lys Gln
    690                 695                 700

Ser Glu Met Glu Val Ala Gly His Ala Asn Val Leu Val Phe Pro Asp
705                 710                 715                 720

Leu Asn Thr Gly Asn Asn Thr Tyr Lys Ala Val Arg Val
                725                 730


<210> SEQ ID NO 34
<211> LENGTH: 2340
<212> TYPE: DNA
<213> ORGANISM: Aphanomyces astaci

<400> SEQUENCE: 34

atgtcccatc aattcactac caagtctgtt gcttctcaat ctaccatgtt gagagtcaga     60

ccattcttgt catctagaaa ggctgctatt actttgttgc caagagctac tacttctaga    120

ttcttcactg atgatgctac caagaagaac gacagattat tggttatgac taacggtggt    180

gttgctaagc actctcattt gttgttgggt ttgatgaaca agttgtctta cacctttcca    240

tccgttggtt actttagacc agttgctcca aatttccatt ctacccatgg tgatcatcac    300

gttgatttga tcagatccga attcaagatc aaggacgaac catatcaatt ggttggtatg    360

acccaagctg atattactca tgctcatttg gaaggtgata ccgattctgt tattgacacc    420

atgttgtcca agttcgaata cttgagagaa aagcacgatt tcgttgttat ggaaggtgct    480

gttttggata cttctccaga attgtcttgg gaattgaacg ttgatattgc caagtctttg    540

aacgctccag ttttgttgac tgttgatgct gatgatttga cagttgatcc agctttacat    600

tggactgctg ctgaatcagt tgcttggttg gcagatcaaa ttactactag agtcttgttg    660

gctaaggata tggctcatgc tgaaggtttg actcatgttg gtactatcgt taacagagtt    720

aagaccgatg atgccttgga attgagagat ttggttcatg ctcaaatcaa ggctagaggt    780

tttgatccaa ctaagttgtt aggtatcttg ccattggatc cagtcttgaa ctctaagaga    840

ttgaacgaag ttgttgctca attgcacgcc aaacaattat acggtaatcc aatgtccaac    900

tccgttgttg ttactgatgg tttgatggct actaccgaat tgaaggattt gttcaagcac    960

atcaacaagc acgatgacgg tttgttggtt atcgtttctt ctgaaagaac cgatgtcatc   1020

ttgggtttgt tagcttcaag attgtctggt gctttgccac aaatttccgg tattatctta   1080
```

```
acaaacggtg gtatcccaca aaacgaatgc caagatattt tgattggttt ggcccaaatt   1140

gataaggcct ctgttccaat ctattccgtt gaattggatt cttacagaac cgctattgcc   1200

ttgtctaagg ttacctgtga tattttgcca acctcccaaa acaaaatcca acaagcctac   1260

attttgttcg acaccaacgt tgaatccgat gaattattgt cccacttgat cgaaagaact   1320

ggtggtcatg gtagaactcc aaagcaattc aaacacttct tgttcgaagc ttccagaaaa   1380

gccgatcaac atatcgtttt gactgaaggt gaagatgaca gaatattgca agctgctgat   1440

gaagttttga gaagaggtat tgctagattg accattttgg gtgatgtcga atctattaac   1500

gctagagcta agaccttgag attggatttg tcacaagcta ccttgttgga cccatctaaa   1560

gctgataagt tggctactta tgccgatcac tacttcgaaa agagaaagtc taaaggtatc   1620

accccagaat tggctaaaga aactgttggt gaagctactt acttcggtac tgttatggtt   1680

gatttggatg atgcagatgg tatggtttct ggtgtttgtc atacaactgc taacactatt   1740

agaccagcct tgcaattgat taagaccaga ccagatattc cattggtttc ttccgttttc   1800

ttcatgtgtt tggaacacga tgttgtcttg tatggtgatt gtgctgttaa tactgatcca   1860

accgctcaac aattggctca aattgctgtt caatcagctg aatctgctgt tgcttttggt   1920

attgaaccta gagttgcttt gttgtcttat gctactggtg attctaacaa gggtccaatc   1980

attgacaaag ttagagaagc tacaaagttg gctcaatcta tggctccagg tgtttctatc   2040

tatggtccta ttcaatatga tgctgccacc aatccatcca ttgctaaaca aaaagttaag   2100

ggtttgaagc aatccgaaat ggaagttgct ggtcatgcta atgttttggt tttcccagat   2160

ttgaacactg gtaacaacac ttacaaggcc gttcaacaat ctactgattg cttggctatt   2220

ggtccaatgt tgcaaggttt gaacaagcca gttaacgatt tgtctagagg tgctacagtt   2280

ggtgatatcg ttactacagt tgcattgact gctatccaag ctaagcaatc taagaactaa   2340
```

<210> SEQ ID NO 35
<211> LENGTH: 764
<212> TYPE: PRT
<213> ORGANISM: Aphanomyces invadans

<400> SEQUENCE: 35

```
Met Leu Arg Cys Arg Pro Phe Leu Ser Gly Arg Lys Ala Ala Ala Thr
1               5                   10                  15

Leu Leu Pro Arg Ala Thr Ala Ser Arg Phe Leu Ser Asp Glu Ala Thr
            20                  25                  30

Lys Lys Asn Asp Arg Leu Leu Val Met Thr Asn Gly Ser Val Ala Lys
        35                  40                  45

His Ser His Val Leu Leu Gly Leu Met Asn Lys Leu Ser Tyr Thr Phe
    50                  55                  60

Pro Ser Val Gly Tyr Phe Arg Pro Val Ala Pro Asn Phe His Ser Ser
65                  70                  75                  80

Tyr Asn Asp His His Val Glu Leu Ile Arg Ser Glu Phe Lys Ile Lys
                85                  90                  95

Asp Glu Pro Tyr Gln Leu Val Gly Met Thr Gln Ser Asp Ile Thr His
            100                 105                 110

Ala His Leu Glu Gly Asp Pro Asp Ser Val Ile Glu Thr Met Leu Ser
        115                 120                 125

Lys Phe Glu Asp Leu Arg Ala Lys His Asp Phe Val Val Met Glu Gly
    130                 135                 140

Ala Lys Leu Asp Ser Ser Pro Glu Leu Ser Trp Glu Leu Asn Val Asp
```

-continued

```
145                 150                 155                 160

Ile Ala Lys Ser Leu Asn Ala Pro Val Leu Leu Thr Val Asp Ala Asp
                165                 170                 175

Asp Leu Val Val Asp Pro Gly Leu His Trp Thr Asp Ala Glu Ala Leu
            180                 185                 190

Ser Trp Leu Ala Asp Gln Ile Thr Thr Arg Val Leu Leu Ala Lys Asp
        195                 200                 205

Met Ala Gln Ala Glu Gly Leu Thr His Val Gly Thr Leu Val Asn Arg
    210                 215                 220

Val Arg Thr Pro Asp Ala Leu Glu Leu Arg Glu His Val His Ala Gln
225                 230                 235                 240

Ile Lys Ala Arg Gly Phe Asp Pro Ser Lys Leu Leu Gly Ile Leu Pro
                245                 250                 255

Val Asp Pro Val Leu Asp Ser Lys Arg Leu Asn Glu Val Val Ala Gln
            260                 265                 270

Leu His Ala Lys Gln Leu Tyr Gly Asn Pro Met Ser Asn Ser Val Val
        275                 280                 285

Val Thr Asp Gly Leu Met Ala Thr Ala Asp Leu Lys Asp Leu Phe Lys
    290                 295                 300

His Ile Asn Lys His Asp Asp Gly Leu Leu Val Ile Val Ser Ala Glu
305                 310                 315                 320

Arg Thr Asp Val Ile Leu Gly Leu Val Ala Ser Arg Leu Ser Gly Ala
                325                 330                 335

Leu Pro Gln Ile Ser Gly Ile Ile Leu Thr Asn Gly Gly Ile Pro Gln
            340                 345                 350

Asn Glu Cys Gln Glu Ile Leu Lys Gly Leu Ser Lys Ile Gly Lys Ala
        355                 360                 365

Ser Val Pro Ile Tyr Ser Val Glu Thr Asp Ser Tyr His Thr Gly Ile
    370                 375                 380

Ala Leu Ser Lys Val Thr Cys Asp Ile Leu Pro Thr Ser Gln Asn Lys
385                 390                 395                 400

Ile Gln His Ala Tyr Ile Leu Phe Asp Lys Asn Val Glu Ser Lys Glu
                405                 410                 415

Leu Leu Ser His Leu Val Glu Gln Ser Gly Gly Asn Arg Arg Thr Pro
            420                 425                 430

Lys Gln Phe Lys His Phe Leu Phe Glu Ala Ser His Lys Ala Asp Gln
        435                 440                 445

His Ile Val Leu Thr Glu Gly Glu Asp Asp Arg Ile Leu Gln Ala Ala
    450                 455                 460

Asp Glu Val Leu Arg Arg Gly Ile Ala Arg Leu Thr Ile Leu Gly Asp
465                 470                 475                 480

Val Asp Ser Ile Asn Ala Arg Ala Lys Thr Leu Arg Leu Asp Leu Ser
                485                 490                 495

Lys Ala Thr Leu Leu Asn Pro Leu Lys Ala Glu Lys Leu Ala Met Tyr
            500                 505                 510

Ala Asp His Tyr Tyr Glu Lys Arg Lys Ala Lys Gly Ile Thr Pro Glu
        515                 520                 525

Leu Ala Lys Glu Thr Val Gly Glu Ala Thr Tyr Phe Gly Thr Val Met
    530                 535                 540

Val Asp Val Asn Asp Ala Asp Gly Met Val Ser Gly Val Cys His Thr
545                 550                 555                 560

Thr Ala Asn Thr Ile Arg Pro Ala Leu Gln Leu Ile Lys Thr Arg Pro
                565                 570                 575
```

-continued

Asp Ile Pro Leu Val Ser Ser Val Phe Phe Met Cys Leu Glu His Asp
580 585 590

Val Val Leu Tyr Gly Asp Cys Ala Val Asn Thr Asp Pro Thr Ala Glu
595 600 605

Gln Leu Ala Gln Ile Ala Val Gln Ser Ala Glu Ser Ala Lys Ala Phe
610 615 620

Asp Ile Glu Pro Arg Val Ala Leu Leu Ser Tyr Ala Thr Gly Asp Ser
625 630 635 640

Asn Lys Gly Pro Ile Ile Asp Lys Val Arg Glu Ala Thr Lys Leu Ala
645 650 655

Gln Thr Met Ala Pro Glu Val Ser Ile Tyr Gly Pro Ile Gln Tyr Asp
660 665 670

Ala Ala Thr Asn Pro Ser Ile Ala Lys Gln Lys Val Lys Gly Leu Lys
675 680 685

Gln Ser Glu Met Asp Val Ala Gly His Ala Asn Val Leu Val Phe Pro
690 695 700

Asp Leu Asn Thr Gly Asn Asn Thr Tyr Lys Ala Val Gln Gln Ser Thr
705 710 715 720

Asp Cys Leu Ala Ile Gly Pro Met Leu Gln Gly Leu Asn Lys Pro Val
725 730 735

Asn Asp Leu Ser Arg Gly Ala Thr Val Gly Asp Ile Val Thr Thr Val
740 745 750

Ala Leu Thr Ala Ile Gln Ala Arg Gln Ser Lys Lys
755 760

<210> SEQ ID NO 36
<211> LENGTH: 2295
<212> TYPE: DNA
<213> ORGANISM: Aphanomyces invadans

<400> SEQUENCE: 36
atgttgagat gcagaccatt cttgtctggt agaaaagctg ctgctacttt gttgccaaga 60
gctactgctt ctagattttt gtctgatgaa gctaccaaga agaacgacag attattggtt 120
atgaccaacg gttccgttgc caaacattct catgttttgt tgggtttgat gaacaagttg 180
tcttacacct ttccatccgt tggttacttt agaccagttg ctccaaattt ccactcctct 240
tacaatgatc atcacgtcga attgattaga tccgaattca agatcaagga cgaaccatat 300
caattggttg gtatgaccca atccgatatt actcatgctc atttggaagg tgatccagat 360
tctgttattg aaaccatgtt gtccaagttc gaagatttga gagctaagca cgatttcgtt 420
gttatggaag gtgctaagtt ggattcttct ccagaattgt cttgggaatt gaacgttgat 480
attgccaagt ctttgaacgc tccagttttg ttgactgttg atgctgatga tttggttgtt 540
gatccaggtt tacattggac tgatgctgaa gctttgtctt ggttggctga tcaaattact 600
actagagtct tgttggctaa ggatatggct caagctgaag gtttgactca tgttggtact 660
ttggttaaca gagttagaac tccagatgcc ttggaattga gagaacacgt tcatgctcaa 720
atcaaggcta gaggttttga tccatctaag ttgttgggta tcttgccagt tgatcctgtt 780
ttggattcta agagattgaa cgaagttgtt gctcaattgc acgccaaaca attatacggt 840
aatccaatgt ccaactccgt tgttgttact gatggtttga tggctactgc tgatttgaag 900
gatttgttca agcacatcaa caagcacgat gacggtttgt tggttatagt ttctgctgaa 960
agaaccgatg tcatcttggg tttggttgct tcaagattgt ctggtgcttt gccacaaatt 1020

-continued

```
tccggtatta tcttgactaa cggtggtatc ccacaaaacg aatgccaaga aattttgaaa   1080

ggtttgtcca agattggtaa ggcctctgtt ccaatctatt ctgttgaaac cgattcttac   1140

catactggta ttgccttgtc taaggttacc tgtgatattt tgccaacctc ccaaaacaaa   1200

atccaacatg cctacatctt gttcgacaag aacgtcgaat ccaaagaatt attgtcccac   1260

ttggttgaac aatccggtgg taatagaaga actccaaagc aattcaagca ctttttgttc   1320

gaagcttccc acaaagctga tcaacatatc gttttgactg aaggtgaaga tgacagaata   1380

ttgcaagctg ctgatgaagt tttgagaaga ggtattgcta gattgaccat tttgggtgat   1440

gttgattcca ttaacgctag agctaagacc ttgagattgg atttgtctaa agctaccttg   1500

ttgaacccat tgaaggctga aaaattggct atgtacgctg atcactacta cgaaaaaaga   1560

aaggctaagg gtattacccc agaattggct aaagaaactg ttggtgaagc tacttacttc   1620

ggtactgtta tggttgatgt taatgatgcc gatggtatgg tttctggtgt ttgtcataca   1680

actgctaaca ctattagacc agccttgcaa ttgattaaga ccagaccaga tattccattg   1740

gtttcttccg ttttcttcat gtgtttggaa cacgatgttg tcttgtatgg tgattgtgct   1800

gttaacactg atccaactgc tgaacaatta gctcaaatcg ctgttcaatc tgctgaatct   1860

gctaaggctt ttgatatcga acctagagtt gctttgttgt cttatgctac tggtgattct   1920

aacaagggtc caatcattga taaggttaga gaagctacta agttggctca aactatggct   1980

cctgaagttt ctatctatgg tccaattcaa tacgatgctg ctaccaatcc atctatcgct   2040

aaacaaaagg ttaagggttt gaagcaatcc gaaatggatg ttgctggtca tgctaatgtt   2100

ttggttttcc cagatttgaa cactggtaac aacacttaca aggccgttca acaatctact   2160

gattgcttgg ctattggtcc aatgttgcaa ggtttgaaca agccagttaa tgacttgtct   2220

agaggtgcaa cagttggtga tatagttact actgttgctt tgaccgctat tcaagctaga   2280

caatctaaga agtaa                                                    2295
```

```
<210> SEQ ID NO 37
<211> LENGTH: 550
<212> TYPE: PRT
<213> ORGANISM: Auxenochlorella protothecoides

<400> SEQUENCE: 37

Met Asp Leu Asn Arg Asp Asn Pro Gly Thr Ala Ser Glu Ile Ala Ser
1               5                   10                  15

Arg Ala Leu Arg His Arg Arg Glu Leu Gln Ala Asp Arg Ala Ser Val
            20                  25                  30

Leu Gly Leu Leu Leu Asn Lys Val Pro Leu Ala Ala His Ala Asp Ile
        35                  40                  45

Val Ser Gly Val Ala Ala Glu Leu Ala Asp Ser Gly Leu Thr Phe Ala
    50                  55                  60

Gly Gly Ile Pro Tyr Asp Arg Ile Ile Gly Thr Ala Arg Val Asn Glu
65                  70                  75                  80

Phe Ala Asn Ala Leu Gly Ala Lys Gln Ile Tyr Gly Arg Pro Glu Leu
                85                  90                  95

Ile Asp Ser Gly Val Trp Gly Gly Arg Glu Asp Asn Arg Phe Gly Gly
            100                 105                 110

Arg Ser Val His Gly Phe Leu Asp Lys Leu Glu Ala Ile Arg Ala Gln
        115                 120                 125

Arg Glu Ala Glu Gly Gln Thr Phe Phe Arg Pro Leu Val Leu Thr Thr
    130                 135                 140
```

```
Lys Asp Arg Gln Asp Leu Val Leu Gly Leu Ala Ala Ala Ser Leu Ser
145                 150                 155                 160

Gly Ala Cys Pro Pro Leu Gly Gly Leu Val Leu Cys Asp Gly Gly Ala
                165                 170                 175

Cys Ala Ile Thr Pro Pro Val His Ala Ile Met Ala Arg Leu Gly Pro
            180                 185                 190

Asp Thr Leu Pro Val Leu Glu Val Pro His Gly Ala Phe Glu Thr Ala
        195                 200                 205

Arg Arg Met Ala Arg Val Asn Pro Gly Ile Leu Pro Thr Ser Val Arg
    210                 215                 220

Lys Val Arg Glu Ala Arg Ala Leu Phe Gly Arg His Val Asp Val Asp
225                 230                 235                 240

Ala Val Ala Ser Gly Met Ala Val His Arg Glu Pro Arg Leu Thr Pro
                245                 250                 255

Lys Arg Phe Pro Gly Glu Val Ala Ala Ala Ala Ala Arg Phe Asn Val
            260                 265                 270

Asp Val Ser Arg Cys Glu Val Glu Asp His Arg Ser Ser Thr Arg Leu
        275                 280                 285

Asp Ala Tyr Ala Asp Phe Leu Val Glu Ala Arg Lys Lys Lys Ala Leu
    290                 295                 300

Thr Lys Ala Ala Ala Leu Asp Gln Leu Thr Asp Ile Asn Met Phe Gly
305                 310                 315                 320

Thr Ile Met Val Ala Met Gly Asp Ala Asp Gly Met Val Ser Gly Ala
                325                 330                 335

Thr Cys Thr Thr Ala Asn Thr Ile Arg Pro Ala Leu Gln Val Leu Lys
            340                 345                 350

Thr Pro Asp Arg Arg Leu Ile Ser Ser Val Phe Phe Met Cys Leu Pro
        355                 360                 365

Asp Arg Val Leu Val Tyr Gly Asp Cys Ala Val Asn Val Glu Pro Thr
    370                 375                 380

Ala Ala Glu Leu Ala Gln Ile Ala Thr Thr Ser Ala Asp Thr Ala Ala
385                 390                 395                 400

Ala Phe Gly Val Glu Pro Arg Val Ala Met Leu Ser Tyr Ser Thr Leu
                405                 410                 415

Gly Ser Gly Ala Gly Pro Gln Val Asp Leu Val Thr Glu Ala Thr Ala
            420                 425                 430

Leu Ala Arg Ala Ala Arg Pro Asp Leu Ala Ile Glu Gly Pro Ile Gln
        435                 440                 445

Tyr Asp Ala Ala Val Asp Pro Gly Val Ala Ala Thr Lys Val Lys Gly
    450                 455                 460

Arg Ser Glu Val Ala Gly Arg Ala Thr Val Cys Val Phe Pro Asp Leu
465                 470                 475                 480

Asn Thr Gly Asn Asn Thr Tyr Lys Ala Val Gln Gln Ser Thr Gly Ala
                485                 490                 495

Ile Ala Ile Gly Pro Leu Met Gln Gly Leu Ala Arg Pro Val Asn Asp
            500                 505                 510

Leu Ser Arg Gly Cys Thr Val Ala Asp Ile Val Asn Thr Val Ala Cys
        515                 520                 525

Thr Ala Val Gln Ala Ala Gly Leu Lys Ala Ala Ala Gln Gln Ala Thr
    530                 535                 540

Ser Ala Ala Ala Ala Ala
545                 550
```

<210> SEQ ID NO 38
<211> LENGTH: 1653
<212> TYPE: DNA
<213> ORGANISM: Auxenochlorella protothecoides

<400> SEQUENCE: 38

```
atggacttga acagagataa tccaggtact gcttctgaaa ttgcttctag agctttgaga      60
cacagaagag aattgcaagc tgatagagct tctgttttgg gtttgttgtt gaacaaagtt     120
ccattggctg ctcatgctga tatagtttct ggtgttgctg ctgaattggc tgattctggt     180
ttgacttttg ctggtggtat tccatacgat agaattattg gtactgccag agttaacgaa     240
tttgctaatg ctttgggtgc caaacaaatc tatggtagac cagaattgat tgactctggt     300
gtttggggtg gtagagaaga taatagattt ggtggtagat ccgttcatgg tttcttggat     360
aagttggaag ctattagagc acaaagagaa gctgaaggtc aaactttttt cagaccattg     420
gttttgacca ccaaggatag acaagatttg gttttaggtt tggctgctgc ttctttgtct     480
ggtgcttgtc caccattggg tggtttggtt ttgtgtgatg gtggtgcatg tgctattact     540
ccaccagttc atgctattat ggctagattg ggtccagata ctttgccagt tttggaagtt     600
ccacatggtg cttttgaaac tgctagaaga atggctagag ttaacccagg tattttgcca     660
acttctgtta gaaaggttag agaagctaga gccttgtttg gtagacatgt tgatgttgat     720
gctgttgctt ctggtatggc tgttcataga gaacctagat tgactccaaa aagattccca     780
ggtgaagttg ctgcagctgc tgctagattc aatgttgacg tttctagatg cgaagtcgaa     840
gatcatagat cctctactag attggatgct tacgctgatt ttttggttga agccagaaaa     900
aagaaggctt tgacaaaagc tgctgccttg gatcaattga ccgatattaa catgttcggt     960
actatcatgg ttgctatggg tgatgctgat ggtatggttt caggtgctac ttgtactact    1020
gctaacacta ttagaccagc cttgcaagtt ttgaaaaccc cagatagaag attgatctcc    1080
tccgtttttt tcatgtgctt gccagataga gttttggttt atggtgattg cgctgttaac    1140
gttgaaccta ctgctgcaga attagctcaa attgctacta cttctgctga tactgctgct    1200
gcatttggtg tcgaacctag agttgctatg ttgtcttatt ctactttggg ttctggtgca    1260
ggtccacaag ttgatttggt tactgaagct actgctttgg ctagagctgc tagacctgat    1320
ttggctattg aaggtccaat tcaatatgat gctgctgttg atccaggtgt tgcagctaca    1380
aaagttaagg gtagatctga agttgcaggt agagctacag tttgtgtttt tccagatttg    1440
aacactggta acaacaccta caaagccgtt caacaatcta ctggtgctat tgctattggt    1500
ccattgatgc aaggtttagc tagaccagtt aatgacttgt ctagaggttg tactgttgcc    1560
gatatcgtta atactgttgc ttgtactgct gttcaagctg ctggtttgaa agctgccgct    1620
caacaagcta catctgctgc cgctgcagct taa                                 1653
```

<210> SEQ ID NO 39
<211> LENGTH: 708
<212> TYPE: PRT
<213> ORGANISM: Beauveria bassiana

<400> SEQUENCE: 39

```
Met Leu Ile Pro Thr Gly Thr Ser Val Gly Leu Thr Ser Val Ser Leu
1               5                   10                  15

Gly Val Ile Arg Ala Met Glu Gln Lys Gly Val Arg Leu Ser Val Phe
            20                  25                  30

Lys Pro Ile Ala Gln Pro Arg Thr Gly Gly Asp Ser Pro Asp Gln Thr
        35                  40                  45
```

```
Thr Ser Ile Ile Arg Ala Asn Ser Thr Ile Pro Ala Ala Glu Pro Leu
    50                  55                  60

Asn Met Gly His Val Glu Ser Leu Leu Ser Ser Asn Gln Gln Asp Val
65                  70                  75                  80

Leu Met Glu Glu Ile Ile Ala Asn Tyr His Ala Thr Ser Lys Asp Ala
                85                  90                  95

Glu Val Val Leu Val Glu Gly Leu Val Pro Thr Arg Lys His Gln Phe
            100                 105                 110

Ala Gln Ala Leu Asn Tyr Glu Ile Ala Lys Thr Leu Asn Ala Glu Ile
        115                 120                 125

Val Phe Val Met Ser Leu Gly Asn Asp Ser Pro Glu Gln Leu Lys Glu
    130                 135                 140

Arg Ile Glu Leu Thr Arg Ser Ser Phe Gly Gly Ser Lys Asn Thr Asn
145                 150                 155                 160

Ile Thr Gly Val Ile Ile Asn Lys Leu Asn Ala Pro Val Asp Glu Gln
                165                 170                 175

Gly Arg Thr Arg Pro Asp Leu Ser Glu Ile Phe Asp Asp Ser Ser Lys
            180                 185                 190

Ala Ser Ile Ala Asn Ile Asp Pro Lys Gln Leu Phe Ala Asp Ser Pro
        195                 200                 205

Leu Pro Val Leu Gly Cys Val Pro Trp Ser Phe Glu Leu Ile Ala Thr
    210                 215                 220

Arg Ala Ile Asp Met Ala Arg His Leu Asn Ala Thr Ile Val Asn Glu
225                 230                 235                 240

Gly Asp Ile Asn Thr Arg Arg Val Lys Ser Val Thr Phe Cys Ala Arg
                245                 250                 255

Ser Ile Pro His Met Leu Glu His Phe Arg Pro Gly Ser Leu Leu Val
            260                 265                 270

Thr Ser Ala Asp Arg Pro Asp Val Leu Val Ala Ala Cys Leu Ala Ala
        275                 280                 285

Met Asn Gly Val Glu Ile Gly Ala Ile Leu Leu Thr Gly Gly Tyr Glu
    290                 295                 300

Met Asp Pro Arg Ile Ser Lys Leu Cys Glu Arg Ala Phe Ala Thr Gly
305                 310                 315                 320

Leu Pro Leu Phe Met Val Glu Thr Asn Thr Trp Gln Thr Ser Leu Ser
                325                 330                 335

Leu Gln Ser Phe Asn Leu Glu Val Pro Thr Asp Asp His Gln Arg Ile
            340                 345                 350

Glu Lys Val Gln Glu Tyr Val Ala Ser His Ile Asp Ala Asn Trp Ile
        355                 360                 365

Glu Ser Leu Thr Ala Thr Ser Glu Arg Ser Arg Arg Leu Ser Pro Pro
    370                 375                 380

Ala Phe Arg Tyr Gln Leu Thr Glu Leu Ala Arg Lys Ala Gly Lys Arg
385                 390                 395                 400

Val Val Leu Pro Glu Gly Asp Glu Pro Arg Thr Val Lys Ala Ala Ala
                405                 410                 415

Ile Cys Ala Glu Arg Gly Ile Ala Thr Cys Val Leu Leu Gly Asn Pro
            420                 425                 430

Asp Glu Ile Thr Arg Val Ala Ala Ala Gln Gly Val Glu Leu Gly Ala
        435                 440                 445

Gly Ile Glu Ile Val Asp Pro Glu Val Val Arg Glu Ser Tyr Val Ala
    450                 455                 460
```

```
Arg Leu Val Glu Leu Arg Lys Ser Lys Gly Met Thr Glu Ala Val Ala
465                 470                 475                 480

Arg Glu Gln Leu Glu Asp Asn Val Val Leu Gly Thr Leu Met Leu Glu
                485                 490                 495

Gln Asp Glu Val Asp Gly Leu Val Ser Gly Ala Val His Thr Thr Ala
            500                 505                 510

Asn Thr Ile Arg Pro Pro Leu Gln Leu Ile Lys Thr Ala Pro Gly Ser
        515                 520                 525

Ser Leu Val Ser Ser Val Phe Phe Met Leu Leu Pro Glu Gln Val Tyr
    530                 535                 540

Val Tyr Gly Asp Cys Ala Ile Asn Pro Asp Pro Thr Ala Glu Gln Leu
545                 550                 555                 560

Ala Glu Ile Ala Ile Gln Ser Ala Asp Ser Ala Ala Ala Phe Gly Ile
                565                 570                 575

Asp Pro Arg Val Ala Met Leu Ser Tyr Ser Thr Gly Asn Ser Gly Ala
            580                 585                 590

Gly Ser Asp Val Glu Lys Val Arg Glu Ala Thr Arg Ile Ala Gln Glu
        595                 600                 605

Lys Arg Pro Asp Leu Val Ile Asp Gly Pro Leu Gln Tyr Asp Ala Ala
    610                 615                 620

Val Met Ala Asp Val Ala Lys Ser Lys Ala Pro Asn Ser Pro Val Ala
625                 630                 635                 640

Gly Arg Ala Thr Val Phe Ile Phe Pro Asp Leu Asn Thr Gly Asn Thr
                645                 650                 655

Thr Tyr Lys Ala Val Gln Arg Ser Ala Asp Leu Ile Ser Ile Gly Pro
            660                 665                 670

Met Leu Gln Gly Met Arg Lys Pro Val Asn Asp Leu Ser Arg Gly Ala
        675                 680                 685

Leu Val Asp Asp Ile Val Tyr Thr Ile Ala Leu Thr Ala Ile Gln Ser
    690                 695                 700

Ala Gln Gln Ala
705
```

<210> SEQ ID NO 40
<211> LENGTH: 2127
<212> TYPE: DNA
<213> ORGANISM: Beauveria bassiana

<400> SEQUENCE: 40

```
atgttgattc caaccggtac ttctgttggt ttgacttctg tttctttggg tgttattaga      60
gccatggaac aaaagggtgt tagattgtct gttttcaagc caattgctca acctagaact     120
ggtggtgatt ctccagatca aactacctct attatcagag ccaactctac tattccagct     180
gctgaaccat tgaatatggg tcatgttgaa tccttgttgt cctccaatca acaagatgtc     240
ttgatggaag aaattatcgc taactaccat gccacttcta aggatgctga agttgttttg     300
gttgaaggtt tggttccaac tagaaagcac caatttgctc aagccttgaa ttacgaaatt     360
gccaagactt tgaacgccga aatcgttttc gttatgtctt tgggtaatga ctccccagaa     420
caattgaaag aaagaatcga attgaccaga tcctctttcg gtggttctaa aaacactaac     480
attaccggtg tcatcatcaa caagttgaat gctccagttg atgaacaagg tagaactaga     540
ccagatttgt ccgaaatctt cgatgattct tccaaggctt ccattgctaa cattgaccca     600
aagcaattat ttgccgattc tccattgcca gttttgggtt gtgttccttg gtcttttgaa     660
ttgattgcta ccagagctat tgatatggcc agacatttga atgctaccat tgtcaatgaa     720
```

```
ggtgacatca acactagaag agttaagtct gttaccttct gcgctagatc tattcctcat    780

atgttggaac atttcagacc aggttctttg ttggttactt ctgctgatag accagacgtt    840

ttagttgctg cttgtttggc tgctatgaac ggtgttgaaa taggtgctat tttgttgact    900

ggtggttacg aaatggatcc aagaatttct aagttgtgcg aaagagcttt tgctactggt    960

ttgcctttgt tcatggttga aactaatact tggcaaacct ccttgtcctt gcaatctttt   1020

aacttggaag ttccaaccga tgaccaccaa agaattgaaa aggttcaaga atacgttgcc   1080

tcccatattg atgctaactg gattgaatct ttgaccgcta cttctgaaag atccagaaga   1140

ttgtctccac cagcttttag ataccaattg actgaattgg ctagaaaggc tggtaaaaga   1200

gttgttttac ctgaaggtga tgaacctaga acagtaaaag ctgctgctat ttgcgctgaa   1260

agaggtattg caacttgcgt tttgttgggt aatccagacg aaattactag agttgctgca   1320

gctcaaggtg ttgaattggg tgcaggtatt gaaatagttg acccagaagt tgtcagagaa   1380

tcttacgttg ctagattggt cgaattgaga aagtctaagg gtatgactga agctgttgcc   1440

agagaacaat tagaagataa tgttgtcttg ggtactttga tgttagaaca agatgaagtc   1500

gacggtttgg tttctggtgc tgttcataca acagctaaca ctattagacc accattgcaa   1560

ttgattaaga ctgctcctgg ttcttcctta gtctcttctg ttttttttcat gttgttgcct   1620

gaacaagtct acgtttatgg tgattgtgct attaacccag atccaacagc tgaacaattg   1680

gccgaaattg ctattcaatc tgctgattct gcagctgctt ttggtattga tccaagagtt   1740

gctatgttga gttactctac tggtaattca ggtgctggtt ctgatgttga aaaagttaga   1800

gaagctacca gaatcgccca agaaaaaaga cctgatttgg ttattgatgg tccattacaa   1860

tacgatgctg ctgttatggc agatgttgct aaatctaaag ctccaaattc tccagttgct   1920

ggtagagcta ctgttttcat tttccagat ttgaacactg gtaacaccac ctacaaagct    1980

gttcaaagaa gtgccgattt gatttccatt ggtccaatgt tgcaaggtat gagaaagcca   2040

gttaacgatt tgtctagagg tgctttggtt gatgatatcg tttacactat tgccttgacc   2100

gcaattcaat cagctcaaca agcttga                                       2127
```

<210> SEQ ID NO 41
<211> LENGTH: 769
<212> TYPE: PRT
<213> ORGANISM: Chlamydomonas reinhardtii

<400> SEQUENCE: 41

```
Met Ala Phe Ala Ser Ser Ser Met Ala Ala Leu Ser Arg Pro Leu Ala
1               5                   10                  15

Ala Val Ser Ser Gly Leu Gly Ser Ala Leu Ser Arg Ala Ser Gln Leu
            20                  25                  30

Leu Thr Ser Gly Ser Leu Ser Ser Ser Pro Thr Ala Ser His Ser Ser
        35                  40                  45

Thr Arg Arg Phe Ile Ser Asp Gly Thr Val Gly Ser Lys Gly Arg Pro
    50                  55                  60

Asp Ser Leu Phe Leu Ser Asp Ile Ser Gly Arg Pro Asn Ala Thr Ala
65                  70                  75                  80

Asn Asp Tyr Tyr Asn Lys Ala Met Val Lys Arg Gln Val Phe Ala Asp
                85                  90                  95

His Lys Val Asp Val Leu Gly Val Val Ile Asn Gly Leu Pro Arg Glu
            100                 105                 110

His His Ala Ile Leu Ser Ser Gln Leu Arg Asp Lys Leu Glu Arg Ala
```

-continued

```
        115                 120                 125

Gly Leu Pro Phe Ala Gly Ala Leu Pro Glu Asp Pro Val Leu Ser Ser
    130                 135                 140

Val Arg Pro Pro Pro Pro Ala Leu Asp Lys Pro Ser Pro Gly Leu Thr
145                 150                 155                 160

Cys Val Ser Ser Cys Ala Pro Ser His Arg Tyr Pro Pro Thr Leu Pro
                165                 170                 175

Pro Leu Gly Leu Gly Leu Leu Leu Cys Pro Cys Pro Val Pro Ala Arg
            180                 185                 190

Leu Gln Leu Ile Ala Ser Gly Lys Gln Ser Glu Val Leu Asp Arg Ile
        195                 200                 205

Tyr Ala Ala Tyr Met Ala Tyr Lys Ala Gly Gly Glu Leu Asp Leu Cys
    210                 215                 220

Leu Val Glu Gly Pro Gly Pro Leu Met Gly Gly Thr Glu Leu Asp Ala
225                 230                 235                 240

Gln Val Val Val Gly Ser Gln Arg Leu Glu Glu Leu Leu Glu Thr Leu
                245                 250                 255

Val Glu Arg Pro Met Gly Arg Pro Leu Val Val Thr Ser Ala Asp Arg
            260                 265                 270

Leu Asp Ile Val Leu Gly Leu Leu Ala Ala Gln Leu Ser Val Arg Gly
        275                 280                 285

Pro Ser Val Ala Gly Val Leu Leu Thr Gln Ala Gly Ala Ser Arg Ile
    290                 295                 300

Thr Arg Ser Tyr Ala Lys Ser Ala Val Asp Asn Ile Phe Ala Gly Leu
305                 310                 315                 320

Ser Asn Asn Thr Gly Ala Ser Gly Gly Gly Pro Asp Gly Ala Ala Ala
                325                 330                 335

Ala Asn Gly Ser Ala Gln Gly Ser Leu Tyr Arg Gly Ala Leu Leu Pro
            340                 345                 350

Val Leu Ser Thr Asp Lys His Leu Ala Glu Ala Leu Ala Val Ile Gly
        355                 360                 365

Arg Met Asp Ala Ser Ile Leu Pro Thr Ser Ile Arg Lys Val Thr Gln
    370                 375                 380

Cys Lys Val Ala Gly Ala Ala Val Met Leu Phe Asp Lys Tyr Ile Asp
385                 390                 395                 400

Ala Asn Ala Val Val Thr Gly Leu Gln Lys Ser Arg Pro Thr Arg Val
                405                 410                 415

Thr Pro Lys Met Phe Gln His Thr Met Lys Ala Met Cys Arg Ala Ser
            420                 425                 430

Pro Gln His Ile Val Leu Pro Glu Ser Val Asp Lys Arg Val Leu Ala
        435                 440                 445

Ala Ala Ala Asp Val Thr Ala Arg Gly Leu Ala Arg Val Thr Leu Leu
    450                 455                 460

Gly Asp Pro Thr Thr Val Gln Gln Glu Pro Pro Pro Ser Pro Ser Thr
465                 470                 475                 480

Pro Ala Ala Met Ala Ala Pro Ala Ser Ala Ser Ser Asp Arg Phe Asp
                485                 490                 495

Lys Tyr Val Asp Met Leu Val Glu Ala Arg Lys Lys Lys Gly Met Thr
            500                 505                 510

Arg Glu Ala Ala Ala Asp Thr Leu His Gly Asp Ile Asn Phe Phe Gly
        515                 520                 525

Thr Met Met Val Ala Ala Gly Asp Ala Asp Gly Met Val Ser Gly Ala
    530                 535                 540
```

```
Ile His Thr Thr Ala Ser Thr Ile Arg Pro Ala Leu Gln Met Leu Lys
545                 550                 555                 560

Asn Pro Ala Ser Ser Leu Val Ser Ser Ile Phe Phe Met Cys Leu Pro
                565                 570                 575

Asp Arg Val Leu Val Tyr Gly Asp Cys Ala Val Asn Val Ser Pro Ser
            580                 585                 590

Ala Ala Asp Leu Ala Ala Ile Ala Thr Thr Ser Ala Asp Thr Ala Ala
        595                 600                 605

Ala Phe Gly Ile Glu Pro Arg Val Ala Met Leu Ser Tyr Ser Thr Leu
    610                 615                 620

Gly Ser Gly Ala Gly Pro Asp Val Gln Lys Val Thr Glu Ala Val Ala
625                 630                 635                 640

Leu Val Lys Gln Gln Arg Gln Asp Ile Lys Val Glu Gly Pro Ile Gln
                645                 650                 655

Tyr Asp Ala Ala Ile Asp Pro Ala Val Ala Ala Val Lys Val Lys Gly
            660                 665                 670

Gly Ser Glu Val Ala Gly Arg Ala Thr Val Phe Val Phe Pro Asp Leu
        675                 680                 685

Asn Thr Gly Asn Asn Thr Tyr Lys Ala Val Gln Gln Ser Thr Gly Ala
    690                 695                 700

Ile Ala Met Gly Pro Val Met Gln Val Cys Val Arg Val Ser Ala Gly
705                 710                 715                 720

Val Gly Gly Leu Leu Lys Pro Val Asn Asp Leu Ser Arg Gly Cys Thr
                725                 730                 735

Val Pro Asp Ile Val Asn Thr Ile Cys Val Thr Ser Ile Gln Ala Met
            740                 745                 750

Gln Phe Lys Gln Arg Thr Gln Ala Ala Val Ala Ala Ala Ala Ala Pro
        755                 760                 765

Lys
```

<210> SEQ ID NO 42
<211> LENGTH: 2310
<212> TYPE: DNA
<213> ORGANISM: Chlamydomonas reinhardtii

<400> SEQUENCE: 42

```
atggctttcg cttcttcttc tatggctgct ttgtctagac ctttggctgc tgtttcttct      60

ggtttgggtt ctgctttatc aagagcctct caattattga cctctggttc tttatcttct     120

tctccaactg cttctcattc ctccactaga agattcattt ctgatggtac tgttggttct     180

aagggtagac cagattcttt gttcttgtcc gatatttctg gtagaccaaa tgctactgct     240

aacgactatt acaacaaggc catggttaag agacaagttt tcgctgatca taaggttgat     300

gttttgggtg ttgttatcaa cggtttgcca agagaacatc atgccatttt gtcatcacaa     360

ttgagagata agttggaaag agctggtttg ccatttgctg gtgctttgcc agaagatcca     420

gttttatctt cagttagacc accacctcca gctttggata agccatctcc aggtttgact     480

tgtgtttctt catgtgctcc atctcataga tatccaccaa ctttgccacc attgggttta     540

ggtttgttgt tgtgtccatg tccagttcca gctagattgc aattgattgc ttctggtaag     600

caatccgaag ttttggatag aatctatgct gcttacatgg cttataaggc tggtggtgaa     660

ttggatttgt gtttggttga aggtccaggt ccattgatgg gtggtactga attagatgct     720

caagttgttg ttggttccca aagattggaa gaattattgg aaaccttggt tgaaagacca     780
```

-continued

```
atgggtagac ctttagttgt tacttctgct gatagattgg atatcgtctt gggtttgttg    840

gctgctcaat tgtctgttag aggtccatct gttgctggtg ttttattgac tcaagctggt    900

gcatctagaa tcactagatc ttatgctaag tccgccgttg acaatatttt cgctggtttg    960

tctaacaata ctggtgctag tggtggtggt ccagatggtg ctgctgctgc aaatggttct   1020

gctcaaggtt cattatacag aggtgctttg ttgccagttt tgtctactga caaacatttg   1080

gctgaagctt tggctgttat tggtagaatg gatgcttcta ttttgccaac ctccattaga   1140

aaggttaccc aatgtaaagt tgccggtgct gcagttatgt tgttcgataa gtatattgat   1200

gccaacgctg ttgtcaccgg tttacaaaaa tctagaccaa ctagagttac cccaaagatg   1260

tttcaacata ccatgaaggc tatgtgtaga gcttctccac aacatatcgt tttgcctgaa   1320

tctgttgata agagagtttt ggctgcagct gctgatgtta ctgctagagg tttggcaaga   1380

gttactttgt tgggtgatcc aactactgtt caacaagaac ctccaccatc tccatctact   1440

ccagctgcta tggcagctcc agcttctgct tcttcagata gatttgataa gtacgtcgac   1500

atgttggtcg aagccagaaa aaagaaaggt atgactagag aagctgctgc agatacttta   1560

catggtgaca ttaacttttt cggtactatg atggttgctg ccggtgatgc tgatggtatg   1620

gtttctggtg ctattcatac aaccgcttct actattagac cagccttgca aatgttgaaa   1680

aacccagctt cttcattggt ttcttccatt tttttcatgt gtttgccaga cagagtcttg   1740

gtttatggtg attgtgctgt taacgtttct ccatctgcag ctgatttggc agctattgct   1800

actacttcag cagatacagc tgctgctttt ggtattgaac ctagagttgc tatgttgtcc   1860

tattctactt tgggttcagg tgctggtcct gatgttcaaa aagttactga agctgttgcc   1920

ttggtcaagc aacaaagaca agatatcaaa gtcgaaggtc caattcaata cgatgctgct   1980

attgatccag ctgttgcagc tgttaaggtt aagggtggtt ctgaagttgc tggtagagct   2040

actgtttttg ttttcccaga tttgaacacc ggtaacaaca cttacaaagc cgttcaacaa   2100

tctacaggtg ctattgcaat gggtccagtt atgcaagttt gtgttagagt ttcagctggt   2160

gttggtggtt tgttgaagcc agttaatgat ttgtcaagag gttgtaccgt tccagatatc   2220

gttaacacta tttgcgttac ctccattcaa gccatgcaat tcaaacaaag aacacaagct   2280

gctgttgctg ctgccgctgc tccaaagtaa                                    2310
```

<210> SEQ ID NO 43
<211> LENGTH: 801
<212> TYPE: PRT
<213> ORGANISM: Coccomyxa subellipsoidea

<400> SEQUENCE: 43

```
Met Leu Pro Arg Ala Leu Arg Ser Ala Lys Ser Ile Phe Ser Ala Val
1               5                   10                  15

Arg Pro Pro Ala Gly Val His Asp Val Leu Ser Leu Pro Gly Ile Gln
            20                  25                  30

His Val Pro Met Glu Ala Val Gln Arg Gln Ala Leu Pro Cys Leu Leu
        35                  40                  45

Pro Arg Met Met Ser Thr Ser Ile Ser Asp Glu His Gln Pro Ser Lys
    50                  55                  60

Lys Ser Leu Tyr Val Leu Asn Val Glu Gly Lys Arg Thr Leu Gly Pro
65                  70                  75                  80

Leu Leu Ile Gly Leu Met Asp Tyr Phe Glu Arg Trp Leu Pro Asn Val
                85                  90                  95

Gly Phe Phe Gln Pro Ile Gly Gly Glu Pro Phe Pro Asp Ser Asp Ser
```

-continued

```
            100                 105                 110

Asp Glu Pro Arg His Val Glu Leu Ile Arg Lys Ala Phe Asp Leu Lys
        115                 120                 125

Asp Asp Pro Arg Ser Met Tyr Ala Val His Arg Arg Glu Ala Ile Ser
    130                 135                 140

Leu Leu Ala His Asp Lys Ala Asp Glu Leu Leu Asp Lys Ile Tyr Ser
145                 150                 155                 160

Ser Phe Glu Glu Tyr Gln Ser Arg His Asp Leu Val Val Ile Glu Gly
                165                 170                 175

Thr His Glu Asp Gly Arg Leu Asn Val Pro Gly Asn Arg Leu Glu Leu
            180                 185                 190

Asn Gly Arg Ile Ala Ala Thr Leu Ala Ala Pro Val Leu Met Val Leu
        195                 200                 205

Asp Ala Gly Asp Asp Ile Ser Val Asp Asp Leu Ile Asp Lys Ala Leu
    210                 215                 220

Leu Ser Lys Asn Gly Leu Glu Glu Gln Arg Cys Glu Val Leu Gly Leu
225                 230                 235                 240

Ile Val Asn Lys Ala Pro Gln Lys Glu His Pro Ile Leu Lys Ala Gln
                245                 250                 255

Leu Ser Lys Lys Leu Ala Glu His Ser Leu Pro Leu Val Gly Val Val
            260                 265                 270

Pro His Asp Pro Leu Ile Ser Ser Val Arg Leu Asp Glu Ile Gln Ala
        275                 280                 285

Ala Leu Ser Ala Lys Val Ile Ala Gly Arg Lys Gly Pro His Asp Leu
    290                 295                 300

Thr Val Asp Lys Val Tyr Val Ala Thr Ala Asp Leu Asp Thr Thr Leu
305                 310                 315                 320

Arg Arg Leu Thr Asp His Thr Ser Ser Arg Pro Leu Ile Val Thr Asp
                325                 330                 335

Ile Gly Arg Ser Asp Leu Ile Leu Gly Leu Thr Ser Ala Asn Glu Ser
            340                 345                 350

Thr Ile Gly Pro His Val Thr Gly Ile Leu Cys Thr Asn Ser Glu Tyr
        355                 360                 365

Gly Arg Arg Asp Met Ser Pro His Val His Ala Ile Leu Gln Ala Lys
    370                 375                 380

His Ser Ala Leu Lys Asp Gln Glu Asp Ala Gly Leu Val Ala Phe Phe
385                 390                 395                 400

Pro Val Met Ser Ser Asp Cys Asn Thr Trp Asp Ala Val Thr Ala Val
                405                 410                 415

Ser Arg Ile Gln Pro Ser Ile Arg Pro Thr Ser Lys Ala Lys Ile Gln
            420                 425                 430

Glu Ala Lys Ala Leu Phe Gln Lys Tyr Val Glu Gly Asn Leu Leu Val
        435                 440                 445

Asp Ala Leu Glu Ala Glu Arg Glu Phe Val Met Thr Pro Lys Met Phe
    450                 455                 460

Met His Asn Ile Asn Arg Ile Cys Leu Ser Asn Arg Gln Arg Val Val
465                 470                 475                 480

Leu Pro Glu Ser Asp Asp Ser Arg Val Leu Ala Ala Ala Glu Glu Leu
                485                 490                 495

Thr His Arg Gly Leu Ala Asp Ile Ile Leu Leu Gly Glu Pro Asp Lys
            500                 505                 510

Val Thr Ala Gln Ala Arg Arg Leu Asp Ile Asp Ile Ser Gln Cys Glu
        515                 520                 525
```

```
Ile Ile Asp Pro Glu Lys Ser Gly Arg Leu Glu Ala Tyr Ile Glu Lys
    530                 535                 540

Leu Val Glu Val Arg Arg Lys Lys Asn Val Thr Pro Asp Met Ala Arg
545                 550                 555                 560

Asp Phe Leu His Asp Pro Asn Tyr Phe Gly Thr Met Met Thr Leu Cys
                565                 570                 575

Gly Asp Ala Asp Gly Met Val Ser Gly Ala Lys His Thr Thr Ala Ala
            580                 585                 590

Thr Ile Arg Pro Gly Leu Gln Val Leu Arg Thr Lys Asp Ser Pro Leu
        595                 600                 605

Val Ser Ser Val Phe Phe Met Cys Leu Pro Asp Lys Val Leu Ile Tyr
    610                 615                 620

Gly Asp Cys Ala Val Asn Val His Pro Ser Ser Asn Glu Leu Ala Gln
625                 630                 635                 640

Ile Ala Val Thr Ser Ala Asp Thr Ala Ala Ala Phe Gly Val Glu Pro
                645                 650                 655

Arg Val Ala Leu Leu Ser Tyr Ser Thr Phe Gly Ser Gly Ser Gly Pro
            660                 665                 670

Glu Val Asp Arg Val Ala Glu Ala Val Arg Ile Ala Lys Glu Met Arg
        675                 680                 685

Pro Asp Leu Lys Leu Glu Gly Pro Ile Gln Tyr Asp Ala Ala Val Asp
    690                 695                 700

Pro Ala Val Ala Arg Gln Lys Val Lys Gly His Ser Glu Val Ala Gly
705                 710                 715                 720

Lys Ala Thr Val Leu Ile Phe Pro Ser Leu Glu Ala Gly Asn Asn Thr
                725                 730                 735

Tyr Lys Ala Val Gln Gln Ser Thr Gly Ala Ile Ala Ile Gly Pro Ile
            740                 745                 750

Leu Gln Gly Leu Ser Arg Pro Val Asn Asp Leu Ser Arg Gly Cys Thr
        755                 760                 765

Val Val Asp Ile Ile Asn Thr Val Thr Cys Thr Cys Val Gln Ala Val
    770                 775                 780

Ala Ile Lys Asp Arg Glu Lys Ser Pro Ala Pro Glu Ala Ala Pro Ala
785                 790                 795                 800

Ala
```

<210> SEQ ID NO 44
<211> LENGTH: 2406
<212> TYPE: DNA
<213> ORGANISM: Coccomyxa subellipsoidea

<400> SEQUENCE: 44

```
atgttgccaa gagctttgag atccgctaag tctatttttt ctgctgttag acctccagct     60

ggtgttcatg atgttttgtc tttgccaggt attcaacacg ttccaatgga agctgttcaa    120

agacaagctt tgccatgttt gttaccaaga atgatgtcca cctccatctc tgatgaacat    180

caaccatcca agaagtcctt gtacgttttg aatgttgaag gtaagagaac cttgggtcct    240

ttgttgattg gtttgatgga ttacttcgaa agatggttgc caaacgttgg tttctttcaa    300

cctattggtg gtgaaccatt tccagattct gattcagatg aacctagaca cgttgaattg    360

attagaaagg ccttcgattt gaaggatgac ccaagatcta tgtacgctgt tcatagaaga    420

gaagccattt ctttgttggc tcatgataag gccgatgaat tattggacaa gatctactcc    480

tcattcgaag aataccaatc cagacacgat ttggttgtta tcgaaggtac tcatgaagat    540
```

```
ggtagattga atgttccagg taacagattg gaattgaacg gtagaattgc tgctactttg    600
gctgctccag ttttgatggt tttggatgct ggtgatgata tctccgttga tgatttgatt    660
gacaaggctt tgttgtccaa gaacggtttg gaagaacaaa gatgtgaagt cttgggtttg    720
atcgttaaca aggctccaca aaaagaacac ccaattttga aggctcaatt gtctaagaag    780
ttggccgaac attctttgcc attggttggt gttgttccac atgatccatt gatctcttca    840
gttagattgg acgaaattca agctgctttg tccgctaaag ttattgctgg tagaaaaggt    900
cctcatgatt tgaccgttga taaggtttat gttgctactg ctgatttgga taccaccttg    960
agaagattga ctgatcatac ttcttccaga ccattgattg tcaccgatat tggtagatcc   1020
gatttgattt tgggtttaac ctctgctaac gaatccacta ttggtccaca tgttactggt   1080
attttgtgca ccaattctga atacggtaga agagatatgt ccccacatgt tcatgctatc   1140
ttgcaagcta aacattctgc cttgaaggat caagaagatg ctggtttggt tgcttttttc   1200
cctgttatgt catctgattg caatacctgg gatgctgtta ctgctgtttc tagaattcaa   1260
ccatctatca gaccaacctc caaggctaaa attcaagaag ctaaagcttt gttccaaaag   1320
tatgtcgaag gtaacttgtt ggttgatgct ttggaagctg aaagagaatt cgttatgact   1380
ccaaagatgt ttatgcacaa catcaacaga atctgcttgt ccaacagaca aagagttgtt   1440
ttgccagaat ccgatgattc tagagtttta gctgctgctg aagaattgac tcatagaggt   1500
ttggctgata tcatcttgtt gggtgaacca gataaggtta ctgctcaagc tagaagattg   1560
gatatcgaca tttcccaatg cgaaatcatc gatccagaaa agtctggtag attagaagcc   1620
tacatcgaaa agttggtcga agttagaaga aagaagaacg ttactccaga tatggccaga   1680
gatttcttgc atgatccaaa ttacttcggt actatgatga ccttgtgtgg tgatgctgat   1740
ggtatggttt ctggtgctaa acatacaact gctgctacaa ttagaccagg tttacaagtc   1800
ttgagaacta aggattctcc attggtcagt tccgttttct ttatgtgttt gccagacaag   1860
gttttgatct acggtgattg tgctgttaac gttcacccat cttctaatga attggctcaa   1920
attgctgtta cctctgctga tactgcagct gcttttggtg tagaacctag agttgctttg   1980
ttatcctact ctacttttgg ttctggttca ggtccagaag ttgatagagt tgcagaagct   2040
gttagaatcg ctaaagaaat gagaccagac ttgaaattgg aaggtccaat tcaatatgat   2100
gctgctgttg atccagctgt tgctagacaa aaagttaagg gtcattctga agttgctggt   2160
aaggctactg ttttgatttt cccatcttta gaagctggta acaacaccta taaggccgtt   2220
caacaatcta ctggtgctat tgcaattggt ccaatattgc aaggtttgtc cagaccagtt   2280
aacgatttgt ctagaggttg taccgttgtt gacattatta acaccgttac ctgtacctgt   2340
gttcaagcag ttgctattaa ggacagagaa aaatctccag ctccagaagc tgctcctgct   2400
gcttaa                                                               2406
```

<210> SEQ ID NO 45
<211> LENGTH: 683
<212> TYPE: PRT
<213> ORGANISM: Guillardia theta

<400> SEQUENCE: 45

```
Met Thr Ala Val Glu Glu Val Gly Leu Leu Tyr Ala Val Leu Pro Arg
1               5                   10                  15

Ala Pro Arg Val Gly Tyr Phe Arg Pro Phe Ala Glu Gly Glu Asn Asp
            20                  25                  30
```

```
Arg Ser Ile Ser Leu Met Arg Ser Ile Phe Arg Leu Asp Asp Ser Pro
        35                  40                  45

Glu Val Met Gln Gly Ile Thr Val Ala Glu Ala Thr Lys Leu Leu Ser
    50                  55                  60

His Gly Gln Glu Lys Glu Leu Phe Asp Gln Ile Leu Ser Lys Tyr Val
65                  70                  75                  80

Glu Tyr Arg Lys Gly Lys Asp Phe Val Leu Val Ser Cys Gly Arg Leu
                85                  90                  95

Glu Asn Asp Ser His Phe Trp Ser Gln Lys Met Ala Ala Ala Leu Asn
            100                 105                 110

Leu Pro Val Leu Leu Ile Ser Asp Val Gly His Glu Ser Asp Leu Ala
        115                 120                 125

Ile Ile Lys Gly Gly Leu Glu Ser Ser Asn Val Lys Ile Ala Gly Val
    130                 135                 140

Leu Met Ser Gly Leu Pro Pro Gly Asn Glu Tyr Ala Glu Thr Ala Asn
145                 150                 155                 160

Glu Cys Lys Glu Ala Ile Glu Gln Leu Gly Leu Arg Ser Val Gly Met
                165                 170                 175

Leu Pro Lys Ser Ala Ile Ile His Gln Val Thr Met Ala Glu Val Val
            180                 185                 190

Asp Ala Leu Gly Ala Lys Val Phe Phe Gly Glu Glu Ser Leu Asp Arg
        195                 200                 205

Ser Ile Val Lys Asp Ile Thr Val Ala Thr Leu Asp Met Asn Arg Met
    210                 215                 220

Leu His Arg Leu Arg Val His Pro Gly Thr Leu Val Ile Val His Ser
225                 230                 235                 240

Gly Arg Ala Asp Val Leu Leu Ser Leu Val Leu Ala Ala Arg Ser Ser
                245                 250                 255

Asn Tyr Pro Arg Pro Ala Gly Ile Leu Leu Thr Gly Ser Arg Asn Leu
            260                 265                 270

Asp Pro Asp Val Asp Asp Ile Leu Cys Gly Leu Asn Gly Ile Ala Met
        275                 280                 285

Pro Val Ile Gly Val Glu Glu Asp Thr Phe Ala Cys Thr Thr Thr Leu
    290                 295                 300

Leu Lys His Arg Pro Val Leu Leu Pro Ser Ser Thr Thr Lys Ile Glu
305                 310                 315                 320

Ala Ala Gln Val Leu Phe Gln Lys His Ile Asp Pro Lys Phe Leu Asn
                325                 330                 335

Gln Leu Val Ala Thr Asn Ala Asp Asp Tyr Val Val Thr Pro Lys Leu
            340                 345                 350

Phe Gln His Asn Ile Phe Ser Ala Ala Arg Thr Asp Lys Gln Arg Ile
        355                 360                 365

Val Leu Pro Glu Gly Asp Asp Pro Arg Val Leu Ala Ala Ala Gly Glu
    370                 375                 380

Leu Leu Ala Arg Asn Leu Cys Glu Val Thr Ile Leu Gly Lys Glu Asp
385                 390                 395                 400

Leu Ile Gln Asn Lys Ala Lys Arg Asn His Val Ser Leu Lys Gly Ala
                405                 410                 415

Lys Ile Val Asp Pro Glu Thr Glu Thr Thr Glu Glu Met Val Asp Ala
            420                 425                 430

Leu Tyr Asn Ala Arg Lys Ser Lys Gly Met Thr Lys Glu Leu Ala Arg
        435                 440                 445

Asp Met Leu Gln Gly Glu Pro Asn Trp Phe Gly Thr Met Met Met Tyr
```

```
    450                 455                 460

Leu Asp Gln Ala Asp Gly Met Val Ser Gly Ala Cys His Ser Thr Ala
465                 470                 475                 480

Ala Thr Met Arg Pro Ala Leu Gln Val Ile Lys Met Ala Pro Gly Phe
                485                 490                 495

Ser Leu Val Ser Ser Val Phe Phe Met Leu Leu Pro Gly Arg Val Leu
            500                 505                 510

Val Phe Gly Asp Cys Ala Ile Asn Val Asp Pro Thr Ala Asp Glu Leu
        515                 520                 525

Ala Glu Ile Ala Val Ala Ser Ala His Thr Ala Arg Ala Phe Gly Ile
    530                 535                 540

Leu Pro Arg Val Ala Met Leu Ser Tyr Ala Thr Gly Asp Ser Asn Gln
545                 550                 555                 560

Gly Pro Met Ile Asp Lys Val Arg Glu Ala Thr Lys Lys Ala Arg Leu
                565                 570                 575

Leu Ala Pro Asn Glu Leu Ile Glu Gly Pro Ile Gln Phe Asp Ala Ala
            580                 585                 590

Val Asp Pro Ala Val Ala Ala Val Lys Tyr Lys Gly Gln Asp Ser Pro
        595                 600                 605

Val Ala Gly Lys Ala Thr Val Leu Val Phe Pro Asp Leu Asn Ala Gly
    610                 615                 620

Asn Asn Ala Tyr Lys Ala Val Gln Gln Ala Ser Lys Ser Ile Ala Val
625                 630                 635                 640

Gly Pro Ile Met Gln Gly Leu Arg Lys Pro Val Asn Asp Leu Ser Arg
                645                 650                 655

Gly Cys Thr Ile Asp Asp Ile Val Asn Thr Val Val Val Thr Cys Leu
            660                 665                 670

Gln Ser Lys Ala Ser Lys Glu Leu Ala Lys Lys
        675                 680
```

<210> SEQ ID NO 46
<211> LENGTH: 2052
<212> TYPE: DNA
<213> ORGANISM: Guillardia theta

<400> SEQUENCE: 46

```
atgaccgctg ttgaagaagt tggtttgttg tacgctgttt tgccaagagc accaagagtt      60

ggttatttta gaccatttgc tgaaggtgaa aacgacagat ccatttcctt gatgagatcc     120

atcttcagat tggatgattc cccagaagtt atgcaaggta ttactgttgc tgaagctacc     180

aagttgttgt ctcatggtca agaaaaagaa ttattcgacc aaatcttgtc caagtacgtc     240

gaatacagaa agggtaagga tttcgttttg gtttcttgcg gtagattgga aaacgattct     300

catttctggt cccaaaaaat ggctgctgct ttgaatttgc cagtcttgtt gatttctgat     360

gtcggtcatg aatctgattt ggccattatt aagggtggtt tggaatcctc caatgttaag     420

attgctggtg ttttgatgtc tggtttgcca ccaggtaatg aatatgctga aactgctaac     480

gaatgcaaag aagccattga acaattgggt ttgagatccg ttggtatgtt gccaaagtct     540

gccattattc atcaagttac catggccgaa gttgttgatg ctttgggtgc taaagttttc     600

ttcggtgaag aatccttgga cagatctatc gttaaggata ttacagttgc caccttggac     660

atgaacagaa tgttgcatag attgagagtt cacccaggta ctttggttat agttcattct     720

ggtagagccg atgtcttgtt gtctttggtt ttggctgcta gatcttctaa ttatccaaga     780

ccagcaggta ttttgttgac cggttctaga aatttggatc cagatgttga tgatatcttg     840
```

```
tgcggtttga atggtattgc catgccagtt attggtgtcg aagaagatac tttcgcttgt    900
actactactt tgttgaagca cagaccagtt ttgttgccat cttctactac taagattgaa    960
gctgcccaag tcttgttcca aaaacatatt gatccaaagt tcttgaatca attggttgct   1020
accaacgccg atgattatgt tgttactcca aagttgttcc aacacaacat tttctctgct   1080
gctagaaccg ataagcaaag aatagttttg ccagaaggtg acgatccaag agttttagct   1140
gctgctggtg aattattggc tagaaacttg tgcgaagtta ctatcttggg taaagaagat   1200
ttgattcaaa acaaggccaa gagaaaccac gtttctttga aaggtgctaa gatcgttgat   1260
ccagaaactg aaactactga agaaatggtt gatgccttgt acaacgctag aaaatctaag   1320
ggtatgacca aagaattggc cagagatatg ttgcaaggtg aacctaattg gttcggtact   1380
atgatgatgt atttggacca agctgatggt atggtttctg gtgcttgtca ttctacagct   1440
gctactatga gaccagcttt acaagttatt aagatggctc caggtttctc cttagtctct   1500
tctgtttttt tcatgttgtt gccaggtaga gtcttggttt ttggtgattg tgctatcaat   1560
gttgatccaa ccgctgatga attggctgaa attgctgttg cttctgctca tactgctaga   1620
gcttttggta ttttgcctag agttgctatg ttgtcttatg ctaccggtga ttctaatcaa   1680
ggtccaatga ttgataaggt tagagaagct actaagaagg ccagattatt ggcaccaaac   1740
gaattgattg aaggtcctat tcaattcgat gctgctgttg atcctgctgt tgcagctgtt   1800
aagtacaaag gtcaagattc tccagttgct ggtaaagcta ctgttttagt tttcccagat   1860
ttgaacgctg gtaacaatgc ttacaaagct gttcaacaag cctccaagtc tattgcagtt   1920
ggtccaatca tgcaaggttt gagaaaacca gttaacgact tgtctagagg ttgcactata   1980
gatgatatcg ttaacaccgt tgttgttacc tgcttgcaat ctaaggcttc taaagaatta   2040
gccaagaagt aa                                                       2052
```

<210> SEQ ID NO 47
<211> LENGTH: 293
<212> TYPE: PRT
<213> ORGANISM: Helicosporidium sp.

<400> SEQUENCE: 47

```
Met Arg Gly Gln Ala Asp Gly Ala Asp Arg Leu Asn Ala Pro Leu Ser
1               5                   10                  15

Ser Ala Ser Pro Pro Ser Ser Ser Ala Pro Ser Leu His Ser Lys Tyr
            20                  25                  30

Thr Gln Leu Leu Leu Ser Arg Arg Ala His Lys Gly Leu Thr Leu Ala
        35                  40                  45

Ser Ala Leu Asp Gln Met Gln Asp Pro Asn Val Val Gly Thr Leu Met
    50                  55                  60

Val Ala Cys Gly Asp Ala Asp Gly Met Val Ser Gly Ala Thr Cys Thr
65                  70                  75                  80

Thr Ala Ala Thr Ile Arg Pro Ala Leu Gln Leu Leu Lys Ala Pro Gly
                85                  90                  95

Arg Leu Val Ser Ser Leu Phe Phe Met Cys Leu Pro Asp Arg Val Leu
            100                 105                 110

Ala Tyr Gly Asp Cys Ala Val Asn Pro Asp Pro Ser Ala Glu Gln Leu
        115                 120                 125

Ala Gln Ile Ala Glu Ser Ala Ala Glu Thr Thr Arg Ala Phe Gly Val
    130                 135                 140

Glu Pro Arg Val Ala Met Leu Ser Tyr Ser Thr Leu Gly Ser Gly Ser
```

-continued

```
145                 150                 155                 160

Gly Pro Ala Val Asp Lys Val Ala Ala Ala Val Glu Lys Leu Gln Ala
                165                 170                 175

Gln Arg Pro Asp Leu Met Val Glu Gly Pro Ile Gln Tyr Asp Ala Ala
            180                 185                 190

Val Asp Ser Thr Val Ala Ala Ala Lys Val Lys Lys Ala Ser Glu Val
        195                 200                 205

Ala Gly Arg Ala Thr Val Cys Val Phe Pro Asp Leu Asn Thr Gly Asn
    210                 215                 220

Asn Thr Tyr Lys Ala Val Gln Gln Ser Thr Gly Ala Leu Ala Val Gly
225                 230                 235                 240

Pro Leu Met Met Gly Leu Gln Arg Pro Val Asn Asp Leu Ser Arg Gly
                245                 250                 255

Cys Thr Val Ala Asp Ile Val Asn Thr Ile Ala Cys Thr Ala Val Gln
            260                 265                 270

Ala Ile Gly Leu Lys Asp Ala Asn Ala Ala Ala Glu Glu Lys Lys Ser
        275                 280                 285

Asp Val Tyr Glu Gly
    290
```

<210> SEQ ID NO 48
<211> LENGTH: 882
<212> TYPE: DNA
<213> ORGANISM: Helicosporidium sp.

<400> SEQUENCE: 48

```
atgagaggtc aagctgatgg tgctgataga ttgaatgctc cattgtcaag tgcttctcca     60

ccatcttcat ctgctccatc tttacattct aagtacaccc aattgttgtt gtctagaaga    120

gcacataagg gtttgacttt ggcttctgct ttggatcaaa tgcaagatcc aaatgttgtc    180

ggtactttga tggttgcttg tggtgatgct gatggtatgg tttctggtgc tacttgtact    240

actgctgcta ctattagacc agccttgcaa ttattgaaag ctccaggtag attggtttcc    300

tccttgtttt ttatgtgctt gccagataga gttttggctt atggtgattg tgctgttaat    360

ccagatccat ctgctgaaca attggctcaa attgctgaat ctgctgctga aactactaga    420

gcttttggtg ttgaacctag agttgctatg ttgtcttatt ctactttggg ttctggttct    480

ggtccagctg ttgataaggt tgctgctgct gttgaaaaat tgcaagctca aagaccagat    540

ttgatggtcg aaggtccaat tcaatatgat gctgcagttg attctactgt tgctgcagct    600

aaagttaaga aggcttctga agttgctggt agagctactg tttgtgtttt tccagacttg    660

aacactggta acaacactta caaagccgtt caacaatcta caggtgcttt ggctgttggt    720

ccattgatga tgggtttaca aagacctgtt aacgacttgt ctagaggttg tacagttgct    780

gatatcgtta acactattgc ttgtactgct gttcaagcca ttggtttgaa agatgctaat    840

gctgctgccg aagaaaaaaa gtctgatgtt tacgaaggtt aa                       882
```

<210> SEQ ID NO 49
<211> LENGTH: 353
<212> TYPE: PRT
<213> ORGANISM: Perkinsus marinus

<400> SEQUENCE: 49

```
Met Leu Ser Arg Ser Thr Ala Arg Cys Ala Pro Ala Ala Leu Ala Gly
1               5                   10                  15

Ile Arg Gln Arg Ala Met Gln Thr Gly Leu Glu Lys Phe Ile Ala Phe
```

```
            20                  25                  30

Pro Glu Val Thr Asp Glu Arg Val Ile Pro Ala Val Ala Lys Val Leu
        35                  40                  45

Lys Glu Lys Ile Ala Gln Pro Val Leu Val Gly Asp Arg Glu Ala Ala
    50                  55                  60

Tyr Lys Cys Ala Lys Ala Asn Asn Val Ser Leu Glu Gly Val Arg Ile
65                  70                  75                  80

Ile Asp Pro Ser Leu His Pro Glu Val Val Glu Gln Thr Ala Thr Val
                85                  90                  95

Leu Phe Gln Lys Arg Gln Lys Lys Gly Met Thr Leu Asp Ala Ala Leu
            100                 105                 110

Asp Thr Val Lys Asn Ser Pro Leu Met Met Ala Asp Leu Met Leu Thr
        115                 120                 125

Thr Gly His Val Gln Gly Cys Val Ala Gly Ala Ser His Thr Ser Ala
    130                 135                 140

Asp Val Ala Arg Ala Ala Leu Gln Thr Val Gly Val Lys Lys Gly Leu
145                 150                 155                 160

Lys Thr Ala Ser Ser Phe Phe Ile Ile Ala Lys Asp Asp Lys Thr Phe
                165                 170                 175

Leu Phe Ser Asp Cys Gly Phe Cys Ile Ala Pro Ser Ile Ser Gln Leu
            180                 185                 190

Ala Glu Ile Ala Ile Thr Thr Ala Gln Thr Cys Glu Asp Val Leu Ala
        195                 200                 205

Thr Thr Pro Arg Val Ala Met Leu Ser Phe Ser Thr Phe Gly Ser Ala
    210                 215                 220

Lys His Glu Tyr Val Thr Arg Val Glu Glu Ala Leu Ala Leu Ala Arg
225                 230                 235                 240

Lys Glu Lys Pro Asp Leu Ala Ile Asp Gly Glu Met Gln Val Asp Ala
                245                 250                 255

Ala Ile Val Pro Glu Val Ala Ala Lys Lys Ala Pro Gly Ser Lys Val
            260                 265                 270

Ala Gly His Ala Asn Val Leu Ile Phe Pro Asp Leu Asn Ala Gly Asn
        275                 280                 285

Ile Ala Tyr Lys Val Ala Glu Arg Phe Gly Gly Tyr Gln Ala Val Gly
    290                 295                 300

Pro Ile Phe Gln Gly Leu Ala Tyr Pro Thr Asn Asp Leu Ser Arg Gly
305                 310                 315                 320

Cys His Ala Glu Asp Val Val Asp Ala Ala Ala Val Thr Val Leu Gln
                325                 330                 335

Gly Ser Ser Ile Pro Ile Pro Thr Gly Pro Ala Pro Gly Asp Ile Leu
            340                 345                 350

Asn

<210> SEQ ID NO 50
<211> LENGTH: 1062
<212> TYPE: DNA
<213> ORGANISM: Perkinsus marinus

<400> SEQUENCE: 50

atgttgtcta gatctactgc tagatgtgct ccagctgctt tggctggtat tagacaaaga      60

gctatgcaaa ctggtttgga aaagttcatt gctttcccag aagttaccga cgaaagagtt     120

attccagctg ttgctaaggt cttgaaagaa aagattgctc aaccagtttt ggtcggtgat     180

agagaagctg cttacaaatg tgctaaggct aacaacgttt ctttggaagg tgttagaatc     240
```

```
atcgatccat cattgcatcc agaagttgtt gaacaaactg ctaccgtttt gttccaaaaa    300

agacaaaaaa agggtatgac cttggatgct gctttagata ctgttaagaa ctccccattg    360

atgatggctg atttgatgtt gactactggt catgttcaag gttgtgttgc tggtgcttct    420

catacttctg ctgatgttgc tagagctgca ttgcaaactg ttggtgttaa gaagggtttg    480

aaaactgcct cctccttctt cattattgcc aaagatgata agaccttctt gttctctgat    540

tgcggtttct gtattgcccc atctatttct caattggccg aaattgctat tactaccgct    600

caaacttgtg aagatgtttt ggctactact ccaagagttg ctatgttgtc tttctctact    660

ttcggttccg ctaaacatga atacgttacc agagttgaag aagctttggc tttggctaga    720

aaagaaaaac cagatttggc cattgacggt gaaatgcaag ttgatgctgc tatagttcct    780

gaagttgctg ctaaaaaagc tccaggttct aaagttgctg gtcatgctaa tgttttgatc    840

ttcccagatt tgaacgctgg taacattgct tataaggttg ctgaaagatt cggtggttat    900

caagctgttg gtccaatttt tcaaggtttg gcttacccaa ctaacgactt gtctagaggt    960

tgtcatgccg aagatgttgt tgatgcagct gctgttactg ttttacaagg ttcctctatt   1020

ccaattccaa ctggtccagc tcctggtgat attttgaact aa                      1062


<210> SEQ ID NO 51
<211> LENGTH: 788
<212> TYPE: PRT
<213> ORGANISM: Physcomitrella patens

<400> SEQUENCE: 51

Met Leu Arg Ala Val Gly Lys Lys Val Arg Arg Val Leu Arg Glu Glu
1               5                   10                  15

Leu Leu Ala Gly Leu Gln Gly Arg Gly Leu Gly Arg Ile Tyr Asp Ala
            20                  25                  30

Ser Gly Thr Gly Val Arg Lys His Gly Trp Gly Ile Ser Ser Arg Glu
        35                  40                  45

Thr His Thr Asn Ser Leu Tyr Ile His His Thr Ile Gly Gly Val Gly
    50                  55                  60

Arg Asp Ser Val Ala Val Thr Val Gly Leu Leu His Ser Leu Glu Arg
65                  70                  75                  80

Leu Gln Pro Gly Ile Gly Tyr Phe Arg Pro Ile Asp Gln Thr Thr Ile
                85                  90                  95

Gly Gly Tyr Arg Ser Lys Leu Ile Lys Ser Val Phe Lys Met Lys Asp
            100                 105                 110

Asp Pro Ala Ile Met Gln Gly Val Thr Gln Asp Arg Ala Tyr Glu Leu
        115                 120                 125

Val Thr Asn Asp Lys Ile Asp Asp Leu Leu Glu Glu Val Leu Lys Ala
    130                 135                 140

Tyr Glu Ala Cys Arg Val Lys His Asp Phe Val Val Val Glu Gly Thr
145                 150                 155                 160

Ser Leu Arg Gly Gly Gly Asp Asp Thr Val Thr Leu Asn Ala Lys Ile
                165                 170                 175

Ala Gln Thr Leu Gly Ser Ser Ala Leu Leu Val Thr Asp Ala Gly Ile
            180                 185                 190

Ala Cys Gly Lys Met Asp Lys Met Lys Asn Trp Asp Gly Phe Asp Trp
        195                 200                 205

Glu Lys Arg Val Val Asn Asn Ala Lys Leu Ser Asp Leu Val Phe Arg
    210                 215                 220
```

Arg Glu His Val Asp Val Val Gly Ala Ile Val His Arg Thr Pro Gln
225 230 235 240

Thr Glu Arg Lys Asp Lys Leu Leu Arg Lys Val Phe Glu Glu Met Lys
245 250 255

Ile Pro Phe Val Gly Ala Leu Pro Glu Asp Ser Val Leu Arg Ser Val
260 265 270

Gln Val Gln Asp Val Ala Lys Lys Leu Glu Ala Gly Leu Leu Tyr Pro
275 280 285

Val Glu Asp Glu Glu Val Ala Met Ser Thr Glu Val Thr Gln Tyr Leu
290 295 300

Val Ala Thr Glu Gln Leu Ser Asp Leu Leu Arg His Leu Pro Arg Tyr
305 310 315 320

Val Asp Pro Thr Lys Gly Ser Ile Val Ile Thr Ser Ala Asn Arg Val
325 330 335

Asp Ile Leu Leu Gly Leu Ile His Leu His Glu Ser Lys Ser Asn Ala
340 345 350

Asn Ile Ala Ala Val Val Leu Ser Gly Gly Lys Pro Pro Pro Arg Glu
355 360 365

Val His Glu Leu Leu Lys Ala Arg Asn Ser Gly Thr Leu Pro Ile Ile
370 375 380

Leu Ser Pro Gln Met Thr Phe Glu Thr Ala Ser Ala Leu Ala Asn Val
385 390 395 400

Glu Gly Tyr Ile Ser Ser Lys Thr Pro Leu Lys Val Glu Arg Ala Gln
405 410 415

Thr Leu Phe Asp Asp Asn Ile Asn Met Lys Leu Ile Lys Asp Ala Met
420 425 430

Phe Gln Glu Arg Pro Val Arg Met Asn Ser Lys Leu Phe Gln His Asn
435 440 445

Leu Phe Thr Arg Ala Lys Gln Cys Ile Gln Thr Ile Val Leu Pro Glu
450 455 460

Gly Glu Glu Pro Arg Thr Leu Gln Ala Ala Gly Thr Val Leu Arg Arg
465 470 475 480

Gly Leu Cys Asn Leu Ile Leu Leu Gly Asp Arg Glu Lys Ile Glu Thr
485 490 495

Leu Ala Lys Gln Phe Arg Val Asp Ile Ser Gln Ala Arg Ile Val Asp
500 505 510

Pro Arg Asp Cys Pro Glu Thr Glu Lys Tyr Ala Arg Tyr Phe Tyr Glu
515 520 525

Ser Arg Lys His Lys Gly Ile Thr Leu Gly Gln Ala His Asn Ile Leu
530 535 540

Ile Gly Asp Val Asn Tyr Phe Gly Thr Cys Met Val Ala Glu Gly Ala
545 550 555 560

Ala Asp Gly Met Val Ser Gly Ala Val His Thr Thr Ala Asn Thr Val
565 570 575

Arg Pro Ala Leu Gln Leu Ile Lys Thr Leu Pro Gly Ile Pro Val Val
580 585 590

Ser Ser Val Phe Phe Met Cys Leu Pro Gly Lys Val Leu Val Tyr Gly
595 600 605

Asp Cys Ala Ile Asn Ser Asp Pro Thr Ser Glu Glu Leu Ala Ala Ile
610 615 620

Ala Ile Ala Ser Ala Asp Thr Ala Ala Ala Phe Gly Ile Lys Pro Arg
625 630 635 640

Val Ala Met Leu Ser Tyr Ala Thr Gly Asp Ser Asn Lys Gly Pro Leu

```
                645                 650                 655

Ile Gln Lys Val Ile Asp Ala Thr Ala Ile Ala Arg Lys Leu Arg Pro
            660                 665                 670

Asp Leu Leu Ile Glu Gly Pro Leu Gln Tyr Asp Ala Ala Val Asp Pro
        675                 680                 685

Val Ile Ala Lys Thr Lys Met Lys Gly Ala Glu Ser Glu Val Ala Gly
    690                 695                 700

Lys Ala Ser Val Leu Ile Phe Pro Asp Leu Asn Thr Gly Asn Asn Thr
705                 710                 715                 720

Tyr Lys Ala Val Gln Gln Thr Thr Gly Ala Val Ala Met Gly Pro Leu
                725                 730                 735

Leu Gln Gly Leu Arg Lys Pro Val Asn Asp Leu Ser Arg Gly Cys Thr
            740                 745                 750

Val Pro Asp Ile Val Thr Thr Ile Ala Leu Thr Ala Val Gln Ala Ala
        755                 760                 765

Ala Met Lys Glu Thr Ala Lys Arg Glu Thr Pro Lys Glu Asn Leu Val
    770                 775                 780

Ala Ser Ala Ala
785


<210> SEQ ID NO 52
<211> LENGTH: 2367
<212> TYPE: DNA
<213> ORGANISM: Physcomitrella patens

<400> SEQUENCE: 52

atgttgagag ctgttggtaa gaaggttaga agagtcttga gagaagaatt attggccggt      60

ttacaaggta gaggtttggg tagaatctat gatgcttctg gtactggtgt tagaaaacat     120

ggttggggta tttcttctag agaaacccat accaactcct tgtacattca tcatacaatt     180

ggtggtgttg gtagagattc tgttgctgtt actgttggtt tgttgcactc tttggaaaga     240

ttacaaccag gtatcggtta cttcagacca attgatcaaa ctaccattgg tggttacaga     300

tccaagttga ttaagtccgt tttcaagatg aaggatgatc cagctattat gcaaggtgtt     360

actcaagata gagcctacga attggttacc aacgataaga tcgatgattt gttggaagaa     420

gtcttgaagg cttacgaagc ttgtagagtt aagcacgatt tcgttgttgt tgaaggtact     480

tctttgagag gtggtggtga tgatactgtt actttgaatg ctaagattgc ccaaaccttg     540

ggttcttctg ctttgttggt tactgatgct ggtattgctt gtggtaagat ggataagatg     600

aagaactggg atggtttcga ttgggaaaaa agagttgtca acaacgccaa gttgtccgat     660

ttggttttta gaagagaaca cgttgatgtt gttggtgcca tagttcatag aactccacaa     720

actgaaagaa aggacaagtt gttgagaaag gttttcgaag aaatgaagat cccattcgtt     780

ggtgctttgc cagaagattc agttttgaga tctgttcaag ttcaagatgt cgccaaaaaa     840

ttggaagcag gtttgttgta tccagttgaa gatgaagaag ttgccatgtc tactgaagtt     900

acccaatatt tggttgccac cgaacaattg tcagatttgt tgagacattt gccaagatac     960

gttgatccaa ctaagggttc tatcgttatt acctctgcta acagagttga catcttgttg    1020

ggtttgattc acttgcacga atctaagtcc aacgctaata ttgctgctgt tgttttgtct    1080

ggtggtaaac caccaccaag agaagttcat gaattattga aggctagaaa ctccggtact    1140

ttgccaatta tcttgtctcc acaaatgact ttcgaaactg cttcagcttt ggctaacgtt    1200

gaaggttaca tttcctctaa gactccattg aaagttgaaa gagcccaaac tttgttcgac    1260
```

```
gataacatca acatgaagtt gatcaaggat gccatgttcc aagaaagacc agttagaatg   1320

aactccaagt tgttccaaca taacttgttc accagagcca agcaatgtat tcaaactatt   1380

gtcttgcctg aaggtgaaga acctagaact ttacaagctg ctggtactgt tttgagaaga   1440

ggtttgtgta acttgatttt gttgggtgac agagaaaaga ttgaaacctt ggctaagcaa   1500

ttcagagtcg atatttctca agccagaatt gtcgatccaa gagattgtcc agaaacagaa   1560

aagtacgcta gatacttcta cgaatccaga aagcacaagg gtattacttt gggtcaagcc   1620

cataacattt tgatcggtga tgttaactac ttcggtactt gtatggttgc tgaaggtgct   1680

gctgatggta tggtttcagg tgctgttcat acaactgcta atactgttag accagccttg   1740

caattgatta agactttgcc aggtattcca gttgtctcct ctgttttttt catgtgtttg   1800

cctggtaagg ttttggttta tggtgattgc gctattaact ctgatccaac ctctgaagaa   1860

ttggctgcta ttgctattgc atctgctgat actgctgctg cttttggtat taagccaaga   1920

gttgctatgt tgtcttatgc tactggtgat tctaacaagg gtccattgat tcaaaaggtt   1980

attgatgcta ctgccattgc cagaaagtta agaccagact tgttaatcga aggtccattg   2040

caatatgatg ctgcagttga tccagttatt gctaagacaa aaatgaaggg tgccgaatct   2100

gaagttgctg gtaaagcttc tgttttgatc ttcccagatt tgaacactgg taacaacact   2160

tacaaggctg ttcaacaaac tactggtgct gttgctatgg gtccattatt gcaaggtttg   2220

agaaagccag tcaacgattt gtctagaggt tgtactgttc cagatatcgt taccactatt   2280

gctttgactg ctgttcaagc tgccgctatg aaggaaactg ctaaaagaga aactccaaaa   2340

gaaaacttgg tagcttctgc tgcttga                                       2367
```

<210> SEQ ID NO 53
<211> LENGTH: 761
<212> TYPE: PRT
<213> ORGANISM: Phytophthora infestans

<400> SEQUENCE: 53

```
Met Trp Thr Leu Arg Asn Thr Phe Arg Arg Thr Ser Val Ala Leu Pro
1               5                   10                  15

Ser Gln Arg Arg Ala Leu Thr Ala Ala Ala Ile Ala Glu Gly Lys Val
            20                  25                  30

Pro Ile Asn Asn Leu Phe Val Thr Ser Thr Glu Val Thr Glu Lys Thr
        35                  40                  45

Ala Pro Val Leu Ile Gly Leu Thr Asn Thr Leu Glu Gln Lys Phe Ala
    50                  55                  60

Arg Val Gly Tyr Phe Arg Pro Ile Gln Pro Ile Val Glu Thr Asp His
65                  70                  75                  80

His Val Asp Val Met Lys Gln Gln Leu Gly Leu Thr Lys Ser Val Glu
                85                  90                  95

Gln Leu Tyr Gly Val Thr Ser Glu Arg Ala Ile Glu Tyr Trp Leu Asn
            100                 105                 110

Gly Lys Gly Asp Asp Leu Val Glu Glu Ile Leu Asp Arg Tyr Glu Ala
        115                 120                 125

Cys Arg Glu Gly His Asp Phe Met Ile Ile Glu Gly Ser Gln Leu Ser
    130                 135                 140

Lys His Glu Ser Ala Met Ser Trp Lys Ile Asn Val Asp Ile Ala Lys
145                 150                 155                 160

Ala Ile Gly Ser Pro Val Leu Thr Ile Ser Asp Phe Ser Glu Ser Ala
                165                 170                 175
```

```
Asn Thr Asn Ser Asp Leu Leu Glu Glu Ile Leu Ser Arg Thr Ala Phe
            180                 185                 190

Asn Lys Asp Gln Val Glu Gly Ala Gly Leu Asn Phe Ile Gly Asn Ile
        195                 200                 205

Ala Asn Arg Val Asn Thr Lys Asp Pro Lys Ala Leu Arg Glu Ala Ile
    210                 215                 220

Arg Ala Lys Leu Arg Glu Lys Asp Leu Pro Phe Leu Gly Phe Leu Pro
225                 230                 235                 240

Lys Asp Asp Phe Ile Ala Ser Lys Arg Leu Asn Glu Val Thr His Gln
                245                 250                 255

Leu Gly Ala Lys Gln Leu Phe Gly Thr Lys Ala Ile Pro Asn Asn Val
            260                 265                 270

Val Val Thr Ser Ala Val Val Ala Thr Ser Ala Leu Lys Asp Leu Phe
        275                 280                 285

Ala His Leu Lys Asn Tyr Lys Asp Gly Ala Leu Val Ile Thr Ser Ala
    290                 295                 300

Asp Arg Ser Asp Val Met Leu Gly Leu Met Ala Ser Arg Leu Pro Gly
305                 310                 315                 320

Ile Leu Pro Asn Val Ser Ala Ile Val Leu Thr Asn Gly Ser Tyr Pro
                325                 330                 335

His Ser Asn Thr Gln Glu Ile Leu Gln Gly Val Glu Ala Leu Asp Lys
            340                 345                 350

Thr Gly Leu Ser Ile Pro Ile Phe Ser Val Pro Glu Asp Thr Phe Thr
        355                 360                 365

Thr Ala Asp Lys Phe Ser Lys Val Ser Thr Asp Ile Leu Pro Thr Ser
    370                 375                 380

Gln Leu Lys Ile Asp Arg Ser Lys Gln Leu Phe Asp Glu Phe Val Gly
385                 390                 395                 400

Lys Glu Gly Ile Ile Gly Glu Leu Asp Glu Gly Met Val Val Asn Arg
                405                 410                 415

Ser Pro Lys Gln Phe Gln His Phe Leu Phe Ser Lys Ser Arg Ala Val
            420                 425                 430

Gln Arg His Ile Val Leu Thr Glu Gly Glu Asp Ile Arg Val Leu Gln
        435                 440                 445

Ala Ala Asp Gln Val Leu Arg Gln Lys Leu Ser Lys Val Thr Ile Leu
    450                 455                 460

Gly Asn Pro Asp Asp Ile Glu Arg His Ala Lys Ser Leu Thr Leu Asp
465                 470                 475                 480

Leu Ser Arg Ala Asn Ile Val Arg Thr Ala Asp Ser Glu Leu Leu Asp
                485                 490                 495

Lys Tyr Val Asp Gln Tyr Phe Glu Lys Arg Lys His Lys Gly Val Thr
            500                 505                 510

Arg Glu Ser Ala Arg Asp Ala Val Leu Glu Glu Thr Cys Phe Gly Thr
        515                 520                 525

Met Met Val Glu Met Gly Asp Ala Asp Gly Met Val Ser Gly Ala Cys
    530                 535                 540

His Thr Thr Ala Asn Thr Ile Arg Pro Ala Leu Gln Leu Ile Lys Thr
545                 550                 555                 560

Thr Pro Asn Arg Pro Ile Val Ser Ser Ile Phe Phe Met Cys Leu Glu
                565                 570                 575

Asp Gly Val Arg Ile Tyr Gly Asp Cys Ala Val Asn Thr Asp Pro Ser
            580                 585                 590

Ala Gln Asp Leu Ala Gln Ile Ala Val Thr Ser Ala Glu Ser Ala Glu
```

```
        595                 600                 605

Ala Phe Gly Leu Ile Pro Lys Val Ala Leu Leu Ser Tyr Ala Thr Gly
    610                 615                 620

Asp Ser Asn Ser Gly Pro Ile Ile Asp Lys Val Arg Glu Ala Thr Lys
625                 630                 635                 640

Met Ala Gln Glu Leu Arg Pro Asp Leu Asp Ile Tyr Gly Pro Ile Gln
                645                 650                 655

Tyr Asp Ala Ala Val Asp Glu Ser Ile Ala Lys Thr Lys Leu Lys Ala
            660                 665                 670

Ile Pro Ser Gly Ala Lys Val Gly Gly Gln Ala Asn Val Leu Ile Phe
        675                 680                 685

Pro Asp Leu Asn Thr Gly Asn Asn Thr Tyr Lys Ala Val Gln Gln Ser
    690                 695                 700

Thr Gly Cys Ile Ala Met Gly Pro Met Leu Gln Gly Leu Arg Lys Pro
705                 710                 715                 720

Val Asn Asp Leu Ser Arg Gly Ala Thr Val Lys Asp Ile Val Thr Thr
                725                 730                 735

Val Ala Ile Thr Ala Ile Gln Ala Asp Gln Val Ile Leu Lys Arg Glu
            740                 745                 750

Ala Lys Ala Lys Val Glu Ala Ala Ala
        755                 760


<210> SEQ ID NO 54
<211> LENGTH: 2286
<212> TYPE: DNA
<213> ORGANISM: Phytophthora infestans

<400> SEQUENCE: 54

atgtggactt tgagaaatac cttcagaaga acctctgttg ctttgccatc tcaaagaaga      60

gctttgactg ctgctgctat tgctgaaggt aaagttccaa tcaacaactt gttcgttacc     120

tctactgaag ttactgaaaa gactgcccca gttttgattg gtttgactaa cactttggaa     180

caaaagttcg ctagagtcgg ttacttcaga ccaattcaac ctatcgttga aaccgatcat     240

cacgttgatg ttatgaagca acaattgggt ttgaccaagt ccgtcgaaca attatatggt     300

gttacttccg aaagagccat cgaatattgg ttgaatggta agggtgatga cttggtcgaa     360

gaaatcttgg atagatacga agcttgtaga gaaggtcacg atttcatgat tatcgaaggt     420

tcccaattgt ccaaacatga atctgctatg tcctggaaga ttaacgttga tattgctaag     480

gctatcggtt ctccagtctt gactatttct gatttttctg aatccgccaa caccaactct     540

gatttgttgg aagaaatttt gtccagaacc gccttcaaca aggatcaagt tgaaggtgct     600

ggtttgaact tcattggtaa cattgctaac agagtcaaca ccaaagatcc aaaggctttg     660

agagaagcta ttagagctaa gttgagagaa aaggacttgc catttttggg tttcttgcca     720

aaggatgatt tcattgcctc taagagattg aacgaagtta cccatcaatt gggtgccaag     780

caattatttg gtacaaaggc tattccaaac aacgtcgttg taacttctgc tgttgttgct     840

acttctgctt tgaaggattt gttcgctcat ttgaagaact acaaggatgg tgctttggtt     900

attacctctg ctgatagatc agatgtcatg ttgggtttaa tggcttctag attgccaggt     960

attttgccaa atgtttccgc tatcgttttg accaatggtt cttacccaca ttctaacacc    1020

caagaaatat tgcaaggtgt tgaagctttg gataagaccg gtttgtctat tccaattttc    1080

tccgttccag aagatacttt cactaccgct gataagttct ctaaggtttc cactgatatc    1140

ttgccaacct cccaattgaa gatcgataga tccaaacaat tattcgatga attcgttggt    1200
```

```
aaagaaggta tcatcggtga attggatgaa ggtatggttg ttaacagatc cccaaagcaa   1260

ttccaacact tcttgttctc taaatccaga gccgttcaaa gacatattgt cttgactgaa   1320

ggtgaagata ttagagtctt gcaagctgct gatcaagtct tgagacaaaa gttgtccaag   1380

gttaccattt tgggtaaccc agatgatatt gaaagacacg ctaagtcttt gaccttggat   1440

ttgtctagag ctaacatcgt tagaaccgcc gattctgaat tattggataa gtacgttgac   1500

caatacttcg aaaaaagaaa gcacaagggt gtcactagag aatcagctag agatgctgtt   1560

ttagaagaaa cctgtttcgg tactatgatg gttgaaatgg gtgatgctga tggtatggtt   1620

tctggtgctt gtcatacaac tgctaacact attagaccag ccttgcaatt gattaagact   1680

actccaaata gaccaattgt ctcctccatt ttcttcatgt gtttggaaga tggtgtcaga   1740

atctatggtg attgtgctgt taatactgat ccatccgctc aagatttggc tcaaattgct   1800

gttacatctg ctgaatcagc tgaagctttt ggtttgattc caaaggttgc tttgttgtct   1860

tatgctaccg gtgattctaa ttccggtcca atcattgata aggttagaga agcaactaag   1920

atggcccaag aattgagacc agatttggat atctatggtc caattcaata cgatgctgcc   1980

gttgatgaat ccattgctaa aactaagttg aaagccattc catccggtgc taaagttggt   2040

ggtcaagcta atgttttgat cttcccagat ttgaacactg gtaacaacac ttacaaggcc   2100

gttcaacaat ctactggttg tattgctatg ggtccaatgt tgcaaggttt aagaaagcca   2160

gttaacgact tatctagagg tgctactgtt aaggatatcg ttactactgt tgctattacc   2220

gctattcaag ccgatcaagt tatcttgaaa agagaagcca aagctaaggt tgaagctgct   2280

gcttaa                                                              2286
```

<210> SEQ ID NO 55
<211> LENGTH: 760
<212> TYPE: PRT
<213> ORGANISM: Phytophthora parasitica

<400> SEQUENCE: 55

```
Met Trp Thr Leu Arg Arg Ser Leu Arg Arg Ser Thr Gly Val Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Thr
    50                  55                  60

Lys Val Gly Tyr Phe Arg Pro Ile Gln Pro Ser Pro Asp Ser Ser Met
65                  70                  75                  80

Ala Asp His His Val Asp Val Met Lys Gln Gln Leu Glu Leu Ser Lys
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175
```

-continued

```
Asp Thr Ser Ala Ala Asn Asp Ala Leu Ile Glu Glu Met Val Ser Arg
            180                 185                 190

Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu Arg
    210                 215                 220

Ala Ser Leu Lys Arg Lys Met Gly Asp Lys Asp Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Thr Gln Leu Phe Gly His Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
305                 310                 315                 320

Pro Gly Val Leu Pro Asn Ile Ser Ala Ile Val Leu Thr Asn Gly Asn
                325                 330                 335

Tyr Pro His Ser Asn Thr Gln Glu Ile Leu Lys Gly Val Gln Ala Leu
            340                 345                 350

Asp Lys Thr Ala Leu Ser Leu Pro Ile Phe Ser Thr Pro Asn Asp Thr
        355                 360                 365

Phe Ser Thr Ala Asp Gly Phe Ala Lys Val Ser Thr Asp Ile Leu Pro
    370                 375                 380

Ser Ser Lys Leu Lys Ile Asp Arg Ser Lys Gln Leu Phe Asp Glu Phe
385                 390                 395                 400

Val Glu Lys Glu Met Leu Ile Gly Glu Leu Asp Glu Gly Met Val Val
                405                 410                 415

Asn Arg Ser Pro Lys Gln Phe Gln His Phe Leu Phe Ser Lys Ser Arg
            420                 425                 430

Ala Val Gln Arg His Ile Val Leu Thr Glu Gly Glu Asp Ile Arg Val
        435                 440                 445

Leu Gln Ala Ala Asp Gln Ile Leu Arg Gln Asn Leu Ser Lys Ile Thr
    450                 455                 460

Ile Leu Gly Asp Pro Asp Glu Ile Leu Leu Asn Ala Lys Met Ala Asn
465                 470                 475                 480

Leu Asp Leu Ser Arg Ala Asn Ile Val Ser Pro Ala Asn Ser Ala Leu
                485                 490                 495

Leu Asp Lys Tyr Val Asp Tyr Phe Tyr Ala Lys Arg Lys His Lys Gly
            500                 505                 510

Val Thr Lys Glu Leu Ala Arg Asp Tyr Cys Lys Asp Glu Thr Tyr Phe
        515                 520                 525

Gly Thr Leu Met Val Glu Leu Gly Asp Ala Asp Gly Met Val Ser Gly
    530                 535                 540

Ala Cys His Thr Thr Ala Asn Thr Ile Arg Pro Ala Leu Gln Leu Ile
545                 550                 555                 560

Lys Thr Ala Pro Asn Arg Pro Ile Val Ser Ser Ile Phe Phe Met Cys
                565                 570                 575

Leu Glu Asp Gly Val Arg Ile Tyr Gly Asp Cys Ala Val Asn Thr Asp
            580                 585                 590
```

-continued

```
Pro Ser Ala Gln Asp Leu Ala Gln Ile Ala Val Thr Ser Ala Glu Ser
        595                 600                 605

Ala Glu Ala Phe Gly Leu Ile Pro Lys Val Ala Leu Leu Ser Tyr Ala
    610                 615                 620

Thr Gly Asp Ser Asn Ser Gly Pro Ile Ile Asp Lys Val Arg Glu Ala
625                 630                 635                 640

Thr Lys Ile Ala Gln Glu Leu Arg Pro Asp Leu Asp Ile Tyr Gly Pro
                645                 650                 655

Ile Gln Tyr Asp Ala Ala Val Asp Glu Ser Ile Ala Lys Thr Lys Leu
            660                 665                 670

Lys Ala Ile Pro Ser Gly Ala Lys Val Gly Gly Gln Ala Asn Val Leu
        675                 680                 685

Ile Phe Pro Asp Leu Asn Thr Gly Asn Asn Thr Tyr Lys Ala Val Gln
    690                 695                 700

Gln Ser Thr Gly Cys Ile Ala Met Gly Pro Met Leu Gln Gly Leu Arg
705                 710                 715                 720

Lys Pro Val Asn Asp Leu Ser Arg Gly Ala Thr Val Lys Asp Ile Val
                725                 730                 735

Thr Thr Val Ala Ile Thr Ala Ile Gln Ala Asp Gln Val Ile Met Lys
            740                 745                 750

Arg Glu Ala Glu Asn Ala Thr Lys
        755                 760
```

<210> SEQ ID NO 56
<211> LENGTH: 2283
<212> TYPE: DNA
<213> ORGANISM: Phytophthora parasitica

<400> SEQUENCE: 56

```
atgtggacct tgagaagaag tttgagaaga tctactggtg ttgctttgcc acatagaaga     60

gctttgactg ctgctgctat ttcacaaggt aaagttccaa tcaacaactt gtacgttacc    120

tctactgaag tcactaagaa aactgcccca gttttgattg gtttggctca tgttttggaa    180

caaaagttca ctaaggtcgg ttacttcaga ccaattcaac catctccaga ttcttctatg    240

gctgatcatc atgttgatgt catgaagcaa caattggaat tgtccaagga cgtcgaagaa    300

ttatacggtg ttacttcttc tagagctatg gaagctatgt tgactggtaa aggtgatgat    360

gttgtcgaag aaatcttgga aagatacgaa caatgcagaa agggtcacga tttcatgatt    420

atcgaaggtt cccaaatctc caaacatgaa tctgctatgt cctggaagat taacgttgat    480

attgctaagg ctatcggttc tcctgttttg atggttactg atttcggtga tacttctgct    540

gctaacgatg ctttgattga agaaatggtt tccagaaccg ttatgggtag agatcaagct    600

gaagatgctg gtttgaatta cttgggtact attgccaata gagtcagagc ctctaatgtt    660

gattctttga gagcttcctt gaagagaaag atgggtgata aggatattcc attcttgggt    720

tttttgccaa tggacgaaat tatcgcctct aagagattga acgaagttac ccatcaattg    780

ggtgccactc aattattcgg tcattccatt gctaatgatg ccgttgttac atctgctgtt    840

gttgctgctt ctgctttgaa agatttgttc gcccatttga aaaagtacaa ggatggtgcc    900

atgatcatta cctctggtga tagatctgat ttgatgttgg gtttgatggt cagtagattg    960

ccaggtgttt tgccaaatat ttccgctatc gttttgacca atggtaacta cccacattct   1020

aacacccaag aaattttgaa gggtgttcaa gctttggata agaccgcttt gtctttgcca   1080

attttctcta ctccaaacga tactttctct accgctgatg gttttgctaa ggtttctact   1140
```

```
gatatcttgc catcctccaa gttgaagatc gatagatcca agcaattatt tgatgaattc   1200

gttgaaaaag aaatgttgat cggtgaattg gacgaaggta tggttgttaa tagatcccca   1260

aagcaattcc aacacttctt gttctctaag tccagagctg ttcaaagaca tattgtcttg   1320

actgaaggtg aagatattag agtcttgcaa gctgccgatc aaatcttgag acaaaacttg   1380

tccaagatca ccattttggg tgatccagac gaaattttgt tgaacgctaa gatggctaac   1440

ttggatttgt ctagagccaa tatcgtttct ccagctaatt ctgccttgtt ggataagtac   1500

gttgattact tctacgccaa gagaaaacat aagggtgtca caaaagaatt ggccagagat   1560

tactgtaagg acgaaactta ctttggtaca ttgatggtcg aattaggtga tgctgatggt   1620

atggtttctg gtgcttgtca tacaactgct aacactatta gaccagcctt gcaattgatt   1680

aagactgctc caaatagacc aatcgtttcc tccattttct tcatgtgctt ggaagatggt   1740

gtcagaatct atggtgattg tgctgttaat actgatccat ctgcacaaga tttggctcaa   1800

attgctgtta ctagtgctga atcagctgaa gcttttggtt tgattccaaa ggttgctttg   1860

ttgtcttatg ctaccggtga ttctaattcc ggtccaatca ttgataaggt tagagaagct   1920

accaagatcg cccaagaatt gagaccagat ttggatatct atggtccaat ccaatatgat   1980

gctgccgttg atgaatctat cgctaagaca aaattgaagg ccattccatc tggtgctaaa   2040

gttggtggtc aagctaatgt tttgatcttc ccagatttga acactggtaa caacacttac   2100

aaggctgttc aacaatctac cggttgtatt gctatgggtc caatgttgca aggtttgaga   2160

aaaccagtta acgacttatc tagaggtgct accgttaagg atatcgttac tactgttgct   2220

attaccgcta ttcaagccga tcaagttatc atgaagagag aagctgaaaa cgctaccaag   2280

tga                                                                 2283
```

<210> SEQ ID NO 57
<211> LENGTH: 762
<212> TYPE: PRT
<213> ORGANISM: Phytophthora ramorum

<400> SEQUENCE: 57

```
Met Trp Thr Leu Arg His Ser Val His Arg Ala Pro Thr Ala Leu Pro
1               5                   10                  15

Gln Arg Arg Ala Leu Thr Ala Ala Ala Ile Ala Gln Gly Lys Val Pro
            20                  25                  30

Ile Asp Asn Leu Phe Val Thr Ser Thr Glu Val Thr Lys Lys Thr Ala
        35                  40                  45

Pro Val Leu Val Gly Leu Ala Asn Thr Leu Glu Gln Lys Phe Ala Lys
    50                  55                  60

Val Gly Tyr Phe Arg Pro Ile Gln Pro Ser Ala Gln Ser Ser Met Ala
65                  70                  75                  80

Asp His His Val Glu Val Met Arg Glu Gln Leu Gly Leu Thr Lys Glu
                85                  90                  95

Val His Glu Leu Phe Gly Val Ser Ser Glu Arg Ala Ile Glu Ser Trp
            100                 105                 110

Leu Ser Gly Lys Glu Asp Asp Leu Val Glu Glu Ile Leu Asp Arg Phe
        115                 120                 125

Glu Gln Cys Arg Glu Gly His Asp Phe Met Ile Ile Glu Gly Ser Gln
    130                 135                 140

Leu Ser Lys His Glu Ser Ala Met Ser Trp Lys Val Asn Val Asp Ile
145                 150                 155                 160

Ala Lys Ala Ile Gly Ser Pro Val Leu Thr Ile Ser Asp Phe Ser Glu
```

```
                165                 170                 175

Ser Thr His Ser Asn Gly Glu Leu Leu Glu Glu Ile Leu Ser Arg Thr
            180                 185                 190

Ala Leu Asn Lys Asp Gln Val Glu Gly Ala Gly Leu Asn Phe Ile Gly
        195                 200                 205

Asn Ile Ala Asn Arg Val Asn Thr Lys Asp Pro Lys Ala Leu Arg Asp
    210                 215                 220

Ala Leu Arg Ser Lys Leu Asn Glu Lys Asp Leu Pro Phe Leu Gly Phe
225                 230                 235                 240

Leu Pro Lys Asp Asp Phe Ile Ala Ser Lys Arg Leu Asn Glu Val Thr
                245                 250                 255

His Gln Leu Gly Ala Thr Gln Leu Phe Gly Thr Lys Ala Ile Pro Asn
            260                 265                 270

Asn Val Val Val Thr Ser Ala Val Val Ala Thr Ser Ala Leu Lys Asp
        275                 280                 285

Leu Phe Ser His Leu Lys Asn Tyr Lys Asp Gly Ala Leu Val Ile Thr
    290                 295                 300

Ser Ala Asp Arg Ser Asp Ile Met Leu Gly Leu Met Ala Ser Arg Leu
305                 310                 315                 320

Pro Gly Ile Leu Pro Asn Val Ser Ala Ile Val Leu Thr Asn Gly Ser
                325                 330                 335

Tyr Pro His Ser Asn Thr Gln Glu Ile Leu Lys Gly Val Glu Ala Leu
            340                 345                 350

Asp Lys Thr Gly Leu Ser Ile Pro Ile Phe Ser Val Pro Glu Asp Thr
        355                 360                 365

Phe Thr Thr Ala Asp Lys Phe Ser Lys Val Ser Thr Asp Ile Leu Pro
    370                 375                 380

Thr Ser Gln Leu Lys Ile Asp Arg Ser Lys Gln Leu Phe Asp Glu Phe
385                 390                 395                 400

Val Gly Lys Glu Asn Leu Ile Gly Glu Leu Asp Glu Gly Met Val Val
                405                 410                 415

Asn Arg Ser Pro Lys Gln Phe Gln His Phe Leu Phe Ser Lys Ser Arg
            420                 425                 430

Ala Val Gln Arg His Ile Val Leu Thr Glu Gly Glu Asp Ile Arg Val
        435                 440                 445

Leu Gln Ala Ala Asp Gln Val Leu Arg Gln Lys Leu Ser Lys Val Thr
    450                 455                 460

Ile Leu Gly Asn Pro Asp Asp Ile Gln Arg His Ala Lys Ser Leu Asn
465                 470                 475                 480

Leu Asp Leu Ser Arg Ala Asn Ile Val Arg Thr Ala Glu Ser Asp Leu
                485                 490                 495

Leu Glu Lys Tyr Val Asp Gln Tyr Phe Glu Lys Arg Lys His Lys Gly
            500                 505                 510

Val Thr Arg Glu Thr Ala Arg Asp Ala Val Leu Glu Glu Thr Cys Phe
        515                 520                 525

Gly Thr Met Met Val Glu Met Gly Asp Ala Asp Gly Met Val Ser Gly
    530                 535                 540

Ala Cys His Thr Thr Ala Asn Thr Ile Arg Pro Ala Leu Gln Leu Ile
545                 550                 555                 560

Lys Thr Thr Pro Asn Arg Pro Ile Val Ser Ser Val Phe Phe Met Cys
                565                 570                 575

Leu Glu Asp Gly Val Arg Ile Tyr Gly Asp Cys Ala Val Asn Thr Asp
            580                 585                 590
```

Pro Ser Ala Ala Asp Leu Ala Gln Ile Ala Val Thr Ser Ala Glu Ser
595 600 605

Ala Glu Ala Phe Gly Leu Ile Pro Lys Val Ala Leu Leu Ser Tyr Ala
610 615 620

Thr Gly Asp Ser Asn Ser Gly Pro Ile Ile Asp Lys Val Arg Glu Ala
625 630 635 640

Thr Lys Ile Ala Gln Glu Leu Arg Pro Asp Leu Asp Ile Tyr Gly Pro
645 650 655

Ile Gln Tyr Asp Ala Ala Val Asp Ala Ser Ile Ala Lys Thr Lys Leu
660 665 670

Lys Ala Ile Pro Ser Gly Ala Lys Val Gly Gly Gln Ala Asn Val Leu
675 680 685

Ile Phe Pro Asp Leu Asn Thr Gly Asn Asn Thr Tyr Lys Ala Val Gln
690 695 700

Gln Ser Thr Gly Cys Val Ala Met Gly Pro Met Leu Gln Gly Leu Arg
705 710 715 720

Lys Pro Val Asn Asp Leu Ser Arg Gly Ala Thr Val Lys Asp Ile Val
725 730 735

Thr Thr Val Ala Ile Thr Ala Ile Gln Ala Asp Gln Val Ile Leu Lys
740 745 750

Arg Glu Ala Gly Ala Ala Ala Ala Lys Leu
755 760

<210> SEQ ID NO 58
<211> LENGTH: 2289
<212> TYPE: DNA
<213> ORGANISM: Phytophthora ramorum

<400> SEQUENCE: 58
atgtggacct tgagacattc tgttcataga gcaccaactg ctttgccaca aagaagagct 60
ttgactgctg ctgctattgc tcaaggtaaa gttccaattg ataacttgtt cgtcacctct 120
actgaagtca ctaagaaaac tgctccagtt ttggttggtt tggctaacac tttggaacaa 180
aagtttgcta aggtcggtta cttcagacca attcaaccat ctgctcaatc ttctatggct 240
gatcatcatg ttgaagttat gagagaacaa ttgggtttga ccaaagaagt ccacgaatta 300
ttcggtgtct cttccgaaag agctattgaa tcttggttgt ccggtaaaga agatgacttg 360
gttgaagaaa tcttggacag attcgaacaa tgcagagaag gtcatgattt catgatcatc 420
gaaggttccc aattgtctaa acatgaatct gctatgtcct ggaaggttaa cgttgatatt 480
gctaaggcta ttggttcccc agttttgacc atttctgatt tctctgaatc cacccattcc 540
aacggtgaat tattggaaga aattttgtcc agaaccgcct tgaacaagga tcaagttgaa 600
ggtgctggtt tgaacttcat tggtaacatt gctaacagag tcaacaccaa agatccaaag 660
gctttgagag atgctttgag atctaagttg aacgaaaagg acttgccatt cttgggtttt 720
ttgccaaagg atgacttcat tgcctctaag agattgaacg aagttaccca tcaattgggt 780
gccactcaat tatttggtac aaaggctatt ccaaacaacg tcgttgtaac ttctgctgtt 840
gttgctactt ctgctttgaa ggatttgttc tcccatttga agaactacaa ggatggtgct 900
ttggttatta cctctgctga tagatccgat atcatgttgg gtttaatggc ttctagattg 960
ccaggtatct tgccaaatgt ttctgctatc gttttgacta acggttccta cccacattct 1020
aacacccaag aaatattgaa gggtgttgaa gctttggata agaccggttt gtctattcca 1080
attttctccg ttccagaaga tactttcact accgctgata agttctctaa ggtttccact 1140

-continued

```
gatattttgc caacctctca attgaagatc gacagatcca agcaattatt cgatgaattc   1200

gttggtaaag aaaacttgat cggtgaattg gatgaaggta tggttgttaa cagatcccca   1260

aagcaattcc aacacttctt gttctctaaa tccagagccg ttcaaagaca tattgtcttg   1320

actgaaggtg aagatatcag agttttacaa gctgctgatc aagtcttgag acaaaagttg   1380

tccaaggtta ccattttggg taacccagat gatatccaaa gacatgccaa gtctttgaat   1440

ttggatttgt ctagagccaa catcgttaga actgctgaat ctgatttgtt ggaaaagtat   1500

gtcgaccaat acttcgaaaa aagaaagcac aagggtgtta ctagagaaac tgctagagat   1560

gctgttttag aagaaacctg tttcggtact atgatggtcg aaatgggtga tgctgatggt   1620

atggtttctg gtgcttgtca tacaactgct aacactatta gaccagcctt gcaattgatt   1680

aagactactc caaatagacc aatcgtttcc tccgttttct tcatgtgttt ggaagatggt   1740

gtcagaatct atggtgattg tgctgttaat actgatccat ctgctgctga tttggctcaa   1800

attgctgtta catctgcaga atctgctgaa gcttttggtt tgattccaaa ggttgctttg   1860

ttgtcttatg ctaccggtga ttctaattcc ggtccaatca ttgataaggt tagagaagct   1920

accaagatcg cccaagaatt gagaccagat ttggacatct atggtccaat tcaatatgat   1980

gctgctgttg atgcctccat tgctaagaca aaattgaaag ctattccatc cggtgctaaa   2040

gttggtggtc aagctaatgt tttgatcttc ccagatttga acactggtaa caacacttac   2100

aaggccgttc aacaatctac tggttgtgtt gctatgggtc caatgttgca aggtttgaga   2160

aaaccagtta acgacttatc tagaggtgct accgttaagg atatcgttac tactgttgct   2220

attaccgcta ttcaagccga ccaagttatt ttgaaaagag aagctggtgc tgctgcagct   2280

aagttgtaa                                                           2289
```

<210> SEQ ID NO 59
<211> LENGTH: 764
<212> TYPE: PRT
<213> ORGANISM: Phytophthora sojae

<400> SEQUENCE: 59

```
Met Trp Thr Leu Arg Arg Ser Leu Arg Arg Ser Pro Val Ser Leu Met
1               5                   10                  15

Leu Pro Ala His Arg Arg Ala Leu Thr Ala Ala Ala Ala Ser Gln Gly
            20                  25                  30

Lys Val Pro Ile Glu Asn Leu Tyr Val Thr Ser Thr Glu Val Thr Lys
        35                  40                  45

Lys Thr Ala Pro Val Leu Ile Gly Leu Ala His Val Leu Glu His Lys
    50                  55                  60

Phe Asp Lys Val Gly Tyr Phe Arg Pro Ile Gln Pro Ser Pro Asp Ser
65                  70                  75                  80

Ser Met Ala Asp His His Val Asp Val Met Lys Gln Gln Leu Glu Leu
                85                  90                  95

Pro His Asn Val Glu Gln Leu Tyr Gly Val Thr Ser Gln Arg Ala Met
            100                 105                 110

Glu Ala Met Leu Asn Gly Lys Gly Asp Asp Ile Val Glu Glu Ile Leu
        115                 120                 125

Glu Arg Tyr Glu Glu Cys Arg Lys Gly His Asp Phe Met Leu Ile Glu
    130                 135                 140

Gly Ser Gln Ile Ser Lys His Glu Ser Ala Met Ser Trp Lys Ile Asn
145                 150                 155                 160
```

-continued

```
Val Asp Ile Ala Lys Ala Ile Gly Ser Pro Val Leu Met Val Thr Asp
                165                 170                 175

Phe Gly Asp Ser Ala Ala Lys Asn Gly Glu Leu Leu Glu Glu Met Val
            180                 185                 190

Ser Arg Thr Val Met Gly Lys Asp Gln Ala Asp Ala Ala Gly Leu Asn
        195                 200                 205

Tyr Leu Gly Thr Ile Ala Asn Arg Val Arg Ala Lys Asp Ala Asp Lys
    210                 215                 220

Leu Arg Ala Asp Leu Lys Glu Lys Leu Asp Glu Lys Asp Ile Pro Phe
225                 230                 235                 240

Leu Gly Phe Leu Pro Met Asp Glu Ile Ile Ala Ser Lys Arg Leu Asn
                245                 250                 255

Glu Val Thr His Gln Leu Gly Ala Thr Gln Leu Phe Gly Asn Thr Ile
            260                 265                 270

Ala Asn Asp Ala Val Val Thr Ser Ala Val Val Ala Ala Ser Ala Leu
        275                 280                 285

Lys Asp Leu Phe Ala His Leu Lys Lys Tyr Lys Asp Gly Ala Met Ile
    290                 295                 300

Ile Thr Ser Gly Asp Arg Ser Asp Leu Met Leu Gly Leu Met Val Ser
305                 310                 315                 320

Arg Leu Pro Gly Val Leu Pro Asn Ile Ser Ala Ile Val Leu Thr Asn
                325                 330                 335

Gly Asn Tyr Pro His Ser Asn Thr Gln Glu Ile Leu Lys Gly Val Glu
            340                 345                 350

Ala Leu Asp Lys Thr Gly Leu Ser Leu Pro Ile Phe Ser Thr Pro Asn
        355                 360                 365

Asp Thr Phe Ser Thr Ala Asp Gly Phe Ala Lys Val Ser Thr Asp Ile
    370                 375                 380

Leu Pro Thr Ser Lys Leu Lys Ile Asp Arg Ser Lys Gln Leu Phe Asp
385                 390                 395                 400

Glu Phe Val Glu Lys Glu Met Leu Ile Gly Glu Leu Asp Gln Gly Met
                405                 410                 415

Val Val Asn Arg Ser Pro Lys Gln Phe Gln His Phe Leu Phe Ser Lys
            420                 425                 430

Ser Arg Ala Val Gln Arg His Ile Val Leu Ser Glu Gly Glu Asp Ile
        435                 440                 445

Arg Val Leu Gln Ala Ala Asp Gln Ile Leu Arg Gln Asn Leu Ser Lys
    450                 455                 460

Ile Thr Ile Leu Gly Asn Pro Asp Glu Ile Leu Leu Asn Ala Lys Thr
465                 470                 475                 480

Ala Asn Leu Asp Leu Ser Arg Ala Asn Ile Val Arg Pro Ser Asp Ser
                485                 490                 495

Glu Leu Leu Asp Lys Tyr Val Asp Tyr Phe Tyr Glu Lys Arg Lys His
            500                 505                 510

Lys Gly Val Thr Lys Glu Leu Ala Arg Asp Tyr Cys Lys Asp Glu Thr
        515                 520                 525

Tyr Phe Gly Thr Leu Met Val Glu Leu Gly Asp Ala Asp Gly Met Val
    530                 535                 540

Ser Gly Ala Cys His Thr Thr Ala Asn Thr Ile Arg Pro Ala Leu Gln
545                 550                 555                 560

Leu Ile Lys Thr Ala Pro Asn Arg Pro Ile Val Ser Ser Val Phe Phe
                565                 570                 575

Met Cys Leu Glu Asp Gly Val Arg Ile Tyr Gly Asp Cys Ala Val Asn
```

-continued

```
            580                 585                 590

Thr Asp Pro Ser Ala Gln Asp Leu Ala Gln Ile Ala Val Thr Ser Ala
        595                 600                 605

Glu Ser Ala Glu Ala Phe Gly Leu Ile Pro Lys Val Ala Leu Leu Ser
    610                 615                 620

Tyr Ala Thr Gly Asp Ser Asn Ser Gly Pro Ile Ile Asp Lys Val Arg
625                 630                 635                 640

Glu Ala Thr Lys Ile Ala Gln Glu Leu Arg Pro Asp Leu Asp Ile Tyr
                645                 650                 655

Gly Pro Ile Gln Tyr Asp Ala Ala Val Asp Ala Ser Ile Ala Lys Thr
            660                 665                 670

Lys Leu Lys Ala Ile Pro Ser Gly Ala Lys Val Gly Gly Gln Ala Asn
        675                 680                 685

Val Leu Ile Phe Pro Asp Leu Asn Thr Gly Asn Asn Thr Tyr Lys Ala
    690                 695                 700

Val Gln Gln Ser Thr Gly Cys Ile Ala Met Gly Pro Met Leu Gln Gly
705                 710                 715                 720

Leu Arg Lys Pro Val Asn Asp Leu Ser Arg Gly Ala Thr Val Lys Asp
                725                 730                 735

Ile Val Thr Thr Val Ala Ile Thr Ala Ile Gln Ala Asp Gln Val Ile
            740                 745                 750

Leu Lys Arg Glu Ala Glu Ala Ala Thr Ala Lys Leu
        755                 760
```

<210> SEQ ID NO 60
<211> LENGTH: 2295
<212> TYPE: DNA
<213> ORGANISM: Phytophthora sojae

<400> SEQUENCE: 60

```
atgtggacct tgagaagatc tttaagaaga tccccagtct ctttgatgtt gccagctcat      60

agaagagctt tgacagctgc tgctgcttca caaggtaaag ttccaattga aaacttgtac     120

gtcacctcta ctgaagtcac taagaaaact gctccagttt tgattggttt ggcccatgtt     180

ttggaacaca agtttgataa ggttggttac ttcagaccaa tccaaccatc tccagattct     240

tcaatggctg atcatcatgt tgatgtcatg aagcaacaat tggaattgcc acacaacgtc     300

gaacaattat acggtgttac ttctcaaaga gctatggaag ctatgttgaa tggtaagggt     360

gatgatatcg tcgaagaaat cttggaaaga tacgaagaat gcagaaaggg tcacgacttt     420

atgttgattg aaggttccca aatctccaag cacgaatctg ctatgtcttg gaagattaac     480

gttgatattg ctaaggccat tggttctcca gtcttaatgg ttactgattt cggtgattct     540

gctgctaaga acggtgaatt attggaagaa atggtttcca gaaccgttat gggtaaagat     600

caagctgatg ctgctggttt gaattacttg ggtactattg ctaacagagt tagagctaag     660

gatgccgata agttgagagc tgatttgaaa gaaaagttgg acgaaaagga catcccattc     720

ttgggttttt tgccaatgga cgaaattatc gcctctaaga gattgaacga agttacccat     780

caattgggtg ccactcaatt attcggtaat accattgcta acgatgccgt tgttacatct     840

gctgttgttg ctgcttctgc tttgaaagat ttgttcgccc atttgaaaaa gtacaaggat     900

ggtgccatga ttatcacctc tggtgataga tctgatttga tgttaggttt gatggtttct     960

agattgccag gtgttttgcc aaacatttct gctatcgttt tgaccaatgg taactaccca    1020

cattctaaca cccaagaaat tttgaagggt gttgaagctt tggataagac cggtttgtct    1080
```

```
ttgccaattt tctctactcc aaacgatact ttctctaccg ctgatggttt tgctaaggtt   1140

tctactgata ttttgccaac ctccaagttg aagatcgaca gatctaagca attatttgat   1200

gaattcgttg aaaaagaaat gttgatcggt gaattggacc aaggtatggt tgttaataga   1260

tccccaaagc aatttcaaca cttcttgttc tctaagtcca gagccgttca aagacatatt   1320

gtcttgtctg aaggtgaaga tatcagagtt ttacaagccg ccgatcaaat cttgagacaa   1380

aacttgtcta agatcaccat cttgggtaac ccagacgaaa ttttgttgaa cgctaagact   1440

gctaacttgg atttgtctag agctaacatc gttagaccat ccgactctga attattagat   1500

aagtacgttg actacttcta cgaaaaaaga aagcacaagg gtgtcaccaa agaattggct   1560

agagattact gtaaggacga aacttacttc ggtactttga tggtagaatt gggtgatgct   1620

gatggtatgg tttctggtgc ttgtcataca actgctaaca ctattagacc agccttgcaa   1680

ttgattaaga ccgctccaaa tagaccaatc gtcagttctg ttttcttcat gtgtttggaa   1740

gatggtgtca gaatctatgg tgattgtgct gttaatactg atccatctgc acaagatttg   1800

gctcaaattg ctgttactag tgctgaatct gctgaagctt ttggtttgat tccaaaggtt   1860

gctttgttgt cttatgccac tggtgattct aattccggtc caattattga caaggttaga   1920

gaagctacca agatcgctca agaattgaga ccagatttgg atatctacgg tccaatccaa   1980

tatgatgctg cagttgatgc ttctattgcc aagacaaaat tgaaggctat tccatccggt   2040

gctaaagttg gtggtcaagc taatgttttg atcttcccag atttgaacac tggtaacaac   2100

acttacaagg ctgttcaaca atctaccggt tgtattgcta tgggtccaat gttgcaaggt   2160

ttaagaaagc cagttaacga cttgtcaaga ggtgctactg ttaaggatat cgttactact   2220

gttgctatta ccgctattca agccgatcaa gttatcttga aaagagaagc tgaagcagct   2280

actgctaagt tgtaa                                                    2295
```

<210> SEQ ID NO 61
<211> LENGTH: 760
<212> TYPE: PRT
<213> ORGANISM: Pythium ultimum

<400> SEQUENCE: 61

```
Met Trp Lys Cys Gly Arg Ser Met Arg Arg Met Thr Ala Leu Val Asn
1               5                   10                  15

Gln Arg Thr Ala Pro His Cys Arg Ala Leu Thr Ala Ala Ala Leu Glu
            20                  25                  30

Gln Gly Arg Val Pro Val Glu Ser Leu Tyr Val Thr Ser Thr Glu Tyr
        35                  40                  45

Thr Lys Lys Thr Ser Pro Val Leu Leu Gly Leu Ala Asn Thr Leu Glu
    50                  55                  60

Gln Lys Phe Ser Ser Val Gly Tyr Phe Arg Pro Ile Ala Pro Gly Lys
65                  70                  75                  80

Ser Ser Gly Ile Glu Asp His His Met Glu Leu Met Lys Ser Glu Leu
                85                  90                  95

Glu Leu Pro Glu Gln Ile Asn Glu Leu Tyr Gly Val Thr Ser Glu Arg
            100                 105                 110

Ala Leu Glu Cys Trp Met Thr Gly Lys Ser Asp Asp Leu Val Glu Glu
        115                 120                 125

Ile Leu Ser Ser Phe Glu His Cys Lys Lys Asn His Asp Phe Met Ile
    130                 135                 140

Ile Glu Gly Ser Pro Val Thr Glu His Glu Ser Ala Met Ser Trp Lys
145                 150                 155                 160
```

-continued

```
Ile Asn Ile Asp Ile Ala Arg Ala Ile Gly Ser Pro Val Leu Leu Leu
                165                 170                 175

Thr Asp Met Ser Ala Met Ser Tyr Thr Asn Gly Asp Leu Val Asp Glu
            180                 185                 190

Ile Val Ser Arg Thr Val Leu Gly Lys Glu Gln Val Glu Ala Ala Gly
        195                 200                 205

Leu Asn Tyr Phe Gly Thr Ile Ala Asn Arg Val Arg Ser Ala Asp Pro
    210                 215                 220

Thr Thr Met Gln Gly Lys Leu Lys Asp Ala Met Ala Lys Lys Asn Leu
225                 230                 235                 240

Pro Phe Leu Gly Phe Leu Pro His Asp Asn Leu Ile Ala Ser Lys Arg
                245                 250                 255

Leu Asn Glu Val Ala His Lys Leu Gly Ala Lys Gln Leu Phe Gly Ser
            260                 265                 270

Lys Glu Ile Ser Asn Asn Val Ile Val Ser Asp Ala Val Val Ala Thr
        275                 280                 285

Ser His Leu Arg Asp Leu Phe Ala His Leu Lys Lys Tyr Asn Asp Gly
    290                 295                 300

Ile Leu Val Ile Thr Ser Ala Asp Arg Ser Asp Ile Leu Leu Gly Leu
305                 310                 315                 320

Leu Ala Ser Arg Ile Pro Gly Val Leu Pro Asn Val Ala Gly Ile Val
                325                 330                 335

Leu Thr Asn Gly Asp Tyr Pro His Ser Asn Thr Gln Glu Ile Leu Gln
            340                 345                 350

Gly Val Ser Glu Leu Asp Lys Thr Gly Leu Ser Ile Pro Ile Phe Val
        355                 360                 365

Val Pro His Asp Thr Tyr Ser Thr Ala Thr Ala Val Ser His Val Ser
    370                 375                 380

Thr Asp Ile Met Pro Thr Ser Val Arg Lys Ile Gly Gln Cys Lys Asn
385                 390                 395                 400

Leu Phe Asp Gln Phe Ile Glu Lys Thr Asn Leu Ile Gly Glu Leu Asp
                405                 410                 415

Glu Gly Val Val Leu His Arg Ser Pro Lys His Phe Asn His Phe Val
            420                 425                 430

Leu Asn Lys Ala Arg Ala Ala Gln Arg His Ile Val Leu Thr Glu Gly
        435                 440                 445

Glu Asp Ile Arg Ile Leu Gln Ala Ala Asp Glu Ile Leu Arg Gln Arg
    450                 455                 460

Leu Ala Lys Leu Thr Ile Leu Gly Asp Pro Asp Glu Ile Arg Leu His
465                 470                 475                 480

Ala Lys Thr Met Asn Leu Asp Leu Ser Gly Ala Asn Ile Ile Lys Pro
                485                 490                 495

Met Asn Ser Asp Arg Leu Gly Ser Tyr Thr Glu Arg Leu Tyr Glu Met
            500                 505                 510

Arg Lys His Lys Gly Met Thr Lys Glu Ile Ala Arg Asp Thr Ile Ala
        515                 520                 525

Glu Glu Thr Tyr Tyr Gly Thr Met Met Val Glu Met Gly Asp Ala Asp
    530                 535                 540

Gly Met Val Ser Gly Ala Cys His Thr Thr Ala Asn Thr Ile Arg Pro
545                 550                 555                 560

Ala Leu Gln Leu Ile Lys Thr Ser Pro Glu Arg Pro Leu Val Ser Ser
                565                 570                 575
```

```
Val Phe Phe Met Cys Leu Glu Asp Gly Val Arg Ile Tyr Gly Asp Cys
            580                 585                 590

Ala Val Asn Thr Ser Pro Thr Ala Glu Glu Leu Ala Gln Ile Ala Val
        595                 600                 605

Thr Ser Ala Glu Ser Ala Glu Ala Phe Gly Met Ile Pro Arg Val Ala
    610                 615                 620

Leu Leu Ser Tyr Ala Thr Gly Asp Ser Asn Lys Gly Pro Ile Ile Asp
625                 630                 635                 640

Lys Val Arg Glu Ala Thr Lys Ile Ala Gln Glu Met Arg Pro Asp Leu
                645                 650                 655

Asp Ile Tyr Gly Pro Ile Gln Tyr Asp Ala Ala Val Asp Glu Ser Ile
            660                 665                 670

Ala Lys Gln Lys Leu Lys Ala Asp Ser Thr Gly Ala Arg Val Ala Gly
        675                 680                 685

Arg Ala Asn Val Leu Ile Phe Pro Asp Leu Asn Thr Gly Asn Asn Thr
    690                 695                 700

Tyr Lys Ala Val Gln Gln Ser Thr Gln Cys Val Ala Met Gly Pro Met
705                 710                 715                 720

Leu Gln Gly Leu Arg Lys Pro Val Asn Asp Leu Ser Arg Gly Ala Thr
                725                 730                 735

Val Lys Asp Ile Ile Thr Thr Val Ala Ile Thr Ala Ile Gln Ala Glu
            740                 745                 750

Gln Met Ile Ala Lys Lys Ala Glu
        755                 760


<210> SEQ ID NO 62
<211> LENGTH: 2283
<212> TYPE: DNA
<213> ORGANISM: Pythium ultimum

<400> SEQUENCE: 62

atgtggaagt gtggtagatc catgagaaga atgactgcct tggttaatca aagaactgct      60

ccacattgca gagctttgac tgctgctgct ttggaacaag gtagagttcc agttgaatcc     120

ttgtacgtta cttctactga atacaccaaa aagacctccc cagttttgtt gggtttggct     180

aatactttag aacaaaagtt ctcctccgtc ggttacttta gaccaattgc tccaggtaaa     240

tcctccggta ttgaagatca tcatatggaa ttgatgaagt ccgaattgga attgccagaa     300

caaatcaacg aattatacgg tgtcacttcc gaaagagctt tggaatgttg gatgactggt     360

aagtctgatg atttggtcga agaaatcttg tcctctttcg aacactgcaa aaagaaccac     420

gatttcatga tcattgaagg ttctccagtt accgaacatg aatctgctat gtcttggaag     480

atcaacattg atattgctag agccattggt tcaccagtct tgttgttgac tgatatgtca     540

gctatgtcct acactaacgg tgatttggtt gacgaaattg tctctagaac cgtcttgggt     600

aaagaacaag ttgaagctgc tggtttgaat tacttcggta ctattgctaa cagagttaga     660

tctgctgatc caactactat gcaaggtaaa ttgaaagatg ctatggccaa gaagaacttg     720

ccatttttgg gtttttttgcc acacgataac ttgatcgctt ctaagagatt gaatgaagtt     780

gcccataagt tgggtgccaa gcaattattt ggttccaaag aaatctccaa caacgtcatc     840

gtttctgatg ctgttgttgc tacttctcac ttgagagatt tgttcgccca tttgaaaaag     900

tacaacgatg gtatcttggt tatcacctct gctgatagat ccgatatctt gttaggtttg     960

ttggcctcta gaattccagg tgttttgcca aatgttgctg gtatcgtttt gaccaatggt    1020

gattacccac attctaacac ccaagaaata ttgcaaggtg tctctgaatt ggataagacc    1080
```

ggtttgtcta ttccaatctt cgttgttcca catgatactt actctactgc tacagctgtt 1140
tctcatgttt ccactgatat tatgccaacc tccgttagaa aaatcggtca atgtaagaac 1200
ttgttcgatc aattcattga aaagaccaac ttgattggtg aattggacga aggtgttgtc 1260
ttgcatagat ctccaaaaca tttcaaccac ttcgttttga acaaagctag agctgctcaa 1320
agacatattg tcttgactga aggtgaagat atcagaatct tgcaagctgc agacgaaatc 1380
ttgagacaaa gattggctaa gttgaccatt ttgggtgatc ctgacgaaat cagattgcat 1440
gctaagacta tgaacttgga tttgtctggt gccaacatta tcaagccaat gaactctgat 1500
agattgggtt cttacaccga aagattatac gaaatgagaa agcacaaggg tatgacaaaa 1560
gaaatcgcca gagataccat tgctgaagaa acttattacg gtactatgat ggtcgaaatg 1620
ggtgatgctg atggtatggt ttctggtgct tgtcatacaa ctgctaacac tattagacca 1680
gccttgcaat tgattaagac ctctccagaa agacctttgg tcagttctgt tttcttcatg 1740
tgtttggaag atggtgtcag aatctatggt gattgtgctg ttaatacttc tccaaccgct 1800
gaagaattgg ctcaaattgc tgttacatct gcagaatctg ctgaagcttt tggtatgatt 1860
ccaagagttg ctttgttgtc ttatgctacc ggtgattcta acaagggtcc aatcattgat 1920
aaggttagag aagctaccaa gatcgctcaa gaaatgagac cagatttgga tatctacggt 1980
ccaatccaat atgatgctgc agttgatgaa tccatagcca agcaaaaatt gaaggctgat 2040
tctactggtg ctagagttgc aggtagagct aatgttttga ttttcccaga tttgaacacc 2100
ggtaacaaca cttacaaagc cgttcaacaa tctacccaat gtgttgctat gggtccaatg 2160
ttgcaaggtt tgagaaaacc agttaacgac ttgtctagag gtgctactgt taaggatatt 2220
atcaccactg ttgctattac cgctattcaa gccgaacaaa tgattgctaa aaaggctgaa 2280
tga 2283

<210> SEQ ID NO 63
<211> LENGTH: 743
<212> TYPE: PRT
<213> ORGANISM: Saprolegnia diclina

<400> SEQUENCE: 63

Met Phe Arg Leu Arg Arg Gln Leu Pro Ser Val Ala Arg Arg Trp Tyr
1 5 10 15

Ser Glu Thr His Lys Val Asn Asp Arg Val Ile Val Leu Ser Asn Asp
20 25 30

Ala Thr Ser His Gln Thr Pro Val Leu Leu Gly Leu Met Asn Thr Leu
35 40 45

Ala Ile Lys Tyr His Ser Val Gly Tyr Phe Arg Pro Ile Ala Pro Pro
50 55 60

Leu Gly Ser Asp His His Val Glu Leu Phe Lys Ser Glu Leu Lys Leu
65 70 75 80

Pro Glu Thr Tyr Glu Gln Leu Val Gly Leu His His Asp Asp Val Val
85 90 95

Asn Ala Arg Leu Thr Gly Asp Leu Asp Ile Ile Thr Asp Thr Ile Val
100 105 110

Ala Lys Phe Glu Ala Leu Arg Ala Lys His Asp Phe Val Val Ile Glu
115 120 125

Gly Ala Thr Phe Glu Ser Ala Pro Glu Leu Ala Trp Asp Ile Asn Val
130 135 140

Glu Leu Ala Lys Thr Leu Gly Ala Pro Val Leu Leu Thr Asn Asp Phe

-continued

```
145                 150                 155                 160

Cys Asp Leu Pro Asp Thr Gln Arg Ile Glu Asp Ala Ile Ala Thr Arg
                165                 170                 175

Val Leu Leu Gly Lys Asp Ala Val Asp Ala Ala Gly Leu Thr Tyr Ile
            180                 185                 190

Gly Ser Ile Ala Asn Arg Val Arg Ser Ser Thr Pro Leu Glu Thr Arg
        195                 200                 205

Lys Arg Val Gln Asp Leu Leu Arg Glu Lys Gly Ala Ala Asp Pro Thr
    210                 215                 220

Ile Phe Leu Gly Ala Leu Pro Leu Asp Ser Ile Leu Ala Ser Lys Arg
225                 230                 235                 240

Leu Asn Glu Val Val Ala Gln Leu Gln Ala Thr Gln Leu Tyr Gly Pro
                245                 250                 255

Ala Ser Pro Asn Ser Val Val Val Thr Asp Gly Leu Ile Gly Thr Ser
            260                 265                 270

Asp Leu Lys Glu Leu Phe Gly His Leu Lys Ala His Asp Asp Gly Leu
        275                 280                 285

Leu Val Ile Thr Ser Ala Asp Arg Thr Asp Val Val Leu Gly Leu Leu
    290                 295                 300

Ala Ser Arg Ala Ser Gly Ala Leu Pro Asn Val Ala Gly Val Ile Leu
305                 310                 315                 320

Thr Asn Gly Ser Tyr Pro Gln Asp His Val Lys Asp Ile Leu Asp Gly
                325                 330                 335

Met Ala Lys Ile Asp Asn Ala Thr Ile Pro Ile Tyr Thr Val Glu Gly
            340                 345                 350

Asp Ala Tyr Lys Thr Ala Asn Ala Leu Ser Arg Val Thr Cys Asp Ile
        355                 360                 365

Leu Pro Thr Ser Gln Thr Lys Ile Gln Gln Ser Asn Ile Leu Phe Asp
    370                 375                 380

Lys Phe Val Ser Arg Ser Ala Leu Met Asp Thr Val Cys Gln Ala Val
385                 390                 395                 400

Lys Ser Thr Lys Arg Thr Pro Lys Gln Phe Lys His Phe Leu Phe Ser
                405                 410                 415

Lys Ala Arg Lys Val Gln Gln His Ile Val Leu Thr Glu Gly Glu Asp
            420                 425                 430

Asp Arg Ile Leu Gln Ala Ala Asp Glu Val Leu Arg Arg Asp Ile Ala
        435                 440                 445

Lys Ile Thr Ile Leu Gly Asp Val Asp Ser Ile Ala Ala Arg Ala Lys
    450                 455                 460

Thr Leu Arg Leu Asp Leu Ser Ala Ala Ser Ile Ile Asp Pro Ser Lys
465                 470                 475                 480

Ala Ala Asp Leu Asp Leu Leu Ala Ala Arg Phe Tyr Glu Lys Arg Lys
                485                 490                 495

Val Lys Gly Val Ser Leu Glu Phe Ala Arg Glu Ser Ala Ser Glu Ala
            500                 505                 510

Thr Cys Tyr Gly Thr Leu Met Val Glu Met Gly Leu Ala Asp Gly Met
        515                 520                 525

Val Ser Gly Ala Cys His Thr Thr Ala Asn Thr Val Arg Pro Ala Leu
    530                 535                 540

Gln Leu Ile Lys Thr Arg Pro Asp Arg Pro Leu Val Ser Ser Ile Phe
545                 550                 555                 560

Phe Met Cys Leu Glu Asp Asp Val Val Val Tyr Gly Asp Cys Ala Ile
                565                 570                 575
```

```
Asn Thr Asp Pro Thr Ala Glu Asp Leu Ala Asn Ile Ala Val Gln Ser
            580                 585                 590

Ala Glu Ser Ala Arg Ala Phe Gly Met Glu Pro Arg Val Ala Leu Leu
        595                 600                 605

Ser Tyr Ala Thr Gly Asp Ser Asn Lys Gly Pro Ile Ile Asp Lys Val
    610                 615                 620

Arg Glu Ala Thr Lys Leu Ala Gln Lys Met Ala Pro Glu Ile Pro Met
625                 630                 635                 640

Tyr Gly Pro Ile Gln Tyr Asp Ala Ala Met Asn Pro Leu Ile Ala Lys
                645                 650                 655

Gln Lys Val Lys Gly Leu Lys Lys Thr Glu Met Glu Val Ala Gly Asn
            660                 665                 670

Ala Asn Val Leu Ile Phe Pro Asp Leu Asn Thr Gly Asn Asn Thr Tyr
        675                 680                 685

Lys Ala Val Gln Gln Ser Thr Asn Cys Leu Ala Met Gly Pro Met Leu
    690                 695                 700

Gln Gly Leu Asn Lys Pro Val Asn Asp Leu Ser Arg Gly Ala Thr Val
705                 710                 715                 720

Gly Asp Ile Val Thr Thr Ile Ala Ile Thr Ala Ile Gln Ala His Gln
                725                 730                 735

Met Asn Glu Ala Ala Ser Thr
            740


<210> SEQ ID NO 64
<211> LENGTH: 2232
<212> TYPE: DNA
<213> ORGANISM: Saprolegnia diclina

<400> SEQUENCE: 64

atgttcagat tgagaagaca attgccatcc gttgctagaa gatggtattc tgaaactcac     60

aaggttaacg atagagtcat cgttttgtct aacgatgcta cttctcatca aaccccagtt    120

ttgttgggtt taatgaacac cttggccatc aagtatcatt ccgttggtta ctttagacca    180

attgctccac cattgggttc tgatcatcat gtcgaattat tcaagtccga attgaagttg    240

ccagaaacct acgaacaatt ggttggttta catcacgatg atgttgttaa cgctagattg    300

actggtgatt tggatattat caccgatacc atcgttgcta agttcgaagc tttgagagct    360

aagcacgatt tcgttgttat tgaaggtgct acttttgaat ccgctccaga attggcttgg    420

gatattaacg ttgaattggc taaaactttg ggtgctcctg ttttgttgac taacgatttt    480

tgtgatttgc cagacaccca aagaatcgaa gatgctattg ctaccagagt cttgttgggt    540

aaagatgctg ttgatgctgc tggtttgact tacattggtt ccattgctaa tagagtcaga    600

tcttctactc cattggaaac cagaaagaga gttcaagact tgttgagaga aaaaggtgct    660

gctgatccaa ctattttctt gggtgctttg ccattggatt ctattttggc ttctaagaga    720

ttgaacgaag ttgtcgctca attgcaagct actcaattat atggtccagc ttctccaaac    780

tctgttgttg ttactgatgg tttgatcggt acttccgatt tgaaagaatt attcggtcat    840

ttgaaggccc atgatgacgg tttgttggtt attacttctg ctgatagaac cgatgttgtc    900

ttgggtttgt tagcttctag agcttctggt gctttaccaa atgttgctgg tgttattttg    960

accaacggtt cttatccaca agatcacgtt aaggatatct tggatggtat ggccaagatt   1020

gataacgcta ctattccaat ctacaccgtt gaaggtgatg cttacaaaac tgctaatgcc   1080

ttgtctagag ttacctgcga tattttgcca acctcccaaa ctaagatcca acaatccaat   1140
```

atcttgttcg acaagttcgt ttccagatcc gctttgatgg atactgtttg tcaagctgtt 1200
aagtctacta agagaacccc aaaacaattc aagcacttct tgttctctaa ggccagaaag 1260
gttcaacaac atattgtctt gactgaaggt gaagatgaca gaatcttgca agctgctgat 1320
gaagttttga gaagagatat tgctaagatc accatcttgg gtgatgttga ttctattgct 1380
gctagagcta agaccttgag attggatttg tctgctgcct ctattatcga tccatctaaa 1440
gctgcagatt tggacttgtt agctgccaga ttttacgaaa aaagaaaggt caagggtgtc 1500
tccttggaat ttgctagaga atctgcttct gaagctactt gttatggtac tttgatggtc 1560
gaaatgggtt tggctgacgg tatggtttca ggtgcttgtc atacaacagc taatactgtt 1620
agaccagcct tacaattgat taagaccaga ccagatagac cattggtttc ttccattttc 1680
ttcatgtgct tggaagatga tgtcgttgtt tatggtgatt gcgccattaa cacagatcca 1740
actgctgaag atttggctaa cattgctgtt caatctgctg aatcagctag agcatttggt 1800
atggaaccta gagttgcttt gttgtcttat gctacaggtg attctaacaa gggtccaatc 1860
attgataagg ttagagaagc tactaagttg gctcaaaaaa tggctccaga aattccaatg 1920
tacggtccaa ttcaatacga tgctgctatg aatccattga tcgctaagca aaaagtcaag 1980
ggtttgaaaa agaccgaaat ggaagttgct ggtaacgcca atgttttgat tttcccagat 2040
ttgaacactg gtaacaacac ctacaaagcc gttcaacaat ctacaaactg tttggctatg 2100
ggtccaatgt tgcaaggttt gaacaaacca gttaacgact tatctagagg tgctacagtt 2160
ggtgatatcg ttactactat tgctattacc gctatccaag cccatcaaat gaatgaagct 2220
gcttctactt ga 2232

<210> SEQ ID NO 65
<211> LENGTH: 763
<212> TYPE: PRT
<213> ORGANISM: Saprolegnia parasitica

<400> SEQUENCE: 65

Met Leu Arg Ala Ser Arg His Leu Leu Pro Thr Arg Arg Ser Ala Leu
1 5 10 15

Leu Ala Arg Ala Ala Thr Ser Arg Leu Phe Ser Asp Ala Pro His Ala
20 25 30

Asn Asp Arg Val Phe Val Met Ser Asn Asp Thr Thr Ser His Gln Ser
35 40 45

Pro Val Leu Leu Gly Leu Met Asn Thr Leu Ser Val Lys Tyr Pro Ser
50 55 60

Val Gly Tyr Phe Arg Pro Ile Ala Pro Asn Lys Asp Pro Arg Val Ser
65 70 75 80

Asp His His Val Glu Val Met Lys Ser Glu Phe Lys Leu Pro Glu Glu
85 90 95

Lys Asp Gln Leu Val Gly Leu Tyr Asn Asp Asp Val Val Gln Ala Arg
100 105 110

Leu Lys Gly Asp Leu Asp Ser Val Thr Asp Thr Ile Ile Ser Lys Phe
115 120 125

Glu Ala Leu Arg Ala Lys His Asp Phe Val Val Ile Glu Gly Ala Met
130 135 140

Phe Glu Ser Ala Pro Asp Leu Ala Trp Asp Ile Asn Val Glu Leu Ala
145 150 155 160

Lys Thr Leu Gly Ala Pro Val Leu Leu Thr Asn Asp Leu Ala Asp Val
165 170 175

```
Glu Ala Asp Glu Ser Leu Ser Glu Asp Glu Arg Thr Lys Lys Leu Val
            180                 185                 190

Asp Thr Ile Val Thr Arg Val Leu Leu Ala Lys Asp Ala Val Gln Asp
        195                 200                 205

Ala Gly Leu Thr Tyr Val Gly Ser Ile Ala Asn Arg Val His Thr Lys
    210                 215                 220

Asp Pro Ile Glu Ile Arg Lys Arg Val Gln Ala Ile Leu Ala Glu Lys
225                 230                 235                 240

Gly Glu Thr Asn Ser Ile Phe His Gly Ala Leu Pro Leu Asp Ser Ile
                245                 250                 255

Leu Ala Ser Lys Arg Leu Asn Glu Val Val Asp Gln Leu His Ala Thr
            260                 265                 270

Gln Leu Tyr Gly Pro Pro Ser Pro Asn Ser Val Val Val Thr Asp Gly
        275                 280                 285

Phe Val Gly Thr Ser Asp Leu Lys Asp Leu Phe Gly His Met Lys Lys
    290                 295                 300

His Asp Asp Gly Leu Leu Val Ile Val Ser Ala Asp Arg Thr Asp Val
305                 310                 315                 320

Met Leu Gly Leu Leu Val Ser Lys Leu Ser Gly Ala Leu Pro Asn Val
                325                 330                 335

Ala Ala Val Ile Leu Thr Asn Gly Lys Phe Pro Gln Asp His Val Lys
            340                 345                 350

Glu Ile Leu Glu Gly Met Ala Lys Ile Asp Asn Ala Thr Ile Pro Ile
        355                 360                 365

Tyr Thr Val Glu Gly Asp Ser Tyr Lys Thr Ala Asn Ala Leu Ser Arg
    370                 375                 380

Val Thr Cys Asp Ile Leu Pro Thr Ser Gln Thr Lys Ile Gln Gln Ser
385                 390                 395                 400

Tyr Ile Leu Phe Asp Lys Tyr Val Ala Arg Asp Ser Val Val Gly Gly
                405                 410                 415

Val Ser Lys Glu Met Ser Thr Lys Arg Thr Pro Lys Gln Phe Lys His
            420                 425                 430

Phe Leu Phe Ser Lys Ala Arg Lys Val Gln Gln His Ile Val Leu Thr
        435                 440                 445

Glu Gly Glu Asp Asp Arg Ile Leu Gln Ala Ala Asp Glu Val Leu Arg
    450                 455                 460

Arg Asp Ile Ala Lys Leu Thr Ile Leu Gly Asp Val Glu Ser Ile Ala
465                 470                 475                 480

Ala Arg Ala Lys Thr Leu Arg Leu Asp Leu Ser Ala Ala Ser Ile Val
                485                 490                 495

Asp Pro Ser Lys Ser Ala Asp Leu Asp Met Tyr Ala Asp Arg Phe Tyr
            500                 505                 510

Glu Lys Arg Lys Ile Lys Gly Val Ser Arg Glu Val Ala Arg Glu Ser
        515                 520                 525

Ala Ala Glu Ala Thr Cys Tyr Gly Thr Leu Met Val Glu Met Gly Leu
    530                 535                 540

Ala Asp Gly Met Val Ser Gly Ala Cys His Thr Thr Ala Asn Thr Val
545                 550                 555                 560

Arg Pro Ala Leu Gln Leu Ile Lys Thr Arg Pro Asp Arg Pro Leu Val
                565                 570                 575

Ser Ser Val Phe Phe Met Cys Leu Asp His Asp Val Val Leu Tyr Gly
            580                 585                 590
```

```
Asp Cys Ala Ile Asn Thr Asp Pro Thr Ala Glu Asp Leu Ala Asn Ile
        595                 600                 605

Ala Val Gln Ser Ala Glu Ser Ala Ile Ala Phe Gly Met Glu Pro Arg
    610                 615                 620

Val Ala Leu Leu Ser Tyr Ala Thr Gly Asp Ser Asn Lys Gly Pro Ile
625                 630                 635                 640

Ile Asp Lys Val Arg Glu Ala Thr Lys Leu Ala Gln Lys Met Ala Pro
                645                 650                 655

Glu Ile Pro Met Tyr Gly Pro Ile Gln Tyr Asp Ala Ala Met Asn Pro
            660                 665                 670

Leu Ile Ala Lys Gln Lys Val Lys Gly Leu Lys Lys Thr Glu Met Glu
        675                 680                 685

Val Ala Gly Asn Ala Asn Val Leu Ile Phe Pro Asp Leu Asn Thr Gly
    690                 695                 700

Asn Asn Thr Tyr Lys Ala Val Gln Gln Ser Thr Asn Cys Leu Ala Met
705                 710                 715                 720

Gly Pro Met Leu Gln Gly Leu Asn Lys Pro Val Asn Asp Leu Ser Arg
                725                 730                 735

Gly Ala Thr Val Gly Asp Ile Val Thr Thr Ile Ala Ile Thr Ala Ile
            740                 745                 750

Gln Ala Asp Gln Met Asn Glu Ala Ala Lys Pro
        755                 760
```

<210> SEQ ID NO 66
<211> LENGTH: 2292
<212> TYPE: DNA
<213> ORGANISM: Saprolegnia parasitica

<400> SEQUENCE: 66

```
atgctgcgag cctcccgaca cctgctgccc acccgacgat ccgccctgct ggcccgagcc     60

gccacctccc gactgttctc cgacgccccc cacgccaacg accgagtctt cgtcatgtcc    120

aacgacacca cctcccacca gtcccccgtc ctgctgggcc tgatgaacac cctgtccgtc    180

aagtacccct ccgtcggcta cttccgaccc atcgccccca acaaggaccc ccgagtctcc    240

gaccaccacg tcgaggtcat gaagtccgag ttcaagctgc ccgaggagaa ggaccagctg    300

gtcggcctgt acaacgacga cgtcgtccag gcccgactga agggcgacct ggactccgtc    360

accgacacca tcatctccaa gttcgaggcc ctgcgagcca agcacgactt cgtcgtcatc    420

gagggcgcca tgttcgagtc cgcccccgac ctggcctggg acatcaacgt cgagctggcc    480

aagaccctgg gcgcccccgt cctgctgacc aacgacctgg ccgacgtcga ggccgacgag    540

tccctgtccg aggacgagcg aaccaagaag ctggtcgaca ccatcgtcac ccgagtcctg    600

ctggccaagg acgccgtcca ggacgccggc ctgacctacg tcggctccat cgccaaccga    660

gtccacacca aggaccccat cgagatccga aagcgagtcc aggccatcct ggccgagaag    720

ggcgagacca actccatctt ccacggcgcc ctgcccctgg actccatcct ggcctccaag    780

cgactgaacg aggtcgtcga ccagctgcac gccacccagc tgtacggccc cccctccccc    840

aactccgtcg tcgtcaccga cggcttcgtc ggcacctccg acctgaagga cctgttcggc    900

cacatgaaga agcacgacga cggcctgctg gtcatcgtct ccgccgaccg aaccgacgtc    960

atgctgggcc tgctggtctc caagctgtcc ggcgccctgc ccaacgtcgc cgccgtcatc   1020

ctgaccaacg gcaagttccc ccaggaccac gtcaaggaga tcctggaggg catggccaag   1080

atcgacaacg ccaccatccc catctacacc gtcgagggcg actcctacaa gaccgccaac   1140
```

```
gccctgtccc gagtcacctg cgacatcctg cccacctccc agaccaagat ccagcagtcc   1200

tacatcctgt tcgacaagta cgtcgcccga gactccgtcg tcggcggcgt ctccaaggag   1260

atgtccacca agcgaacccc caagcagttc aagcacttcc tgttctccaa ggcccgaaag   1320

gtccagcagc acatcgtcct gaccgagggc gaggacgacc gaatcctgca ggccgccgac   1380

gaggtcctgc gacgagacat cgccaagctg accatcctgg gcgacgtcga gtccatcgcc   1440

gcccgagcca agaccctgcg actggacctg tccgccgcct ccatcgtcga cccctccaag   1500

tccgccgacc tggacatgta cgccgaccga ttctacgaga agcgaaagat caagggcgtc   1560

tcccgagagg tcgcccgaga gtccgccgcc gaggccacct gctacggcac cctgatggtc   1620

gagatgggcc tggccgacgg catggtctcc ggcgcctgcc acaccaccgc caacaccgtc   1680

cgacccgccc tgcagctgat caagacccga cccgaccgac ccctggtctc ctccgtcttc   1740

ttcatgtgcc tggaccacga cgtcgtcctg tacggcgact gcgccatcaa caccgacccc   1800

accgccgagg acctggccaa catcgccgtc cagtccgccg agtccgccat cgccttcggc   1860

atggagcccc gagtcgccct gctgtcctac gccaccggcg actccaacaa gggccccatc   1920

atcgacaagg tccgagaggc caccaagctg gcccagaaga tggcccccga gatccccatg   1980

tacggcccca tccagtacga cgccgccatg aacccccctga tcgccaagca gaaggtcaag   2040

ggcctgaaga agaccgagat ggaggtcgcc ggcaacgcca acgtcctgat cttccccgac   2100

ctgaacaccg gcaacaacac ctacaaggcc gtccagcagt ccaccaactg cctggccatg   2160

ggccccatgc tgcagggcct gaacaagccc gtcaacgacc tgtcccgagg cgccaccgtc   2220

ggcgacatcg tcaccaccat cgccatcacc gccatccagg ccgaccagat gaacgaggcc   2280

gccaagccct aa                                                         2292
```

<210> SEQ ID NO 67
<211> LENGTH: 422
<212> TYPE: PRT
<213> ORGANISM: Selaginella moellendorffii

<400> SEQUENCE: 67

```
Met Trp Gly Ile Asp Arg Arg Lys Ala Leu Glu Phe Leu Ala Asn Gly
1               5                   10                  15

Asp Leu Asp Glu Met Leu Glu Gln Ile Tyr Val Ala Tyr Glu Glu Leu
            20                  25                  30

Lys Arg Arg His Glu Cys Val Leu Ile Glu Gly Thr Gln Phe Cys Arg
        35                  40                  45

Asp Ala Ser Ala Leu Asp Ala His Ile Ala Ser Ala Leu Gly Ser Pro
    50                  55                  60

Val Leu Leu Ala Thr Asn Val Asp Ala Leu Arg Gln Leu Trp Ser Ser
65                  70                  75                  80

Lys Asp His Ala Gly Asn Leu Gln Asp Trp Ala Thr Glu Ile Ala Thr
                85                  90                  95

Tyr Thr Arg Cys Ser Ala Leu Ala Phe Glu Lys Leu Lys Val Arg Val
            100                 105                 110

Val Gly Gly Phe Val Tyr Gly Ser Ser Asp Ala Pro Asp Met Arg Lys
        115                 120                 125

Val Phe Ser Lys Trp Lys Leu Gln Phe Val Gly Ala Leu Pro Gly Phe
    130                 135                 140

Asp Glu Arg Glu Asn Pro Val Lys Ala Phe Ala Asn Asn Ile Glu Met
145                 150                 155                 160

Glu Ala Leu Lys Arg Asn Met Pro Glu Glu Asn Ala Ala Arg Val Ser
```

```
                165                 170                 175

Pro Leu Leu Phe Arg Asn Ser Leu Phe Ser Arg Ala Lys Glu Asn Asn
            180                 185                 190

Gln Val Ile Leu Leu Pro Glu Gly Asp Glu Pro Arg Thr Val Gln Ala
        195                 200                 205

Ala Gly Phe Ile Leu Gln His Gly Leu Cys Ser Leu Ile Leu Leu Gly
    210                 215                 220

Glu Arg Glu Lys Leu Leu Glu Ala Ala Lys Val Ser Asn Val Asp Leu
225                 230                 235                 240

Arg Ser Ala Ile Ile Lys Asp Pro Ser Asp Pro Gln Glu Leu Glu Lys
                245                 250                 255

Tyr Ala Thr Val Tyr Tyr Gln Thr Arg Lys His Lys Gly Met Thr Leu
            260                 265                 270

Glu Lys Ala Arg Glu Ile Leu Gly Asn Asp Pro Ile Thr Leu Gly Thr
        275                 280                 285

Cys Met Val Ser Ala Gly Asp Ala Asp Gly Met Val Cys Gly Ala Val
    290                 295                 300

His Thr Thr Ala Asn Thr Val Arg Pro Ala Leu Gln Ile Ile Lys Thr
305                 310                 315                 320

Asp Pro Ala Thr Pro Ile Val Ser Ser Val Met Phe Ile Cys Leu Glu
                325                 330                 335

Asp Ala Val Val Ala Tyr Ala Asp Val Ala Ile Asn Ala Ser Pro Ser
            340                 345                 350

Ala Asp Glu Leu Ala Thr Ile Ala Ile Ala Ser Ala Asp Thr Val Thr
        355                 360                 365

Ala Phe Gly Leu Glu Pro Arg Val Ala Leu Leu Ser Tyr Ala Thr Gly
    370                 375                 380

Asp Ser Asn Ala Gly Arg Gly Arg Cys Gln His Arg Lys Ile Gln Thr
385                 390                 395                 400

Pro Gly Phe Ile Thr Arg Gly Thr Ile Pro Gly Ala Ala Ser Ile Cys
                405                 410                 415

Leu Pro Arg Ser Gln Gly
            420
```

<210> SEQ ID NO 68
<211> LENGTH: 1269
<212> TYPE: DNA
<213> ORGANISM: Selaginella moellendorffii

<400> SEQUENCE: 68

```
atgtggggta tcgatagaag aaaggctttg gaatttttgg ccaatggtga tttggacgaa      60

atgttggaac aaatctacgt tgcctacgaa gaattgaaga gaagacatga atgcgtcttg     120

atcgaaggta ctcaattctg tagagatgct tctgctttgg atgctcatat tgcttcagct     180

ttaggttctc cagttttgtt ggctactaat gttgatgcct tgagacaatt gtggtcctct     240

aaagatcatg ctggtaactt gcaagattgg gctactgaaa ttgctactta cactagatgt     300

tccgctttgg cttttgaaaa gttgaaggtt agagttgttg gtggtttcgt ttacggttct     360

tctgatgctc cagatatgag aaaggttttc tctaagtgga agttgcaatt cgttggtgct     420

ttgccaggtt ttgacgaaag agaaaatcca gttaaggctt tcgccaacaa cattgaaatg     480

gaagccttga aaagaaacat gccagaagaa aacgctgcta gagtttcacc tttgttgttc     540

agaaactcct tgttctccag agccaaagaa aacaatcaag tcatcttgtt gcctgaaggt     600

gatgaaccta gaactgttca agctgctggt tttatcttgc aacatggttt gtgttccttg     660
```

```
atcttgttgg gtgaaagaga aaagttgttg gaagctgcta aggtttccaa cgttgatttg    720

agatctgcca ttatcaagga tccatctgat ccacaagaat tggaaaagta cgctaccgtt    780

tactaccaaa ctagaaaaca taagggtatg acctttggaaa aggccagaga aattttgggt    840

aacgatccaa ttactttggg tacttgtatg gtttctgctg gtgatgctga tggtatggtt    900

tgcggtgctg ttcatacaac tgctaatact gttagaccag ccttgcaaat tatcaagact    960

gatccagcta ctccaatcgt ttcttccgtt atgttcattt gcttggaaga tgctgttgtt   1020

gcttacgctg atgttgctat taacgcttct ccatctgctg atgaattagc tactattgct   1080

attgcttctg ccgatactgt tactgctttt ggtttggaac ctagagttgc tttgttgtct   1140

tatgctactg gtgattctaa tgctggtaga ggtagatgtc aacacagaaa gattcaaacc   1200

ccaggtttca ttaccagagg tactattcca ggtgctgctt ctatttgttt gccaagatct   1260

caaggttaa                                                             1269
```

<210> SEQ ID NO 69
<211> LENGTH: 240
<212> TYPE: PRT
<213> ORGANISM: Tetraselmis sp.
<220> FEATURE:
<221> NAME/KEY: MOD_RES
<222> LOCATION: (98)..(98)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (139)..(139)
<223> OTHER INFORMATION: Any amino acid
<220> FEATURE:
<221> NAME/KEY: MOD_RES
<222> LOCATION: (183)..(183)
<223> OTHER INFORMATION: Any amino acid

<400> SEQUENCE: 69

```
Met Arg Pro Ala Leu Gln Val Ile Lys Cys Ala Pro Gly Ala Asn Met
1               5                   10                  15

Val Ser Ser Ala Phe Phe Met Leu Leu Asp Ser Gly Val Lys Val Phe
            20                  25                  30

Ala Asp Cys Ala Ile Val Glu Ser Pro Thr Ala Glu Gln Leu Ala Glu
        35                  40                  45

Ile Gly Ala Ala Ser Ala Val Thr Ala Ala Ser Phe Gly Leu Ser Pro
    50                  55                  60

Arg Ile Ala Met Leu Ser Tyr Ala Thr Gly Asp Ser Asn Ser Gly Pro
65                  70                  75                  80

Met Ile Thr Lys Val Arg Glu Ala Thr Glu Leu Leu Arg Arg His Pro
                85                  90                  95

Leu Xaa Val Xaa Arg Gly Tyr Pro Val Glu Gly Pro Ile Gln Phe Asp
            100                 105                 110

Ala Ala Val Asp Pro Met Val Ala Glu Val Lys Phe Arg Gly Ser Pro
        115                 120                 125

Gly Pro Val Ala Gly Arg Ala Asn Val Cys Xaa Phe Pro Asp Leu Asn
    130                 135                 140

Ala Gly Asn Asn Ala Tyr Lys Ala Val Gln Gln Ala Ser Gly Cys Val
145                 150                 155                 160

Ala Ile Gly Pro Val Met Gln Gly Leu Lys Leu Pro Val Asn Asp Leu
                165                 170                 175
```

```
Ser Arg Gly Cys Thr Val Xaa Asp Ile Val Gln Thr Val Ile Val Thr
            180                 185                 190

Cys Val Gln Ala Ile Ala Ala Lys Gln Ala Gln Met Pro Glu Glu Glu
        195                 200                 205

Val Leu Ser Pro Lys Pro Ile Lys Asp Arg His Leu Leu Ile Lys Ala
    210                 215                 220

Val Glu Ser Arg Gly Ser Leu Asn Asn Leu Thr Ser His Pro Leu Asn
225                 230                 235                 240


<210> SEQ ID NO 70
<211> LENGTH: 723
<212> TYPE: DNA
<213> ORGANISM: Tetraselmis sp.
<220> FEATURE:
<221> NAME/KEY: modified_base
<222> LOCATION: (292)..(294)
<223> OTHER INFORMATION: a, c, t, g, unknown or other
<220> FEATURE:
<221> NAME/KEY: modified_base
<222> LOCATION: (298)..(300)
<223> OTHER INFORMATION: a, c, t, g, unknown or other
<220> FEATURE:
<221> NAME/KEY: modified_base
<222> LOCATION: (415)..(417)
<223> OTHER INFORMATION: a, c, t, g, unknown or other
<220> FEATURE:
<221> NAME/KEY: modified_base
<222> LOCATION: (547)..(549)
<223> OTHER INFORMATION: a, c, t, g, unknown or other

<400> SEQUENCE: 70

atgcgacccg ccctgcaggt catcaagtgc gcccccggcg ccaacatggt ctcctccgcc      60

ttcttcatgc tgctggactc cggcgtcaag gtcttcgccg actgcgccat cgtcgagtcc     120

cccaccgccg agcagctggc cgagatcggc gccgcctccg ccgtcaccgc cgcctccttc     180

ggcctgtccc cccgaatcgc catgctgtcc tacgccaccg gcgactccaa ctccggcccc     240

atgatcacca aggtccgaga ggccaccgag ctgctgcgac gacacccccct gnnngtcnnn    300

cgaggctacc ccgtcgaggg ccccatccag ttcgacgccg ccgtcgaccc catggtcgcc     360

gaggtcaagt tccgaggctc ccccggcccc gtcgccggcc gagccaacgt ctgcnnnttc     420

cccgacctga acgccggcaa caacgcctac aaggccgtcc agcaggcctc cggctgcgtc     480

gccatcggcc ccgtcatgca gggcctgaag ctgcccgtca acgacctgtc ccgaggctgc     540

accgtcnnng acatcgtcca gaccgtcatc gtcacctgcg tccaggccat cgccgccaag     600

caggcccaga tgcccgagga ggaggtcctg tcccccaagc ccatcaagga ccgacacctg     660

ctgatcaagg ccgtcgagtc ccgaggctcc ctgaacaacc tgacctccca ccccctgaac     720

taa                                                                    723


<210> SEQ ID NO 71
<211> LENGTH: 803
<212> TYPE: PRT
<213> ORGANISM: Volvox carteri

<400> SEQUENCE: 71

Met Ala Ala His Leu Gln Arg Cys Arg Pro Cys Asp Ser Asp Thr Gly
1               5                   10                  15

Ala Ser Phe Ile Pro Glu Ser Ala Leu Thr Arg Arg Ala Ala Leu Pro
            20                  25                  30

Pro Ala Gly Arg Ile Leu His Arg Arg Ser Tyr Ser Ala Val Ala Pro
        35                  40                  45
```

```
Ile Ala Arg Ala Ser Arg Ser Ser Ser Lys Gln Ser Ser Asn Ser Gly
    50                  55                  60

Leu Gln Ser Leu Phe Leu Ser Asp Ile Ser Leu Ile Gly Gln Arg Thr
65                  70                  75                  80

Pro Leu Leu Leu Gly Phe Phe Asn Tyr Phe Glu Arg His Leu Pro His
                85                  90                  95

Val Gly Phe Phe Glu Pro Ile Ala His Glu Ala Leu Ala Ser Ser Glu
            100                 105                 110

Leu Lys Ile Asp Arg His Val Glu Leu Val Tyr Lys Val Phe Asn Leu
        115                 120                 125

Lys Gly Asp Ala Thr Arg Met Thr Gly Val Gln Asp Ala Glu Ala Ala
    130                 135                 140

Arg Met Ile Ala Asn Gly Gln His Ser Glu Leu Leu Asp Arg Ile Tyr
145                 150                 155                 160

Ala Asn Phe Val Ser Tyr Lys Glu Gly His Asp Leu Val Leu Val Glu
                165                 170                 175

Gly Pro Gly Pro Leu Met Gly Gly Thr Glu Leu Asp Ala Gln Ile Ala
            180                 185                 190

Ala Thr Ile Asn Ala Pro Val Leu Met Thr Met Thr Gly Ser Pro Asn
        195                 200                 205

Cys Ser Val Ser Asp Tyr Tyr Asn Arg Ala Met Val Lys Arg Gln Val
    210                 215                 220

Phe Leu Asp His Lys Val Glu Val Leu Gly Leu Val Met Asn Gly Leu
225                 230                 235                 240

Pro Arg Asn Ser His Ala Leu Met Thr Ala Gln Leu Lys Ala Arg Phe
                245                 250                 255

Asn Gln Ser Gly Leu Pro Phe Ala Gly Ala Ile Pro Gln Asp Pro Ile
            260                 265                 270

Leu Lys Asn Val Arg Leu Asp Glu Val Gln Thr Ala Leu Gln Ala Val
        275                 280                 285

Arg Leu Tyr Gly Asp Ser Leu Leu Thr Asp Val Glu Phe Asp Asp Val
    290                 295                 300

Val Val Gly Cys Gln Arg Leu Glu Glu Leu Leu Glu Ile Leu Gly Glu
305                 310                 315                 320

Arg Pro Gly Gly Arg Pro Leu Val Ile Thr Ser Ala Asp Arg Leu Asp
                325                 330                 335

Ile Val Leu Gly Leu Leu Ala Ala Gln Leu Ser Val Ser Gly Pro Gly
            340                 345                 350

Val Ala Gly Val Leu Leu Thr Gln Ala Gly Ser Ser Arg Ser Gly Arg
        355                 360                 365

Asn Tyr Ala Arg Asp Thr Ile Asp Arg Ile Phe Ala Gly Leu Val Asn
    370                 375                 380

Ser Gly Leu Tyr Lys Gly Ser Leu Leu Pro Arg Leu Phe Glu Gln Tyr
385                 390                 395                 400

Val Asp Ala Asn Ala Val Val Ala Glu Leu Gln Arg Ile Lys Pro Thr
                405                 410                 415

Arg Met Thr Pro Lys Met Phe Met His Thr Leu Lys Thr Met Cys Arg
            420                 425                 430

Glu Asn Pro Gln His Ile Ile Leu Pro Glu Ser Asp Asp Lys Arg Val
        435                 440                 445

Leu Ala Ala Ala Ala Asp Val Thr Thr Arg Gly Leu Ala Lys Ile Thr
    450                 455                 460
```

```
Leu Leu Gly Asp Pro Thr Thr Ile Thr Ala Glu Ala Ala Lys Leu Gly
465                 470                 475                 480

Leu Asp Leu Ser Gln Cys Asn Ile His Asn Pro Asn Thr Ala Gly Arg
                485                 490                 495

Phe Asp Ala Tyr Ala Glu Leu Leu Val Glu Leu Arg Lys His Lys Gly
            500                 505                 510

Met Thr Pro Asp Arg Ala Leu Asp Thr Leu His Gly Asp Met Asn Phe
        515                 520                 525

Tyr Ala Thr Met Met Ile Ala Ala Gly Asp Ala Asp Gly Met Val Ser
    530                 535                 540

Gly Ala Cys His Thr Thr Ala Ser Thr Val Arg Pro Ala Met Gln Val
545                 550                 555                 560

Leu Lys Ser Ala Asp Ser Pro Leu Val Ser Ser Val Phe Ile Met Cys
                565                 570                 575

Leu Pro Asp Arg Val Val Val Tyr Gly Asp Cys Ala Val Asn Val Asn
            580                 585                 590

Pro Thr Ala Ala Glu Leu Ala Thr Ile Ala Ile Thr Ser Ala Asp Thr
        595                 600                 605

Ala Ala Ala Phe Gly Ile Glu Pro Arg Val Ala Met Leu Ser Tyr Ser
    610                 615                 620

Thr Leu Gly Ser Gly Thr Gly Pro Asp Val Leu Lys Val Glu Glu Ala
625                 630                 635                 640

Val Ala Leu Ala Lys Ala Arg Arg Pro Asp Leu Lys Ile Glu Gly Pro
                645                 650                 655

Ile Gln Tyr Asp Ala Ala Ile Asp Pro Lys Val Ala Ala Val Lys Val
            660                 665                 670

Thr Gly Gly Ser Glu Val Ala Gly Lys Ala Thr Val Phe Val Phe Pro
        675                 680                 685

Asp Leu Asn Thr Gly Asn Asn Thr Tyr Lys Ala Val Gln Gln Ser Ser
    690                 695                 700

Gly Ala Ile Ala Met Gly Pro Ile Met Gln Val Pro Val Trp Gly Gly
705                 710                 715                 720

Trp Pro Tyr Leu Pro Trp Pro Gly Leu Leu Lys Pro Val Asn Asp Leu
                725                 730                 735

Ser Arg Gly Cys Thr Val Pro Asp Ile Val Asn Thr Ile Cys Val Thr
            740                 745                 750

Ser Ile Gln Ala Ser Arg Leu Arg Arg Gly Asn Arg Gln Ser Ala Asp
        755                 760                 765

Ser Thr Pro Thr Gln Ser Met Asp Gly Gly Pro Gly Pro Ser Asn Gly
    770                 775                 780

Asn Gly Asn Gly Asn Gly Asn Gly Ser Gly Val Ile Pro Pro Gln Leu
785                 790                 795                 800

Ala Ile Val
```

<210> SEQ ID NO 72
<211> LENGTH: 2412
<212> TYPE: DNA
<213> ORGANISM: Volvox carteri

<400> SEQUENCE: 72

```
atggctgctc acttgcaaag atgtagacca tgtgattctg atactggtgc ttctttcatt      60

ccagaatctg ctttgactag aagagctgct ttgccaccag caggtagaat attgcataga     120

agatcttatt ctgccgttgc tccaattgct agagcttcta gatcttcctc taaacaatct     180
```

-continued

```
tccaactccg gtttacaatc cttgttcttg tccgatattt ccttgattgg tcaaagaacc    240
cctttgttgt tgggtttctt taactacttc gaaagacact tgccacacgt tggtttttt    300
gaacctattg ctcatgaagc tttggcctct tccgaattga aaatcgatag acatgttgaa    360
ttggtctaca aggttttcaa cttgaagggt gatgctacta gaatgactgg tgttcaagat    420
gctgaagctg ctagaatgat tgctaatggt caacactccg aattattgga tagaatctac    480
gccaacttcg tttcctacaa agaaggtcac gatttggttt tggttgaagg tccaggtcca    540
ttgatgggtg gtactgaatt ggatgctcaa attgctgcta ctattaacgc tccagttttg    600
atgactatga ctggttctcc aaactgctct gtttctgatt actacaatag agccatggtc    660
aagagacaag ttttcttgga tcataaggtt gaagtcttgg gtttggttat gaatggtttg    720
ccaagaaact ctcatgcttt gatgacagct caattgaagg ccagattcaa tcaatcaggt    780
ttgccatttg ctggtgctat tccacaagat ccaattttga agaacgtcag attggatgaa    840
gttcaaactg cattgcaagc cgttagatta tacggtgatt ctttgttgac tgacgttgaa    900
ttcgatgatg ttgttgtcgg ttgtcaaaga ttggaagaat tattagaaat cttgggtgaa    960
agaccaggtg gtagaccatt ggttattaca tctgctgata gattggatat cgttttgggt   1020
ttgttagctg cccaattgtc tgtttcaggt cctggtgttg ctggtgtttt gttaactcaa   1080
gctggttctt caagatccgg tagaaattat gctagagata ccatcgatag aattttcgct   1140
ggtttggtca attccggttt gtacaagggt tctttattgc caagattatt cgaacaatac   1200
gttgatgcta acgctgttgt tgctgaattg caaagaatca agccaacaag aatgacccca   1260
aagatgttca tgcatacctt gaaaactatg tgcagagaaa accctcaaca catcattttg   1320
ccagaatccg atgataagag agttttggct gctgctgcag atgttactac tagaggtttg   1380
gctaagatta ccttgttggg tgatccaact actattactg ctgaagcagc aaagttgggt   1440
ttagatttgt ctcaatgcaa catccataac ccaaatactg ctggtagatt cgatgcttac   1500
gctgaattat tggttgaatt gagaaagcac aagggtatga ctccagatag agctttggat   1560
actttacacg gtgatatgaa cttctacgcc actatgatga ttgctgctgg tgatgctgat   1620
ggtatggttt ctggtgcttg tcatacaact gcttctactg ttagaccagc tatgcaagtt   1680
ttgaagtctg ctgattctcc attggtcagt tccgttttca ttatgtgttt gccagacaga   1740
gttgttgttt atggtgattg tgccgttaat gttaatccaa ctgctgctga attagctacc   1800
attgctatta cttcagcaga tacagctgct gcttttggta ttgaacctag agttgctatg   1860
ttgtcctatt ccactttggg ttctggtact ggtccagatg ttttgaaagt tgaagaagct   1920
gttgctttgg ctaaagctag aagaccagat ttgaagatcg aaggtccaat tcaatacgat   1980
gctgctattg atccaaaagt tgctgctgtt aaggttactg gtggttctga agttgctggt   2040
aaagctactg tttttgtttt cccagacttg aacactggta acaacactta caaagccgtc   2100
caacaatcat caggtgctat tgctatgggt ccaatcatgc aagttccagt ttggggtggt   2160
tggccatatt tgccatggcc aggtttgttg aaaccagtta atgatttgtc tagaggttgc   2220
accgttccag atatcgttaa cactatttgc gttacctcca ttcaagcctc tagattgaga   2280
agaggtaata gacaatccgc tgattctact ccaactcaat ctatggatgg tggtcctggt   2340
ccatctaatg gtaacggtaa tggtaatggt aacggttctg gtgttattcc accacaattg   2400
gctatcgtct aa                                                       2412
```

<210> SEQ ID NO 73
<211> LENGTH: 323

<212> TYPE: PRT
<213> ORGANISM: Bacillus subtilis

<400> SEQUENCE: 73

Met Ala Asp Leu Phe Ser Thr Val Gln Glu Lys Val Ala Gly Lys Asp
1 5 10 15

Val Lys Ile Val Phe Pro Glu Gly Leu Asp Glu Arg Ile Leu Glu Ala
20 25 30

Val Ser Lys Leu Ala Gly Asn Lys Val Leu Asn Pro Ile Val Ile Gly
35 40 45

Asn Glu Asn Glu Ile Gln Ala Lys Ala Lys Glu Leu Asn Leu Thr Leu
50 55 60

Gly Gly Val Lys Ile Tyr Asp Pro His Thr Tyr Glu Gly Met Glu Asp
65 70 75 80

Leu Val Gln Ala Phe Val Glu Arg Arg Lys Gly Lys Ala Thr Glu Glu
85 90 95

Gln Ala Arg Lys Ala Leu Leu Asp Glu Asn Tyr Phe Gly Thr Met Leu
100 105 110

Val Tyr Lys Gly Leu Ala Asp Gly Leu Val Ser Gly Ala Ala His Ser
115 120 125

Thr Ala Asp Thr Val Arg Pro Ala Leu Gln Ile Ile Lys Thr Lys Glu
130 135 140

Gly Val Lys Lys Thr Ser Gly Val Phe Ile Met Ala Arg Gly Glu Glu
145 150 155 160

Gln Tyr Val Phe Ala Asp Cys Ala Ile Asn Ile Ala Pro Asp Ser Gln
165 170 175

Asp Leu Ala Glu Ile Ala Ile Glu Ser Ala Asn Thr Ala Lys Met Phe
180 185 190

Asp Ile Glu Pro Arg Val Ala Met Leu Ser Phe Ser Thr Lys Gly Ser
195 200 205

Ala Lys Ser Asp Glu Thr Glu Lys Val Ala Asp Ala Val Lys Ile Ala
210 215 220

Lys Glu Lys Ala Pro Glu Leu Thr Leu Asp Gly Glu Phe Gln Phe Asp
225 230 235 240

Ala Ala Phe Val Pro Ser Val Ala Glu Lys Lys Ala Pro Asp Ser Glu
245 250 255

Ile Lys Gly Asp Ala Asn Val Phe Val Phe Pro Ser Leu Glu Ala Gly
260 265 270

Asn Ile Gly Tyr Lys Ile Ala Gln Arg Leu Gly Asn Phe Glu Ala Val
275 280 285

Gly Pro Ile Leu Gln Gly Leu Asn Met Pro Val Asn Asp Leu Ser Arg
290 295 300

Gly Cys Asn Ala Glu Asp Val Tyr Asn Leu Ala Leu Ile Thr Ala Ala
305 310 315 320

Gln Ala Leu

<210> SEQ ID NO 74
<211> LENGTH: 972
<212> TYPE: DNA
<213> ORGANISM: Bacillus subtilis

<400> SEQUENCE: 74
atggccgatt tgttctctac cgttcaagaa aaagttgctg gtaaggatgt caagatcgtt 60
tttccagaag gtttggacga aagaattttg gaagctgttt ctaaattggc cggtaacaag 120

-continued

```
gttttgaacc caatcgttat tggtaacgaa aacgaaattc aagccaaggc caaagaattg    180

aacttgactt tgggtggtgt taagatctac gatccacata cttatgaagg tatggaagat    240

ttggttcaag ccttcgttga aagaagaaaa ggtaaggcta ctgaagaaca agctagaaaa    300

gctttgttag acgaaaacta cttcggtact atgttggtct acaaaggttt ggctgatggt    360

ttggtttctg gtgctgctca ttctactgct gatactgtta gaccagcatt gcaaatcatc    420

aagacaaaag aaggtgtcaa aaagacctcc ggtgttttca ttatggctag aggtgaagaa    480

caatacgttt tcgctgattg cgctattaac attgctccag attctcaaga tttggccgaa    540

attgctattg aatctgctaa cactgctaag atgttcgaca ttgaacctag agttgctatg    600

ttgtcattct ctacaaaagg ttctgctaag tctgacgaaa ctgaaaaggt tgctgatgca    660

gttaagatcg ctaaagaaaa agctccagaa ttgaccttgg atggtgaatt tcaatttgat    720

gctgctttcg ttccatccgt tgctgaaaaa aaagcaccag attctgaaat caagggtgat    780

gccaatgttt tcgtattccc atctttagaa gctggtaaca tcggttacaa gattgctcaa    840

agattgggta actttgaagc tgttggtcca atattgcaag gtttgaatat gccagttaac    900

gatttgtcta gaggttgcaa tgcagaagat gtttacaact tggctttgat tactgctgct    960

caagctttgt aa                                                        972
```

<210> SEQ ID NO 75
<211> LENGTH: 328
<212> TYPE: PRT
<213> ORGANISM: Thermoanaerobacterium saccharolyticum

<400> SEQUENCE: 75

```
Met Ser Ile Ile Gln Asn Ile Ile Glu Lys Ala Lys Ser Asp Lys Lys
1               5                   10                  15

Lys Ile Val Leu Pro Glu Gly Ala Glu Pro Arg Thr Leu Lys Ala Ala
            20                  25                  30

Glu Ile Val Leu Lys Glu Gly Ile Ala Asp Leu Val Leu Leu Gly Asn
        35                  40                  45

Glu Asp Glu Ile Arg Asn Ala Ala Lys Asp Leu Asp Ile Ser Lys Ala
    50                  55                  60

Glu Ile Ile Asp Pro Val Lys Ser Glu Met Phe Asp Arg Tyr Ala Asn
65                  70                  75                  80

Asp Phe Tyr Glu Leu Arg Lys Asn Lys Gly Ile Thr Leu Glu Lys Ala
                85                  90                  95

Arg Glu Thr Ile Lys Asp Asn Ile Tyr Phe Gly Cys Met Met Val Lys
            100                 105                 110

Glu Gly Tyr Ala Asp Gly Leu Val Ser Gly Ala Ile His Ala Thr Ala
        115                 120                 125

Asp Leu Leu Arg Pro Ala Phe Gln Ile Ile Lys Thr Ala Pro Gly Ala
    130                 135                 140

Lys Ile Val Ser Ser Phe Phe Ile Met Glu Val Pro Asn Cys Glu Tyr
145                 150                 155                 160

Gly Glu Asn Gly Val Phe Leu Phe Ala Asp Cys Ala Val Asn Pro Ser
                165                 170                 175

Pro Asn Ala Glu Glu Leu Ala Ser Ile Ala Val Gln Ser Ala Asn Thr
            180                 185                 190

Ala Lys Asn Leu Leu Gly Phe Glu Pro Lys Val Ala Met Leu Ser Phe
        195                 200                 205

Ser Thr Lys Gly Ser Ala Ser His Glu Leu Val Asp Lys Val Arg Lys
    210                 215                 220
```

```
Ala Thr Glu Ile Ala Lys Glu Leu Met Pro Asp Val Ala Ile Asp Gly
225                 230                 235                 240

Glu Leu Gln Leu Asp Ala Ala Leu Val Lys Glu Val Ala Glu Leu Lys
                245                 250                 255

Ala Pro Gly Ser Lys Val Ala Gly Cys Ala Asn Val Leu Ile Phe Pro
            260                 265                 270

Asp Leu Gln Ala Gly Asn Ile Gly Tyr Lys Leu Val Gln Arg Leu Ala
        275                 280                 285

Lys Ala Asn Ala Ile Gly Pro Ile Thr Gln Gly Met Gly Ala Pro Val
    290                 295                 300

Asn Asp Leu Ser Arg Gly Cys Ser Tyr Arg Asp Ile Val Asp Val Ile
305                 310                 315                 320

Ala Thr Thr Ala Val Gln Ala Gln
                325


<210> SEQ ID NO 76
<211> LENGTH: 987
<212> TYPE: DNA
<213> ORGANISM: Thermoanaerobacterium saccharolyticum

<400> SEQUENCE: 76

atgtccatca tccaaaacat catcgaaaag gccaagtccg ataagaagaa aatcgttttg      60

ccagaaggtg ctgaacctag aactttgaaa gctgctgaaa tcgtcttgaa agaaggtatt     120

gctgatttgg tcttgttggg taacgaagac gaaattagaa atgctgccaa ggatttggat     180

atctccaagg ccgaaattat cgatccagtt aagtctgaaa tgttcgacag atacgctaac     240

gacttctacg aattgagaaa gaacaagggt atcaccttgg aaaaggctag agaaaccatt     300

aaggacaaca tctacttcgg ttgcatgatg gtcaaagaag gttacgctga cggtttggtt     360

tctggtgcta ttcatgctac agctgatttg ttaagaccag ccttccaaat tatcaaaact     420

gctccaggtg ctaagatcgt cagttcattt ttcattatgg aagtcccaaa ctgcgaatac     480

ggtgaaaatg gtgttttttt gttcgctgat tgtgccgtta atccatctcc aaatgctgaa     540

gaattggctt ccattgctgt tcaatctgct aatactgcta agaatttgtt gggtttcgaa     600

cctaaggttg ccatgttgtc tttttcaaca aaaggttccg cttcccatga attggttgat     660

aaggttagaa aggctaccga aatcgccaaa gaattgatgc cagatgttgc tattgatggt     720

gaattacaat tggatgctgc cttggtaaaa gaagttgctg aattgaaagc tccaggttca     780

aaagttgctg gttgtgctaa tgttttgatc ttcccagact tacaagctgg taacattggt     840

tacaagttgg ttcaaagatt ggctaaggct aatgccattg gtccaattac tcaaggtatg     900

ggtgctccag ttaatgattt gtctagaggt tgttcctaca gagatatcgt tgatgttatt     960

gctactaccg ctgttcaagc tcaataa                                         987


<210> SEQ ID NO 77
<211> LENGTH: 733
<212> TYPE: PRT
<213> ORGANISM: Aphanomyces astaci

<400> SEQUENCE: 77

Met Ser His Gln Phe Thr Thr Lys Ser Val Ala Ser Gln Ser Thr Met
1               5                   10                  15

Leu Arg Val Arg Pro Phe Leu Ser Ser Arg Lys Ala Ala Ile Thr Leu
            20                  25                  30

Leu Pro Arg Ala Thr Thr Ser Arg Phe Phe Thr Asp Asp Ala Thr Lys
```

```
        35                  40                  45

Lys Asn Asp Arg Leu Leu Val Met Thr Asn Gly Gly Val Ala Lys His
    50                  55                  60

Ser His Leu Leu Leu Gly Leu Met Asn Lys Leu Ser Tyr Thr Phe Pro
65                  70                  75                  80

Ser Val Gly Tyr Phe Arg Pro Val Ala Pro Asn Phe His Ser Thr His
                85                  90                  95

Gly Asp His His Val Asp Leu Ile Arg Ser Glu Phe Lys Ile Lys Asp
            100                 105                 110

Glu Pro Tyr Gln Leu Val Gly Met Thr Gln Ala Asp Ile Thr His Ala
        115                 120                 125

His Leu Glu Gly Asp Thr Asp Ser Val Ile Asp Thr Met Leu Ser Lys
    130                 135                 140

Phe Glu Tyr Leu Arg Glu Lys His Asp Phe Val Val Met Glu Gly Ala
145                 150                 155                 160

Val Leu Asp Thr Ser Pro Glu Leu Ser Trp Glu Leu Asn Val Asp Ile
                165                 170                 175

Ala Lys Ser Leu Asn Ala Pro Val Leu Leu Thr Val Asp Ala Asp Asp
            180                 185                 190

Leu Thr Val Asp Pro Ala Leu His Trp Thr Ala Ala Glu Ser Val Ala
        195                 200                 205

Trp Leu Ala Asp Gln Ile Thr Thr Arg Val Leu Leu Ala Lys Asp Met
    210                 215                 220

Ala His Ala Glu Gly Leu Thr His Val Gly Thr Ile Val Asn Arg Val
225                 230                 235                 240

Lys Thr Asp Asp Ala Leu Glu Leu Arg Asp Leu Val His Ala Gln Ile
                245                 250                 255

Lys Ala Arg Gly Phe Asp Pro Thr Lys Leu Leu Gly Ile Leu Pro Leu
            260                 265                 270

Asp Pro Val Leu Asn Ser Lys Arg Leu Asn Glu Val Val Ala Gln Leu
        275                 280                 285

His Ala Lys Gln Leu Tyr Gly Asn Pro Met Ser Asn Ser Val Val Val
    290                 295                 300

Thr Asp Gly Leu Met Ala Thr Thr Glu Leu Lys Asp Leu Phe Lys His
305                 310                 315                 320

Ile Asn Lys His Asp Asp Gly Leu Leu Val Ile Val Ser Ser Glu Arg
                325                 330                 335

Thr Asp Val Ile Leu Gly Leu Leu Ala Ser Arg Leu Ser Gly Ala Leu
            340                 345                 350

Pro Gln Ile Ser Gly Ile Ile Leu Thr Asn Gly Gly Ile Pro Gln Asn
        355                 360                 365

Glu Cys Gln Asp Ile Leu Ile Gly Leu Ala Gln Ile Asp Lys Ala Ser
    370                 375                 380

Val Pro Ile Tyr Ser Val Glu Leu Asp Ser Tyr Arg Thr Ala Ile Ala
385                 390                 395                 400

Leu Ser Lys Val Thr Cys Asp Ile Leu Pro Thr Ser Gln Asn Lys Ile
                405                 410                 415

Gln Gln Ala Tyr Ile Leu Phe Asp Thr Asn Val Glu Ser Asp Glu Leu
            420                 425                 430

Leu Ser His Leu Ile Glu Arg Thr Gly Gly His Gly Arg Thr Pro Lys
        435                 440                 445

Gln Phe Lys His Phe Leu Phe Glu Ala Ser Arg Lys Ala Asp Gln His
    450                 455                 460
```

```
Ile Val Leu Thr Glu Gly Glu Asp Asp Arg Ile Leu Gln Ala Ala Asp
465                 470                 475                 480

Glu Val Leu Arg Arg Gly Ile Ala Arg Leu Thr Ile Leu Gly Asp Val
                485                 490                 495

Glu Ser Ile Asn Ala Arg Ala Lys Thr Leu Arg Leu Asp Leu Ser Gln
            500                 505                 510

Ala Thr Leu Leu Asp Pro Ser Lys Ala Asp Lys Leu Ala Thr Tyr Ala
        515                 520                 525

Asp His Tyr Phe Glu Lys Arg Lys Ser Lys Gly Ile Thr Pro Glu Leu
    530                 535                 540

Ala Lys Glu Thr Val Gly Glu Ala Thr Tyr Phe Gly Thr Val Met Val
545                 550                 555                 560

Asp Leu Asp Asp Ala Asp Gly Met Val Ser Gly Val Cys His Thr Thr
                565                 570                 575

Ala Asn Thr Ile Arg Pro Ala Leu Gln Leu Ile Lys Thr Arg Pro Asp
            580                 585                 590

Ile Pro Leu Val Ser Ser Val Phe Phe Met Cys Leu Glu His Asp Val
        595                 600                 605

Val Leu Tyr Gly Asp Cys Ala Val Asn Thr Asp Pro Thr Ala Gln Gln
    610                 615                 620

Leu Ala Gln Ile Ala Val Gln Ser Ala Glu Ser Ala Val Ala Phe Gly
625                 630                 635                 640

Ile Glu Pro Arg Val Ala Leu Leu Ser Tyr Ala Thr Gly Asp Ser Asn
                645                 650                 655

Lys Gly Pro Ile Ile Asp Lys Val Arg Glu Ala Thr Lys Leu Ala Gln
            660                 665                 670

Ser Met Ala Pro Gly Val Ser Ile Tyr Gly Pro Ile Gln Tyr Asp Ala
        675                 680                 685

Ala Thr Asn Pro Ser Ile Ala Lys Gln Lys Val Lys Gly Leu Lys Gln
    690                 695                 700

Ser Glu Met Glu Val Ala Gly His Ala Asn Val Leu Val Phe Pro Asp
705                 710                 715                 720

Leu Asn Thr Gly Asn Asn Thr Tyr Lys Ala Val Arg Val
                725                 730


<210> SEQ ID NO 78
<211> LENGTH: 2202
<212> TYPE: DNA
<213> ORGANISM: Aphanomyces astaci

<400> SEQUENCE: 78

atgtcccacc agttcaccac caagtccgtc gcctcccagt ccaccatgct gcgagtccga      60

cccttcctgt cctcccgaaa ggccgccatc accctgctgc cccgagccac cacctcccga     120

ttcttcaccg acgacgccac caagaagaac gaccgactgc tggtcatgac caacggcggc     180

gtcgccaagc actcccacct gctgctgggc ctgatgaaca agctgtccta caccttcccc     240

tccgtcggct acttccgacc cgtcgccccc aacttccact ccacccacgg cgaccaccac     300

gtcgacctga tccgatccga gttcaagatc aaggacgagc cctaccagct ggtcggcatg     360

acccaggccg acatcaccca cgcccacctg gagggcgaca ccgactccgt catcgacacc     420

atgctgtcca agttcgagta cctgcgagag aagcacgact tcgtcgtcat ggagggcgcc     480

gtcctggaca cctcccccga gctgtcctgg gagctgaacg tcgacatcgc caagtccctg     540

aacgcccccg tcctgctgac cgtcgacgcc gacgacctga ccgtcgaccc cgccctgcac     600
```

```
tggaccgccg ccgagtccgt cgcctggctg gccgaccaga tcaccacccg agtcctgctg    660

gccaaggaca tggcccacgc cgagggcctg acccacgtcg gcaccatcgt caaccgagtc    720

aagaccgacg acgccctgga gctgcgagac ctggtccacg cccagatcaa ggcccgaggc    780

ttcgacccca ccaagctgct gggcatcctg cccctggacc ccgtcctgaa ctccaagcga    840

ctgaacgagg tcgtcgccca gctgcacgcc aagcagctgt acggcaaccc catgtccaac    900

tccgtcgtcg tcaccgacgg cctgatggcc accaccgagc tgaaggacct gttcaagcac    960

atcaacaagc acgacgacgg cctgctggtc atcgtctcct ccgagcgaac cgacgtcatc   1020

ctgggcctgc tggcctcccg actgtccggc gccctgcccc agatctccgg catcatcctg   1080

accaacggcg gcatccccca gaacgagtgc caggacatcc tgatcggcct ggcccagatc   1140

gacaaggcct ccgtccccat ctactccgtc gagctggact cctaccgaac cgccatcgcc   1200

ctgtccaagg tcacctgcga catcctgccc acctcccaga acaagatcca gcaggcctac   1260

atcctgttcg acaccaacgt cgagtccgac gagctgctgt cccacctgat cgagcgaacc   1320

ggcggccacg gccgaacccc caagcagttc aagcacttcc tgttcgaggc ctcccgaaag   1380

gccgaccagc acatcgtcct gaccgagggc gaggacgacc gaatcctgca ggccgccgac   1440

gaggtcctgc gacgaggcat cgcccgactg accatcctgg gcgacgtcga gtccatcaac   1500

gcccgagcca agaccctgcg actggacctg tcccaggcca ccctgctgga cccctccaag   1560

gccgacaagc tggccaccta cgccgaccac tacttcgaga agcgaaagtc caagggcatc   1620

acccccgagc tggccaagga gaccgtcggc gaggccacct acttcggcac cgtcatggtc   1680

gacctggacg acgccgacgg catggtctcc ggcgtctgcc acaccaccgc caacaccatc   1740

cgacccgccc tgcagctgat caagacccga cccgacatcc ccctggtctc ctccgtcttc   1800

ttcatgtgcc tggagcacga cgtcgtcctg tacggcgact gcgccgtcaa caccgacccc   1860

accgcccagc agctggccca gatcgccgtc cagtccgccg agtccgccgt cgccttcggc   1920

atcgagcccc gagtcgccct gctgtcctac gccaccggcg actccaacaa gggccccatc   1980

atcgacaagg tccgagaggc caccaagctg gcccagtcca tggcccccgg cgtctccatc   2040

tacggcccca tccagtacga cgccgccacc aacccctcca tcgccaagca gaaggtcaag   2100

ggcctgaagc agtccgagat ggaggtcgcc ggccacgcca acgtcctggt cttccccgac   2160

ctgaacaccg gcaacaacac ctacaaggcc gtccgagtct aa                      2202
```

<210> SEQ ID NO 79
<211> LENGTH: 792
<212> TYPE: PRT
<213> ORGANISM: Chlamydomonas reinhardtii

<400> SEQUENCE: 79

```
Met Ser Leu Asn Ser Ser Thr Met Ser Arg Arg Gln Ala Val Ala Gly
1               5                   10                  15

Ala Pro Ala Val Ala Pro Phe Arg His Ala Gly Leu Phe Pro Arg Val
            20                  25                  30

Arg Leu Cys Ala Asn Arg Arg Val Ala Arg Val Ala Pro Lys Ala Ala
        35                  40                  45

Gly Asn Gly Asn Ile Ala Gln Gly Glu Gln Gly Phe Asp Thr Leu Phe
    50                  55                  60

Leu Ser Asp Ile Ser Leu Val Gly Gln Arg Thr Pro Leu Leu Leu Gly
65                  70                  75                  80

Phe Phe Asn Tyr Phe Glu Arg His Leu Pro His Val Gly Phe Phe Glu
```

-continued

```
                85                  90                  95

Pro Ile Ala Ala Glu Ala Leu Ala Ser Ser Glu Leu Arg Ile Asp Arg
            100                 105                 110

His Val Glu Leu Val Tyr Lys Val Phe Asn Leu Lys Gly Asp Val Arg
        115                 120                 125

Ala Met Thr Gly Val Gln Asp Ala Glu Ala Ala Arg Met Ile Ala Asn
    130                 135                 140

Gly Gln His Ser Glu Leu Leu Asp Lys Ile Tyr Ser Gln Tyr Ala Ser
145                 150                 155                 160

Tyr Lys Glu Gly Gln Asp Leu Val Leu Val Glu Gly Pro Gly Pro Leu
                165                 170                 175

Met Gly Gly Thr Glu Leu Asp Ala Gln Ile Ala Ala Ala Leu Asn Ala
            180                 185                 190

Pro Val Leu Met Thr Met Thr Gly Gln Pro Asn Ala Thr Val Ala Asp
        195                 200                 205

Tyr Tyr Asn Arg Ala Met Val Lys Arg Gln Val Phe Leu Asp His His
    210                 215                 220

Val Glu Val Leu Gly Leu Val Met Asn Gly Leu Pro Arg Gln Ser His
225                 230                 235                 240

Ala Ile Leu Ser Gly Gln Leu Arg Asp Lys Phe Ala Ala Ala Gly Leu
                245                 250                 255

Pro Phe Ala Gly Ala Ile Pro Thr Asp Ile Met Leu Arg Asn Val Arg
            260                 265                 270

Leu Asp Glu Val Gln Thr Ala Met Gly Ala Gln Arg Leu Tyr Gly Asp
        275                 280                 285

Ser Leu Leu Thr Asp Val Glu Phe Asp Asp Val Val Val Ala Ser Gln
    290                 295                 300

Arg Leu Glu Glu Leu Leu Glu Ile Leu Ala Glu Arg Pro Met Gly Arg
305                 310                 315                 320

Pro Leu Val Val Thr Ser Ala Asp Arg Leu Asp Ile Val Leu Gly Leu
                325                 330                 335

Leu Ala Ala Gln Leu Ser Val Ser Gly Pro Gly Val Ala Gly Ile Leu
            340                 345                 350

Leu Thr Gln Ala Gly Ser Ala Arg Ser Gly Arg Asn Tyr Ala Arg Asp
        355                 360                 365

Thr Ile Asp Arg Ile Phe Ala Gly Leu Ser Ser Ser Gly Leu Tyr Lys
    370                 375                 380

Gly Ser Leu Leu Pro Val Leu Val Thr Asp Met Pro Leu Arg Asp Ala
385                 390                 395                 400

Ile Arg Lys Leu Asp Asn Leu Asp Ala Ala Ile Leu Pro Ser Ser Thr
                405                 410                 415

Arg Lys Ile Ser Gln Cys Lys Arg Leu Phe Glu Gln Tyr Val Asp Ala
            420                 425                 430

Asn Ala Val Val Ala Arg Leu Gln Asn Met Val Arg Pro Asn Arg Met
        435                 440                 445

Thr Pro Lys Met Phe Met His Thr Leu Lys Ser Met Cys Asn Ala Thr
    450                 455                 460

Pro Gln His Ile Val Leu Pro Glu Ser Glu Asp Lys Arg Val Leu Ala
465                 470                 475                 480

Ala Ala Ala Asp Val Val Gln Arg Gly Leu Ala Lys Ile Thr Leu Leu
                485                 490                 495

Gly Asp Pro Thr Thr Ile Leu Ala Glu Ala Ala Lys Leu Gly Leu Asp
            500                 505                 510
```

```
Leu Ser Gly Cys Asn Ile His Asn Pro Asn Thr Ser Asp Arg Phe Asp
        515                 520                 525

Lys Tyr Val Asp Met Leu Val Glu Ala Arg Lys Lys Lys Gly Met Thr
    530                 535                 540

Arg Glu Val Ala Ala Asp Thr Leu His Gly Asp Val Asn Phe Phe Ala
545                 550                 555                 560

Thr Met Met Ile Val Ala Gly Asp Ala Asp Gly Met Val Ser Gly Ala
                565                 570                 575

Val His Thr Thr Ala Ser Thr Val Arg Pro Ala Leu Gln Val Leu Lys
            580                 585                 590

Ser Pro Asp Thr Pro Leu Val Ser Ser Val Phe Ile Met Cys Leu Pro
        595                 600                 605

Asp Arg Val Val Val Tyr Gly Asp Cys Ala Val Asn Val Asn Pro Ser
    610                 615                 620

Ala Ala Asp Leu Ala Gln Ile Ala Ile Thr Ser Asn Asp Thr Ala Ala
625                 630                 635                 640

Ala Phe Gly Ile Glu Pro Arg Val Ala Met Leu Ser Tyr Ser Thr Leu
                645                 650                 655

Gly Ser Gly Ser Gly Pro Asp Val Gln Lys Val Ser Glu Ala Val Ala
            660                 665                 670

Ile Val Lys Gln Arg Arg Pro Asp Ile Lys Val Glu Gly Pro Ile Gln
        675                 680                 685

Tyr Asp Ala Ala Ile Asp Pro Lys Val Ala Ala Val Lys Val Gln Gly
    690                 695                 700

Leu Ser Glu Val Ala Gly Lys Ala Thr Val Phe Ile Phe Pro Asp Leu
705                 710                 715                 720

Asn Thr Gly Asn Asn Thr Tyr Lys Ala Val Gln Gln Ser Thr Gly Ala
                725                 730                 735

Ile Ala Met Gly Pro Val Met Gln Gly Leu Leu Arg Pro Val Asn Asp
            740                 745                 750

Leu Ser Arg Gly Cys Thr Val Pro Asp Ile Ile Asn Thr Ile Cys Val
        755                 760                 765

Thr Ser Ile Gln Ala Ser Arg Met Ser Ser Ala Ala Arg Ala Ala Ala
    770                 775                 780

Ala Lys Ala Ala Val Ala Ala Val
785                 790
```

<210> SEQ ID NO 80
<211> LENGTH: 2379
<212> TYPE: DNA
<213> ORGANISM: Chlamydomonas reinhardtii

<400> SEQUENCE: 80

```
atgtccctga actcctccac catgtcccga cgacaggccg tcgccggcgc ccccgccgtc      60

gccccccttcc gacacgccgg cctgttcccc cgagtccgac tgtgcgccaa ccgacgagtc    120

gcccgagtcg cccccaaggc cgccggcaac ggcaacatcg cccagggcga gcagggcttc    180

gacaccctgt tcctgtccga catctccctg gtcggccagc gaaccccccct gctgctgggc    240

ttcttcaact acttcgagcg acacctgccc cacgtcggct tcttcgagcc catcgccgcc    300

gaggccctgg cctcctccga gctgcgaatc gaccgacacg tcgagctggt ctacaaggtc    360

ttcaacctga agggcgacgt ccgagccatg accggcgtcc aggacgccga ggccgcccga    420

atgatcgcca acggccagca ctccgagctg ctggacaaga tctactccca gtacgcctcc    480
```

```
tacaaggagg gccaggacct ggtcctggtc gagggccccg gccccctgat gggcggcacc    540
gagctggacg cccagatcgc cgccgccctg aacgccccccg tcctgatgac catgaccggc    600
cagcccaacg ccaccgtcgc cgactactac aaccgagcca tggtcaagcg acaggtcttc    660
ctggaccacc acgtcgaggt cctgggcctg gtcatgaacg gcctgccccg acagtcccac    720
gccatcctgt ccggccagct gcgagacaag ttcgccgccg ccggcctgcc cttcgccggc    780
gccatcccca ccgacatcat gctgcgaaac gtccgactgg acgaggtcca gaccgccatg    840
ggcgcccagc gactgtacgg cgactccctg ctgaccgacg tcgagttcga cgacgtcgtc    900
gtcgcctccc agcgactgga ggagctgctg gagatcctgg ccgagcgacc catgggccga    960
cccctggtcg tcacctccgc cgaccgactg gacatcgtcc tgggcctgct ggccgcccag   1020
ctgtccgtct ccggccccgg cgtcgccggc atcctgctga cccaggccgg ctccgcccga   1080
tccggccgaa actacgcccg agacaccatc gaccgaatct tcgccggcct gtcctcctcc   1140
ggcctgtaca agggctccct gctgcccgtc ctggtcaccg acatgcccct gcgagacgcc   1200
atccgaaagc tggacaacct ggacgccgcc atcctgccct cctccacccg aaagatctcc   1260
cagtgcaagc gactgttcga gcagtacgtc gacgccaacg ccgtcgtcgc ccgactgcag   1320
aacatggtcc gacccaaccg aatgaccccc aagatgttca tgcacaccct gaagtccatg   1380
tgcaacgcca ccccccagca catcgtcctg cccgagtccg aggacaagcg agtcctggcc   1440
gccgccgccg acgtcgtcca gcgaggcctg gccaagatca ccctgctggg cgaccccacc   1500
accatcctgg ccgaggccgc caagctgggc ctggacctgt ccggctgcaa catccacaac   1560
cccaacacct ccgaccgatt cgacaagtac gtcgacatgc tggtcgaggc ccgaaagaag   1620
aagggcatga cccgagaggt cgccgccgac accctgcacg gcgacgtcaa cttcttcgcc   1680
accatgatga tcgtcgccgg cgacgccgac ggcatggtct ccggcgccgt ccacaccacc   1740
gcctccaccg tccgacccgc cctgcaggtc ctgaagtccc ccgacacccc cctggtctcc   1800
tccgtcttca tcatgtgcct gcccgaccga gtcgtcgtct acggcgactg cgccgtcaac   1860
gtcaacccct ccgccgccga cctggcccag atcgccatca cctccaacga caccgccgcc   1920
gccttcggca tcgagccccg agtcgccatg ctgtcctact ccaccctggg ctccggctcc   1980
ggccccgacg tccagaaggt ctccgaggcc gtcgccatcg tcaagcagcg acgacccgac   2040
atcaaggtcg agggccccat ccagtacgac gccgccatcg accccaaggt cgccgccgtc   2100
aaggtccagg gcctgtccga ggtcgccggc aaggccaccg tcttcatctt ccccgacctg   2160
aacaccggca acaacaccta caaggccgtc cagcagtcca ccggcgccat cgccatgggc   2220
cccgtcatgc agggcctgct gcgacccgtc aacgacctgt cccgaggctg caccgtcccc   2280
gacatcatca acaccatctg cgtcacctcc atccaggcct cccgaatgtc ctccgccgcc   2340
cgagccgccg ccgccaaggc cgccgtcgcc gccgtctaa                          2379
```

<210> SEQ ID NO 81
<211> LENGTH: 353
<212> TYPE: PRT
<213> ORGANISM: Perkinsus marinus

<400> SEQUENCE: 81

```
Met Leu Ser Arg Ser Thr Ala Arg Cys Ala Pro Ala Ala Leu Ala Gly
1               5                   10                  15

Ile Arg Gln Arg Ala Met Gln Thr Gly Leu Lys Lys Phe Ile Ala Phe
            20                  25                  30

Pro Glu Val Ser Asp Glu Arg Val Ile Pro Ala Val Ala Lys Val Leu
```

-continued

```
        35                  40                  45

Lys Glu Lys Ile Ala Gln Pro Val Leu Val Gly Asp Arg Glu Ala Ala
    50                  55                  60

Tyr Lys Cys Ala Lys Ala Asn Asn Val Ser Leu Glu Gly Val Arg Ile
65                  70                  75                  80

Ile Asp Pro Ala Leu His Pro Glu Val Val Glu Gln Thr Ala Thr Val
            85                  90                  95

Leu Phe Gln Lys Arg Gln Lys Lys Gly Met Thr Ile Asp Ala Ala Leu
            100                 105                 110

Asp Thr Val Lys Asn Ser Pro Leu Met Met Ala Asn Leu Met Leu Thr
        115                 120                 125

Thr Gly His Val Gln Gly Cys Val Ala Gly Ala Ser His Thr Ser Ala
    130                 135                 140

Asp Val Ala Arg Ala Ala Leu Gln Thr Val Gly Val Lys Lys Gly Leu
145                 150                 155                 160

Lys Thr Ala Ser Ser Phe Phe Ile Ile Ala Lys Asp Asp Lys Thr Phe
            165                 170                 175

Leu Phe Ser Asp Cys Gly Phe Cys Ile Ala Pro Ser Ile Ser Gln Leu
            180                 185                 190

Ala Glu Ile Ala Ile Thr Thr Ala Gln Thr Cys Glu Asp Val Leu Ala
        195                 200                 205

Ser Thr Pro Arg Ile Ala Met Leu Ser Phe Ser Thr Phe Gly Ser Ala
    210                 215                 220

Lys His Glu Tyr Val Thr Arg Val Glu Glu Ala Leu Ala Leu Ala Arg
225                 230                 235                 240

Lys Glu Arg Pro Asp Leu Ala Ile Asp Gly Glu Met Gln Val Asp Ala
            245                 250                 255

Ala Ile Val Pro Glu Val Ala Ala Lys Lys Ala Pro Gly Ser Lys Val
            260                 265                 270

Ala Gly His Ala Asn Val Leu Ile Phe Pro Asp Leu Asn Ala Gly Asn
        275                 280                 285

Ile Ala Tyr Lys Val Ala Glu Arg Phe Gly Gly Tyr Gln Ala Val Gly
    290                 295                 300

Pro Val Phe Gln Gly Leu Ala Tyr Pro Thr Asn Asp Leu Ser Arg Gly
305                 310                 315                 320

Cys His Ala Glu Asp Val Val Asp Ala Ala Ala Val Thr Val Leu Gln
            325                 330                 335

Gly Ala Ser Ile Pro Ile Pro Thr Gly Pro Ala Pro Gly Asp Val Leu
            340                 345                 350

Asn
```

<210> SEQ ID NO 82
<211> LENGTH: 1062
<212> TYPE: DNA
<213> ORGANISM: Perkinsus marinus

<400> SEQUENCE: 82

```
atgctgtccc gatccaccgc ccgatgcgcc cccgccgccc tggccggcat ccgacagcga      60

gccatgcaga ccggcctgaa gaagttcatc gccttccccg aggtctccga cgagcgagtc     120

atccccgccg tcgccaaggt cctgaaggag aagatcgccc agcccgtcct ggtcggcgac     180

cgagaggccg cctacaagtg cgccaaggcc aacaacgtct ccctggaggg cgtccgaatc     240

atcgaccccg ccctgcaccc cgaggtcgtc gagcagaccg ccaccgtcct gttccagaag     300
```

```
cgacagaaga agggcatgac catcgacgcc gccctggaca ccgtcaagaa ctcccccctg    360

atgatggcca acctgatgct gaccaccggc cacgtccagg gctgcgtcgc cggcgcctcc    420

cacacctccg ccgacgtcgc ccgagccgcc ctgcagaccg tcggcgtcaa gaagggcctg    480

aagaccgcct cctccttctt catcatcgcc aaggacgaca agaccttcct gttctccgac    540

tgcggcttct gcatcgcccc ctccatctcc cagctggccg agatcgccat caccaccgcc    600

cagacctgcg aggacgtcct ggcctccacc ccccgaatcg ccatgctgtc cttctccacc    660

ttcggctccg ccaagcacga gtacgtcacc cgagtcgagg aggccctggc cctggcccga    720

aaggagcgac ccgacctggc catcgacggc gagatgcagg tcgacgccgc catcgtcccc    780

gaggtcgccg ccaagaaggc ccccggctcc aaggtcgccg gccacgccaa cgtcctgatc    840

ttccccgacc tgaacgccgg caacatcgcc tacaaggtcg ccgagcgatt cggcggctac    900

caggccgtcg gccccgtctt ccagggcctg gcctacccca ccaacgacct gtcccgaggc    960

tgccacgccg aggacgtcgt cgacgccgcc gccgtcaccg tcctgcaggg cgcctccatc   1020

cccatcccca ccggccccgc ccccggcgac gtcctgaact aa                      1062


<210> SEQ ID NO 83
<211> LENGTH: 297
<212> TYPE: PRT
<213> ORGANISM: Perkinsus marinus

<400> SEQUENCE: 83

Val Gly Gly Arg Pro Arg Gly Asn Tyr Lys Cys Ala Lys Ala Asn Asn
1               5                   10                  15

Val Ser Leu Glu Gly Val Arg Ile Ile Asp Pro Ala Leu His Pro Glu
            20                  25                  30

Val Val Glu Gln Thr Ala Thr Val Leu Phe Gln Lys Arg Gln Lys Lys
        35                  40                  45

Gly Met Thr Ile Asp Ala Ala Leu Asp Thr Val Lys Asn Ser Pro Leu
    50                  55                  60

Met Met Ala Asn Leu Met Leu Thr Thr Gly His Val Gln Gly Cys Val
65                  70                  75                  80

Ala Gly Ala Ser His Thr Ser Ala Asp Val Ala Arg Ala Ala Leu Gln
                85                  90                  95

Thr Val Gly Val Lys Lys Gly Leu Lys Thr Ala Ser Ser Phe Phe Ile
            100                 105                 110

Ile Ala Lys Asp Asp Lys Thr Phe Leu Phe Ser Asp Cys Gly Phe Cys
        115                 120                 125

Ile Ala Pro Ser Ile Ser Gln Leu Ala Glu Ile Ala Ile Thr Thr Ala
    130                 135                 140

Gln Thr Cys Glu Asp Val Leu Ala Ser Thr Pro Arg Ile Ala Met Leu
145                 150                 155                 160

Ser Phe Ser Thr Phe Gly Ser Ala Lys His Glu Tyr Val Thr Arg Val
                165                 170                 175

Glu Glu Ala Leu Ala Leu Ala Arg Lys Glu Arg Pro Asp Leu Ala Ile
            180                 185                 190

Asp Gly Glu Met Gln Val Asp Ala Ala Ile Val Pro Glu Val Ala Ala
        195                 200                 205

Lys Lys Ala Pro Gly Ser Lys Val Ala Gly Gln Ala Asn Val Leu Ile
    210                 215                 220

Phe Pro Asp Leu Asn Ala Gly Asn Ile Ala Tyr Lys Val Ala Glu Arg
225                 230                 235                 240
```

```
Phe Gly Gly Tyr Gln Ala Val Gly Pro Val Phe Gln Gly Leu Ala Tyr
                245                 250                 255

Pro Thr Asn Asp Leu Ser Arg Gly Cys His Ala Glu Asp Val Val Asp
            260                 265                 270

Ala Ala Ala Val Thr Val Leu Gln Gly Ala Ser Ile Pro Ile Pro Thr
        275                 280                 285

Gly Pro Ala Pro Gly Asp Val Leu Asn
    290                 295


<210> SEQ ID NO 84
<211> LENGTH: 894
<212> TYPE: DNA
<213> ORGANISM: Perkinsus marinus

<400> SEQUENCE: 84

gtcggcggcc gaccccgagg caactacaag tgcgccaagg ccaacaacgt ctccctggag      60

ggcgtccgaa tcatcgaccc cgccctgcac cccgaggtcg tcgagcagac cgccaccgtc     120

ctgttccaga agcgacagaa gaagggcatg accatcgacg ccgccctgga caccgtcaag     180

aactcccccc tgatgatggc caacctgatg ctgaccaccg gccacgtcca gggctgcgtc     240

gccggcgcct cccacacctc cgccgacgtc gcccgagccg ccctgcagac cgtcggcgtc     300

aagaagggcc tgaagaccgc ctcctccttc ttcatcatcg ccaaggacga caagaccttc     360

ctgttctccg actgcggctt ctgcatcgcc ccctccatct cccagctggc cgagatcgcc     420

atcaccaccg cccagacctg cgaggacgtc ctggcctcca ccccccgaat cgccatgctg     480

tccttctcca ccttcggctc cgccaagcac gagtacgtca cccgagtcga ggaggccctg     540

gccctggccc gaaaggagcg acccgacctg gccatcgacg gcgagatgca ggtcgacgcc     600

gccatcgtcc ccgaggtcgc cgccaagaag gcccccggct ccaaggtcgc cggccaggcc     660

aacgtcctga tcttccccga cctgaacgcc ggcaacatcg cctacaaggt cgccgagcga     720

ttcggcggct accaggccgt cggccccgtc ttccagggcc tggcctaccc caccaacgac     780

ctgtcccgag gctgccacgc cgaggacgtc gtcgacgccg ccgccgtcac cgtcctgcag     840

ggcgcctcca tccccatccc caccggcccc gcccccggcg acgtcctgaa ctaa           894


<210> SEQ ID NO 85
<211> LENGTH: 219
<212> TYPE: PRT
<213> ORGANISM: Perkinsus marinus

<400> SEQUENCE: 85

Val Ser Pro Gly Ala Ser His Thr Ser Ala Asp Val Ala Arg Ala Ala
1               5                   10                  15

Leu Gln Thr Val Gly Val Lys Lys Gly Leu Lys Thr Ala Ser Ser Phe
            20                  25                  30

Phe Ile Ile Ala Lys Asp Asp Lys Thr Phe Leu Phe Ser Asp Cys Gly
        35                  40                  45

Phe Cys Ile Ala Pro Ser Ile Ser Gln Leu Ala Glu Ile Ala Ile Thr
    50                  55                  60

Thr Ala Gln Thr Cys Glu Asp Val Leu Ala Thr Thr Pro Arg Val Ala
65                  70                  75                  80

Met Leu Ser Phe Ser Thr Phe Gly Ser Ala Lys His Glu Tyr Val Thr
                85                  90                  95

Arg Val Glu Glu Ala Leu Ala Leu Ala Arg Lys Glu Lys Pro Asp Leu
            100                 105                 110
```

```
Ala Ile Asp Gly Glu Met Gln Val Asp Ala Ala Ile Val Pro Glu Val
        115                 120                 125

Ala Ala Lys Lys Ala Pro Gly Ser Lys Val Ala Gly His Ala Asn Val
    130                 135                 140

Leu Ile Phe Pro Asp Leu Asn Ala Gly Asn Ile Ala Tyr Lys Val Ala
145                 150                 155                 160

Glu Arg Phe Gly Gly Tyr Gln Ala Val Gly Pro Ile Phe Gln Gly Leu
                165                 170                 175

Ala Tyr Pro Thr Asn Asp Leu Ser Arg Gly Cys His Ala Glu Asp Val
            180                 185                 190

Val Asp Ala Ala Ala Val Thr Val Leu Gln Gly Ser Ser Ile Pro Ile
        195                 200                 205

Pro Thr Gly Pro Ala Pro Gly Asp Ile Leu Asn
    210                 215


<210> SEQ ID NO 86
<211> LENGTH: 660
<212> TYPE: DNA
<213> ORGANISM: Perkinsus marinus

<400> SEQUENCE: 86

gtctccccg gcgcctccca cacctccgcc gacgtcgccc gagccgccct gcagaccgtc      60

ggcgtcaaga agggcctgaa gaccgcctcc tccttcttca tcatcgccaa ggacgacaag    120

accttcctgt tctccgactg cggcttctgc atcgccccct ccatctccca gctggccgag    180

atcgccatca ccaccgccca gacctgcgag gacgtcctgg ccaccacccc ccgagtcgcc    240

atgctgtcct tctccacctt cggctccgcc aagcacgagt acgtcacccg agtcgaggag    300

gccctggccc tggcccgaaa ggagaagccc gacctggcca tcgacggcga gatgcaggtc    360

gacgccgcca tcgtccccga ggtcgccgcc aagaaggccc ccggctccaa ggtcgccggc    420

cacgccaacg tcctgatctt ccccgacctg aacgccggca acatcgccta caaggtcgcc    480

gagcgattcg gcggctacca ggccgtcggc cccatcttcc agggcctggc ctaccccacc    540

aacgacctgt cccgaggctg ccacgccgag gacgtcgtcg acgccgccgc cgtcaccgtc    600

ctgcagggct cctccatccc catccccacc ggccccgccc ccggcgacat cctgaactaa    660


<210> SEQ ID NO 87
<211> LENGTH: 771
<212> TYPE: PRT
<213> ORGANISM: Phytophthora infestans

<400> SEQUENCE: 87

Met Trp Thr Leu Arg His Ser Leu Arg Arg Ser Val Gly Met Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Thr
    50                  55                  60

Lys Val Gly Tyr Phe Arg Pro Ile Gln Pro Ser Pro Asp Ser Ser Met
65                  70                  75                  80

Ala Asp His His Val Asp Val Met Lys His Gln Leu Glu Leu Ser Lys
                85                  90                  95

Asp Val Glu Glu Leu Tyr Gly Val Thr Ser Ser Arg Ala Met Glu Ala
            100                 105                 110
```

```
Met Leu Thr Gly Lys Gly Asp Asp Ile Val Glu Glu Ile Leu Glu Arg
        115                 120                 125

Tyr Glu Glu Cys Arg Lys Gly His Asp Phe Met Ile Ile Glu Gly Ser
    130                 135                 140

Gln Val Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ser Ser Asn Ala Leu Leu Glu Glu Met Val Ser Arg
            180                 185                 190

Thr Val Met Gly Arg Asp Gln Ala Glu Ala Ala Gly Leu Asn Tyr Leu
        195                 200                 205

Gly Thr Ile Ala Asn Arg Val Arg Ala Lys Asp Val Ala Thr Leu Arg
    210                 215                 220

Glu Asp Leu Lys Leu Lys Met Gly Lys Lys Glu Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Lys Gln Leu Phe Gly Asn Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
305                 310                 315                 320

Pro Gly Val Leu Pro Asn Ile Ser Ala Ile Val Leu Thr Asn Gly Asn
                325                 330                 335

Tyr Pro His Ser Asn Thr Gln Glu Ile Leu Lys Gly Val Glu Ala Leu
            340                 345                 350

Asp Lys Thr Gly Leu Ser Leu Pro Ile Phe Ser Thr Pro Asn Asp Thr
        355                 360                 365

Asn Ser Thr Ala Asp Gly Phe Ala Lys Val Ser Thr Tyr Ile Leu Pro
    370                 375                 380

Ser Ser Lys Leu Lys Ile Asp Arg Ser Lys Gln Leu Phe Asp Glu Phe
385                 390                 395                 400

Val Glu Lys Glu Met Leu Ile Gly Glu Leu Asp Glu Gly Met Val Val
                405                 410                 415

Ser Arg Ser Pro Lys Gln Phe Gln His Phe Leu Phe Ser Lys Ser Arg
            420                 425                 430

Ala Val Gln Arg His Ile Val Leu Thr Glu Gly Glu Asp Ile Arg Val
        435                 440                 445

Leu Gln Ala Ala Asp Gln Ile Leu Arg Gln Asn Leu Ser Arg Ile Thr
    450                 455                 460

Ile Leu Gly Asp Pro Asp Glu Ile Thr Val Asn Ala Lys Met Ala Asn
465                 470                 475                 480

Leu Asp Leu Ser Arg Ala Asn Ile Ile Arg Pro Val Asp Ser His Leu
                485                 490                 495

Leu Asp Lys Tyr Val Asp Tyr Phe Tyr Ala Lys Arg Lys His Lys Gly
            500                 505                 510

Val Thr Arg Glu Leu Ala Arg Asp Tyr Cys Lys Asp Glu Thr Tyr Phe
        515                 520                 525
```

```
Gly Thr Leu Met Val Glu Leu Gly Asp Ala Asp Gly Met Val Ser Gly
    530                 535                 540

Ala Cys His Thr Thr Ala Asn Thr Ile Arg Pro Ala Leu Gln Leu Ile
545                 550                 555                 560

Lys Thr Thr Pro Asn Arg Pro Ile Val Ser Ser Ile Phe Phe Met Cys
                565                 570                 575

Leu Lys Asp Gly Val Arg Ile Tyr Gly Asp Cys Ala Val Asn Thr Asp
            580                 585                 590

Pro Ser Ala Gln Asp Leu Ala Gln Ile Ala Val Thr Ser Ala Glu Ser
        595                 600                 605

Ala Glu Ala Phe Gly Leu Ile Pro Lys Val Ala Leu Leu Ser Tyr Ala
    610                 615                 620

Thr Gly Asp Ser Asn Ser Gly Pro Ile Ile Asp Lys Val Arg Glu Ala
625                 630                 635                 640

Thr Lys Met Ala Gln Glu Leu Arg Pro Asp Leu Asp Ile Tyr Gly Pro
                645                 650                 655

Ile Gln Tyr Asp Ala Ala Val Asp Glu Ser Ile Ala Lys Thr Lys Leu
            660                 665                 670

Lys Ala Ile Pro Ser Gly Ala Lys Val Gly Gly Gln Ala Asn Val Leu
        675                 680                 685

Ile Phe Pro Asp Leu Asn Thr Gly Asn Asn Thr Tyr Lys Ala Val Gln
    690                 695                 700

Gln Ser Thr Gly Cys Ile Ala Met Gly Pro Met Leu Gln Gly Leu Arg
705                 710                 715                 720

Lys Pro Val Asn Asp Leu Ser Arg Gly Ala Thr Val Lys Asp Ile Val
                725                 730                 735

Thr Thr Val Ala Ile Thr Ala Ile Gln Ala Asp Gln Val Ile Leu Lys
            740                 745                 750

Arg Glu Ala Glu Asn Ser Lys Asn Gln Asn Gly Glu Phe Leu Glu Ser
        755                 760                 765

Ala Thr Met
    770
```

<210> SEQ ID NO 88
<211> LENGTH: 2316
<212> TYPE: DNA
<213> ORGANISM: Phytophthora infestans

<400> SEQUENCE: 88

```
atgtggaccc tgcgacactc cctgcgacga tccgtcggca tggccctgcc ccaccgacga      60

gccctgaccg ccgccgccat ctcccagggc aaggtcccca tcaacaacct gtacgtcacc     120

tccaccgagg tcaccaagaa gaccgccccc gtcctgatcg gcctggccca cgtcctggag     180

cagaagttca ccaaggtcgg ctacttccga cccatccagc cctcccccga ctcctccatg     240

gccgaccacc acgtcgacgt catgaagcac cagctggagc tgtccaagga cgtcgaggag     300

ctgtacggcg tcacctcctc ccgagccatg gaggccatgc tgaccggcaa gggcgacgac     360

atcgtcgagg agatcctgga gcgatacgag gagtgccgaa agggccacga cttcatgatc     420

atcgagggct cccaggtctc caagcacgag tccgccatgt cctggaagat caacgtcgac     480

atcgccaagg ccatcggctc cccgtcctg atggtcaccg acttcggcga cacctccgcc     540

tcctccaacg ccctgctgga ggagatggtc tcccgaaccg tcatgggccg agaccaggcc     600

gaggccgccg gcctgaacta cctgggcacc atcgccaacc gagtccgagc caaggacgtc     660

gccaccctgc gagaggacct gaagctgaag atgggcaaga aggagatccc cttcctgggc     720
```

```
ttcctgccca tggacgagat catcgcctcc aagcgactga acgaggtcac ccaccagctg    780

ggcgccaagc agctgttcgg caactccatc gccaacgacg ccgtcgtcac ctccgccgtc    840

gtcgccgcct ccgccctgaa ggacctgttc gcccacctga agaagtacaa ggacggcgcc    900

atgatcatca cctccggcga ccgatccgac ctgatgctgg gcctgatggt ctcccgactg    960

cccggcgtcc tgcccaacat ctccgccatc gtcctgacca acggcaacta cccccactcc   1020

aacacccagg agatcctgaa gggcgtcgag gccctggaca agaccggcct gtccctgccc   1080

atcttctcca cccccaacga caccaactcc accgccgacg gcttcgccaa ggtctccacc   1140

tacatcctgc cctcctccaa gctgaagatc gaccgatcca agcagctgtt cgacgagttc   1200

gtcgagaagg agatgctgat cggcgagctg gacgagggca tggtcgtctc ccgatccccc   1260

aagcagttcc agcacttcct gttctccaag tcccgagccg tccagcgaca catcgtcctg   1320

accgagggcg aggacatccg agtcctgcag gccgccgacc agatcctgcg acagaacctg   1380

tcccgaatca ccatcctggg cgaccccgac gagatcaccg tcaacgccaa gatggccaac   1440

ctggacctgt cccgagccaa catcatccga cccgtcgact cccacctgct ggacaagtac   1500

gtcgactact tctacgccaa gcgaaagcac aagggcgtca cccgagagct ggcccgagac   1560

tactgcaagg acgagaccta cttcggcacc ctgatggtcg agctgggcga cgccgacggc   1620

atggtctccg gcgcctgcca caccaccgcc aacaccatcc gacccgccct gcagctgatc   1680

aagaccaccc ccaaccgacc catcgtctcc tccatcttct tcatgtgcct gaaggacggc   1740

gtccgaatct acggcgactg cgccgtcaac accgacccct ccgcccagga cctggcccag   1800

atcgccgtca cctccgccga gtccgccgag gccttcggcc tgatccccaa ggtcgccctg   1860

ctgtcctacg ccaccggcga ctccaactcc ggccccatca tcgacaaggt ccgagaggcc   1920

accaagatgg cccaggagct gcgacccgac ctggacatct acggccccat ccagtacgac   1980

gccgccgtcg acgagtccat cgccaagacc aagctgaagg ccatcccctc cggcgccaag   2040

gtcggcggcc aggccaacgt cctgatcttc cccgacctga acaccggcaa caacacctac   2100

aaggccgtcc agcagtccac cggctgcatc gccatgggcc ccatgctgca gggcctgcga   2160

aagcccgtca acgacctgtc ccgaggcgcc accgtcaagg acatcgtcac caccgtcgcc   2220

atcaccgcca tccaggccga ccaggtcatc ctgaagcgag aggccgagaa ctccaagaac   2280

cagaacggcg agttcctgga gtccgccacc atgtaa                             2316
```

<210> SEQ ID NO 89
<211> LENGTH: 760
<212> TYPE: PRT
<213> ORGANISM: Phytophthora parasitica

<400> SEQUENCE: 89

```
Met Trp Thr Leu Arg Arg Ser Leu Arg His Ser Thr Gly Val Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Thr
    50                  55                  60

Lys Val Gly Tyr Phe Arg Pro Ile Gln Pro Ser Pro Asp Ser Ser Met
65                  70                  75                  80

Ala Asp His His Val Asp Val Met Lys Gln Gln Leu Glu Leu Ser Lys
```

```
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ala Asn Asp Ala Leu Ile Glu Glu Met Val Ser Arg
            180                 185                 190

Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu Arg
    210                 215                 220

Ala Ser Leu Lys Arg Lys Met Gly Asp Lys Asp Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Thr Gln Leu Phe Gly His Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
305                 310                 315                 320

Pro Gly Val Leu Pro Asn Ile Ser Ala Ile Val Leu Thr Asn Gly Asn
                325                 330                 335

Tyr Pro His Ser Asn Thr Gln Glu Ile Leu Lys Gly Val Gln Ala Leu
            340                 345                 350

Asp Lys Thr Ala Leu Ser Leu Pro Ile Phe Ser Thr Pro Asn Asp Thr
        355                 360                 365

Phe Ser Thr Ala Asp Gly Phe Ala Lys Val Ser Thr Asp Ile Leu Pro
    370                 375                 380

Ser Ser Lys Leu Lys Ile Asp Arg Ser Lys Gln Leu Phe Asp Glu Phe
385                 390                 395                 400

Val Glu Lys Glu Met Leu Ile Gly Glu Leu Asp Glu Gly Met Val Val
                405                 410                 415

Asn Arg Ser Pro Lys Gln Phe Gln His Phe Leu Phe Ser Lys Ser Arg
            420                 425                 430

Ala Val Gln Arg His Ile Val Leu Thr Glu Gly Glu Asp Ile Arg Val
        435                 440                 445

Leu Gln Ala Ala Asp Gln Ile Leu Arg Gln Asn Leu Ser Lys Ile Thr
    450                 455                 460

Ile Leu Gly Asp Pro Asp Glu Ile Leu Leu Asn Ala Lys Met Ala Asn
465                 470                 475                 480

Leu Asp Leu Ser Arg Ala Asn Ile Val Ser Pro Ala Asn Ser Ala Leu
                485                 490                 495

Leu Asp Lys Tyr Val Asp Tyr Phe Tyr Ala Lys Arg Lys His Lys Gly
            500                 505                 510
```

```
Val Thr Lys Glu Leu Ala Arg Asp Tyr Cys Lys Asp Glu Thr Tyr Phe
        515                 520                 525

Gly Thr Leu Met Val Glu Leu Gly Asp Ala Asp Gly Met Val Ser Gly
    530                 535                 540

Ala Cys His Thr Thr Ala Asn Thr Ile Arg Pro Ala Leu Gln Leu Ile
545                 550                 555                 560

Lys Thr Ala Pro Asn Arg Pro Ile Val Ser Ser Ile Phe Phe Met Cys
                565                 570                 575

Leu Glu Asp Gly Val Arg Ile Tyr Gly Asp Cys Ala Val Asn Thr Asp
            580                 585                 590

Pro Ser Ala Gln Asp Leu Ala Gln Ile Ala Val Thr Ser Ala Glu Ser
        595                 600                 605

Ala Glu Ala Phe Gly Leu Ile Pro Lys Val Ala Leu Leu Ser Tyr Ala
    610                 615                 620

Thr Gly Asp Ser Asn Ser Gly Pro Ile Ile Asp Lys Val Arg Glu Ala
625                 630                 635                 640

Thr Lys Ile Ala Gln Glu Leu Arg Pro Asp Leu Asp Ile Tyr Gly Pro
                645                 650                 655

Ile Gln Tyr Asp Ala Ala Val Asp Glu Ser Ile Ala Lys Thr Lys Leu
            660                 665                 670

Lys Ala Ile Pro Ser Gly Ala Lys Val Gly Gly Gln Ala Asn Val Leu
        675                 680                 685

Ile Phe Pro Asp Leu Asn Thr Gly Asn Asn Thr Tyr Lys Ala Val Gln
    690                 695                 700

Gln Ser Thr Gly Cys Ile Ala Met Gly Pro Met Leu Gln Gly Leu Arg
705                 710                 715                 720

Lys Pro Val Asn Asp Leu Ser Arg Gly Ala Thr Val Lys Asp Ile Val
                725                 730                 735

Thr Thr Val Ala Ile Thr Ala Ile Gln Ala Asp Gln Val Ile Met Lys
            740                 745                 750

Arg Glu Ala Glu Asn Ala Thr Lys
        755                 760
```

<210> SEQ ID NO 90
<211> LENGTH: 2283
<212> TYPE: DNA
<213> ORGANISM: Phytophthora parasitica

<400> SEQUENCE: 90

```
atgtggaccc tgcgacgatc cctgcgacac tccaccggcg tcgccctgcc ccaccgacga     60

gccctgaccg ccgccgccat ctcccagggc aaggtcccca tcaacaacct gtacgtcacc    120

tccaccgagg tcaccaagaa gaccgccccc gtcctgatcg gcctggccca cgtcctggag    180

cagaagttca ccaaggtcgg ctacttccga cccatccagc cctcccccga ctcctccatg    240

gccgaccacc acgtcgacgt catgaagcag cagctggagc tgtccaagga cgtcgaggag    300

ctgtacggcg tcacctcctc ccgagccatg gaggccatgc tgaccggcaa gggcgacgac    360

gtcgtcgagg agatcctgga gcgatacgag cagtgccgaa agggccacga cttcatgatc    420

atcgagggct cccagatctc caagcacgag tccgccatgt cctggaagat caacgtcgac    480

atcgccaagg ccatcggctc ccccgtcctg atggtcaccg acttcggcga cacctccgcc    540

gccaacgacg ccctgatcga ggagatggtc tcccgaaccg tcatgggccg agaccaggcc    600

gaggacgccg gcctgaacta cctgggcacc atcgccaacc gagtccgagc ctccaacgtc    660
```

-continued

```
gactccctgc gagcctccct gaagcgaaag atgggcgaca aggacatccc cttcctgggc    720

ttcctgccca tggacgagat catcgcctcc aagcgactga acgaggtcac ccaccagctg    780

ggcgccaccc agctgttcgg ccactccatc gccaacgacg ccgtcgtcac ctccgccgtc    840

gtcgccgcct ccgccctgaa ggacctgttc gcccacctga agaagtacaa ggacggcgcc    900

atgatcatca cctccggcga ccgatccgac ctgatgctgg gcctgatggt ctcccgactg    960

cccggcgtcc tgcccaacat ctccgccatc gtcctgacca acggcaacta cccccactcc   1020

aacacccagg agatcctgaa gggcgtccag gccctggaca agaccgccct gtccctgccc   1080

atcttctcca cccccaacga caccttctcc accgccgacg gcttcgccaa ggtctccacc   1140

gacatcctgc cctcctccaa gctgaagatc gaccgatcca agcagctgtt cgacgagttc   1200

gtcgagaagg agatgctgat cggcgagctg gacgagggca tggtcgtcaa ccgatccccc   1260

aagcagttcc agcacttcct gttctccaag tcccgagccg tccagcgaca catcgtcctg   1320

accgagggcg aggacatccg agtcctgcag gccgccgacc agatcctgcg acagaacctg   1380

tccaagatca ccatcctggg cgacccccgac gagatcctgc tgaacgccaa gatggccaac   1440

ctggacctgt cccgagccaa catcgtctcc cccgccaact ccgccctgct ggacaagtac   1500

gtcgactact tctacgccaa gcgaaagcac aagggcgtca ccaaggagct ggcccgagac   1560

tactgcaagg acgagaccta cttcggcacc ctgatggtcg agctgggcga cgccgacggc   1620

atggtctccg gcgcctgcca caccaccgcc aacaccatcc gacccgccct gcagctgatc   1680

aagaccgccc ccaaccgacc catcgtctcc tccatcttct tcatgtgcct ggaggacggc   1740

gtccgaatct acggcgactg cgccgtcaac accgacccct ccgcccagga cctggcccag   1800

atcgccgtca cctccgccga gtccgccgag gccttcggcc tgatccccaa ggtcgccctg   1860

ctgtcctacg ccaccggcga ctccaactcc ggccccatca tcgacaaggt ccgagaggcc   1920

accaagatcg cccaggagct gcgacccgac ctggacatct acggccccat ccagtacgac   1980

gccgccgtcg acgagtccat cgccaagacc aagctgaagg ccatcccctc cggcgccaag   2040

gtcggcggcc aggccaacgt cctgatcttc cccgacctga acaccggcaa caacacctac   2100

aaggccgtcc agcagtccac cggctgcatc gccatgggcc ccatgctgca gggcctgcga   2160

aagcccgtca acgacctgtc ccgaggcgcc accgtcaagg acatcgtcac caccgtcgcc   2220

atcaccgcca tccaggccga ccaggtcatc atgaagcgag aggccgagaa cgccaccaag   2280

taa                                                                 2283
```

<210> SEQ ID NO 91
<211> LENGTH: 761
<212> TYPE: PRT
<213> ORGANISM: Phytophthora parasitica

<400> SEQUENCE: 91

```
Met Trp Thr Leu Arg Arg Ser Leu Arg His Ser Thr Gly Val Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Ala
    50                  55                  60

Lys Val Gly Tyr Phe Arg Pro Ile Gln Pro Ser Pro Asp Ser Ser Met
65                  70                  75                  80
```

```
Ala Asp His His Val Asp Val Met Lys Gln Gln Leu Glu Leu Ser Lys
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ala Asn Asp Ala Leu Ile Glu Glu Met Val Ser Arg
            180                 185                 190

Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu Arg
    210                 215                 220

Ala Ser Leu Lys Arg Lys Met Gly Asp Lys Asp Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Thr Gln Leu Phe Gly His Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
305                 310                 315                 320

Pro Gly Val Leu Pro Asn Ile Ser Ala Ile Val Leu Thr Asn Gly Asn
                325                 330                 335

Tyr Pro His Ser Asn Thr Gln Glu Ile Leu Lys Gly Val Gln Ala Leu
            340                 345                 350

Asp Lys Thr Ala Leu Ser Leu Pro Ile Phe Ser Thr Pro Asn Asp Thr
        355                 360                 365

Phe Ser Thr Ala Asp Gly Phe Ala Lys Val Ser Thr Asp Ile Leu Pro
    370                 375                 380

Ser Ser Lys Leu Lys Ile Asp Arg Ser Lys Gln Leu Phe Asp Glu Phe
385                 390                 395                 400

Val Glu Lys Glu Met Leu Ile Gly Glu Leu Asp Glu Gly Met Val Val
                405                 410                 415

Asn Arg Ser Pro Lys Gln Phe Gln His Phe Leu Phe Ser Lys Ser Arg
            420                 425                 430

Ala Val Gln Arg His Ile Val Leu Thr Glu Gly Glu Asp Ile Arg Val
        435                 440                 445

Leu Gln Ala Ala Asp Gln Ile Leu Arg Gln Asn Leu Ser Lys Ile Thr
    450                 455                 460

Ile Leu Gly Asp Pro Asp Glu Ile Leu Leu Asn Ala Lys Met Ala Asn
465                 470                 475                 480

Leu Asp Leu Ser Arg Ala Asn Ile Val Ser Pro Ala Asn Ser Ala Leu
                485                 490                 495

Leu Asp Lys Tyr Val Asp Tyr Phe Tyr Ala Lys Arg Lys His Lys Gly
```

500 505 510

Val Thr Lys Glu Leu Ala Arg Asp Tyr Cys Lys Asp Glu Thr Tyr Phe
515 520 525

Gly Thr Leu Met Val Glu Leu Gly Asp Ala Asp Gly Met Val Ser Gly
530 535 540

Ala Cys His Thr Thr Ala Asn Thr Ile Arg Pro Ala Leu Gln Leu Ile
545 550 555 560

Lys Thr Ala Pro Asn Arg Pro Ile Val Ser Ser Ile Phe Phe Met Cys
565 570 575

Leu Glu Asp Gly Val Arg Ile Tyr Gly Asp Cys Ala Val Asn Thr Asp
580 585 590

Pro Ser Ala Gln Asp Leu Ala Gln Ile Ala Val Thr Ser Ala Glu Ser
595 600 605

Ala Glu Ala Phe Gly Leu Ile Pro Lys Val Ala Leu Leu Ser Tyr Ala
610 615 620

Thr Gly Asp Ser Asn Ser Gly Pro Ile Ile Asp Lys Val Arg Glu Ala
625 630 635 640

Thr Lys Ile Ala Gln Glu Leu Arg Pro Asp Leu Asp Ile Tyr Gly Pro
645 650 655

Ile Gln Tyr Asp Ala Ala Val Asp Glu Ser Ile Ala Lys Thr Lys Leu
660 665 670

Lys Ala Ile Pro Ser Gly Ala Lys Val Gly Gly Gln Ala Asn Val Leu
675 680 685

Ile Phe Pro Asp Leu Asn Thr Gly Asn Asn Thr Tyr Lys Ala Val Gln
690 695 700

Gln Ser Thr Gly Cys Ile Ala Met Gly Pro Met Leu Gln Gly Leu Arg
705 710 715 720

Lys Pro Val Asn Asp Leu Ser Arg Gly Ala Thr Val Lys Asp Ile Val
725 730 735

Thr Thr Val Ala Ile Thr Ala Ile Gln Ala Asp Gln Val Ile Leu Lys
740 745 750

Arg Glu Ala Glu Thr Glu Ala Ala Ala
755 760

<210> SEQ ID NO 92
<211> LENGTH: 2286
<212> TYPE: DNA
<213> ORGANISM: Phytophthora parasitica

<400> SEQUENCE: 92
atgtggaccc tgcgacgatc cctgcgacac tccaccggcg tcgccctgcc ccaccgacga 60
gccctgaccg ccgccgccat ctcccagggc aaggtcccca tcaacaacct gtacgtcacc 120
tccaccgagg tcaccaagaa gaccgccccc gtcctgatcg gcctggccca cgtcctggag 180
cagaagttcg ccaaggtcgg ctacttccga cccatccagc cctcccccga ctcctccatg 240
gccgaccacc acgtcgacgt catgaagcag cagctggagc tgtccaagga cgtcgaggag 300
ctgtacggcg tcacctcctc ccgagccatg gaggccatgc tgaccggcaa gggcgacgac 360
gtcgtcgagg agatcctgga gcgatacgag cagtgccgaa agggccacga cttcatgatc 420
atcgagggct cccagatctc caagcacgag tccgccatgt cctggaagat caacgtcgac 480
atcgccaagg ccatcggctc ccccgtcctg atggtcaccg acttcggcga cacctccgcc 540
gccaacgacg ccctgatcga ggagatggtc tcccgaaccg tcatgggccg agaccaggcc 600
gaggacgccg gcctgaacta cctgggcacc atcgccaacc gagtccgagc ctccaacgtc 660

```
gactccctgc gagcctccct gaagcgaaag atgggcgaca aggacatccc cttcctgggc    720
ttcctgccca tggacgagat catcgcctcc aagcgactga acgaggtcac ccaccagctg    780
ggcgccaccc agctgttcgg ccactccatc gccaacgacg ccgtcgtcac ctccgccgtc    840
gtcgccgcct ccgccctgaa ggacctgttc gcccacctga agaagtacaa ggacggcgcc    900
atgatcatca cctccggcga ccgatccgac ctgatgctgg gcctgatggt ctcccgactg    960
cccggcgtcc tgcccaacat ctccgccatc gtcctgacca acggcaacta cccccactcc   1020
aacacccagg agatcctgaa gggcgtccag gccctggaca agaccgccct gtccctgccc   1080
atcttctcca cccccaacga caccttctcc accgccgacg gcttcgccaa ggtctccacc   1140
gacatcctgc cctcctccaa gctgaagatc gaccgatcca agcagctgtt cgacgagttc   1200
gtcgagaagg agatgctgat cggcgagctg gacgagggca tggtcgtcaa ccgatccccc   1260
aagcagttcc agcacttcct gttctccaag tcccgagccg tccagcgaca catcgtcctg   1320
accgagggcg aggacatccg agtcctgcag gccgccgacc agatcctgcg acagaacctg   1380
tccaagatca ccatcctggg cgaccccgac gagatcctgc tgaacgccaa gatggccaac   1440
ctggacctgt cccgagccaa catcgtctcc cccgccaact ccgccctgct ggacaagtac   1500
gtcgactact tctacgccaa gcgaaagcac aagggcgtca ccaaggagct ggcccgagac   1560
tactgcaagg acgagaccta cttcggcacc ctgatggtcg agctgggcga cgccgacggc   1620
atggtctccg gcgcctgcca caccaccgcc aacaccatcc gacccgccct gcagctgatc   1680
aagaccgccc ccaaccgacc catcgtctcc tccatcttct tcatgtgcct ggaggacggc   1740
gtccgaatct acggcgactg cgccgtcaac accgacccct ccgcccagga cctggcccag   1800
atcgccgtca cctccgccga gtccgccgag gccttcggcc tgatccccaa ggtcgccctg   1860
ctgtcctacg ccaccggcga ctccaactcc ggccccatca tcgacaaggt ccgagaggcc   1920
accaagatcg cccaggagct gcgacccgac ctggacatct acggccccat ccagtacgac   1980
gccgccgtcg acgagtccat cgccaagacc aagctgaagg ccatcccctc cggcgccaag   2040
gtcggcggcc aggccaacgt cctgatcttc cccgacctga acaccggcaa caacacctac   2100
aaggccgtcc agcagtccac cggctgcatc gccatgggcc ccatgctgca gggcctgcga   2160
aagcccgtca acgacctgtc ccgaggcgcc accgtcaagg acatcgtcac caccgtcgcc   2220
atcaccgcca tccaggccga ccaggtcatc ctgaagcgag aggccgagac cgaggccgcc   2280
gcctaa                                                              2286
```

<210> SEQ ID NO 93
<211> LENGTH: 761
<212> TYPE: PRT
<213> ORGANISM: Phytophthora parasitica

<400> SEQUENCE: 93

```
Met Trp Thr Leu Arg Arg Ser Leu Arg His Ser Thr Gly Val Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Thr
    50                  55                  60

Lys Val Gly Tyr Phe Arg Pro Ile Gln Pro Ser Pro Asp Ser Ser Met
65                  70                  75                  80
```

```
Ala Asp His His Val Asp Val Met Lys Gln Gln Leu Glu Leu Ser Lys
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ala Asn Asp Ala Leu Ile Glu Glu Met Val Ser Arg
            180                 185                 190

Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu Arg
    210                 215                 220

Ala Ser Leu Lys Arg Lys Met Gly Asp Lys Asp Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Thr Gln Leu Phe Gly His Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
305                 310                 315                 320

Pro Gly Val Leu Pro Asn Ile Ser Ala Ile Val Leu Thr Asn Gly Asn
                325                 330                 335

Tyr Pro His Ser Asn Thr Gln Glu Ile Leu Lys Gly Val Gln Ala Leu
            340                 345                 350

Asp Lys Thr Ala Leu Ser Leu Pro Ile Phe Ser Thr Pro Asn Asp Thr
        355                 360                 365

Phe Ser Thr Ala Asp Gly Phe Ala Lys Val Ser Thr Asp Ile Leu Pro
    370                 375                 380

Ser Ser Lys Leu Lys Ile Asp Arg Ser Lys Gln Leu Phe Asp Glu Phe
385                 390                 395                 400

Val Glu Lys Glu Met Leu Ile Gly Glu Leu Asp Glu Gly Met Val Val
                405                 410                 415

Asn Arg Ser Pro Lys Gln Phe Gln His Phe Leu Phe Ser Lys Ser Arg
            420                 425                 430

Ala Val Gln Arg His Ile Val Leu Thr Glu Gly Glu Asp Ile Arg Val
        435                 440                 445

Leu Gln Ala Ala Asp Gln Ile Leu Arg Gln Asn Leu Ser Lys Ile Thr
    450                 455                 460

Ile Leu Gly Asp Pro Asp Glu Ile Leu Leu Asn Ala Lys Met Ala Asn
465                 470                 475                 480

Leu Asp Leu Ser Arg Ala Asn Ile Val Ser Pro Ala Asn Ser Ala Leu
                485                 490                 495
```

```
Leu Asp Lys Tyr Val Asp Tyr Phe Tyr Ala Lys Arg Lys His Lys Gly
            500                 505                 510

Val Thr Lys Glu Leu Ala Arg Asp Tyr Cys Lys Asp Glu Thr Tyr Phe
        515                 520                 525

Gly Thr Leu Met Val Glu Leu Gly Asp Ala Asp Gly Met Val Ser Gly
    530                 535                 540

Ala Cys His Thr Thr Ala Asn Thr Ile Arg Pro Ala Leu Gln Leu Ile
545                 550                 555                 560

Lys Thr Ala Pro Asn Arg Pro Ile Val Ser Ser Ile Phe Phe Met Cys
                565                 570                 575

Leu Glu Asp Gly Val Arg Ile Tyr Gly Asp Cys Ala Val Asn Thr Asp
            580                 585                 590

Pro Ser Ala Gln Asp Leu Ala Gln Ile Ala Val Thr Ser Ala Glu Ser
        595                 600                 605

Ala Glu Ala Phe Gly Leu Ile Pro Lys Val Ala Leu Leu Ser Tyr Ala
    610                 615                 620

Thr Gly Asp Ser Asn Ser Gly Pro Ile Ile Asp Lys Val Arg Glu Ala
625                 630                 635                 640

Thr Lys Ile Ala Gln Glu Leu Arg Pro Asp Leu Asp Ile Tyr Gly Pro
                645                 650                 655

Ile Gln Tyr Asp Ala Ala Val Asp Glu Ser Ile Ala Lys Thr Lys Leu
            660                 665                 670

Lys Ala Ile Pro Ser Gly Ala Lys Val Gly Gly Gln Ala Asn Val Leu
        675                 680                 685

Ile Phe Pro Asp Leu Asn Thr Gly Asn Asn Thr Tyr Lys Ala Val Gln
    690                 695                 700

Gln Ser Thr Gly Cys Ile Ala Met Gly Pro Met Leu Gln Gly Leu Arg
705                 710                 715                 720

Lys Pro Val Asn Asp Leu Ser Arg Gly Ala Thr Val Lys Asp Ile Val
                725                 730                 735

Thr Thr Val Ala Ile Thr Ala Ile Gln Ala Asp Gln Val Ile Leu Lys
            740                 745                 750

Arg Glu Ala Glu Thr Glu Ala Ala Ala
        755                 760


<210> SEQ ID NO 94
<211> LENGTH: 2286
<212> TYPE: DNA
<213> ORGANISM: Phytophthora parasitica

<400> SEQUENCE: 94

atgtggaccc tgcgacgatc cctgcgacac tccaccggcg tcgccctgcc ccaccgacga      60

gccctgaccg ccgccgccat ctcccagggc aaggtcccca tcaacaacct gtacgtcacc     120

tccaccgagg tcaccaagaa gaccgccccc gtcctgatcg gcctggccca cgtcctggag     180

cagaagttca ccaaggtcgg ctacttccga cccatccagc cctcccccga ctcctccatg     240

gccgaccacc acgtcgacgt catgaagcag cagctggagc tgtccaagga cgtcgaggag     300

ctgtacggcg tcacctcctc ccgagccatg gaggccatgc tgaccggcaa gggcgacgac     360

gtcgtcgagg agatcctgga gcgatacgag cagtgccgaa agggccacga cttcatgatc     420

atcgagggct cccagatctc caagcacgag tccgccatgt cctggaagat caacgtcgac     480

atcgccaagg ccatcggctc ccccgtcctg atggtcaccg acttcggcga cacctccgcc     540

gccaacgacg ccctgatcga ggagatggtc tcccgaaccg tcatgggccg agaccaggcc     600
```

```
gaggacgccg gcctgaacta cctgggcacc atcgccaacc gagtccgagc ctccaacgtc    660

gactccctgc gagcctccct gaagcgaaag atgggcgaca aggacatccc cttcctgggc    720

ttcctgccca tggacgagat catcgcctcc aagcgactga acgaggtcac ccaccagctg    780

ggcgccaccc agctgttcgg ccactccatc gccaacgacg ccgtcgtcac ctccgccgtc    840

gtcgccgcct ccgccctgaa ggacctgttc gcccacctga agaagtacaa ggacggcgcc    900

atgatcatca cctccggcga ccgatccgac ctgatgctgg gcctgatggt ctcccgactg    960

cccggcgtcc tgcccaacat ctccgccatc gtcctgacca acggcaacta cccccactcc   1020

aacacccagg agatcctgaa gggcgtccag gccctggaca agaccgccct gtccctgccc   1080

atcttctcca cccccaacga caccttctcc accgccgacg gcttcgccaa ggtctccacc   1140

gacatcctgc cctcctccaa gctgaagatc gaccgatcca agcagctgtt cgacgagttc   1200

gtcgagaagg agatgctgat cggcgagctg gacgagggca tggtcgtcaa ccgatccccc   1260

aagcagttcc agcacttcct gttctccaag tcccgagccg tccagcgaca catcgtcctg   1320

accgagggcg aggacatccg agtcctgcag gccgccgacc agatcctgcg acagaacctg   1380

tccaagatca ccatcctggg cgaccccgac gagatcctgc tgaacgccaa gatggccaac   1440

ctggacctgt cccgagccaa catcgtctcc cccgccaact ccgccctgct ggacaagtac   1500

gtcgactact tctacgccaa gcgaaagcac aagggcgtca ccaaggagct ggcccgagac   1560

tactgcaagg acgagaccta cttcggcacc ctgatggtcg agctgggcga cgccgacggc   1620

atggtctccg gcgcctgcca caccaccgcc aacaccatcc gacccgccct gcagctgatc   1680

aagaccgccc ccaaccgacc catcgtctcc tccatcttct tcatgtgcct ggaggacggc   1740

gtccgaatct acggcgactg cgccgtcaac accgacccct ccgcccagga cctggcccag   1800

atcgccgtca cctccgccga gtccgccgag gccttcggcc tgatccccaa ggtcgccctg   1860

ctgtcctacg ccaccggcga ctccaactcc ggccccatca tcgacaaggt ccgagaggcc   1920

accaagatcg cccaggagct gcgacccgac ctggacatct acggccccat ccagtacgac   1980

gccgccgtcg acgagtccat cgccaagacc aagctgaagg ccatcccctc cggcgccaag   2040

gtcggcggcc aggccaacgt cctgatcttc cccgacctga acaccggcaa caacacctac   2100

aaggccgtcc agcagtccac cggctgcatc gccatgggcc ccatgctgca gggcctgcga   2160

aagcccgtca acgacctgtc ccgaggcgcc accgtcaagg acatcgtcac caccgtcgcc   2220

atcaccgcca tccaggccga ccaggtcatc ctgaagcgag aggccgagac cgaggccgcc   2280

gcctaa                                                              2286
```

<210> SEQ ID NO 95
<211> LENGTH: 684
<212> TYPE: PRT
<213> ORGANISM: Phytophthora parasitica

<400> SEQUENCE: 95

```
Met Trp Thr Leu Arg Asn Thr Phe Arg Arg Thr Ser Ala Ala Phe Ala
1               5                   10                  15

Pro Gln Arg Arg Ala Leu Thr Ala Ala Ala Ile Ala Glu Gly Lys Val
            20                  25                  30

Pro Ile Asn Asn Leu Phe Val Thr Ser Thr Glu Val Thr Lys Lys Thr
        35                  40                  45

Ala Pro Val Leu Ile Gly Leu Thr Asn Thr Leu Glu Gln Lys Phe Thr
    50                  55                  60

Lys Val Gly Tyr Phe Arg Pro Ile Gln Pro Ile Val Glu Thr Asp His
```

-continued

```
65                  70                  75                  80

His Ile Asp Val Met Lys Gln Gln Leu Gly Leu Thr Lys Ser Val Asp
                85                  90                  95

Gln Leu Tyr Gly Val Thr Ser Glu Arg Ala Ile Glu Tyr Trp Leu Asn
            100                 105                 110

Gly Lys Gly Asp Asp Leu Val Glu Glu Ile Leu Glu Arg Tyr Glu Ala
        115                 120                 125

Cys Arg Glu Gly His Asp Phe Met Ile Ile Glu Gly Ser Gln Ile Ser
    130                 135                 140

Lys His Glu Ser Ala Met Ser Trp Lys Ile Asn Val Asp Ile Ala Lys
145                 150                 155                 160

Ala Ile Gly Ser Pro Val Leu Thr Ile Ser Asp Phe Ser Glu Ser Ala
                165                 170                 175

Asn Thr Asn Gly Glu Leu Leu Glu Glu Ile Leu Ser Arg Thr Ala Leu
            180                 185                 190

Asn Lys Asp Gln Val Glu Gly Ala Gly Leu Asn Phe Ile Gly Asn Ile
        195                 200                 205

Ala Asn Arg Val Asn Thr Lys Asp Pro Lys Ala Leu Arg Asp Ala Ile
    210                 215                 220

Arg Ser Lys Leu Arg Glu Lys Asp Leu Pro Phe Leu Gly Phe Leu Pro
225                 230                 235                 240

Arg Asp Asp Phe Ile Ala Ser Lys Arg Leu Asn Glu Val Thr His Gln
                245                 250                 255

Leu Gly Ala Lys Gln Leu Phe Gly Thr Lys Ala Ile Pro Asn Asn Val
            260                 265                 270

Val Val Thr Ser Ala Val Val Ala Thr Ser Ala Leu Lys Asp Leu Phe
        275                 280                 285

Ala His Leu Lys Asn Tyr Lys Asp Gly Ala Leu Val Ile Thr Ser Ala
    290                 295                 300

Asp Arg Ser Asp Val Met Leu Gly Leu Met Ala Ser Arg Leu Pro Gly
305                 310                 315                 320

Ile Leu Pro Asn Val Ser Ala Ile Val Leu Thr Asn Gly Ser Tyr Pro
                325                 330                 335

His Ser Asn Thr Gln Glu Ile Leu Gln Gly Val Glu Ala Leu Asp Lys
            340                 345                 350

Thr Gly Leu Ser Ile Pro Ile Phe Ser Val Pro Glu Asp Thr Phe Thr
        355                 360                 365

Thr Ala Asp Lys Phe Ser Lys Val Ser Thr Asp Ile Leu Pro Thr Ser
    370                 375                 380

Ser Leu Lys Ile Asp Arg Ser Lys Gln Leu Phe Asp Glu Phe Val Gly
385                 390                 395                 400

Lys Glu Ser Ile Ile Gly Glu Leu Asp Glu Gly Met Val Val Asn Arg
                405                 410                 415

Ser Pro Lys Gln Phe Gln His Phe Leu Phe Ser Lys Ser Arg Ala Val
            420                 425                 430

Gln Arg His Ile Val Leu Thr Glu Gly Glu Asp Ile Arg Val Leu Gln
        435                 440                 445

Ala Ala Asp Gln Val Leu Arg Gln Lys Leu Ser Lys Val Thr Ile Leu
    450                 455                 460

Gly Asn Pro Asp Asp Ile Glu Arg His Ala Lys Ser Leu Asn Leu Asp
465                 470                 475                 480

Leu Ser Arg Ala Asn Ile Val Arg Thr Ala Asp Ser Asp Leu Leu Glu
                485                 490                 495
```

```
Arg Tyr Val Asp Gln Tyr Phe Glu Lys Arg Lys His Lys Gly Val Thr
            500                 505                 510

Arg Glu Ser Ala Arg Asp Ala Val Leu Glu Glu Thr Cys Phe Gly Thr
        515                 520                 525

Met Met Val Glu Met Gly Asp Ala Asp Gly Met Val Ser Gly Ala Cys
    530                 535                 540

His Thr Thr Ala Asn Thr Ile Arg Pro Ala Leu Gln Leu Ile Lys Thr
545                 550                 555                 560

Ala Pro Asn Arg Pro Ile Val Ser Ser Ile Phe Phe Met Cys Leu Glu
                565                 570                 575

Asp Gly Val Arg Ile Tyr Gly Asp Cys Ala Val Asn Thr Asp Pro Ser
            580                 585                 590

Ala Gln Asp Leu Ala Gln Ile Ala Val Thr Ser Ala Glu Ser Ala Glu
        595                 600                 605

Ala Phe Gly Leu Ile Pro Lys Val Ala Leu Leu Ser Tyr Ala Thr Gly
    610                 615                 620

Asp Ser Asn Ser Gly Pro Ile Ile Asp Lys Val Arg Glu Ala Thr Lys
625                 630                 635                 640

Ile Ala Gln Glu Leu Arg Pro Asp Leu Asp Ile Tyr Gly Pro Ile Gln
                645                 650                 655

Tyr Asp Ala Ala Val Asp Glu Ser Ile Ala Lys Thr Lys Leu Lys Ala
            660                 665                 670

Ile Pro Ser Gly Ala Lys Val Gly Gly Gln Ala Asn
        675                 680
```

<210> SEQ ID NO 96
<211> LENGTH: 2055
<212> TYPE: DNA
<213> ORGANISM: Phytophthora parasitica

<400> SEQUENCE: 96

```
atgtggaccc tgcgaaacac cttccgacga acctccgccg ccttcgcccc ccagcgacga     60

gccctgaccg ccgccgccat cgccgagggc aaggtcccca tcaacaacct gttcgtcacc    120

tccaccgagg tcaccaagaa gaccgccccc gtcctgatcg gcctgaccaa caccctggag    180

cagaagttca ccaaggtcgg ctacttccga cccatccagc ccatcgtcga gaccgaccac    240

cacatcgacg tcatgaagca gcagctgggc ctgaccaagt ccgtcgacca gctgtacggc    300

gtcacctccg agcgagccat cgagtactgg ctgaacggca agggcgacga cctggtcgag    360

gagatcctgg agcgatacga ggcctgccga gagggccacg acttcatgat catcgagggc    420

tcccagatct ccaagcacga gtccgccatg tcctggaaga tcaacgtcga catcgccaag    480

gccatcggct cccccgtcct gaccatctcc gacttctccg agtccgccaa caccaacggc    540

gagctgctgg aggagatcct gtcccgaacc gccctgaaca aggaccaggt cgagggcgcc    600

ggcctgaact tcatcggcaa catcgccaac cgagtcaaca ccaaggaccc caaggccctg    660

cgagacgcca tccgatccaa gctgcgagag aaggacctgc ccttcctggg cttcctgccc    720

cgagacgact tcatcgcctc caagcgactg aacgaggtca cccaccagct gggcgccaag    780

cagctgttcg gcaccaaggc catccccaac aacgtcgtcg tcacctccgc cgtcgtcgcc    840

acctccgccc tgaaggacct gttcgcccac ctgaagaact acaaggacgg cgccctggtc    900

atcacctccg ccgaccgatc cgacgtcatg ctgggcctga tggcctcccg actgcccggc    960

atcctgccca acgtctccgc catcgtcctg accaacggct cctaccccca ctccaacacc   1020
```

-continued

```
caggagatcc tgcagggcgt cgaggccctg gacaagaccg gcctgtccat ccccatcttc   1080

tccgtccccg aggacacctt caccaccgcc gacaagttct ccaaggtctc caccgacatc   1140

ctgcccacct cctccctgaa gatcgaccga tccaagcagc tgttcgacga gttcgtcggc   1200

aaggagtcca tcatcggcga gctggacgag ggcatggtcg tcaaccgatc cccccaagcag   1260

ttccagcact tcctgttctc caagtcccga gccgtccagc gacacatcgt cctgaccgag   1320

ggcgaggaca tccgagtcct gcaggccgcc gaccaggtcc tgcgacagaa gctgtccaag   1380

gtcaccatcc tgggcaaccc cgacgacatc gagcgacacg ccaagtccct gaacctggac   1440

ctgtcccgag ccaacatcgt ccgaaccgcc gactccgacc tgctggagcg atacgtcgac   1500

cagtacttcg agaagcgaaa gcacaagggc gtcacccgag agtccgcccg agacgccgtc   1560

ctggaggaga cctgcttcgg caccatgatg gtcgagatgg gcgacgccga cggcatggtc   1620

tccggcgcct gccacaccac cgccaacacc atccgacccg ccctgcagct gatcaagacc   1680

gcccccaacc gacccatcgt ctcctccatc ttcttcatgt gcctggagga cggcgtccga   1740

atctacggcg actgcgccgt caacaccgac ccctccgccc aggacctggc ccagatcgcc   1800

gtcacctccg ccgagtccgc cgaggccttc ggcctgatcc ccaaggtcgc cctgctgtcc   1860

tacgccaccg gcgactccaa ctccggcccc atcatcgaca aggtccgaga ggccaccaag   1920

atcgcccagg agctgcgacc cgacctggac atctacggcc ccatccagta cgacgccgcc   1980

gtcgacgagt ccatcgccaa gaccaagctg aaggccatcc cctccggcgc caaggtcggc   2040

ggccaggcca actaa                                                    2055


<210> SEQ ID NO 97
<211> LENGTH: 675
<212> TYPE: PRT
<213> ORGANISM: Phytophthora parasitica

<400> SEQUENCE: 97

Met Trp Thr Leu Arg Arg Ser Leu Arg His Ser Thr Gly Val Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Ala
    50                  55                  60

Lys Val Gly Tyr Phe Arg Pro Ile Gln Pro Ser Pro Asp Ser Ser Met
65                  70                  75                  80

Ala Asp His His Val Asp Val Met Lys Gln Gln Leu Glu Leu Ser Lys
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ala Asn Asp Ala Leu Ile Glu Glu Met Val Ser Arg
            180                 185                 190
```

```
Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu His
    210                 215                 220

Ile Pro Phe Leu Gly Phe Leu Pro Met Asp Glu Ile Ile Ala Ser Lys
225                 230                 235                 240

Arg Leu Asn Glu Val Thr His Gln Leu Gly Ala Thr Gln Leu Phe Gly
                245                 250                 255

His Ser Ile Ala Asn Asp Ala Val Val Thr Ser Ala Val Val Ala Ala
            260                 265                 270

Ser Ala Leu Lys Asp Leu Phe Ala His Leu Lys Lys Tyr Lys Asp Gly
        275                 280                 285

Ala Met Ile Ile Thr Ser Gly Asp Arg Ser Asp Leu Met Leu Gly Leu
    290                 295                 300

Met Val Ser Arg Leu Pro Gly Val Leu Pro Asn Ile Ser Ala Ile Val
305                 310                 315                 320

Leu Thr Asn Gly Asn Tyr Pro His Ser Asn Thr Gln Glu Ile Leu Lys
                325                 330                 335

Gly Val Gln Ala Leu Asp Lys Thr Ala Leu Ser Leu Pro Ile Phe Ser
            340                 345                 350

Thr Pro Asn Asp Thr Phe Ser Thr Ala Asp Gly Phe Ala Lys Val Ser
        355                 360                 365

Thr Asp Ile Leu Pro Ser Ser Lys Leu Lys Ile Asp Arg Ser Lys Gln
    370                 375                 380

Leu Phe Asp Glu Phe Val Glu Lys Glu Met Leu Ile Gly Glu Leu Asp
385                 390                 395                 400

Glu Gly Met Val Val Asn Arg Ser Pro Lys Gln Phe Gln His Phe Leu
                405                 410                 415

Phe Ser Lys Ser Arg Ala Val Gln Arg His Ile Val Leu Thr Glu Gly
            420                 425                 430

Glu Asp Ile Arg Val Leu Gln Ala Ala Asp Gln Ile Leu Arg Gln Asn
        435                 440                 445

Leu Ser Lys Ile Thr Ile Leu Gly Asp Pro Asp Glu Ile Leu Leu Asn
    450                 455                 460

Ala Lys Met Ala Asn Leu Asp Leu Ser Arg Ala Asn Ile Val Ser Pro
465                 470                 475                 480

Ala Asn Ser Ala Leu Leu Asp Lys Tyr Val Asp Tyr Phe Tyr Ala Lys
                485                 490                 495

Arg Lys His Lys Gly Val Thr Lys Glu Leu Ala Arg Asp Tyr Cys Lys
            500                 505                 510

Asp Glu Thr Tyr Phe Gly Thr Leu Met Val Glu Leu Gly Asp Ala Asp
        515                 520                 525

Gly Met Val Ser Gly Ala Cys His Thr Thr Ala Asn Thr Ile Arg Pro
    530                 535                 540

Ala Leu Gln Leu Ile Lys Thr Ala Pro Asn Arg Pro Ile Val Ser Ser
545                 550                 555                 560

Ile Phe Phe Met Cys Leu Glu Asp Gly Val Arg Ile Tyr Gly Asp Cys
                565                 570                 575

Ala Val Asn Thr Asp Pro Ser Ala Gln Asp Leu Ala Gln Ile Ala Val
            580                 585                 590

Thr Ser Ala Glu Ser Ala Glu Ala Phe Gly Leu Ile Pro Lys Val Ala
        595                 600                 605
```

-continued

```
Leu Leu Ser Tyr Ala Thr Gly Asp Ser Asn Ser Gly Pro Ile Ile Asp
    610                 615                 620

Lys Val Arg Glu Ala Thr Lys Ile Ala Gln Glu Leu Arg Pro Asp Leu
625                 630                 635                 640

Asp Ile Tyr Gly Pro Ile Gln Tyr Asp Ala Ala Val Asp Glu Ser Ile
                645                 650                 655

Ala Lys Thr Lys Leu Lys Ala Ile Pro Ser Gly Ala Lys Val Gly Gly
            660                 665                 670

Gln Ala Asn
        675


<210> SEQ ID NO 98
<211> LENGTH: 2028
<212> TYPE: DNA
<213> ORGANISM: Phytophthora parasitica

<400> SEQUENCE: 98

atgtggaccc tgcgacgatc cctgcgacac tccaccggcg tcgccctgcc ccaccgacga      60

gccctgaccg ccgccgccat ctcccagggc aaggtcccca tcaacaacct gtacgtcacc     120

tccaccgagg tcaccaagaa gaccgccccc gtcctgatcg gcctggccca cgtcctggag     180

cagaagttcg ccaaggtcgg ctacttccga cccatccagc cctcccccga ctcctccatg     240

gccgaccacc acgtcgacgt catgaagcag cagctggagc tgtccaagga cgtcgaggag     300

ctgtacggcg tcacctcctc ccgagccatg gaggccatgc tgaccggcaa gggcgacgac     360

gtcgtcgagg agatcctgga gcgatacgag cagtgccgaa agggccacga cttcatgatc     420

atcgagggct cccagatctc caagcacgag tccgccatgt cctggaagat caacgtcgac     480

atcgccaagg ccatcggctc ccccgtcctg atggtcaccg acttcggcga cacctccgcc     540

gccaacgacg ccctgatcga ggagatggtc tcccgaaccg tcatgggccg agaccaggcc     600

gaggacgccg gcctgaacta cctgggcacc atcgccaacc gagtccgagc ctccaacgtc     660

gactccctgc acatcccctt cctgggcttc ctgcccatgg acgagatcat cgcctccaag     720

cgactgaacg aggtcaccca ccagctgggc gccacccagc tgttcggcca ctccatcgcc     780

aacgacgccg tcgtcacctc cgccgtcgtc gccgcctccg ccctgaagga cctgttcgcc     840

cacctgaaga agtacaagga cggcgccatg atcatcacct ccggcgaccg atccgacctg     900

atgctgggcc tgatggtctc ccgactgccc ggcgtcctgc ccaacatctc cgccatcgtc     960

ctgaccaacg gcaactaccc ccactccaac acccaggaga tcctgaaggg cgtccaggcc    1020

ctggacaaga ccgccctgtc cctgcccatc ttctccaccc ccaacgacac cttctccacc    1080

gccgacggct tcgccaaggt ctccaccgac atcctgccct cctccaagct gaagatcgac    1140

cgatccaagc agctgttcga cgagttcgtc gagaaggaga tgctgatcgg cgagctggac    1200

gagggcatgg tcgtcaaccg atcccccaag cagttccagc acttcctgtt ctccaagtcc    1260

cgagccgtcc agcgacacat cgtcctgacc gagggcgagg acatccgagt cctgcaggcc    1320

gccgaccaga tcctgcgaca gaacctgtcc aagatcacca tcctgggcga ccccgacgag    1380

atcctgctga acgccaagat ggccaacctg gacctgtccc gagccaacat cgtctccccc    1440

gccaactccg ccctgctgga caagtacgtc gactacttct acgccaagcg aaagcacaag    1500

ggcgtcacca aggagctggc ccgagactac tgcaaggacg agacctactt cggcaccctg    1560

atggtcgagc tgggcgacgc cgacggcatg gtctccggcg cctgccacac caccgccaac    1620

accatccgac ccgccctgca gctgatcaag accgccccca accgacccat cgtctcctcc    1680
```

-continued

```
atcttcttca tgtgcctgga ggacggcgtc cgaatctacg gcgactgcgc cgtcaacacc   1740

gacccctccg cccaggacct ggcccagatc gccgtcacct ccgccgagtc cgccgaggcc   1800

ttcggcctga tccccaaggt cgccctgctg tcctacgcca ccggcgactc caactccggc   1860

cccatcatcg acaaggtccg agaggccacc aagatcgccc aggagctgcg acccgacctg   1920

gacatctacg gccccatcca gtacgacgcc gccgtcgacg agtccatcgc caagaccaag   1980

ctgaaggcca tcccctccgg cgcccaaggtc ggcggccagg ccaactaa               2028


<210> SEQ ID NO 99
<211> LENGTH: 686
<212> TYPE: PRT
<213> ORGANISM: Phytophthora parasitica

<400> SEQUENCE: 99

Met Trp Thr Leu Arg Arg Ser Leu Arg His Ser Thr Gly Val Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Ala
    50                  55                  60

Lys Val Gly Tyr Phe Arg Pro Ile Gln Pro Ser Pro Asp Ser Ser Met
65                  70                  75                  80

Ala Asp His His Val Asp Val Met Lys Gln Gln Leu Glu Leu Ser Lys
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ala Asn Asp Ala Leu Ile Glu Glu Met Val Ser Arg
            180                 185                 190

Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu Arg
    210                 215                 220

Ala Ser Leu Lys Arg Lys Met Gly Asp Lys Asp Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Thr Gln Leu Phe Gly His Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
305                 310                 315                 320
```

Pro Gly Val Leu Pro Asn Ile Ser Ala Ile Val Leu Thr Asn Gly Asn
325 330 335

Tyr Pro His Ser Asn Thr Gln Glu Ile Leu Lys Gly Val Gln Ala Leu
340 345 350

Asp Lys Thr Ala Leu Ser Leu Pro Ile Phe Ser Thr Pro Asn Asp Thr
355 360 365

Phe Ser Thr Ala Asp Gly Phe Ala Lys Val Ser Thr Asp Ile Leu Pro
370 375 380

Ser Ser Lys Leu Lys Ile Asp Arg Ser Lys Gln Leu Phe Asp Glu Phe
385 390 395 400

Val Glu Lys Glu Met Leu Ile Gly Glu Leu Asp Glu Gly Met Val Val
405 410 415

Asn Arg Ser Pro Lys Gln Phe Gln His Phe Leu Phe Ser Lys Ser Arg
420 425 430

Ala Val Gln Arg His Ile Val Leu Thr Glu Gly Glu Asp Ile Arg Val
435 440 445

Leu Gln Ala Ala Asp Gln Ile Leu Arg Gln Asn Leu Ser Lys Ile Thr
450 455 460

Ile Leu Gly Asp Pro Asp Glu Ile Leu Leu Asn Ala Lys Met Ala Asn
465 470 475 480

Leu Asp Leu Ser Arg Ala Asn Ile Val Ser Pro Ala Asn Ser Ala Leu
485 490 495

Leu Asp Lys Tyr Val Asp Tyr Phe Tyr Ala Lys Arg Lys His Lys Gly
500 505 510

Val Thr Lys Glu Leu Ala Arg Asp Tyr Cys Lys Asp Glu Thr Tyr Phe
515 520 525

Gly Thr Leu Met Val Glu Leu Gly Asp Ala Asp Gly Met Val Ser Gly
530 535 540

Ala Cys His Thr Thr Ala Asn Thr Ile Arg Pro Ala Leu Gln Leu Ile
545 550 555 560

Lys Thr Ala Pro Asn Arg Pro Ile Val Ser Ser Ile Phe Phe Met Cys
565 570 575

Leu Glu Asp Gly Val Arg Ile Tyr Gly Asp Cys Ala Val Asn Thr Asp
580 585 590

Pro Ser Ala Gln Asp Leu Ala Gln Ile Ala Val Thr Ser Ala Glu Ser
595 600 605

Ala Glu Ala Phe Gly Leu Ile Pro Lys Val Ala Leu Leu Ser Tyr Ala
610 615 620

Thr Gly Asp Ser Asn Ser Gly Pro Ile Ile Asp Lys Val Arg Glu Ala
625 630 635 640

Thr Lys Ile Ala Gln Glu Leu Arg Pro Asp Leu Asp Ile Tyr Gly Pro
645 650 655

Ile Gln Tyr Asp Ala Ala Val Asp Glu Ser Ile Ala Lys Thr Lys Leu
660 665 670

Lys Ala Ile Pro Ser Gly Ala Lys Val Gly Gly Gln Ala Asn
675 680 685

<210> SEQ ID NO 100
<211> LENGTH: 2061
<212> TYPE: DNA
<213> ORGANISM: Phytophthora parasitica

<400> SEQUENCE: 100
atgtggaccc tgcgacgatc cctgcgacac tccaccggcg tcgccctgcc ccaccgacga 60

```
gccctgaccg ccgccgccat ctcccagggc aaggtcccca tcaacaacct gtacgtcacc    120
tccaccgagg tcaccaagaa gaccgccccc gtcctgatcg gcctggccca cgtcctggag    180
cagaagttcg ccaaggtcgg ctacttccga cccatccagc cctcccccga ctcctccatg    240
gccgaccacc acgtcgacgt catgaagcag cagctggagc tgtccaagga cgtcgaggag    300
ctgtacggcg tcacctcctc ccgagccatg gaggccatgc tgaccggcaa gggcgacgac    360
gtcgtcgagg agatcctgga gcgatacgag cagtgccgaa agggccacga cttcatgatc    420
atcgagggct cccagatctc caagcacgag tccgccatgt cctggaagat caacgtcgac    480
atcgccaagg ccatcggctc ccccgtcctg atggtcaccg acttcggcga cacctccgcc    540
gccaacgacg ccctgatcga ggagatggtc tcccgaaccg tcatgggccg agaccaggcc    600
gaggacgccg gcctgaacta cctgggcacc atcgccaacc gagtccgagc ctccaacgtc    660
gactccctgc gagcctccct gaagcgaaag atgggcgaca aggacatccc cttcctgggc    720
ttcctgccca tggacgagat catcgcctcc aagcgactga acgaggtcac ccaccagctg    780
ggcgccaccc agctgttcgg ccactccatc gccaacgacg ccgtcgtcac ctccgccgtc    840
gtcgccgcct ccgccctgaa ggacctgttc gcccacctga agaagtacaa ggacggcgcc    900
atgatcatca cctccggcga ccgatccgac ctgatgctgg gcctgatggt ctcccgactg    960
cccggcgtcc tgcccaacat ctccgccatc gtcctgacca acggcaacta cccccactcc   1020
aacacccagg agatcctgaa gggcgtccag gccctggaca agaccgccct gtccctgccc   1080
atcttctcca cccccaacga caccttctcc accgccgacg gcttcgccaa ggtctccacc   1140
gacatcctgc cctcctccaa gctgaagatc gaccgatcca agcagctgtt cgacgagttc   1200
gtcgagaagg agatgctgat cggcgagctg gacgagggca tggtcgtcaa ccgatccccc   1260
aagcagttcc agcacttcct gttctccaag tcccgagccg tccagcgaca catcgtcctg   1320
accgagggcg aggacatccg agtcctgcag gccgccgacc agatcctgcg acagaacctg   1380
tccaagatca ccatcctggg cgaccccgac gagatcctgc tgaacgccaa gatggccaac   1440
ctggacctgt cccgagccaa catcgtctcc cccgccaact ccgccctgct ggacaagtac   1500
gtcgactact tctacgccaa gcgaaagcac aagggcgtca ccaaggagct ggcccgagac   1560
tactgcaagg acgagaccta cttcggcacc ctgatggtcg agctgggcga cgccgacggc   1620
atggtctccg gcgcctgcca caccaccgcc aacaccatcc gacccgccct gcagctgatc   1680
aagaccgccc ccaaccgacc catcgtctcc tccatcttct tcatgtgcct ggaggacggc   1740
gtccgaatct acggcgactg cgccgtcaac accgacccct ccgcccagga cctggcccag   1800
atcgccgtca cctccgccga gtccgccgag gccttcggcc tgatccccaa ggtcgccctg   1860
ctgtcctacg ccaccggcga ctccaactcc ggccccatca tcgacaaggt ccgagaggcc   1920
accaagatcg cccaggagct gcgacccgac ctggacatct acggccccat ccagtacgac   1980
gccgccgtcg acgagtccat cgccaagacc aagctgaagg ccatcccctc cggcgccaag   2040
gtcggcggcc aggccaacta a                                             2061
```

```
<210> SEQ ID NO 101
<211> LENGTH: 676
<212> TYPE: PRT
<213> ORGANISM: Phytophthora parasitica

<400> SEQUENCE: 101

Met Trp Thr Leu Arg Arg Ser Leu Arg His Ser Thr Gly Val Ala Leu
1               5                   10                  15
```

```
Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Ala
    50                  55                  60

Lys Val Gly Tyr Phe Arg Pro Ile Gln Pro Ser Pro Asp Ser Ser Met
65                  70                  75                  80

Ala Asp His His Val Asp Val Met Lys Gln Gln Leu Glu Leu Ser Lys
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ala Asn Asp Ala Leu Ile Glu Glu Met Val Ser Arg
            180                 185                 190

Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu Arg
    210                 215                 220

Ala Ser Leu Lys Arg Lys Met Gly Asp Lys Asp Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Thr Gln Leu Phe Gly His Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
305                 310                 315                 320

Pro Gly Val Leu Pro Asn Ile Ser Ala Ile Val Leu Thr Asn Gly Asn
                325                 330                 335

Tyr Pro His Ser Asn Thr Gln Glu Ile Leu Lys Gly Val Gln Ala Leu
            340                 345                 350

Asp Lys Thr Ala Leu Ser Leu Pro Ile Phe Ser Thr Pro Asn Asp Thr
        355                 360                 365

Phe Ser Thr Ala Asp Gly Phe Ala Lys Val Ser Thr Asp Ile Leu Pro
    370                 375                 380

Ser Ser Lys Leu Lys Ile Asp Arg Ser Lys Gln Leu Phe Asp Glu Phe
385                 390                 395                 400

Val Glu Lys Glu Met Leu Ile Gly Glu Leu Asp Glu Gly Met Val Val
                405                 410                 415

Asn Arg Ser Pro Lys Gln Phe Gln His Phe Leu Phe Ser Lys Ser Arg
            420                 425                 430
```

```
Ala Val Gln Arg His Ile Val Leu Thr Glu Gly Glu Asp Ile Arg Val
        435                 440                 445

Leu Gln Ala Ala Asp Gln Ile Leu Arg Gln Asn Leu Ser Gln Ile Thr
    450                 455                 460

Ile Leu Gly Asp Pro Asp Glu Ile Leu Leu Asn Ala Lys Met Ala Asn
465                 470                 475                 480

Leu Asp Leu Ser Arg Ala Asn Ile Val Ser Pro Ala Asn Ser Ala Leu
                485                 490                 495

Leu Asp Lys Tyr Val Asp Tyr Phe Tyr Ala Lys Arg Lys His Lys Gly
            500                 505                 510

Val Thr Lys Glu Leu Ala Arg Asp Tyr Cys Lys Asp Glu Thr Tyr Phe
        515                 520                 525

Gly Thr Leu Met Val Glu Leu Gly Asp Ala Asp Gly Met Val Ser Gly
    530                 535                 540

Ala Cys His Thr Thr Ala Asn Thr Ile Arg Pro Ala Leu Gln Leu Ile
545                 550                 555                 560

Lys Thr Ala Pro Asn Arg Pro Ile Val Ser Ser Ile Phe Phe Met Cys
                565                 570                 575

Leu Glu Asp Gly Val Arg Ile Tyr Gly Asp Cys Ala Val Asn Thr Asp
            580                 585                 590

Pro Ser Ala Gln Asp Leu Ala Gln Ile Ala Val Thr Ser Ala Glu Ser
        595                 600                 605

Ala Glu Ala Phe Gly Leu Ile Pro Lys Val Ala Leu Leu Ser Tyr Ala
    610                 615                 620

Thr Gly Asp Ser Asn Ser Gly Pro Ile Ile Asp Lys Val Arg Glu Ala
625                 630                 635                 640

Thr Lys Ile Ala Gln Glu Leu Arg Pro Asp Leu Asp Ile Tyr Gly Pro
                645                 650                 655

Ile Gln Tyr Asp Ala Ala Val Asp Glu Ser Ile Ala Lys Thr Lys Leu
            660                 665                 670

Lys Ala Ile Pro
        675
```

<210> SEQ ID NO 102
<211> LENGTH: 2031
<212> TYPE: DNA
<213> ORGANISM: Phytophthora parasitica

<400> SEQUENCE: 102

```
atgtggaccc tgcgacgatc cctgcgacac tccaccggcg tcgccctgcc ccaccgacga      60

gccctgaccg ccgccgccat ctcccagggc aaggtcccca tcaacaacct gtacgtcacc     120

tccaccgagg tcaccaagaa gaccgccccc gtcctgatcg gcctggccca cgtcctggag     180

cagaagttcg ccaaggtcgg ctacttccga cccatccagc cctcccccga ctcctccatg     240

gccgaccacc acgtcgacgt catgaagcag cagctggagc tgtccaagga cgtcgaggag     300

ctgtacggcg tcacctcctc ccgagccatg gaggccatgc tgaccggcaa gggcgacgac     360

gtcgtcgagg agatcctgga gcgatacgag cagtgccgaa agggccacga cttcatgatc     420

atcgagggct cccagatctc caagcacgag tccgccatgt cctggaagat caacgtcgac     480

atcgccaagg ccatcggctc ccccgtcctg atggtcaccg acttcggcga cacctccgcc     540

gccaacgacg ccctgatcga ggagatggtc tcccgaaccg tcatgggccg agaccaggcc     600

gaggacgccg gcctgaacta cctgggcacc atcgccaacc gagtccgagc ctccaacgtc     660

gactccctgc gagcctccct gaagcgaaag atgggcgaca aggacatccc cttcctgggc     720
```

```
ttcctgccca tggacgagat catcgcctcc aagcgactga acgaggtcac ccaccagctg    780
ggcgccaccc agctgttcgg ccactccatc gccaacgacg ccgtcgtcac ctccgccgtc    840
gtcgccgcct ccgccctgaa ggacctgttc gcccacctga agaagtacaa ggacggcgcc    900
atgatcatca cctccggcga ccgatccgac ctgatgctgg gcctgatggt ctcccgactg    960
cccggcgtcc tgcccaacat ctccgccatc gtcctgacca acggcaacta cccccactcc   1020
aacacccagg agatcctgaa gggcgtccag gccctggaca agaccgccct gtccctgccc   1080
atcttctcca cccccaacga caccttctcc accgccgacg gcttcgccaa ggtctccacc   1140
gacatcctgc cctcctccaa gctgaagatc gaccgatcca agcagctgtt cgacgagttc   1200
gtcgagaagg agatgctgat cggcgagctg gacgagggca tggtcgtcaa ccgatccccc   1260
aagcagttcc agcacttcct gttctccaag tcccgagccg tccagcgaca catcgtcctg   1320
accgagggcg aggacatccg agtcctgcag gccgccgacc agatcctgcg acagaacctg   1380
tcccagatca ccatcctggg cgaccccgac gagatcctgc tgaacgccaa gatggccaac   1440
ctggacctgt cccgagccaa catcgtctcc cccgccaact ccgccctgct ggacaagtac   1500
gtcgactact tctacgccaa gcgaaagcac aagggcgtca ccaaggagct ggcccgagac   1560
tactgcaagg acgagaccta cttcggcacc ctgatggtcg agctgggcga cgccgacggc   1620
atggtctccg gcgcctgcca caccaccgcc aacaccatcc gacccgccct gcagctgatc   1680
aagaccgccc ccaaccgacc catcgtctcc tccatcttct tcatgtgcct ggaggacggc   1740
gtccgaatct acggcgactg cgccgtcaac accgacccct ccgcccagga cctggcccag   1800
atcgccgtca cctccgccga gtccgccgag gccttcggcc tgatccccaa ggtcgccctg   1860
ctgtcctacg ccaccggcga ctccaactcc ggccccatca tcgacaaggt ccgagaggcc   1920
accaagatcg cccaggagct gcgacccgac ctggacatct acggccccat ccagtacgac   1980
gccgccgtcg acgagtccat cgccaagacc aagctgaagg ccatccccta a            2031
```

<210> SEQ ID NO 103
<211> LENGTH: 655
<212> TYPE: PRT
<213> ORGANISM: Phytophthora parasitica

<400> SEQUENCE: 103

```
Met Trp Thr Leu Arg Asn Thr Phe Arg Arg Thr Ser Ala Ala Phe Ala
1               5                   10                  15

Pro Gln Arg Arg Ala Leu Thr Ala Ala Ala Ile Ala Glu Gly Lys Val
            20                  25                  30

Pro Ile Asn Asn Leu Phe Val Thr Ser Thr Glu Val Thr Lys Lys Thr
        35                  40                  45

Ala Pro Val Leu Ile Gly Leu Thr Asn Thr Leu Glu Gln Lys Phe Thr
    50                  55                  60

Lys Val Gly Tyr Phe Arg Pro Ile Gln Pro Ile Val Glu Thr Asp His
65                  70                  75                  80

His Ile Asp Val Met Lys Gln Gln Leu Gly Leu Thr Lys Ser Val Asp
                85                  90                  95

Gln Leu Tyr Gly Val Thr Ser Glu Arg Ala Ile Glu Tyr Trp Leu Asn
            100                 105                 110

Gly Lys Gly Asp Asp Leu Val Glu Glu Ile Leu Glu Arg Tyr Glu Ala
        115                 120                 125

Cys Arg Glu Gly His Asp Phe Met Ile Ile Glu Gly Ser Gln Ile Ser
    130                 135                 140
```

```
Lys His Glu Ser Ala Met Ser Trp Lys Ile Asn Val Asp Ile Ala Lys
145                 150                 155                 160

Ala Ile Gly Ser Pro Val Leu Thr Ile Ser Asp Phe Ser Glu Ser Ala
                165                 170                 175

Asn Thr Asn Gly Glu Leu Leu Glu Glu Ile Leu Ser Arg Thr Ala Leu
            180                 185                 190

Asn Lys Asp Gln Val Glu Gly Ala Gly Leu Asn Phe Ile Gly Asn Ile
        195                 200                 205

Ala Asn Arg Val Asn Thr Lys Asp Pro Lys Ala Leu Arg Asp Ala Ile
    210                 215                 220

Arg Ser Lys Leu Arg Glu Lys Asp Leu Pro Phe Leu Gly Phe Leu Pro
225                 230                 235                 240

Arg Asp Asp Phe Ile Ala Ser Lys Arg Leu Asn Glu Val Thr His Gln
                245                 250                 255

Leu Gly Ala Lys Gln Leu Phe Gly Thr Lys Ala Ile Pro Asn Asn Val
            260                 265                 270

Val Val Thr Ser Ala Val Val Ala Thr Ser Ala Leu Lys Asp Leu Phe
        275                 280                 285

Ala His Leu Lys Asn Tyr Lys Asp Gly Ala Leu Val Ile Thr Ser Ala
    290                 295                 300

Asp Arg Ser Asp Val Met Leu Gly Leu Met Ala Ser Arg Leu Pro Gly
305                 310                 315                 320

Ile Leu Pro Asn Val Ser Ala Ile Val Leu Thr Asn Gly Ser Tyr Pro
                325                 330                 335

His Ser Asn Thr Gln Glu Ile Leu Gln Gly Val Glu Ala Leu Asp Lys
            340                 345                 350

Thr Gly Leu Ser Ile Pro Ile Phe Ser Val Pro Glu Asp Thr Phe Thr
        355                 360                 365

Thr Ala Asp Lys Phe Ser Lys Val Ser Thr Asp Ile Leu Pro Thr Ser
    370                 375                 380

Ser Leu Lys Ile Asp Arg Ser Lys Gln Leu Phe Asp Glu Phe Val Gly
385                 390                 395                 400

Lys Glu Ser Ile Ile Gly Glu Leu Asp Glu Gly Met Val Val Asn Arg
                405                 410                 415

Ser Pro Lys Gln Phe Gln His Phe Leu Phe Ser Lys Ser Arg Ala Val
            420                 425                 430

Gln Arg His Ile Val Leu Thr Glu Gly Glu Asp Ile Arg Val Leu Gln
        435                 440                 445

Ala Ala Asp Gln Val Leu Arg Gln Lys Leu Ser Lys Val Thr Ile Leu
    450                 455                 460

Gly Asn Pro Asp Asp Ile Glu Arg His Ala Lys Ser Leu Asn Leu Asp
465                 470                 475                 480

Leu Ser Arg Ala Asn Ile Val Arg Thr Ala Asp Ser Asp Leu Leu Glu
                485                 490                 495

Arg Tyr Val Asp Gln Tyr Phe Glu Lys Arg Lys His Lys Gly Val Thr
            500                 505                 510

Arg Glu Ser Ala Arg Asp Ala Val Leu Glu Glu Thr Cys Phe Gly Thr
        515                 520                 525

Met Met Val Glu Met Gly Asp Ala Asp Gly Met Val Ser Gly Ala Cys
    530                 535                 540

His Thr Thr Ala Asn Thr Ile Arg Pro Ala Leu Gln Leu Ile Lys Thr
545                 550                 555                 560
```

```
Ala Pro Asn Arg Pro Ile Val Ser Ser Ile Phe Phe Met Cys Leu Glu
                565                 570                 575

Asp Gly Val Arg Ile Tyr Gly Asp Cys Ala Val Asn Thr Asp Pro Ser
            580                 585                 590

Ala Gln Asp Leu Ala Gln Ile Ala Val Thr Ser Ala Glu Ser Ala Glu
        595                 600                 605

Ala Phe Gly Leu Ile Pro Lys Val Ala Leu Leu Ser Tyr Ala Thr Gly
    610                 615                 620

Asp Ser Asn Ser Gly Pro Ile Ile Asp Lys Val Arg Glu Ala Thr Lys
625                 630                 635                 640

Ile Ala Gln Glu Leu Arg Pro Asp Leu Asp Ile Tyr Gly Pro Ile
                645                 650                 655


<210> SEQ ID NO 104
<211> LENGTH: 1968
<212> TYPE: DNA
<213> ORGANISM: Phytophthora parasitica

<400> SEQUENCE: 104

atgtggaccc tgcgaaacac cttccgacga acctccgccg ccttcgcccc ccagcgacga     60

gccctgaccg ccgccgccat cgccgagggc aaggtcccca tcaacaacct gttcgtcacc    120

tccaccgagg tcaccaagaa gaccgccccc gtcctgatcg gcctgaccaa caccctggag    180

cagaagttca ccaaggtcgg ctacttccga cccatccagc ccatcgtcga gaccgaccac    240

cacatcgacg tcatgaagca gcagctgggc ctgaccaagt ccgtcgacca gctgtacggc    300

gtcacctccg agcgagccat cgagtactgg ctgaacggca agggcgacga cctggtcgag    360

gagatcctgg agcgatacga ggcctgccga gagggccacg acttcatgat catcgagggc    420

tcccagatct ccaagcacga gtccgccatg tcctggaaga tcaacgtcga catcgccaag    480

gccatcggct cccccgtcct gaccatctcc gacttctccg agtccgccaa caccaacggc    540

gagctgctgg aggagatcct gtcccgaacc gccctgaaca aggaccaggt cgagggcgcc    600

ggcctgaact tcatcggcaa catcgccaac cgagtcaaca ccaaggaccc caaggccctg    660

cgagacgcca tccgatccaa gctgcgagag aaggacctgc ccttcctggg cttcctgccc    720

cgagacgact tcatcgcctc caagcgactg aacgaggtca cccaccagct gggcgccaag    780

cagctgttcg gcaccaaggc catccccaac aacgtcgtcg tcacctccgc cgtcgtcgcc    840

acctccgccc tgaaggacct gttcgcccac ctgaagaact acaaggacgg cgccctggtc    900

atcacctccg ccgaccgatc cgacgtcatg ctgggcctga tggcctcccg actgcccggc    960

atcctgccca acgtctccgc catcgtcctg accaacggct cctaccccca ctccaacacc   1020

caggagatcc tgcagggcgt cgaggccctg gacaagaccg gcctgtccat ccccatcttc   1080

tccgtccccg aggacacctt caccaccgcc gacaagttct ccaaggtctc caccgacatc   1140

ctgcccacct cctccctgaa gatcgaccga tccaagcagc tgttcgacga gttcgtcggc   1200

aaggagtcca tcatcggcga gctggacgag ggcatggtcg tcaaccgatc ccccaagcag   1260

ttccagcact tcctgttctc caagtcccga gccgtccagc gacacatcgt cctgaccgag   1320

ggcgaggaca tccgagtcct gcaggccgcc gaccaggtcc tgcgacagaa gctgtccaag   1380

gtcaccatcc tgggcaaccc cgacgacatc gagcgacacg ccaagtccct gaacctggac   1440

ctgtcccgag ccaacatcgt ccgaaccgcc gactccgacc tgctggagcg atacgtcgac   1500

cagtacttcg agaagcgaaa gcacaagggc gtcacccgag agtccgcccg agacgccgtc   1560

ctggaggaga cctgcttcgg caccatgatg gtcgagatgg gcgacgccga cggcatggtc   1620
```

```
tccggcgcct gccacaccac cgccaacacc atccgacccg ccctgcagct gatcaagacc   1680

gcccccaacc gacccatcgt ctcctccatc ttcttcatgt gcctggagga cggcgtccga   1740

atctacggcg actgcgccgt caacaccgac ccctccgccc aggacctggc ccagatcgcc   1800

gtcacctccg ccgagtccgc cgaggccttc ggcctgatcc ccaaggtcgc cctgctgtcc   1860

tacgccaccg gcgactccaa ctccggcccc atcatcgaca aggtccgaga ggccaccaag   1920

atcgcccagg agctgcgacc cgacctggac atctacggcc ccatctaa                1968


<210> SEQ ID NO 105
<211> LENGTH: 657
<212> TYPE: PRT
<213> ORGANISM: Phytophthora parasitica

<400> SEQUENCE: 105

Met Trp Thr Leu Arg Arg Ser Leu Arg His Ser Thr Gly Val Ala Leu
1               5                   10                  15

Pro His Arg Arg Ala Leu Thr Ala Ala Ala Ile Ser Gln Gly Lys Val
            20                  25                  30

Pro Ile Asn Asn Leu Tyr Val Thr Ser Thr Glu Val Thr Lys Lys Thr
        35                  40                  45

Ala Pro Val Leu Ile Gly Leu Ala His Val Leu Glu Gln Lys Phe Thr
    50                  55                  60

Lys Val Gly Tyr Phe Arg Pro Ile Gln Pro Ser Pro Asp Ser Ser Met
65                  70                  75                  80

Ala Asp His His Val Asp Val Met Lys Gln Gln Leu Glu Leu Ser Lys
                85                  90                  95

Asp Val Glu Glu Leu Tyr Gly Val Thr Ser Ser Arg Ala Met Glu Ala
            100                 105                 110

Met Leu Thr Gly Lys Gly Asp Asp Val Val Glu Glu Ile Leu Glu Arg
        115                 120                 125

Tyr Glu Gln Cys Arg Lys Gly His Asp Phe Met Ile Ile Glu Gly Ser
    130                 135                 140

Gln Ile Ser Lys His Glu Ser Ala Met Ser Trp Lys Ile Asn Val Asp
145                 150                 155                 160

Ile Ala Lys Ala Ile Gly Ser Pro Val Leu Met Val Thr Asp Phe Gly
                165                 170                 175

Asp Thr Ser Ala Ala Asn Asp Ala Leu Ile Glu Glu Met Val Ser Arg
            180                 185                 190

Thr Val Met Gly Arg Asp Gln Ala Glu Asp Ala Gly Leu Asn Tyr Leu
        195                 200                 205

Gly Thr Ile Ala Asn Arg Val Arg Ala Ser Asn Val Asp Ser Leu Arg
    210                 215                 220

Ala Ser Leu Lys Arg Lys Met Gly Asp Lys Asp Ile Pro Phe Leu Gly
225                 230                 235                 240

Phe Leu Pro Met Asp Glu Ile Ile Ala Ser Lys Arg Leu Asn Glu Val
                245                 250                 255

Thr His Gln Leu Gly Ala Thr Gln Leu Phe Gly His Ser Ile Ala Asn
            260                 265                 270

Asp Ala Val Val Thr Ser Ala Val Val Ala Ala Ser Ala Leu Lys Asp
        275                 280                 285

Leu Phe Ala His Leu Lys Lys Tyr Lys Asp Gly Ala Met Ile Ile Thr
    290                 295                 300

Ser Gly Asp Arg Ser Asp Leu Met Leu Gly Leu Met Val Ser Arg Leu
```

305 310 315 320

Pro Gly Val Leu Pro Asn Ile Ser Ala Ile Val Leu Thr Asn Gly Asn
325 330 335

Tyr Pro His Ser Asn Thr Gln Glu Ile Leu Lys Gly Val Gln Ala Leu
340 345 350

Asp Lys Thr Ala Leu Ser Leu Pro Ile Phe Ser Thr Pro Asn Asp Thr
355 360 365

Phe Ser Thr Ala Asp Gly Phe Ala Lys Val Ser Thr Asp Ile Leu Pro
370 375 380

Ser Ser Lys Leu Lys Ile Asp Arg Ser Lys Gln Leu Phe Asp Glu Phe
385 390 395 400

Val Glu Lys Glu Met Leu Ile Gly Glu Leu Asp Glu Gly Met Val Val
405 410 415

Asn Arg Ser Pro Lys Gln Phe Gln His Phe Leu Phe Ser Lys Ser Arg
420 425 430

Ala Val Gln Arg His Ile Val Leu Thr Glu Gly Glu Asp Ile Arg Val
435 440 445

Leu Gln Ala Ala Asp Gln Ile Leu Arg Gln Asn Leu Ser Lys Ile Thr
450 455 460

Ile Leu Gly Asp Pro Asp Glu Ile Leu Leu Asn Ala Lys Met Ala Asn
465 470 475 480

Leu Asp Leu Ser Arg Ala Asn Ile Val Ser Pro Ala Asn Ser Ala Leu
485 490 495

Leu Asp Lys Tyr Val Asp Tyr Phe Tyr Ala Lys Arg Lys His Lys Gly
500 505 510

Val Thr Lys Glu Leu Ala Arg Asp Tyr Cys Lys Asp Glu Thr Tyr Phe
515 520 525

Gly Thr Leu Met Val Glu Leu Gly Asp Ala Asp Gly Met Val Ser Gly
530 535 540

Ala Cys His Thr Thr Ala Asn Thr Ile Arg Pro Ala Leu Gln Leu Ile
545 550 555 560

Lys Thr Ala Pro Asn Arg Pro Ile Val Ser Ser Ile Phe Phe Met Cys
565 570 575

Leu Glu Asp Gly Val Arg Ile Tyr Gly Asp Cys Ala Val Asn Thr Asp
580 585 590

Pro Ser Ala Gln Asp Leu Ala Gln Ile Ala Val Thr Ser Ala Glu Ser
595 600 605

Ala Glu Ala Phe Gly Leu Ile Pro Lys Val Ala Leu Leu Ser Tyr Ala
610 615 620

Thr Gly Asp Ser Asn Ser Gly Pro Ile Ile Asp Lys Val Arg Glu Ala
625 630 635 640

Thr Lys Ile Ala Gln Glu Leu Arg Pro Asp Leu Asp Ile Tyr Gly Pro
645 650 655

Ile

<210> SEQ ID NO 106
<211> LENGTH: 1974
<212> TYPE: DNA
<213> ORGANISM: Phytophthora parasitica

<400> SEQUENCE: 106
atgtggaccc tgcgacgatc cctgcgacac tccaccggcg tcgccctgcc ccaccgacga 60
gccctgaccg ccgccgccat ctcccagggc aaggtcccca tcaacaacct gtacgtcacc 120

-continued

```
tccaccgagg tcaccaagaa gaccgccccc gtcctgatcg gcctggccca cgtcctggag    180
cagaagttca ccaaggtcgg ctacttccga cccatccagc cctcccccga ctcctccatg    240
gccgaccacc acgtcgacgt catgaagcag cagctggagc tgtccaagga cgtcgaggag    300
ctgtacggcg tcacctcctc ccgagccatg gaggccatgc tgaccggcaa gggcgacgac    360
gtcgtcgagg agatcctgga gcgatacgag cagtgccgaa agggccacga cttcatgatc    420
atcgagggct cccagatctc caagcacgag tccgccatgt cctggaagat caacgtcgac    480
atcgccaagg ccatcggctc ccccgtcctg atggtcaccg acttcggcga cacctccgcc    540
gccaacgacg ccctgatcga ggagatggtc tcccgaaccg tcatgggccg agaccaggcc    600
gaggacgccg gcctgaacta cctgggcacc atcgccaacc gagtccgagc ctccaacgtc    660
gactccctgc gagcctccct gaagcgaaag atgggcgaca aggacatccc cttcctgggc    720
ttcctgccca tggacgagat catcgcctcc aagcgactga acgaggtcac ccaccagctg    780
ggcgccaccc agctgttcgg ccactccatc gccaacgacg ccgtcgtcac ctccgccgtc    840
gtcgccgcct ccgccctgaa ggacctgttc gcccacctga agaagtacaa ggacggcgcc    900
atgatcatca cctccggcga ccgatccgac ctgatgctgg gcctgatggt ctcccgactg    960
cccggcgtcc tgcccaacat ctccgccatc gtcctgacca acggcaacta cccccactcc   1020
aacacccagg agatcctgaa gggcgtccag gccctggaca agaccgccct gtccctgccc   1080
atcttctcca cccccaacga caccttctcc accgccgacg gcttcgccaa ggtctccacc   1140
gacatcctgc cctcctccaa gctgaagatc gaccgatcca agcagctgtt cgacgagttc   1200
gtcgagaagg agatgctgat cggcgagctg gacgagggca tggtcgtcaa ccgatccccc   1260
aagcagttcc agcacttcct gttctccaag tcccgagccg tccagcgaca catcgtcctg   1320
accgagggcg aggacatccg agtcctgcag gccgccgacc agatcctgcg acagaacctg   1380
tccaagatca ccatcctggg cgacccccgac gagatcctgc tgaacgccaa gatggccaac   1440
ctggacctgt cccgagccaa catcgtctcc cccgccaact ccgccctgct ggacaagtac   1500
gtcgactact tctacgccaa gcgaaagcac aagggcgtca ccaaggagct ggcccgagac   1560
tactgcaagg acgagaccta cttcggcacc ctgatggtcg agctgggcga cgccgacggc   1620
atggtctccg gcgcctgcca caccaccgcc aacaccatcc gacccgccct gcagctgatc   1680
aagaccgccc ccaaccgacc catcgtctcc tccatcttct tcatgtgcct ggaggacggc   1740
gtccgaatct acggcgactg cgccgtcaac accgacccct ccgcccagga cctggcccag   1800
atcgccgtca cctccgccga gtccgccgag gccttcggcc tgatccccaa ggtcgccctg   1860
ctgtcctacg ccaccggcga ctccaactcc ggccccatca tcgacaaggt ccgagaggcc   1920
accaagatcg cccaggagct gcgacccgac ctggacatct acggccccat ctaa          1974
```

<210> SEQ ID NO 107
<211> LENGTH: 760
<212> TYPE: PRT
<213> ORGANISM: Phytophthora ramorum

<400> SEQUENCE: 107

```
Met Trp Thr Leu Arg Arg Ser Leu Arg Arg Ser Thr Ala Ser Ala Thr
1               5                   10                  15

Leu Pro Thr Arg Arg Ala Leu Thr Ala Ala Ser Ile Ala Gln Gly Lys
            20                  25                  30

Val Pro Ile Glu Asn Leu Tyr Val Thr Ser Thr Glu Val Thr Lys Lys
        35                  40                  45
```

```
Thr Ala Pro Val Leu Ile Gly Leu Ala His Val Leu Glu Gln Lys Phe
    50                  55                  60

Ser Lys Val Gly Tyr Phe Arg Pro Ile Gln Pro Ser Arg Asp Ser Ser
65                  70                  75                  80

Met Ala Asp His His Val Asp Val Met Arg Gln Gln Leu Glu Leu Ser
                85                  90                  95

Gln Asp Val Glu Gln Leu Tyr Gly Val Thr Ser Ser Arg Ala Met Glu
            100                 105                 110

Ala Met Leu Thr Gly Lys Gly Asp Asp Val Val Glu Glu Ile Leu Asp
        115                 120                 125

Arg Tyr Glu Gln Cys Arg Lys Gly His Asp Phe Met Ile Ile Glu Gly
    130                 135                 140

Ser Gln Ile Ser Lys His Glu Ser Ala Met Ser Trp Lys Ile Asn Val
145                 150                 155                 160

Asp Ile Ala Lys Ala Ile Gly Ser Pro Val Leu Met Val Thr Asp Phe
                165                 170                 175

Gly Asp Ser Ser Ala Val Asn Gly Glu Leu Leu Glu Glu Met Val Ser
            180                 185                 190

Arg Thr Leu Met Gly Arg Asp Gln Ala Asp Ala Ala Gly Leu Asn Tyr
        195                 200                 205

Leu Gly Thr Ile Ala Asn Arg Val Arg Ala Lys Asp Ala Glu Ala Leu
    210                 215                 220

Arg Ala Glu Leu Lys Lys Thr Val Ser Gly Lys Glu Ile Pro Phe Leu
225                 230                 235                 240

Gly Phe Leu Pro Met Asp Glu Ile Ile Ala Ser Lys Arg Leu Asn Glu
                245                 250                 255

Val Thr His Gln Leu Gly Ala Thr Gln Leu Phe Gly Asn Ser Ile Ala
            260                 265                 270

Asn Asp Ala Val Val Thr Ser Ala Val Val Ala Ala Ser Ala Leu Lys
        275                 280                 285

Asp Leu Phe Ala His Leu Lys Lys Tyr Lys Asp Gly Ala Met Ile Ile
    290                 295                 300

Thr Ser Gly Asp Arg Ser Asp Leu Met Leu Gly Leu Met Val Ser Arg
305                 310                 315                 320

Leu Pro Gly Val Leu Pro Asn Ile Ser Ala Ile Val Leu Thr Asn Gly
                325                 330                 335

Asn Tyr Pro His Ser Asn Thr Gln Glu Ile Leu Lys Gly Val Glu Ala
            340                 345                 350

Leu Asp Lys Thr Gly Leu Ser Leu Pro Ile Phe Ser Thr Pro Asn Asp
        355                 360                 365

Thr Phe Ser Thr Ala Asp Gly Phe Ala Lys Val Ser Thr Asp Ile Leu
    370                 375                 380

Pro Ser Ser Lys Leu Lys Ile Asp Arg Ser Lys Gln Leu Phe Asp Glu
385                 390                 395                 400

Phe Val Glu Lys Glu Met Leu Ile Gly Glu Leu Asp Gln Gly Met Val
                405                 410                 415

Val Asn Arg Ser Pro Lys Gln Phe Gln His Phe Leu Phe Ser Lys Ser
            420                 425                 430

Arg Ala Val Gln Arg Arg Ile Val Leu Thr Glu Gly Glu Asp Ile Arg
        435                 440                 445

Val Leu Gln Ala Ala Asp Gln Ile Leu Arg Gln Asn Leu Ser Lys Ile
    450                 455                 460

Thr Ile Leu Gly Asp Pro Asp Glu Ile Leu Leu Asn Ala Lys Thr Ser
```

-continued 465 470 475 480

Asn Leu Asp Leu Ser Arg Ala Asn Ile Val Arg Pro Ala Asp Ser Asp
485 490 495

Leu Leu Glu Lys Tyr Val Asp Tyr Phe Tyr Glu Lys Arg Lys His Lys
500 505 510

Gly Val Thr Lys Glu Leu Ala Arg Asp Tyr Cys Lys Asp Glu Thr Tyr
515 520 525

Phe Gly Thr Leu Met Val Glu Met Gly Asp Ala Asp Gly Met Val Ser
530 535 540

Gly Ala Cys His Thr Thr Ala Asn Thr Ile Arg Pro Ala Leu Gln Leu
545 550 555 560

Ile Lys Thr Thr Pro Asn Arg Pro Ile Val Ser Ser Val Phe Phe Met
565 570 575

Cys Leu Glu Asp Gly Val Arg Ile Tyr Gly Asp Cys Ala Val Asn Thr
580 585 590

Asp Pro Ser Ala Ala Asp Leu Ala Gln Ile Ala Val Thr Ser Ala Glu
595 600 605

Ser Ala Glu Ala Phe Gly Leu Ile Pro Lys Val Ala Leu Leu Ser Tyr
610 615 620

Ala Thr Gly Asp Ser Asn Ser Gly Pro Ile Ile Asp Lys Val Arg Glu
625 630 635 640

Ala Thr Lys Ile Ala Gln Glu Leu Arg Pro Asp Leu Asp Ile Tyr Gly
645 650 655

Pro Ile Gln Tyr Asp Ala Ala Val Asp Ala Ser Ile Ala Lys Thr Lys
660 665 670

Leu Lys Ala Ile Pro Ser Gly Ala Lys Val Gly Gly Gln Ala Asn Val
675 680 685

Leu Ile Phe Pro Asp Leu Asn Thr Gly Asn Asn Thr Tyr Lys Ala Val
690 695 700

Gln Gln Ser Thr Gly Cys Val Ala Met Gly Pro Met Leu Gln Gly Leu
705 710 715 720

Arg Lys Pro Val Asn Asp Leu Ser Arg Gly Ala Thr Val Lys Asp Ile
725 730 735

Val Thr Thr Val Ala Ile Thr Ala Ile Gln Ala Asp Gln Val Ile Leu
740 745 750

Lys Arg Glu Ala Ala Thr Lys Lys
755 760

<210> SEQ ID NO 108
<211> LENGTH: 2283
<212> TYPE: DNA
<213> ORGANISM: Phytophthora ramorum

<400> SEQUENCE: 108
atgtggaccc tgcgacgatc cctgcgacga tccaccgcct ccgccaccct gcccacccga 60
cgagccctga ccgccgcctc catcgcccag ggcaaggtcc ccatcgagaa cctgtacgtc 120
acctccaccg aggtcaccaa gaagaccgcc cccgtcctga tcggcctggc ccacgtcctg 180
gagcagaagt tctccaaggt cggctacttc cgacccatcc agccctcccg agactcctcc 240
atggccgacc accacgtcga cgtcatgcga cagcagctgg agctgtccca ggacgtcgag 300
cagctgtacg gcgtcacctc ctcccgagcc atggaggcca tgctgaccgg caagggcgac 360
gacgtcgtcg aggagatcct ggaccgatac gagcagtgcc gaaagggcca cgacttcatg 420
atcatcgagg gctcccagat ctccaagcac gagtccgcca tgtcctggaa gatcaacgtc 480

```
gacatcgcca aggccatcgg ctcccccgtc ctgatggtca ccgacttcgg cgactcctcc    540
gccgtcaacg gcgagctgct ggaggagatg gtctcccgaa ccctgatggg ccgagaccag    600
gccgacgccg ccggcctgaa ctacctgggc accatcgcca accgagtccg agccaaggac    660
gccgaggccc tgcgagccga gctgaagaag accgtctccg gcaaggagat cccccttcctg    720
ggcttcctgc ccatggacga gatcatcgcc tccaagcgac tgaacgaggt cacccaccag    780
ctgggcgcca cccagctgtt cggcaactcc atcgccaacg acgccgtcgt cacctccgcc    840
gtcgtcgccg cctccgccct gaaggacctg ttcgcccacc tgaagaagta caaggacggc    900
gccatgatca tcacctccgg cgaccgatcc gacctgatgc tgggcctgat ggtctcccga    960
ctgcccggcg tcctgcccaa catctccgcc atcgtcctga ccaacggcaa ctaccccccac   1020
tccaacaccc aggagatcct gaagggcgtc gaggccctgg acaagaccgg cctgtccctg   1080
cccatcttct ccacccccaa cgacaccttc tccaccgccg acggcttcgc caaggtctcc   1140
accgacatcc tgccctcctc caagctgaag atcgaccgat ccaagcagct gttcgacgag   1200
ttcgtcgaga aggagatgct gatcggcgag ctggaccagg gcatggtcgt caaccgatcc   1260
cccaagcagt tccagcactt cctgttctcc aagtcccgag ccgtccagcg acgaatcgtc   1320
ctgaccgagg gcgaggacat ccgagtcctg caggccgccg accagatcct gcgacagaac   1380
ctgtccaaga tcaccatcct gggcgacccc gacgagatcc tgctgaacgc caagacctcc   1440
aacctggacc tgtcccgagc caacatcgtc cgacccgccg actccgacct gctggagaag   1500
tacgtcgact acttctacga gaagcgaaag cacaagggcg tcaccaagga gctggcccga   1560
gactactgca aggacgagac ctacttcggc accctgatgg tcgagatggg cgacgccgac   1620
ggcatggtct ccggcgcctg ccacaccacc gccaacacca tccgacccgc cctgcagctg   1680
atcaagacca cccccaaccg acccatcgtc tcctccgtct tcttcatgtg cctggaggac   1740
ggcgtccgaa tctacggcga ctgcgccgtc aacaccgacc cctccgccgc cgacctggcc   1800
cagatcgccg tcacctccgc cgagtccgcc gaggccttcg gcctgatccc caaggtcgcc   1860
ctgctgtcct acgccaccgg cgactccaac tccggcccca tcatcgacaa ggtccgagag   1920
gccaccaaga tcgcccagga gctgcgaccc gacctggaca tctacggccc catccagtac   1980
gacgccgccg tcgacgcctc catcgccaag accaagctga aggccatccc ctccggcgcc   2040
aaggtcggcg gccaggccaa cgtcctgatc ttccccgacc tgaacaccgg caacaacacc   2100
tacaaggccg tccagcagtc caccggctgc gtcgccatgg gccccatgct gcagggcctg   2160
cgaaagcccg tcaacgacct gtcccgaggc gccaccgtca aggacatcgt caccaccgtc   2220
gccatcaccg ccatccaggc cgaccaggtc atcctgaagc gagaggccgc caccaagaag   2280
taa                                                                  2283
```

<210> SEQ ID NO 109
<211> LENGTH: 743
<212> TYPE: PRT
<213> ORGANISM: Saprolegnia parasitica

<400> SEQUENCE: 109

```
Met Phe Arg Leu Arg Arg Pro Leu Gln Ser Ala Pro Arg Arg Trp Tyr
1               5                   10                  15

Ser Glu Thr His Lys Val Asn Asp Arg Val Val Val Leu Ser Asn Asp
            20                  25                  30

Ala Thr Ser His Gln Thr Pro Val Leu Leu Gly Leu Met Asn Thr Leu
        35                  40                  45
```

```
Ala Ile Lys Tyr His Ser Val Gly Tyr Phe Arg Pro Ile Ala Pro Pro
    50                  55                  60

Val Gly Ser Asp His His Val Glu Leu Phe Lys Ser Glu Leu Lys Leu
65                  70                  75                  80

Pro Glu Thr Tyr Glu Gln Leu Val Gly Leu His His Asp Asp Val Val
                85                  90                  95

Asn Ala Arg Leu Ser Gly Asp Leu Asp Val Val Thr Asp Thr Ile Val
            100                 105                 110

Ala Lys Phe Glu Ala Leu Arg Ala Lys His Asp Phe Val Val Ile Glu
        115                 120                 125

Gly Ala Thr Phe Glu Ser Ala Pro Asp Leu Ala Trp Asp Ile Asn Val
    130                 135                 140

Glu Leu Ala Lys Thr Leu Gly Ala Pro Val Leu Leu Thr Asn Asp Phe
145                 150                 155                 160

Gly Asp Val Pro Glu Val Gln Arg Ile Glu Asp Ala Ile Ala Thr Arg
                165                 170                 175

Val Leu Leu Gly Lys Asp Ala Val Asp Ala Ala Gly Leu Thr Tyr Ile
            180                 185                 190

Gly Ser Ile Ala Asn Arg Val Arg Ser Ser Thr Pro Leu Glu Thr Arg
        195                 200                 205

Gln Arg Val His Asp Leu Leu Arg Glu Lys Gly Ala Ala Asp Pro Thr
    210                 215                 220

Ile Phe Leu Gly Ala Leu Pro Leu Asp Ser Ile Leu Ala Ser Lys Arg
225                 230                 235                 240

Leu Asn Glu Val Val Ala Gln Leu Gln Ala Thr Gln Leu Tyr Gly Pro
                245                 250                 255

Ala Ser Pro Asn Ser Val Val Val Thr Glu Gly Leu Ile Gly Thr Ser
            260                 265                 270

Asp Leu Lys Glu Leu Phe Gly His Leu Lys Ala His Asp Asp Gly Leu
        275                 280                 285

Leu Val Ile Thr Ser Ala Asp Arg Thr Asp Val Val Leu Gly Leu Leu
    290                 295                 300

Ala Ser Arg Ala Ser Gly Ala Leu Pro Asn Val Ala Gly Val Val Leu
305                 310                 315                 320

Thr Asn Gly Ala Tyr Pro Gln Asp His Val Lys Asn Ile Leu Asp Gly
                325                 330                 335

Met Ala Lys Ile Asp Asn Ala Thr Ile Pro Ile Tyr Thr Val Glu Gly
            340                 345                 350

Asp Ala Tyr Lys Thr Ala Asn Ala Leu Ser Arg Val Thr Cys Asp Ile
        355                 360                 365

Leu Pro Thr Ser Gln Thr Lys Ile Gln Gln Ser Asn Ile Leu Phe Asp
    370                 375                 380

Lys Phe Val Ser Arg Ser Ala Leu Met Asp Thr Val Cys Gln Ala Val
385                 390                 395                 400

Lys Ser Thr Lys Arg Thr Pro Lys Gln Phe Lys His Phe Leu Phe Ser
                405                 410                 415

Lys Ala Arg Lys Val Gln Gln His Ile Val Leu Thr Glu Gly Glu Asp
            420                 425                 430

Asp Arg Ile Leu Gln Ala Ala Asp Glu Val Leu Arg Arg Asp Ile Ala
        435                 440                 445

Lys Leu Thr Ile Leu Gly Asp Val Glu Ser Ile Ala Ala Arg Ala Lys
    450                 455                 460
```

```
Thr Leu Arg Leu Asp Leu Ser Ala Ala Ser Ile Val Asp Pro Ser Lys
465                 470                 475                 480

Ser Ala Asp Leu Asp Leu Leu Ala Ala Arg Phe Tyr Glu Lys Arg Lys
                485                 490                 495

Val Lys Gly Val Ser Leu Glu Phe Ala Arg Glu Ser Ala Ala Glu Ala
            500                 505                 510

Thr Cys Tyr Gly Thr Leu Met Val Glu Met Gly Leu Ala Asp Gly Met
        515                 520                 525

Val Ser Gly Ala Cys His Thr Thr Ala Asn Thr Val Arg Pro Ala Leu
    530                 535                 540

Gln Leu Ile Lys Thr Arg Pro Asp Arg Pro Leu Val Ser Ser Val Phe
545                 550                 555                 560

Phe Met Cys Leu Glu Asp Asp Val Val Val Tyr Gly Asp Cys Ala Ile
                565                 570                 575

Asn Thr Asp Pro Thr Ala Glu Asp Leu Ala Asn Ile Ala Val Gln Ser
            580                 585                 590

Ala Glu Ser Ala Ile Ala Phe Gly Met Glu Pro Arg Val Ala Leu Leu
        595                 600                 605

Ser Tyr Ala Thr Gly Asp Ser Asn Lys Gly Pro Ile Ile Asp Lys Val
    610                 615                 620

Arg Glu Ala Thr Lys Leu Ala Gln Lys Met Ala Pro Glu Ile Pro Met
625                 630                 635                 640

Tyr Gly Pro Ile Gln Tyr Asp Ala Ala Met Asn Pro Leu Ile Ala Lys
                645                 650                 655

Gln Lys Val Lys Gly Leu Lys Lys Thr Glu Met Glu Val Ala Gly Asn
            660                 665                 670

Ala Asn Val Leu Ile Phe Pro Asp Leu Asn Thr Gly Asn Asn Thr Tyr
        675                 680                 685

Lys Ala Val Gln Gln Ser Thr Asn Cys Leu Ala Met Gly Pro Met Leu
    690                 695                 700

Gln Gly Leu Asn Lys Pro Val Asn Asp Leu Ser Arg Gly Ala Thr Val
705                 710                 715                 720

Gly Asp Ile Val Thr Thr Ile Ala Ile Thr Ala Ile Gln Ala Asp Gln
                725                 730                 735

Met Arg Thr Ala Ala Ser Leu
            740


<210> SEQ ID NO 110
<211> LENGTH: 2232
<212> TYPE: DNA
<213> ORGANISM: Saprolegnia parasitica

<400> SEQUENCE: 110

atgttccgac tgcgacgacc cctgcagtcc gcccccgac gatggtactc cgagacccac      60

aaggtcaacg accgagtcgt cgtcctgtcc aacgacgcca cctcccacca gacccccgtc     120

ctgctgggcc tgatgaacac cctggccatc aagtaccact ccgtcggcta cttccgaccc     180

atcgcccccc ccgtcggctc cgaccaccac gtcgagctgt tcaagtccga gctgaagctg     240

cccgagacct acgagcagct ggtcggcctg caccacgacg acgtcgtcaa cgcccgactg     300

tccggcgacc tggacgtcgt caccgacacc atcgtcgcca agttcgaggc cctgcgagcc     360

aagcacgact tcgtcgtcat cgagggcgcc accttcgagt ccgcccccga cctggcctgg     420

gacatcaacg tcgagctggc caagaccctg ggcgcccccg tcctgctgac caacgacttc     480

ggcgacgtcc ccgaggtcca gcgaatcgag gacgccatcg ccacccgagt cctgctgggc     540
```

```
aaggacgccg tcgacgccgc cggcctgacc tacatcggct ccatcgccaa ccgagtccga    600

tcctccaccc ccctggagac ccgacagcga gtccacgacc tgctgcgaga gaagggcgcc    660

gccgacccca ccatcttcct gggcgccctg cccctggact ccatcctggc ctccaagcga    720

ctgaacgagg tcgtcgccca gctgcaggcc acccagctgt acggccccgc ctcccccaac    780

tccgtcgtcg tcaccgaggg cctgatcggc acctccgacc tgaaggagct gttcggccac    840

ctgaaggccc acgacgacgg cctgctggtc atcacctccg ccgaccgaac cgacgtcgtc    900

ctgggcctgc tggcctcccg agcctccggc gccctgccca acgtcgccgg cgtcgtcctg    960

accaacggcg cctaccccca ggaccacgtc aagaacatcc tggacggcat ggccaagatc   1020

gacaacgcca ccatccccat ctacaccgtc gagggcgacg cctacaagac cgccaacgcc   1080

ctgtcccgag tcacctgcga catcctgccc acctcccaga ccaagatcca gcagtccaac   1140

atcctgttcg acaagttcgt ctcccgatcc gccctgatgg acaccgtctg ccaggccgtc   1200

aagtccacca agcgaacccc caagcagttc aagcacttcc tgttctccaa ggcccgaaag   1260

gtccagcagc acatcgtcct gaccgagggc gaggacgacc gaatcctgca ggccgccgac   1320

gaggtcctgc gacgagacat cgccaagctg accatcctgg gcgacgtcga gtccatcgcc   1380

gcccgagcca agaccctgcg actggacctg tccgccgcct ccatcgtcga cccctccaag   1440

tccgccgacc tggacctgct ggccgcccga ttctacgaga agcgaaaggt caagggcgtc   1500

tccctggagt tcgcccgaga gtccgccgcc gaggccacct gctacggcac cctgatggtc   1560

gagatgggcc tggccgacgg catggtctcc ggcgcctgcc acaccaccgc caacaccgtc   1620

cgacccgccc tgcagctgat caagacccga cccgaccgac ccctggtctc ctccgtcttc   1680

ttcatgtgcc tggaggacga cgtcgtcgtc tacggcgact gcgccatcaa caccgacccc   1740

accgccgagg acctggccaa catcgccgtc cagtccgccg agtccgccat cgccttcggc   1800

atggagcccc gagtcgccct gctgtcctac gccaccggcg actccaacaa gggccccatc   1860

atcgacaagg tccgagaggc caccaagctg gcccagaaga tggcccccga gatccccatg   1920

tacggcccca tccagtacga cgccgccatg aaccccctga tcgccaagca gaaggtcaag   1980

ggcctgaaga agaccgagat ggaggtcgcc ggcaacgcca acgtcctgat cttccccgac   2040

ctgaacaccg gcaacaacac ctacaaggcc gtccagcagt ccaccaactg cctggccatg   2100

ggccccatgc tgcagggcct gaacaagccc gtcaacgacc tgtcccgagg cgccaccgtc   2160

ggcgacatcg tcaccaccat cgccatcacc gccatccagg ccgaccagat gcgaaccgcc   2220

gcctccctgt aa                                                       2232
```

```
<210> SEQ ID NO 111
<211> LENGTH: 343
<212> TYPE: PRT
<213> ORGANISM: Selaginella moellendorffii

<400> SEQUENCE: 111

Phe Arg Asn Ser Leu Phe Ser Arg Ala Lys Glu Asn Asn Gln Val Ile
1               5                   10                  15

Leu Leu Pro Glu Gly Asp Glu Pro Arg Thr Val Gln Ala Ala Gly Phe
            20                  25                  30

Ile Leu Gln His Gly Leu Cys Ser Leu Ile Leu Leu Gly Glu Arg Glu
        35                  40                  45

Lys Leu Leu Glu Ala Ala Lys Val Tyr Asn Val Asp Leu Arg Ser Ala
    50                  55                  60
```

-continued

```
Ile Ile Lys Asp Pro Ser Asp Pro Gln Glu Leu Glu Lys Tyr Ala Thr
65                  70                  75                  80

Val Tyr Tyr Gln Thr Arg Lys His Lys Gly Met Thr Leu Glu Lys Ala
                85                  90                  95

Arg Glu Ile Leu Gly Asn Asp Pro Ile Thr Leu Gly Thr Cys Met Val
            100                 105                 110

Ser Ala Gly Asp Ala Asp Gly Met Val Cys Gly Ala Val His Thr Thr
        115                 120                 125

Ala Asn Thr Val Arg Pro Ala Leu Gln Ile Ile Lys Thr Asp Pro Ala
    130                 135                 140

Thr Pro Ile Val Ser Ser Val Met Phe Ile Cys Leu Glu Asp Ala Val
145                 150                 155                 160

Val Ala Tyr Ala Asp Val Ala Ile Asn Ala Ser Pro Ser Ala Asp Glu
                165                 170                 175

Leu Ala Thr Ile Ala Ile Ala Ser Ala Asp Thr Val Thr Ala Phe Gly
            180                 185                 190

Leu Glu Pro Arg Val Ala Leu Leu Ser Tyr Ala Thr Gly Asp Ser Asn
        195                 200                 205

Ala Gly Pro Leu Val Gln Lys Val Ala Asp Ala Ala Ser Ile Ala Arg
    210                 215                 220

Ser Arg Arg Pro Asp Leu Leu Leu Glu Gly Pro Phe Gln Tyr Asp Ala
225                 230                 235                 240

Ala Val Asn Ala Ala Ala Ala Lys Ile Lys Leu Lys Gly Lys Asn Ser
                245                 250                 255

Glu Val Ala Gly Lys Ala Asn Val Phe Ile Phe Pro Asp Leu Asn Ser
            260                 265                 270

Ser Asn Ile Ala Cys Lys Val Val Gln Gln His Thr Gly Ala Thr Val
        275                 280                 285

Ile Gly Pro Ile Leu Gln Gly Leu Arg Lys Pro Val Asn Asp Leu Ser
    290                 295                 300

Arg Gly Cys Thr Val Lys Asp Ile Ile Ala Thr Ile Ala Thr Thr Ala
305                 310                 315                 320

Ile Gln Ala Ala Ala Glu Lys Lys Lys Ser Lys Ala Val Ala Val Glu
                325                 330                 335

Ala Met Lys Ala Arg Lys Glu
            340


<210> SEQ ID NO 112
<211> LENGTH: 1032
<212> TYPE: DNA
<213> ORGANISM: Selaginella moellendorffii

<400> SEQUENCE: 112

ttccgaaact ccctgttctc ccgagccaag gagaacaacc aggtcatcct gctgcccgag      60

ggcgacgagc cccgaaccgt ccaggccgcc ggcttcatcc tgcagcacgg cctgtgctcc     120

ctgatcctgc tgggcgagcg agagaagctg ctggaggccg ccaaggtcta caacgtcgac     180

ctgcgatccg ccatcatcaa ggacccctcc gacccccagg agctggagaa gtacgccacc     240

gtctactacc agacccgaaa gcacaagggc atgaccctgg agaaggcccg agagatcctg     300

ggcaacgacc ccatcaccct gggcacctgc atggtctccg ccggcgacgc cgacggcatg     360

gtctgcggcg ccgtccacac caccgccaac accgtccgac ccgccctgca gatcatcaag     420

accgaccccg ccacccccat cgtctcctcc gtcatgttca tctgcctgga ggacgccgtc     480

gtcgcctacg ccgacgtcgc catcaacgcc tccccctccg ccgacgagct ggccaccatc     540
```

```
gccatcgcct ccgccgacac cgtcaccgcc ttcggcctgg agccccgagt cgccctgctg    600

tcctacgcca ccggcgactc caacgccggc cccctggtcc agaaggtcgc cgacgccgcc    660

tccatcgccc gatcccgacg acccgacctg ctgctggagg gcccccttcca gtacgacgcc    720

gccgtcaacg ccgccgccgc caagatcaag ctgaagggca agaactccga ggtcgccggc    780

aaggccaacg tcttcatctt ccccgacctg aactcctcca acatcgcctg caaggtcgtc    840

cagcagcaca ccggcgccac cgtcatcggc cccatcctgc agggcctgcg aaagcccgtc    900

aacgacctgt cccgaggctg caccgtcaag gacatcatcg ccaccatcgc caccaccgcc    960

atccaggccg ccgccgagaa gaagaagtcc aaggccgtcg ccgtcgaggc catgaaggcc   1020

cgaaaggagt aa                                                       1032
```

```
<210> SEQ ID NO 113
<211> LENGTH: 329
<212> TYPE: PRT
<213> ORGANISM: Gluconacetobacter diazotrophicus

<400> SEQUENCE: 113

Met Met Ala Pro Pro Thr Pro Gly His Gly Met Thr Asp Glu Val Thr
1               5                   10                  15

Asp Ala Lys Met Asp Ala Met Ile Ala Gly Pro Gly Phe Leu Asp Thr
            20                  25                  30

Leu Ser Ala Arg Leu Ala Gly Ser Pro Pro Val Asp Ala Ala Val Ile
        35                  40                  45

Tyr Pro Cys Ser Leu Pro Ser Leu Gln Ala Ala Val Gly Leu Gly Gln
    50                  55                  60

Gln Gly Ile Val Gln Pro Ile Leu Ile Gly Pro Gly Glu Arg Ile Arg
65                  70                  75                  80

Ala Leu Ala Arg Ser Ala Ser Leu Asp Leu Ala Ala Cys Arg Leu Val
                85                  90                  95

Glu Ala Ala Asp Glu His Leu Ala Ala Ala Arg Gly Val Ala Leu Ala
            100                 105                 110

Arg Asp Gly Thr Ala Arg Met Leu Met Lys Gly Ser Leu His Ser Ser
        115                 120                 125

Ile Phe Leu Arg Glu Ile Gly His His Glu Ser Gly Leu Arg Thr Asp
    130                 135                 140

Arg Arg Met Ser His Val Phe Val Leu Asp Val Pro Thr Cys Ser Arg
145                 150                 155                 160

Pro Leu Leu Val Thr Asp Gly Ala Val Asn Ile Ala Pro Asp Leu Pro
                165                 170                 175

Ala Arg Arg Asp Ile Val Gln Asn Ala Ile Asp Leu Ala Arg Thr Ile
            180                 185                 190

Gly Ile Ser Arg Pro Arg Val Ala Ile Leu Ser Ala Ile Glu Thr Val
        195                 200                 205

Asn Pro Glu Leu Pro Ser Thr Val Asp Ala Ala Leu Leu Ala Lys Met
    210                 215                 220

Ala Glu Arg Gly Gln Ile Thr Gly Gly Ile Val Asp Gly Pro Leu Ala
225                 230                 235                 240

Leu Asp Asn Ala Leu Ser Ala Glu Ala Ala Arg Cys Lys Gly Val Glu
                245                 250                 255

Ser Pro Val Ala Gly Cys Ala Asp Ile Leu Val Val Pro Asp Leu Glu
            260                 265                 270

Ala Gly Asn Met Leu Ala Lys Gln Leu Thr Phe Met Gly Gly Ala Ser
```

```
        275                 280                 285

Ala Ala Gly Val Val Leu Gly Ala Arg Val Pro Val Val Leu Thr Ser
    290                 295                 300

Arg Ala Asp Ser Val Arg Thr Arg Ile Leu Ser Gly Ile Leu Ala Ala
305                 310                 315                 320

Val Leu Ala Gln Ala Arg Gly Met Asp
                325


<210> SEQ ID NO 114
<211> LENGTH: 990
<212> TYPE: DNA
<213> ORGANISM: Gluconacetobacter diazotrophicus

<400> SEQUENCE: 114

atgatggctc ctcctacacc tggtcatggt atgacagatg aagtaacaga tgctaaaatg      60

gatgctatga tagctggtcc tggtttttta gatacattat cagctagatt agctggttca     120

cctcctgtag atgctgctgt aatatatcct tgttcattac cttcattaca agctgctgta     180

ggtttaggtc aacaaggtat agtacaacct atattaatag gtcctggtga aagaataaga     240

gctttagcta gatcagcttc attagattta gctgcttgta gattagtaga agctgctgat     300

gaacatttag ctgctgctag aggtgtagct ttagctagag atggtacagc tagaatgtta     360

atgaaaggtt cattacattc atcaatattt ttaagagaaa taggtcatca tgaatcaggt     420

ttaagaacag atagaagaat gtcacatgta tttgtattag atgtacctac atgttcaaga     480

cctttattag taacagatgg tgctgtaaat atagctcctg atttacctgc tagaagagat     540

atagtacaaa atgctataga tttagctaga acaataggta tatcaagacc tagagtagct     600

atattatcag ctatagaaac agtaaatcct gaattacctt caacagtaga tgctgcttta     660

ttagctaaaa tggctgaaag aggtcaaata acaggtggta tagtagatgg tcctttagct     720

ttagataatg ctttatcagc tgaagctgct agatgtaaag gtgtagaatc acctgtagct     780

ggttgtgctg atatattagt agtacctgat ttagaagctg gtaatatgtt agctaaacaa     840

ttaacattta tgggtggtgc ttcagctgct ggtgtagtat taggtgctag agtacctgta     900

gtattaacat caagagctga ttcagtaaga acaagaatat tatcaggtat attagctgct     960

gtattagctc aagctagagg tatggattga                                      990


<210> SEQ ID NO 115
<211> LENGTH: 953
<212> TYPE: PRT
<213> ORGANISM: Yarrowia lipolytica

<400> SEQUENCE: 115

Met Ile Glu Gly Ile Ser Phe Ala Ser Phe Val Thr His Glu Lys Pro
1               5                   10                  15

Lys Phe Val Arg Ala Leu Asp Phe Tyr Lys Ala Leu Gly Phe Leu Pro
            20                  25                  30

Thr Lys Glu Tyr Lys His Gly Thr Asp His His Ala Thr Asp Glu Glu
        35                  40                  45

Gly Ala Gly Ser Ile Gln Glu Val Trp Leu Thr Ser Ser Arg Ala Gly
    50                  55                  60

Val Pro Ser Val Thr Val Lys Leu Arg Leu Ser Arg His Gly Asn Glu
65                  70                  75                  80

His Val Ser Leu Pro Asn Leu Lys His Asp Trp Arg Ser Leu Val Pro
                85                  90                  95
```

-continued

```
Ser Leu Val Tyr Tyr Ala Pro Asp Leu Asp Ala Val Arg Ala Ala Ile
            100                 105                 110

Thr Pro Phe Leu His Glu Asp His Ser Thr Leu Leu Glu Arg Pro Ser
        115                 120                 125

His Thr Asn Phe Ile Glu Leu Tyr Ala Ile Asp Pro Met Gly Asn Leu
    130                 135                 140

Val Gly Phe Ser Arg Arg Glu Asn Pro Tyr Ser Ser Ala Met Gln Lys
145                 150                 155                 160

Pro Phe Ser Ala Asp Asp Ile Gly Pro Gln Asn Phe Ser Lys Pro Asn
                165                 170                 175

Glu Thr Lys Ile Lys Gly Lys Lys Arg Ile Gly Val Met Thr Ser Gly
            180                 185                 190

Gly Asp Ala Pro Gly Met Cys Ala Ala Val Arg Ala Val Val Arg Ala
        195                 200                 205

Gly Ile Ala Arg Gly Cys Glu Val Tyr Ala Val Arg Glu Gly Tyr Glu
    210                 215                 220

Gly Leu Val Lys Gly Gly Asp Leu Ile Glu Pro Leu Ser Trp Glu Asp
225                 230                 235                 240

Val Arg Gly Trp Leu Ser Leu Gly Gly Thr Leu Ile Gly Thr Ala Arg
                245                 250                 255

Cys Lys Glu Phe Arg Glu Arg Glu Gly Arg Leu Ala Gly Ala Leu Asn
            260                 265                 270

Met Val Lys Asn Gly Ile Asp Ala Leu Ile Val Ile Gly Gly Asp Gly
        275                 280                 285

Ser Leu Thr Gly Ala Asp Leu Phe Arg Glu Glu Trp Pro Ser Leu Ile
    290                 295                 300

Glu Glu Leu Val Thr Asn Gly Ser Ile Thr Ala Glu Gln Ala Glu Arg
305                 310                 315                 320

His Arg His Leu Asp Ile Cys Gly Met Val Gly Ser Ile Asp Asn Asp
                325                 330                 335

Met Ala Thr Thr Asp Val Thr Ile Gly Ala Tyr Ser Ser Leu Asp Arg
            340                 345                 350

Ile Cys Glu Leu Val Asp Phe Ile Asp Ala Thr Ala Gln Ser His Ser
        355                 360                 365

Arg Ala Phe Val Val Glu Val Met Gly Arg His Cys Gly Trp Leu Ala
    370                 375                 380

Leu Met Ala Gly Thr Ala Thr Gly Ala Asp Tyr Ile Phe Ile Pro Glu
385                 390                 395                 400

Ala Ala Pro Asp Ala Thr Gln Trp Ala Glu Lys Met Thr Arg Val Val
                405                 410                 415

Lys Arg His Arg Ser Gln Gly Lys Arg Lys Thr Val Val Ile Val Ala
            420                 425                 430

Glu Gly Ala Ile Asp Ser Asp Leu Asn Pro Ile Thr Ala Lys Met Val
        435                 440                 445

Lys Asp Val Leu Asp Gly Ile Gly Leu Asp Thr Arg Ile Ser Thr Leu
    450                 455                 460

Gly His Val Gln Arg Gly Gly Pro Pro Val Ala Ala Asp Arg Val Leu
465                 470                 475                 480

Ala Ser Leu Gln Gly Val Glu Ala Ile Asp Ala Ile Leu Ser Leu Thr
                485                 490                 495

Pro Glu Thr Pro Ser Pro Met Ile Ala Leu Asn Glu Asn Lys Ile Thr
            500                 505                 510

Arg Lys Pro Leu Val Glu Ser Val Ala Leu Thr Lys Lys Val Ala Asp
```

```
        515                 520                 525

Ala Ile Gly Asn Lys Asp Phe Ala Glu Ala Met Arg Leu Arg Asn Pro
    530                 535                 540

Glu Phe Val Glu Gln Leu Gln Gly Phe Leu Leu Thr Asn Ser Ala Asp
545                 550                 555                 560

Lys Asp Arg Pro Gln Glu Pro Ala Lys Asp Pro Leu Arg Val Ala Ile
                565                 570                 575

Val Cys Thr Gly Ala Pro Ala Gly Gly Met Asn Ala Ala Ile Arg Ser
            580                 585                 590

Ala Val Leu Tyr Gly Leu Ala Arg Gly His Gln Met Phe Ala Ile His
        595                 600                 605

Asn Gly Trp Ser Gly Leu Val Lys Asn Gly Asp Asp Ala Val Arg Glu
    610                 615                 620

Leu Thr Trp Leu Glu Val Glu Pro Leu Cys Gln Lys Gly Gly Cys Glu
625                 630                 635                 640

Ile Gly Thr Asn Arg Ser Leu Pro Glu Cys Asp Leu Gly Met Ile Ala
                645                 650                 655

Tyr His Phe Gln Arg Gln Arg Phe Asp Gly Leu Ile Val Ile Gly Gly
            660                 665                 670

Phe Glu Ala Phe Arg Ala Leu Asn Gln Leu Asp Asp Ala Arg His Ala
        675                 680                 685

Tyr Pro Ala Leu Arg Ile Pro Met Val Gly Ile Pro Ala Thr Ile Ser
    690                 695                 700

Asn Asn Val Pro Gly Thr Asp Tyr Ser Leu Gly Ala Asp Thr Cys Leu
705                 710                 715                 720

Asn Ser Leu Val Gln Tyr Cys Asp Val Leu Lys Thr Ser Ala Ser Ala
                725                 730                 735

Thr Arg Leu Arg Leu Phe Val Val Glu Val Gln Gly Gly Asn Ser Gly
            740                 745                 750

Tyr Ile Ala Thr Val Ala Gly Leu Ile Thr Gly Ala Tyr Val Val Tyr
        755                 760                 765

Thr Pro Glu Ser Gly Ile Asn Leu Arg Leu Leu Gln His Asp Ile Ser
    770                 775                 780

Tyr Leu Lys Asp Thr Phe Ala His Gln Ala Asp Val Asn Arg Thr Gly
785                 790                 795                 800

Lys Leu Leu Leu Arg Asn Glu Arg Ser Ser Asn Val Phe Thr Thr Asp
                805                 810                 815

Val Ile Thr Gly Ile Ile Asn Glu Glu Ala Lys Gly Ser Phe Asp Ala
            820                 825                 830

Arg Thr Ala Ile Pro Gly His Val Gln Gln Gly Gly His Pro Ser Pro
        835                 840                 845

Thr Asp Arg Val Arg Ala Gln Arg Phe Ala Ile Lys Ala Val Gln Phe
    850                 855                 860

Ile Glu Glu His His Gly Ser Lys Asn Asn Ala Asp His Cys Val Ile
865                 870                 875                 880

Leu Gly Val Arg Gly Ser Lys Phe Lys Tyr Thr Ser Val Ser His Leu
                885                 890                 895

Tyr Ala His Lys Thr Glu His Gly Ala Arg Arg Pro Lys His Ser Tyr
            900                 905                 910

Trp His Ala Ile Gly Asp Ile Ala Asn Met Leu Val Gly Arg Lys Ala
        915                 920                 925

Pro Pro Leu Pro Glu Thr Leu Asn Asp Glu Ile Glu Lys Asn Ile Ala
    930                 935                 940
```

```
Lys Glu Gln Gly Ile Ile Asp Pro Cys
945                 950


<210> SEQ ID NO 116
<211> LENGTH: 972
<212> TYPE: DNA
<213> ORGANISM: Bacillus subtilis

<400> SEQUENCE: 116

atggcagatt tattttcaac agtgcaagaa aaagtagctg gaaaagacgt taaaattgta      60

tttcctgaag gcttagacga gcgtatttta gaagcggtca gcaagcttgc aggaaacaaa     120

gtgctgaatc cgattgtgat cggcaatgaa aatgagatcc aagcaaaagc aaaagaattg     180

aaccttacgc tgggcggcgt taagatttat gatcctcata catatgaagg catggaagac     240

cttgtacaag cattcgtaga acgccgcaaa ggcaaagcga ctgaagaaca ggctcgtaaa     300

gcattattag acgagaacta cttcggtaca atgctggtgt ataaaggact tgcagacgga     360

cttgtaagcg gagctgctca ctcaactgct gacactgtcc gcccggctct tcaaatcatc     420

aaaacaaaag aaggcgtgaa aaagacttca ggcgtgttca tcatggctcg cggagaagag     480

caatacgtat tcgcagattg cgcgatcaac attgcacctg acagccaaga tcttgccgag     540

attgcgatcg aaagtgccaa tacggcaaaa atgttcgaca ttgagcctcg cgtggcaatg     600

ctcagcttct ctacaaaagg ctcagcaaaa tctgatgaaa cagaaaaagt agcggatgca     660

gtgaaaatcg cgaaagaaaa agcgcctgaa ctgacacttg acggcgaatt ccaatttgat     720

gctgcatttg ttccatctgt agctgagaaa aaagcgccgg attccgagat caaaggggac     780

gctaacgtat tcgtattccc aagtcttgaa gcaggaaaca tcggctataa aatcgctcag     840

cgtttgggca actttgaagc ggtaggacca atcctgcaag gtttaaatat gcctgtaaac     900

gacctttcaa gaggatgtaa cgctgaagat gtttacaatc tcgcattaat tacagcggcg     960

caagcactgt aa                                                         972


<210> SEQ ID NO 117
<211> LENGTH: 333
<212> TYPE: PRT
<213> ORGANISM: Clostridium acetobutylicum

<400> SEQUENCE: 117

Met Asp Leu Ile Glu Ser Ile Trp Glu Cys Ala Lys Gln Asp Lys Lys
1               5                   10                  15

Arg Ile Ile Leu Ala Glu Gly Glu Glu Lys Arg Asn Leu Ile Ala Ala
            20                  25                  30

Asp Lys Ile Ile Lys Glu Gly Leu Ala Glu Leu Val Leu Val Gly Asp
        35                  40                  45

Glu Asn Lys Ile Lys Glu Lys Ala Ser Glu Leu Asn Leu Asp Ile Ser
    50                  55                  60

Lys Ala Glu Ile Met Asp Pro Glu Thr Ser Leu Lys Thr Glu Thr Tyr
65                  70                  75                  80

Ala Arg Asp Phe Tyr Glu Leu Arg Lys His Lys Gly Met Thr Ile Glu
                85                  90                  95

Lys Ser Glu Lys Met Val Arg Asp Pro Leu Tyr Phe Ala Thr Met Ala
            100                 105                 110

Leu Lys Asp Gly Tyr Val Asp Gly Met Val Ser Gly Ala Val His Thr
        115                 120                 125

Thr Gly Asp Leu Leu Arg Pro Gly Leu Gln Ile Ile Lys Thr Ala Pro
```

```
    130                 135                 140

Gly Val Lys Ile Val Ser Gly Phe Phe Val Met Ile Ile Pro Asp Cys
145                 150                 155                 160

Asp Tyr Gly Glu Glu Gly Leu Leu Leu Phe Ala Asp Cys Ala Val Asn
                165                 170                 175

Pro Asn Pro Thr Ser Asp Glu Leu Ala Asp Ile Ala Ile Thr Thr Ala
            180                 185                 190

Glu Thr Ala Arg Lys Leu Cys Asn Val Glu Pro Lys Val Ala Met Leu
        195                 200                 205

Ser Phe Ser Thr Met Gly Ser Ala Lys Gly Glu Met Val Asp Lys Val
    210                 215                 220

Lys Asn Ala Val Glu Ile Thr Lys Lys Phe Arg Pro Asp Leu Ala Ile
225                 230                 235                 240

Asp Gly Glu Leu Gln Leu Asp Ala Ala Ile Asp Ser Glu Val Ala Ala
                245                 250                 255

Leu Lys Ala Pro Ser Ser Asn Val Ala Gly Asn Ala Asn Val Leu Val
            260                 265                 270

Phe Pro Asp Leu Gln Thr Gly Asn Ile Gly Tyr Lys Leu Val Gln Arg
        275                 280                 285

Phe Ala Lys Ala Lys Ala Ile Gly Pro Ile Cys Gln Gly Phe Ala Lys
    290                 295                 300

Pro Ile Asn Asp Leu Ser Arg Gly Cys Ser Ser Glu Asp Ile Val Asn
305                 310                 315                 320

Val Val Ala Ile Thr Val Val Gln Ala Gln Arg Gly Ile
                325                 330


<210> SEQ ID NO 118
<211> LENGTH: 1002
<212> TYPE: DNA
<213> ORGANISM: Clostridium acetobutylicum

<400> SEQUENCE: 118

atggatttaa tagaaagcat atgggagtgt gctaagcaag acaaaaaaag gataatatta      60

gctgaaggtg aagaaaaaag aaatctaatt gccgcagata aaattatcaa agagggatta     120

gcagagcttg ttcttgtagg tgatgaaaat aaaattaaag aaaaagcaag tgagttgaat     180

cttgacattt cgaaggctga aataatggat ccagagacat cactaaaaac agaaacatat     240

gctagagatt tttatgaact tagaaaacac aaaggaatga ctattgaaaa atctgaaaaa     300

atggtaagag atcctcttta ttttgcaaca atggctttaa aagatggcta tgttgatgga     360

atggtttcag gagctgttca cacaactgga gatttattaa gaccaggact tcaaattata     420

aaaactgcac caggagttaa aatagtatca ggattctttg ttatgataat acctgactgc     480

gattatggtg aagagggtct tttattattt gcagattgtg ctgtaaatcc taacccaaca     540

tcagatgaac tagctgatat tgctataact acagctgaaa cagctagaaa attatgtaac     600

gtagagccta aagttgcgat gctttcattc tcaactatgg gaagtgcaaa aggcgaaatg     660

gtagataagg ttaaaaatgc tgttgaaatc acaaagaaat tcagaccgga tcttgctatt     720

gatggtgagc ttcagcttga tgctgcaata gatagtgaag tagcggcttt aaaagcacct     780

tctagtaatg ttgcaggaaa tgcaaatgtt cttgtattcc cagatcttca aacaggaaac     840

attgggtaca agcttgttca aagatttgca aaagcaaaag caataggacc tatatgtcaa     900

ggatttgcaa aacctattaa tgatttatca agaggctgta gctcagagga tatagtaaat     960

gttgttgcta taactgttgt tcaggctcaa agaggtatat aa                       1002
```

<210> SEQ ID NO 119
<211> LENGTH: 328
<212> TYPE: PRT
<213> ORGANISM: Thermoanaerobacterium saccharolyticum

<400> SEQUENCE: 119

```
Met Ser Ile Ile Gln Asn Ile Ile Glu Lys Ala Lys Ser Asp Lys Lys
1               5                   10                  15

Lys Ile Val Leu Pro Glu Gly Ala Glu Pro Arg Thr Leu Lys Ala Ala
            20                  25                  30

Glu Ile Val Leu Lys Glu Gly Ile Ala Asp Leu Val Leu Leu Gly Asn
        35                  40                  45

Glu Asp Glu Ile Arg Asn Ala Ala Lys Asp Leu Asp Ile Ser Lys Ala
    50                  55                  60

Glu Ile Ile Asp Pro Val Lys Ser Glu Met Phe Asp Arg Tyr Ala Asn
65                  70                  75                  80

Asp Phe Tyr Glu Leu Arg Lys Asn Lys Gly Ile Thr Leu Glu Lys Ala
                85                  90                  95

Arg Glu Thr Ile Lys Asp Asn Ile Tyr Phe Gly Cys Met Met Val Lys
            100                 105                 110

Glu Gly Tyr Ala Asp Gly Leu Val Ser Gly Ala Ile His Ala Thr Ala
        115                 120                 125

Asp Leu Leu Arg Pro Ala Phe Gln Ile Ile Lys Thr Ala Pro Gly Ala
    130                 135                 140

Lys Ile Val Ser Ser Phe Phe Ile Met Glu Val Pro Asn Cys Glu Tyr
145                 150                 155                 160

Gly Glu Asn Gly Val Phe Leu Phe Ala Asp Cys Ala Val Asn Pro Ser
                165                 170                 175

Pro Asn Ala Glu Glu Leu Ala Ser Ile Ala Val Gln Ser Ala Asn Thr
            180                 185                 190

Ala Lys Asn Leu Leu Gly Phe Glu Pro Lys Val Ala Met Leu Ser Phe
        195                 200                 205

Ser Thr Lys Gly Ser Ala Ser His Glu Leu Val Asp Lys Val Arg Lys
    210                 215                 220

Ala Thr Glu Ile Ala Lys Glu Leu Met Pro Asp Val Ala Ile Asp Gly
225                 230                 235                 240

Glu Leu Gln Leu Asp Ala Ala Leu Val Lys Glu Val Ala Glu Leu Lys
                245                 250                 255

Ala Pro Gly Ser Lys Val Ala Gly Cys Ala Asn Val Leu Ile Phe Pro
            260                 265                 270

Asp Leu Gln Ala Gly Asn Ile Gly Tyr Lys Leu Val Gln Arg Leu Ala
        275                 280                 285

Lys Ala Asn Ala Ile Gly Pro Ile Thr Gln Gly Met Gly Ala Pro Val
    290                 295                 300

Asn Asp Leu Ser Arg Gly Cys Ser Tyr Arg Asp Ile Val Asp Val Ile
305                 310                 315                 320

Ala Thr Thr Ala Val Gln Ala Gln
                325
```

<210> SEQ ID NO 120
<211> LENGTH: 987
<212> TYPE: DNA
<213> ORGANISM: Thermoanaerobacterium saccharolyticum

<400> SEQUENCE: 120

```
atgagcatta ttcaaaacat cattgaaaaa gctaaaagcg ataaaaagaa aattgttctg     60

ccagaaggtg cagaacccag gacattaaaa gctgctgaaa tagttttaaa agaagggatt    120

gcagatttag tgcttcttgg aaatgaagat gagataagaa atgctgcaaa agacttggac    180

atatccaaag ctgaaatcat tgaccctgta aagtctgaaa tgtttgatag gtatgctaat    240

gatttctatg agttaaggaa gaacaaagga atcacgttgg aaaaagccag agaaacaatc    300

aaggataata tctattttgg atgtatgatg gttaaagaag gttatgctga tggattggta    360

tctggcgcta ttcatgctac tgcagattta ttaagacctg catttcagat aattaaaacg    420

gctccaggag caaagatagt atcaagcttt tttataatgg aagtgcctaa ttgtgaatat    480

ggtgaaaatg gtgtattctt gtttgctgat tgtgcggtca acccatcgcc taatgcagaa    540

gaacttgctt ctattgccgt acaatctgct aatactgcaa agaatttgtt gggctttgaa    600

ccaaaagttg ccatgctatc attttctaca aaaggtagtg catcacatga attagtagat    660

aaagtaagaa aagcgacaga gatagcaaaa gaattgatgc cagatgttgc tatcgacggt    720

gaattgcaat tggatgctgc tcttgttaaa gaagttgcag agctaaaagc gccgggaagc    780

aaagttgcgg gatgtgcaaa tgtgcttata ttccctgatt tacaagctgg taatatagga    840

tataagcttg tacagaggtt agctaaggca aatgcaattg gacctataac acaaggaatg    900

ggtgcaccgg ttaatgattt atcaagagga tgcagctata gagatattgt tgacgtaata    960

gcaacaacag ctgtgcaggc tcaataa                                        987
```

<210> SEQ ID NO 121
<211> LENGTH: 813
<212> TYPE: PRT
<213> ORGANISM: Leuconostoc mesenteroides

<400> SEQUENCE: 121

```
Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Lys Ala Glu Asp Val
        35                  40                  45

Lys Val Lys Pro Ile Gly His Trp Gly Thr Ile Ser Gly Gln Thr Phe
    50                  55                  60

Leu Tyr Ala His Ala Asn Arg Leu Ile Asn Lys Tyr Gly Leu Asn Met
65                  70                  75                  80

Phe Tyr Val Gly Gly Pro Gly His Gly Gly Gln Val Met Val Thr Asn
                85                  90                  95

Ala Tyr Leu Asp Gly Ala Tyr Thr Glu Asp Tyr Pro Glu Ile Thr Gln
            100                 105                 110

Asp Ile Glu Gly Met Ser His Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160

Asp Asn Pro Asp Gln Val Ala Phe Ala Val Val Gly Asp Gly Glu Ala
                165                 170                 175

Glu Thr Gly Pro Ser Met Ala Ser Trp His Ser Ile Lys Phe Leu Asn
            180                 185                 190
```

```
Ala Lys Asn Asp Gly Ala Val Leu Pro Val Leu Asp Leu Asn Gly Phe
        195                 200                 205

Lys Ile Ser Asn Pro Thr Ile Phe Ser Arg Met Ser Asp Glu Glu Ile
    210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Thr Tyr His Gln Leu Ala Ala Asn Ile
                245                 250                 255

Leu Asp Gln Ala Ile Glu Asp Ile Gln Ala Ile Gln Asn Asp Ala Arg
            260                 265                 270

Glu Asn Gly Lys Tyr Gln Asp Gly Glu Ile Pro Ala Trp Pro Val Ile
        275                 280                 285

Ile Ala Arg Leu Pro Lys Gly Trp Gly Gly Pro Thr His Asp Ala Ser
    290                 295                 300

Asn Asn Pro Ile Glu Asn Ser Phe Arg Ala His Gln Val Pro Leu Pro
305                 310                 315                 320

Leu Glu Gln His Asp Leu Ala Thr Leu Pro Glu Phe Glu Asp Trp Met
                325                 330                 335

Asn Ser Tyr Lys Pro Glu Glu Leu Phe Asn Ala Asp Gly Ser Leu Lys
            340                 345                 350

Asp Glu Leu Lys Ala Ile Ala Pro Lys Gly Asp Lys Arg Met Ser Ala
        355                 360                 365

Asn Pro Ile Thr Asn Gly Gly Ala Asp Arg Ser Asp Leu Lys Leu Pro
    370                 375                 380

Asn Trp Arg Glu Phe Ala Asn Asp Ile Asn Asp Asp Thr Arg Gly Lys
385                 390                 395                 400

Glu Phe Ala Asp Ser Lys Arg Asn Met Asp Met Ala Thr Leu Ser Asn
                405                 410                 415

Tyr Leu Gly Ala Val Ser Gln Leu Asn Pro Thr Arg Phe Arg Phe Phe
            420                 425                 430

Gly Pro Asp Glu Thr Met Ser Asn Arg Leu Trp Gly Leu Phe Asn Val
        435                 440                 445

Thr Pro Arg Gln Trp Met Glu Glu Ile Lys Glu Pro Gln Asp Gln Leu
    450                 455                 460

Leu Ser Pro Thr Gly Arg Ile Ile Asp Ser Gln Leu Ser Glu His Gln
465                 470                 475                 480

Ala Glu Gly Trp Leu Glu Gly Tyr Thr Leu Thr Gly Arg Val Gly Ile
                485                 490                 495

Phe Ala Ser Tyr Glu Ser Phe Leu Arg Val Val Asp Thr Met Val Thr
            500                 505                 510

Gln His Phe Lys Trp Leu Arg His Ala Ser Glu Gln Ala Trp Arg Asn
        515                 520                 525

Asp Tyr Pro Ser Leu Asn Leu Ile Ala Thr Ser Thr Ala Phe Gln Gln
    530                 535                 540

Asp His Asn Gly Tyr Thr His Gln Asp Pro Gly Met Leu Thr His Leu
545                 550                 555                 560

Ala Glu Lys Lys Ser Asn Phe Ile Arg Glu Tyr Leu Pro Ala Asp Gly
                565                 570                 575

Asn Ser Leu Leu Ala Val Gln Glu Arg Ala Phe Ser Glu Arg His Lys
            580                 585                 590

Val Asn Leu Leu Ile Ala Ser Lys Gln Pro Arg Gln Gln Trp Phe Thr
        595                 600                 605

Val Glu Glu Ala Glu Val Leu Ala Asn Glu Gly Leu Lys Ile Ile Asp
```

```
    610                 615                 620

Trp Ala Ser Thr Ala Pro Ser Gly Asp Val Asp Ile Thr Phe Ala Ser
625                 630                 635                 640

Ala Gly Thr Glu Pro Thr Ile Glu Thr Leu Ala Ala Leu Trp Leu Ile
                645                 650                 655

Asn Gln Ala Phe Pro Asp Val Lys Phe Arg Tyr Val Asn Val Val Glu
            660                 665                 670

Leu Leu Arg Leu Gln Lys Lys Ser Glu Pro Asn Met Asn Asp Glu Arg
        675                 680                 685

Glu Leu Ser Ala Glu Glu Phe Asn Lys Tyr Phe Gln Ala Asp Thr Pro
    690                 695                 700

Val Ile Phe Gly Phe His Ala Tyr Glu Asn Leu Ile Glu Ser Phe Phe
705                 710                 715                 720

Phe Glu Arg Lys Phe Thr Gly Asp Val Tyr Val His Gly Tyr Arg Glu
                725                 730                 735

Asp Gly Asp Ile Thr Thr Thr Tyr Asp Met Arg Val Tyr Ser His Leu
            740                 745                 750

Asp Arg Phe His Gln Ala Lys Glu Ala Ala Glu Ile Leu Ser Ala Asn
        755                 760                 765

Gly Lys Ile Asp Gln Ala Ala Ala Asp Thr Phe Ile Ala Lys Met Asp
    770                 775                 780

Asp Thr Leu Ala Lys His Phe Gln Val Thr Arg Asn Glu Gly Arg Asp
785                 790                 795                 800

Ile Glu Glu Phe Thr Asp Trp Thr Trp Ser Pro Leu Lys
                805                 810
```

<210> SEQ ID NO 122
<211> LENGTH: 2442
<212> TYPE: DNA
<213> ORGANISM: Leuconostoc mesenteroides

<400> SEQUENCE: 122

```
atggcagatt tcgattcaaa agagtacttg gaacttgttg ataagtggtg gcgcgcaact      60

aactatttgt cagctgggat gatctttttg aagagcaacc cattgttctc agttactaat     120

acacctatca aggctgaaga tgtaaaagtt aagccaatcg gacactgggg tactatctca     180

ggtcagacat tcttgtatgc acatgctaac cgtttgatca acaagtatgg tttgaacatg     240

ttttacgttg gtggccctgg tcacggtggc caagttatgg ttactaacgc ttacttagac     300

ggcgcatata ctgaagatta tcctgaaatc actcaagata tcgaaggtat gagccacttg     360

ttcaagcgtt tctcattccc tggcggtatt ggatcacaca tgacagctca aacacctggt     420

tcattacacg aaggtggtga attgggctat tcattgagcc acgcttttgg tgccgttttg     480

gacaatcctg accaagttgc tttcgcagtt gttggtgatg gtgaagctga aacaggtcct     540

tcaatggctt catggcactc aattaagttt ttgaatgcta agaatgatgg tgccgttttg     600

cctgtcttgg atttgaacgg attcaagatt tcaaacccaa ctatcttctc acgtatgagt     660

gatgaagaaa tcacaaagtt ctttgaaggt ttgggttatt cacctcgctt catcgaaaac     720

gatgatattc atgactacgc aacataccac caacttgcag caaacatttt ggatcaagct     780

attgaagata ttcaagctat tcaaaatgat gcacgtgaaa atggtaagta tcaagatggt     840

gaaatccctg catggccagt aattattgct cgcttgccaa agggctgggg tggaccaacg     900

cacgatgcaa gtaacaatcc tattgaaaac tcattccgtg cgcaccaagt gccattgcct     960

cttgaacaac acgatcttgc aacattgcct gaattcgaag actggatgaa ctcatacaag    1020
```

cctgaagaat tattcaatgc tgatggttct ttgaaggatg aattgaaagc tatcgctcct 1080
aagggtgaca agcgtatgtc agctaaccct attacaaatg gtggtgctga tcgttcagac 1140
ttgaagttgc ctaactggag agaattcgct aacgatatca atgatgatac acgtggtaag 1200
gaattcgctg atagcaagcg caatatggac atggcaacat tgtcaaacta cttgggtgct 1260
gtttcacaat tgaacccaac tcgtttccgc ttcttcggtc ctgatgaaac aatgtcaaac 1320
cgtttgtggg gattgttcaa tgttacacca cgtcaatgga tggaagaaat caaggaacca 1380
caagatcaat tattgagccc tacgggtcgc attattgatt cacaattgtc tgaacatcaa 1440
gctgaaggtt ggcttgaagg atatactttg actggtcgtg ttggaatctt cgcatcatac 1500
gagtcattct tgcgtgttgt cgatacaatg gttacgcaac acttcaagtg gttgcgtcac 1560
gcttcagaac aagcatggcg taatgactat ccatcattga acttgattgc aacttcaact 1620
gctttccaac aagatcacaa tggatatact caccaagatc caggtatgtt gactcacttg 1680
gctgaaaaga agtctaactt tattcgtgaa tatttgccag ctgatggtaa ctcattgttg 1740
gctgttcaag aacgtgcctt ctcagaacgt cataaggtta acttgttgat tgcttctaag 1800
caaccacgtc aacaatggtt tacagttgaa gaagctgaag tattggctaa cgaaggtttg 1860
aagatcattg attgggcttc tactgcacct tctggtgatg ttgatattac attcgcatct 1920
gctggtactg aaccaacaat tgaaactttg gctgctttgt ggttgattaa ccaagcattc 1980
ccagatgtta agttccgtta tgttaacgtt gttgaattac tacgtttgca aaagaagtca 2040
gaacctaaca tgaatgatga acgtgaatta tcagccgaag aattcaacaa gtatttccaa 2100
gctgatacac cagttatctt cggtttccat gcttatgaaa acttgattga atcattcttc 2160
ttcgaacgta agttcacggg tgatgtatac gttcatggat atcgtgaaga tggtgacatc 2220
acaacgacat atgatatgcg tgtatattca cacttggatc gcttccatca agctaaggaa 2280
gctgctgaaa tcttgtctgc aaatggtaag attgatcaag ctgctgctga tacattcatc 2340
gctaagatgg atgatacttt ggcaaagcat ttccaagtta ctcgtaacga aggtcgtgat 2400
atcgaagaat tcactgactg gacatggtca ccacttaagt aa 2442

<210> SEQ ID NO 123
<211> LENGTH: 822
<212> TYPE: PRT
<213> ORGANISM: Lactococcus lactis

<400> SEQUENCE: 123

Met Thr Glu Tyr Asn Ser Glu Ala Tyr Leu Lys Lys Leu Asp Lys Trp
1               5                   10                  15

Trp Arg Ala Ala Thr Tyr Leu Gly Ala Gly Met Ile Phe Leu Lys Glu
            20                  25                  30

Asn Pro Leu Phe Ser Val Thr Gly Thr Pro Ile Lys Ala Glu Asn Leu
        35                  40                  45

Lys Ala Asn Pro Ile Gly His Trp Gly Thr Val Ser Gly Gln Thr Phe
    50                  55                  60

Leu Tyr Ala His Ala Asn Arg Leu Ile Asn Lys Tyr Asp Gln Lys Met
65                  70                  75                  80

Phe Tyr Met Gly Gly Pro Gly His Gly Gly Gln Ala Met Val Val Pro
                85                  90                  95

Ser Tyr Leu Asp Gly Ser Tyr Thr Glu Ala Tyr Pro Glu Ile Thr Gln
            100                 105                 110

Asp Leu Glu Gly Met Ser Arg Leu Phe Lys Arg Phe Ser Phe Pro Gly

```
        115                 120                 125

Gly Ile Gly Ser His Met Thr Ala Gln Thr Pro Gly Ser Leu His Glu
    130                 135                 140

Gly Gly Glu Leu Gly Tyr Val Leu Ser His Ala Thr Gly Ala Ile Leu
145                 150                 155                 160

Asp Gln Pro Glu Gln Ile Ala Phe Ala Val Val Gly Asp Gly Glu Ala
                165                 170                 175

Glu Thr Gly Pro Leu Met Thr Ser Trp His Ser Ile Lys Phe Ile Asn
            180                 185                 190

Pro Lys Asn Asp Gly Ala Ile Leu Pro Ile Leu Asp Leu Asn Gly Phe
        195                 200                 205

Lys Ile Ser Asn Pro Thr Leu Phe Ala Arg Thr Ser Asp Val Asp Ile
    210                 215                 220

Arg Lys Phe Phe Glu Gly Leu Gly Tyr Ser Pro Arg Tyr Ile Glu Asn
225                 230                 235                 240

Asp Asp Ile His Asp Tyr Met Ala Tyr His Lys Leu Ala Ala Glu Val
                245                 250                 255

Phe Asp Lys Ala Ile Glu Asp Ile His Gln Ile Gln Lys Asp Ala Arg
            260                 265                 270

Glu Asp Asn Arg Tyr Gln Asn Gly Glu Ile Pro Ala Trp Pro Ile Val
        275                 280                 285

Ile Ala Arg Leu Pro Lys Gly Trp Gly Gly Pro Arg Tyr Asn Asp Trp
    290                 295                 300

Ser Gly Pro Lys Phe Asp Gly Lys Gly Met Pro Ile Glu His Ser Phe
305                 310                 315                 320

Arg Ala His Gln Val Pro Leu Pro Leu Ser Ser Lys Asn Met Gly Thr
                325                 330                 335

Leu Pro Glu Phe Val Lys Trp Met Thr Ser Tyr Gln Pro Glu Thr Leu
            340                 345                 350

Phe Asn Ala Asp Gly Ser Leu Lys Glu Glu Leu Arg Asp Phe Ala Pro
        355                 360                 365

Lys Gly Glu Met Arg Met Ala Ser Asn Pro Val Thr Asn Gly Gly Val
    370                 375                 380

Asp Ser Ser Asn Leu Val Leu Pro Asp Trp Gln Glu Phe Ala Asn Pro
385                 390                 395                 400

Ile Ser Glu Asn Asn Arg Gly Lys Leu Leu Pro Asp Thr Asn Asp Asn
                405                 410                 415

Met Asp Met Asn Val Leu Ser Lys Tyr Phe Ala Glu Ile Val Lys Leu
            420                 425                 430

Asn Pro Thr Arg Phe Arg Leu Phe Gly Pro Asp Glu Thr Met Ser Asn
        435                 440                 445

Arg Phe Trp Glu Met Phe Lys Val Thr Asn Arg Gln Trp Met Gln Val
    450                 455                 460

Ile Lys Asn Pro Asn Asp Glu Phe Ile Ser Pro Glu Gly Arg Ile Ile
465                 470                 475                 480

Asp Ser Gln Leu Ser Glu His Gln Ala Glu Gly Trp Leu Glu Gly Tyr
                485                 490                 495

Thr Leu Thr Gly Arg Thr Gly Ala Phe Ala Ser Tyr Glu Ser Phe Leu
            500                 505                 510

Arg Val Val Asp Ser Met Leu Thr Gln His Phe Lys Trp Ile Arg Gln
        515                 520                 525

Ala Ala Asp Gln Lys Trp Arg His Asp Tyr Pro Ser Leu Asn Val Ile
    530                 535                 540
```

```
Ser Thr Ser Thr Val Phe Gln Gln Asp His Asn Gly Tyr Thr His Gln
545                 550                 555                 560

Asp Pro Gly Met Leu Thr His Leu Ala Glu Lys Lys Ser Asp Phe Ile
                565                 570                 575

Arg Gln Tyr Leu Pro Ala Asp Gly Asn Thr Leu Leu Ala Val Phe Asp
            580                 585                 590

Arg Ala Phe Gln Asp Arg Ser Lys Ile Asn His Ile Val Ala Ser Lys
        595                 600                 605

Gln Pro Arg Gln Gln Trp Phe Thr Lys Glu Glu Ala Glu Lys Leu Ala
    610                 615                 620

Thr Asp Gly Ile Ala Thr Ile Asp Trp Ala Ser Thr Ala Lys Asp Gly
625                 630                 635                 640

Glu Ala Val Asp Leu Val Phe Ala Ser Ala Gly Ala Glu Pro Thr Ile
                645                 650                 655

Glu Thr Leu Ala Ala Leu His Leu Val Asn Glu Val Phe Pro Gln Ala
            660                 665                 670

Lys Phe Arg Tyr Val Asn Val Val Glu Leu Gly Arg Leu Gln Lys Lys
        675                 680                 685

Lys Gly Ala Leu Asn Gln Glu Arg Glu Leu Ser Asp Glu Glu Phe Glu
    690                 695                 700

Lys Tyr Phe Gly Pro Ser Gly Thr Pro Val Ile Phe Gly Phe His Gly
705                 710                 715                 720

Tyr Glu Asp Leu Ile Glu Ser Ile Phe Tyr Gln Arg Gly His Asp Gly
                725                 730                 735

Leu Ile Val His Gly Tyr Arg Glu Asp Gly Asp Ile Thr Thr Thr Tyr
            740                 745                 750

Asp Met Arg Val Tyr Ser Glu Leu Asp Arg Phe His Gln Ala Ile Asp
        755                 760                 765

Ala Met Gln Val Leu Tyr Val Asn Arg Lys Val Asn Gln Gly Leu Ala
    770                 775                 780

Lys Ala Phe Ile Asp Arg Met Lys Arg Thr Leu Val Lys His Phe Glu
785                 790                 795                 800

Val Thr Arg Asn Glu Gly Val Asp Ile Pro Asp Phe Thr Glu Trp Val
                805                 810                 815

Trp Ser Asp Leu Lys Lys
            820
```

<210> SEQ ID NO 124
<211> LENGTH: 2469
<212> TYPE: DNA
<213> ORGANISM: Lactococcus lactis

<400> SEQUENCE: 124

```
atgacagaat ataattcaga agcttatttg aaaaagcttg ataaatggtg gcgagcagca      60

acttatcttg gagcaggaat gatcttcttg aaagaaaatc cattgttctc tgtgacaggt     120

actccaatta aagcggaaaa ccttaaagcc aatcctattg ggcactgggg gacggtttca     180

ggacaaactt tcctctatgc tcatgctaat cgtctaatca ataaatatga tcaaaagatg     240

ttttacatgg gtggccccgg acatggtgga caagctatgg ttgttccttc ttatcttgat     300

ggctcatata cagaagctta tccagagatt acccaagatt tggaaggaat gtcacgtttg     360

tttaaacgtt tctcatttcc tggaggaata gggtcgcata tgacagcaca aacccctggt     420

tcacttcatg aaggaggtga gttgggttat gtgctatcac atgcaacagg ggctattctt     480
```

```
gatcaacctg aacagattgc ttttgctgtt gttggggatg gagaagctga aactggaccg    540
ttgatgacaa gttggcactc tattaaattc attaatccta agaatgatgg ggcgatttta    600
ccaattcttg atttaaatgg ttttaaaatt tcaaatccta ctttgttcgc tcgaacttca    660
gatgttgata ttcgtaaatt ctttgaagga ctgggttact cacctcgtta tattgaaaat    720
gatgatattc atgattacat ggcttatcat aaattagcag ctgaagtttt tgataaagcg    780
attgaagaca ttcatcaaat tcagaaagat gcgcgtgaag ataatcgtta tcaaaatgga    840
gagattccag cttggccaat tgttatcgca cgtttaccaa aaggttgggg tggtccacgt    900
tataatgatt ggtcaggtcc taaatttgac ggtaagggaa tgccaattga acatagtttc    960
cgtgcgcatc aagttccact tccgttatct tctaaaaata tgggaacttt accagaattt   1020
gtaaaatgga tgacttctta ccaaccagaa actttattta atgctgatgg aagtttgaaa   1080
gaagagttgc gtgattttgc accaaaaggt gagatgcgaa tggcttcaaa ccctgtaaca   1140
aatgggggag ttgattcttc taatttggtt ttaccagatt ggcaagaatt tgcaaatcca   1200
atttctgaaa ataatcgagg gaaattactc cctgatacaa atgacaatat ggatatgaat   1260
gttttgtcaa aatattttgc tgaaatagtc aaacttaatc ctacgcgttt ccgtttgttt   1320
ggtcctgatg aaaccatgtc taatcgtttt tgggaaatgt ttaaggtgac gaatcgtcag   1380
tggatgcaag tcataaaaaa tccaaatgat gaatttatct cacctgaggg tcgcattatt   1440
gattctcaat tatcagaaca ccaagcagaa ggttggcttg aaggttatac tttaaccgga   1500
cgcacaggag catttgcaag ttatgaatca ttcttgcgag tcgtagattc aatgttaact   1560
caacatttca aatggattcg tcaagctgca gaccaaaaat ggcgccatga ttatccttcg   1620
cttaatgtta tttcgacctc aaccgttttc caacaagacc ataatggtta tactcaccaa   1680
gatcctggaa tgttgactca tttggctgaa aagaaatctg attttatcag acaatacttg   1740
ccggctgatg ggaatacttt gcttgccgta tttgaccgtg cttttcaaga tagaagtaaa   1800
attaatcata ttgtagcctc taaacaacct cgtcaacaat ggtttactaa agaagaagct   1860
gaaaaattgg cgactgacgg aattgcaaca attgattggg cttcaacggc taaagatgga   1920
gaagcagtag atttagtttt tgcctcagca ggagctgagc ctacaattga aacactggca   1980
gctttacatc ttgtaaacga agttttccca caggcaaaat tccgttatgt gaacgtggtt   2040
gaattgggtc ggttgcaaaa gaaaaaggga gcactcaatc aagaacgtga actctcagat   2100
gaagaatttg aaaaatactt tggcccttca ggcactccag taatttttgg attccatgga   2160
tatgaagatt taatcgaatc cattttctat caaagaggac atgatggttt gattgttcat   2220
ggttaccgtg aagatggtga catcacgacg acttatgata tgcgggttta ctctgagctt   2280
gaccgtttcc accaagcgat tgatgccatg caagttctat atgtcaaccg aaaagttaat   2340
caaggtctag cgaaagcttt cattgaccga atgaaacgga cactagttaa acactttgaa   2400
gtgacaagaa atgaaggagt tgatattcct gattttactg aatgggtttg gtcggattta   2460
aagaaatag                                                           2469
```

<210> SEQ ID NO 125
<211> LENGTH: 780
<212> TYPE: PRT
<213> ORGANISM: Aspergillus nidulans

<400> SEQUENCE: 125

```
Met Pro Gly Glu Val Ile Glu Arg Pro Asn Pro Ala Pro Lys Pro Ser
1               5                   10                  15
```

-continued

```
His Val Pro Asp Leu Val Glu Lys Leu Ile Ile Pro Ala Gln Lys Thr
            20                  25                  30

Lys Leu Glu Lys Ser Asp Cys Asp Ala Leu His Lys Tyr Arg Arg Ala
        35                  40                  45

Ala Ala Tyr Ile Ala Ala Gly His Trp Gly Thr Cys Pro Gly Leu Ile
    50                  55                  60

Leu Val Tyr Ser His Leu Asn Tyr Leu Ile Lys Lys Gln Asn Leu Asp
65                  70                  75                  80

Met Leu Tyr Val Val Gly Pro Gly His Gly Ala Pro Gly Leu Leu Ala
                85                  90                  95

Ser Leu Trp Leu Glu Gly Ser Leu Gly Lys Phe Tyr Pro Gln Tyr Thr
            100                 105                 110

Lys Asp Lys Glu Gly Leu His Asn Leu Ile Ser Thr Phe Ser Thr Ser
        115                 120                 125

Ala Gly Leu Pro Ser His Ile Asn Ala Glu Thr Pro Gly Ala Ile His
    130                 135                 140

Glu Gly Gly Glu Leu Gly Tyr Ala Leu Ser Val Ser Phe Gly Ala Val
145                 150                 155                 160

Met Asp Asn Pro Asp Leu Ile Val Thr Cys Val Val Gly Asp Gly Glu
                165                 170                 175

Ala Glu Thr Gly Pro Thr Ala Thr Ser Trp His Ala Ile Lys Tyr Ile
            180                 185                 190

Asp Pro Ala Glu Ser Gly Ala Val Leu Pro Ile Leu His Val Asn Gly
        195                 200                 205

Phe Lys Ile Ser Glu Arg Thr Ile Phe Gly Cys Met Asp Asn Arg Glu
    210                 215                 220

Ile Val Cys Leu Phe Thr Gly Tyr Gly Tyr Gln Val Arg Ile Val Glu
225                 230                 235                 240

Asp Leu Glu Asp Ile Asp Asn Asp Leu His Ser Ala Met Ser Trp Ala
                245                 250                 255

Val Glu Glu Ile Arg Asn Ile Gln Lys Ala Ala Arg Ser Gly Lys Pro
            260                 265                 270

Ile Met Lys Pro Gln Trp Pro Met Ile Val Leu Arg Thr Pro Lys Gly
        275                 280                 285

Trp Ser Gly Pro Lys Glu Leu His Gly Gln Phe Ile Glu Gly Ser Phe
    290                 295                 300

His Ser His Gln Val Pro Leu Pro Asn Ala Lys Lys Asp Asp Glu Glu
305                 310                 315                 320

Leu Gln Ala Leu Gln Lys Trp Leu Ser Ser Tyr Lys Pro Asp Glu Leu
                325                 330                 335

Phe Thr Glu Ser Gly Asp Val Ile Asp Glu Ile Leu Ser Ile Ile Pro
            340                 345                 350

Ser Asp Asp Lys Lys Leu Gly Met Arg Pro Glu Ala Tyr Lys Thr His
        355                 360                 365

Leu Pro Pro Asp Leu Pro Asp Trp Arg Gln Phe Cys Val Lys Lys Gly
    370                 375                 380

Asp Gln Phe Ser Ala Met Lys Ala Ile Gly Ser Phe Ile Asp Gln Val
385                 390                 395                 400

Phe Val Lys Asn Pro His Thr Val Arg Leu Phe Ser Pro Asp Glu Leu
                405                 410                 415

Glu Ser Asn Lys Leu Ser Ala Ala Leu Ser His Thr Gly Arg Asn Phe
            420                 425                 430

Gln Trp Asp Glu Phe Ser Asn Ala Lys Gly Gly Arg Val Ile Glu Val
```

-continued

```
        435                 440                 445

Leu Ser Glu His Leu Cys Gln Gly Phe Met Gln Gly Tyr Thr Leu Thr
    450                 455                 460

Gly Arg Thr Gly Ile Phe Pro Ser Tyr Glu Ser Phe Leu Gly Ile Ile
465                 470                 475                 480

His Thr Met Met Val Gln Tyr Ala Lys Phe Ala Lys Met Ala Lys Glu
                485                 490                 495

Thr Ala Trp His His Asp Val Ser Ser Ile Asn Tyr Ile Glu Thr Ser
            500                 505                 510

Thr Trp Ala Arg Gln Glu His Asn Gly Phe Ser His Gln Asn Pro Ser
        515                 520                 525

Phe Ile Gly Ala Val Leu Lys Leu Lys Pro Tyr Ala Ala Arg Val Tyr
    530                 535                 540

Leu Pro Pro Asp Ala Asn Thr Phe Leu Thr Thr Leu His His Cys Leu
545                 550                 555                 560

Lys Ser Lys Asn Tyr Ile Asn Leu Met Val Gly Ser Lys Gln Pro Thr
                565                 570                 575

Pro Val Tyr Leu Ser Pro Glu Glu Ala Glu Ser His Cys Arg Ala Gly
            580                 585                 590

Ala Ser Ile Phe Lys Phe Cys Ser Thr Asp Gly Gly Leu Arg Pro Asp
        595                 600                 605

Val Val Leu Val Gly Ile Gly Val Glu Val Met Phe Glu Val Ile Lys
    610                 615                 620

Ala Ala Ala Ile Leu Arg Glu Arg Cys Pro Glu Leu Arg Val Arg Val
625                 630                 635                 640

Val Asn Val Thr Asp Leu Phe Ile Leu Glu Asn Glu Gly Ala His Pro
                645                 650                 655

His Ala Leu Lys His Glu Ala Phe Asp Asn Leu Phe Thr Glu Asp Arg
            660                 665                 670

Ser Ile His Phe Asn Tyr His Gly Tyr Val Asn Glu Leu Gln Gly Leu
        675                 680                 685

Leu Phe Gly Arg Pro Arg Leu Asp Arg Ala Thr Ile Lys Gly Tyr Lys
    690                 695                 700

Glu Glu Gly Ser Thr Thr Thr Pro Phe Asp Met Met Leu Val Asn Glu
705                 710                 715                 720

Val Ser Arg Tyr His Val Ala Lys Ala Ala Val Thr Gly Gly Ala Arg
                725                 730                 735

Phe Asn Glu Lys Val Lys Leu Arg His Gln Glu Leu Cys Ser Glu Phe
            740                 745                 750

Asp His Asn Ile Ala Glu Thr Arg Lys Tyr Ile Met Asn Asn His Gln
        755                 760                 765

Asp Pro Glu Asp Thr Tyr Asn Met Pro Ser Phe Asn
    770                 775                 780


<210> SEQ ID NO 126
<211> LENGTH: 2343
<212> TYPE: DNA
<213> ORGANISM: Aspergillus nidulans

<400> SEQUENCE: 126

atgccaggag aagtcatcga gcgaccaaac ccggcgccaa agccgtcgca tgtccccgat      60

ttagtagaaa aactcataat tcccgcgcag aagacgaagc tggagaaaag cgattgtgat     120

gcgttgcaca agtatcgtcg cgcggcggcg tatattgctg ctggacactg gggaacatgt     180
```

-continued

```
cctgggttga tcctcgttta ctctcacctg aactacctga tcaagaagca gaacctcgat    240
atgctgtatg ttgttgggcc agggcatgga gcaccgggct tgctagcatc gttgtggctt    300
gagggctcgc tggggaagtt ttatccgcag tataccaagg acaaggaggg tctgcacaac    360
ctcatctcga cgttcagtac cagtgccgga ctgcctagcc acatcaatgc tgaaacaccc    420
ggcgctatcc acgaaggagg agagctgggc tatgcgctgt ctgtctcctt cggcgcagtc    480
atggataacc ccgatttgat tgtaacatgt gtagttggag acggagaggc ggaaactggt    540
ccaacagcca catcatggca tgcgatcaag tacatcgatc cagctgagtc aggagccgtg    600
cttccaatcc tgcatgtgaa tggcttcaag atcagtgagc gcactatttt tgggtgcatg    660
gataacaggg agatagtctg cctgttcaca gggtacgggt atcaggtgcg cattgtcgag    720
gacctcgagg acatcgacaa cgaccttcac agcgctatgt cctgggcggt tgaggaaatc    780
cgtaatattc agaaagcagc gcgctccgga aagcctatca tgaagcctca atggcccatg    840
attgtcttgc gaacgcccaa gggttggtca gggccgaaag agctgcatgg ccagttcatc    900
gaaggatcgt tccactccca ccaggttccc ctccctaatg ctaagaaaga cgatgaggag    960
ctccaggctc tgcagaaatg gctttcctct tacaaacccg atgagctgtt taccgagtct   1020
ggcgacgtta tcgacgaaat cctatccatt attccttcgg atgataagaa actcggcatg   1080
agacccgagg cctacaagac tcatctaccg ccggacctcc ctgactggag acagttctgc   1140
gtgaaaaaag gggatcagtt cagcgcaatg aaggccattg gtagcttcat cgaccaggtt   1200
ttcgtcaaga acccgcatac cgtccggtta ttctcacccg acgagctgga aagcaacaag   1260
ttgagcgctg ccctatcaca tacgggaagg aatttccagt gggatgagtt ctcgaatgca   1320
aaaggtgggc gggtgatcga ggtcctgagt gagcatttgt gtcagggctt catgcagggg   1380
tatacattga ccggccggac gggcatcttc ccatcatatg agagtttctt gggtattata   1440
cataccatga tggtccagta tgccaagttc gcaaagatgg ctaaagaaac ggcatggcac   1500
catgacgtga gtagtatcaa ctacatcgag accagcacct gggcccgaca ggagcacaat   1560
ggcttctctc accaaaatcc atccttcatc ggcgcggttc tcaaactgaa gccgtacgcc   1620
gcccgcgtct acctgcctcc cgacgccaac acatttctta ccactttgca ccactgcctg   1680
aaatcaaaga attatatcaa cctcatggtc ggctcaaagc aacccacccc agtctacctg   1740
agccccgagg aagcggaaag ccactgccga gccggagcct cgatcttcaa gttctgcagt   1800
accgacggtg ggctccgccc ggatgtcgta ctcgttggaa tcggtgttga ggtcatgttc   1860
gaagttatca aggcggcagc catactgcga gaacgatgcc ctgagctgcg tgttcgtgta   1920
gtcaacgtga cggatttatt cattctcgag aacgagggtg cccacccccca cgccttgaag   1980
cacgaggcct tcgacaacct cttcaccgag gatcgctcca tccatttcaa ctatcatgga   2040
tatgtgaacg aactccaggg cctgctcttt ggccgcccta ggctcgaccg ggcaaccatc   2100
aagggatata aggaagaggg aagcaccaca actccatttg acatgatgct tgtgaatgaa   2160
gtatcgcggt accacgtcgc gaaggcagcc gtcacgggag gagcgaggtt caatgagaaa   2220
gtcaagctgc ggcaccagga gctttgctct gaattcgatc ataacattgc tgagacgcgc   2280
aagtacatca tgaacaatca tcaagatccc gaagacacat acaatatgcc ctcatttaac   2340
tag                                                                 2343
```

<210> SEQ ID NO 127
<211> LENGTH: 408
<212> TYPE: PRT
<213> ORGANISM: Methanosarcina acetivorans

<400> SEQUENCE: 127

Met Lys Val Leu Val Ile Asn Ala Gly Ser Ser Ser Leu Lys Tyr Gln
1               5                   10                  15

Leu Ile Asp Met Thr Asn Glu Ser Pro Leu Ala Ile Gly Leu Cys Glu
            20                  25                  30

Arg Ile Gly Ile Asp Asn Ser Ile Ile Thr Gln Lys Arg Ser Asp Gly
        35                  40                  45

Lys Lys Leu Glu Lys Gln Thr Asp Leu Pro Asn His Lys Val Ala Leu
    50                  55                  60

Glu Glu Val Val Lys Ala Leu Thr Asp Ser Glu Leu Gly Val Ile Lys
65                  70                  75                  80

Ser Met Asp Glu Ile Asn Ala Val Gly His Arg Val Val His Gly Gly
                85                  90                  95

Glu Lys Phe Thr Ser Ser Ala Leu Ile Asp Glu Gly Val Glu Gln Ala
            100                 105                 110

Ile Lys Asp Cys Phe Glu Leu Ala Pro Leu His Asn Pro Pro Asn Met
        115                 120                 125

Met Gly Ile Thr Ala Cys Gln Glu Ile Met Pro Gly Val Pro Met Val
    130                 135                 140

Ala Val Phe Asp Thr Ala Phe His Gln Thr Ile Pro Ala Tyr Ala Tyr
145                 150                 155                 160

Met Tyr Ala Leu Pro Tyr Thr Leu Tyr Glu Lys Tyr Gly Ile Arg Lys
                165                 170                 175

Tyr Gly Phe His Gly Thr Ser His Phe Tyr Val Ala Arg Arg Ala Ala
            180                 185                 190

Ala Met Leu Gly Lys Pro Glu Glu Glu Val Lys Val Ile Thr Cys His
        195                 200                 205

Leu Gly Asn Gly Ser Ser Ile Thr Ala Val Asn Gly Gly Lys Ser Val
    210                 215                 220

Glu Thr Thr Met Gly Phe Thr Pro Leu Glu Gly Val Ala Met Gly Thr
225                 230                 235                 240

Arg Cys Gly Ser Ile Asp Pro Ala Val Val Pro Phe Val Met Glu Lys
                245                 250                 255

Glu Gly Leu Thr Thr Arg Glu Ile Asp Thr Leu Met Asn Lys Lys Ser
            260                 265                 270

Gly Val Leu Gly Val Ser Gly Leu Ser Asn Asp Phe Arg Asp Leu Asp
        275                 280                 285

Glu Ala Ala Ser Lys Gly Asn Gln Arg Ala Glu Leu Ala Leu Glu Ile
    290                 295                 300

Phe Ala Tyr Lys Ile Lys Lys Val Ile Gly Glu Tyr Ser Ala Val Leu
305                 310                 315                 320

Asn Gly Ala Asp Ala Val Val Phe Thr Ala Gly Ile Gly Glu Asn Ser
                325                 330                 335

Ala Ser Ile Arg Lys Arg Ile Leu Ser Gly Leu Asp Gly Leu Gly Ile
            340                 345                 350

Glu Ile Asp Glu Glu Lys Asn Lys Ile Arg Gly Gln Glu Ile Asp Ile
        355                 360                 365

Ser Thr Pro Asp Ala Lys Val Arg Val Leu Val Ile Pro Thr Asn Glu
    370                 375                 380

Glu Leu Thr Ile Ala Arg Asp Thr Lys Glu Ile Cys Glu Thr Glu Val
385                 390                 395                 400

Lys Leu Arg Arg Ser Val Ser Ile

405

<210> SEQ ID NO 128
<211> LENGTH: 1227
<212> TYPE: DNA
<213> ORGANISM: Methanosarcina acetivorans

<400> SEQUENCE: 128

```
atgaaagtac tggttataaa cgcagggagt tcttctctca aatatcaatt aattgatatg      60

acaaacgagt cccctcttgc aatagggctc tgtgagagga taggcatcga caactcgatc     120

attacccaga agaggtctga cggcaagaaa ctggaaaagc agaccgacct tcctaaccac     180

aaggttgccc ttgaggaagt cgtcaaggct cttacggact ccgagctcgg tgtcatcaaa     240

agcatggacg aaatcaatgc agtcgggcac agagttgtgc acggtggaga aaagttcact     300

tcctcggctt tgatcgatga aggcgtagaa caggcaatca aggactgctt tgaactggct     360

cctctccaca atcctccaaa catgatggga attactgcct gtcaggagat catgccaggc     420

gtcccgatgg ttgctgtttt tgacacagca ttccaccaga caatcccggc ctatgcctac     480

atgtatgctc tgccgtacac actgtacgaa aagtacggga tcagaaaata cggtttccac     540

ggcacttctc acttttacgt tgccagaagg gctgccgcta tgctcggaaa acccgaagaa     600

gaagtcaaag tcatcacctg ccacctagga aacggctcaa gcattacggc tgttaacggc     660

ggaaaatccg ttgagacaac aatgggcttt accccgctcg aaggagttgc aatgggtacc     720

aggtgcggtt cgattgaccc tgcagtagtc cccttcgtta tggaaaagga aggccttacg     780

acccgagaaa tcgataccct catgaacaag aagtcaggcg tgcttggagt ctccgggctc     840

agcaacgact tcagggacct cgatgaagca gcttccaaag gcaaccagag agccgaactc     900

gcccttgaaa tctttgcata caagattaag aaggtcatag gtgagtattc agccgtactc     960

aatggtgcgg atgcggtagt ctttacagca ggcattggag aaaacagtgc aagtatcagg    1020

aagagaatcc tctccggcct tgacggtctc ggcatagaga tcgacgaaga aaagaacaag    1080

atcagaggtc aggaaatcga tatcagcact cctgatgcaa aagtaagagt ccttgttatc    1140

ccgaccaacg aagaactaac cattgcaagg gacacaaagg aaatctgtga gaccgaagta    1200

aagctgcgca gatcagtatc aatctga                                        1227
```

<210> SEQ ID NO 129
<211> LENGTH: 408
<212> TYPE: PRT
<213> ORGANISM: Methanosarcina barkeri

<400> SEQUENCE: 129

```
Met Lys Val Leu Val Ile Asn Ala Gly Ser Ser Ser Leu Lys Tyr Gln
1               5                   10                  15

Leu Ile Asp Met Ile Asn Glu Ser Pro Leu Ala Val Gly Leu Cys Glu
            20                  25                  30

Arg Val Gly Ile Asp Asn Ser Ile Ile Thr Gln Lys Arg Phe Asp Gly
        35                  40                  45

Lys Lys Leu Glu Lys Gln Val Asp Leu Pro Thr His Arg Val Ala Leu
    50                  55                  60

Glu Glu Val Val Lys Ala Leu Thr Asp Pro Glu Phe Gly Val Ile Thr
65                  70                  75                  80

Asp Met Gly Glu Ile Asn Ala Val Gly His Arg Val Val His Gly Gly
                85                  90                  95

Glu Lys Phe Thr Thr Ser Ala Leu Phe Asp Ala Gly Val Glu Glu Ala
```

```
            100                 105                 110

Ile Arg Asp Cys Phe Asp Leu Ala Pro Leu His Asn Pro Pro Asn Met
        115                 120                 125

Met Gly Ile Ser Ala Cys Ala Glu Ile Met Pro Gly Thr Pro Met Val
    130                 135                 140

Ile Val Phe Asp Thr Ala Phe His Gln Thr Met Pro Ala Tyr Ala Tyr
145                 150                 155                 160

Met Tyr Ala Leu Pro Tyr Asp Leu Tyr Glu Lys Tyr Gly Val Arg Lys
                165                 170                 175

Tyr Gly Phe His Gly Thr Ser His Lys Tyr Val Ala Gly Arg Ala Ala
            180                 185                 190

Leu Met Leu Gly Lys Pro Ile Glu Asp Thr Lys Ile Ile Thr Cys His
        195                 200                 205

Leu Gly Asn Gly Ser Ser Ile Ala Ala Val Lys Gly Gly Lys Ser Ile
    210                 215                 220

Asp Thr Ser Met Gly Phe Thr Pro Leu Glu Gly Val Ala Met Gly Thr
225                 230                 235                 240

Arg Cys Gly Ser Ile Asp Pro Ala Val Val Pro Phe Val Met Asp Lys
                245                 250                 255

Glu Ser Leu Ser Ser Arg Glu Val Asp Thr Leu Met Asn Lys Lys Ser
            260                 265                 270

Gly Val Leu Gly Val Ser Gly Ile Ser Asn Asp Phe Arg Asp Leu Asp
        275                 280                 285

Glu Ala Ala Ser His Gly Asn Glu Arg Ala Glu Leu Ala Leu Glu Ile
    290                 295                 300

Phe Ala Tyr Ser Val Lys Arg Val Ile Gly Glu Tyr Leu Ala Val Leu
305                 310                 315                 320

Asn Gly Ala Asp Ala Ile Val Phe Thr Ala Gly Ile Gly Glu Asn Ser
                325                 330                 335

Ala Ser Ile Arg Lys Arg Ile Leu Thr Gly Leu Glu Gly Leu Gly Ile
            340                 345                 350

Lys Ile Asp Glu Glu Lys Asn Lys Ile Arg Gly Gln Glu Ile Asp Ile
        355                 360                 365

Ser Thr Pro Asp Ser Ser Ile Arg Val Phe Val Ile Pro Thr Asn Glu
    370                 375                 380

Glu Leu Ala Ile Ala Arg Glu Thr Lys Glu Ile Val Glu Thr Glu Ala
385                 390                 395                 400

Lys Leu Arg Lys Ser Val Pro Val
                405
```

<210> SEQ ID NO 130
<211> LENGTH: 1227
<212> TYPE: DNA
<213> ORGANISM: Methanosarcina barkeri

<400> SEQUENCE: 130

```
atgaaggtat tggtaataaa tgcaggaagc tcatcgctga aatatcagtt aattgatatg     60

atcaatgaat cccctcttgc agtcggtctt tgcgaaaggg tgggaatcga taactcgatc    120

attactcaga agaggttcga tggcaagaag ctggaaaagc aggttgacct gccaacccac    180

agagtagccc ttgaagaagt tgtcaaggct cttacggatc cggaatttgg tgtcatcaca    240

gacatgggtg aaatcaacgc ggtcggacac agggttgtgc acggtggcga gaagttcaca    300

acatctgctt tatttgatgc aggtgtcgag gaagctatta gagattgctt cgatctggct    360
```

```
cctctccaca accctccaaa catgatggga atttcagcct gtgcagagat catgcctgga    420

acgcccatgg ttattgtttt tgacactgca ttccatcaga ccatgcctgc gtatgcctac    480

atgtatgctt tgccatatga cctctacgaa aagtatggag tgcgaaaata cggtttccac    540

gggacttccc acaagtatgt cgctggaaga gccgctctta tgcttggaaa gcctatagaa    600

gatacaaaga ttatcacctg tcacctcgga aatggttcaa gtattgcagc agtgaaaggt    660

ggaaaatcta ttgataccag catgggcttt actcctcttg aaggggttgc aatgggtacc    720

agatgcggtt ccattgatcc ggcagtcgtt cccttcgtta tggataaaga aagcctgtca    780

agcagagagg ttgatactct catgaacaag aagtctggcg tacttggagt ttccgggata    840

agcaacgact tcagagacct tgatgaggct gcctctcatg gaaacgagag agctgagctt    900

gcccttgaga tcttcgcata tagtgtcaag agagtcattg gtgagtattt agccgtgctc    960

aatggtgcag atgcgattgt ctttaccgca ggtatcggag aaaacagcgc aagcatcaga   1020

aagagaatcc ttactggtct tgaaggtctc ggtataaaaa tcgatgagga aaagaacaag   1080

atcagaggcc aggaaatcga catcagtacc cctgattcga gtataagggt ttttgtcatt   1140

ccaaccaatg aagaacttgc cattgcaagg gaaacaaagg aaattgttga gaccgaagct   1200

aaactacgta aatcggtacc tgtttga                                       1227


<210> SEQ ID NO 131
<211> LENGTH: 346
<212> TYPE: PRT
<213> ORGANISM: Gluconacetobacter diazotrophicus

<400> SEQUENCE: 131

Met Leu Val Asp Arg Thr Trp Pro Arg Pro Asp Thr Gly Ala Asp Pro
1               5                   10                  15

His Gln Gly Pro Val Gly Ser Leu Ile Asp Trp Val Ala Ser His Leu
            20                  25                  30

Gly Asp Val Pro Leu Val Gly Val Gly His Arg Val Val His Gly Gly
        35                  40                  45

Pro Asp Phe Ile Ala Pro Val Arg Ile Thr Pro Asp Val Leu Ala Arg
    50                  55                  60

Leu Asp Ala Leu Thr Pro Phe Ala Pro Leu His Gln Pro Ala Ser Leu
65                  70                  75                  80

Gly Pro Ile Arg Ala Leu Thr Ala Leu His Pro Asp Leu Pro Gln Val
                85                  90                  95

Ala Cys Phe Asp Thr Ala Phe His His Thr Met Pro Ala Thr Ala Thr
            100                 105                 110

Arg Leu Ala Leu Pro Asp Ala Tyr Gly Arg Lys Gly Val Arg Arg Tyr
        115                 120                 125

Gly Phe His Gly Leu Ser Tyr Glu Tyr Ile Ala Ser Cys Leu Pro Gly
    130                 135                 140

Leu Ser Pro Arg Leu Ala Ala Gly Arg Thr Leu Val Ala His Leu Gly
145                 150                 155                 160

Asn Gly Ala Ser Leu Cys Ala Met Gln Ala Gly Arg Ser Ile Glu Thr
                165                 170                 175

Thr Met Gly Phe Ser Val Leu Asp Gly Leu Val Met Gly Thr Arg Cys
            180                 185                 190

Gly Gln Leu Asp Pro Gly Val Ile Leu Tyr Met Leu Arg Ala Glu Lys
        195                 200                 205

Leu Asp Val Ala Gly Ile Glu Asp Val Leu Tyr Arg Gln Ser Gly Leu
    210                 215                 220
```

Leu Gly Leu Ser Gly Val Ser Ser Asp Met Arg Asp Leu Gln Glu Arg
225 230 235 240

Ala Ala Gly Asn Asp Gly Ala Arg Gln Ala Leu Glu Met Phe Thr Tyr
245 250 255

Arg Leu Val Gln Gln Ala Gly Ser Met Val Ala Val Leu Gly Gly Leu
260 265 270

Asp Gly Leu Val Phe Thr Ala Gly Ile Gly Glu His Asp Ala Pro Ile
275 280 285

Arg Ala Ala Ala Cys Ala Arg Leu Ser Trp Leu Gly Leu Arg Leu Asp
290 295 300

Ala Ala Ala Asn Ala Ala His Ala Pro Val Ile Ser Thr Pro Asp Ser
305 310 315 320

Ala Val Glu Val Arg Val Ile Pro Thr Asp Glu Glu Ser Met Ile Arg
325 330 335

Arg His Val Ala Asp Cys Leu Ala Gly Glu
340 345

<210> SEQ ID NO 132
<211> LENGTH: 1041
<212> TYPE: DNA
<213> ORGANISM: Gluconacetobacter diazotrophicus

<400> SEQUENCE: 132
atgctggtcg accggacatg gcccaggccc gacacagggg ccgatcccca tcagggcccg 60
gtcggcagcc tgattgactg ggtggcctcg cacctggggg acgttccgct ggtcggggta 120
gggcaccggg tggtgcatgg cggtcccgac ttcatcgccc cggtgcggat cacgcccgat 180
gtcctggcgc ggctggacgc gctgacaccg ttcgcgccgt tgcaccagcc ggccagcctg 240
gggccgatcc gcgccctgac ggccctgcat cccgacctgc cgcaggtcgc ctgcttcgat 300
accgccttcc accacaccat gcccgccacg gccacgcggc tggcgctgcc ggacgcctat 360
gggcgcaagg gggtgcggcg gtatgggttc cacggcctgt cctacgaata tatcgcctcc 420
tgcctgcccg gcctgtcgcc ccggctggcg gccgggcgca cgctggtggc gcatctgggc 480
aatggggcca gcctgtgcgc gatgcaggcg gggcgcagca tcgagaccac gatggggttc 540
tcggtactgg acgggctggt gatgggcacg cgctgcggcc agctcgatcc cggcgtcatc 600
ctgtacatgc tgcgcgcgga aaaactggac gtggcgggga tcgaggacgt gctgtaccgc 660
cagtcgggcc tgctgggcct gtcgggcgtt tccagcgaca tgcgcgacct gcaggaacgc 720
gcggccggga atgacggcgc ccgccaggcg ctggagatgt tcacataccg cctggtccag 780
caggcgggtt cgatggtcgc ggtgctgggt ggactggacg gactggtctt taccgccggc 840
atcggcgagc atgacgcccc gatccgggcg gcggcgtgcg cgcgcctgtc ctggctgggg 900
ctccgcctgg acgctgccgc caacgcggcc cacgccccgg tgatcagcac gccggacagc 960
gcggtggagg tccgcgtcat tcccacggac gaggaaagca tgatccgccg ccacgtcgcg 1020
gattgcctgg cgggggaatg a 1041

<210> SEQ ID NO 133
<211> LENGTH: 417
<212> TYPE: PRT
<213> ORGANISM: Aspergillus niger

<400> SEQUENCE: 133

Met Ala Arg Lys Ser Ile Leu Ser Val Asn Ala Gly Ser Ser Ser Val
1 5 10 15

-continued

```
Lys Leu Thr Phe Tyr Thr Tyr Glu Lys Thr Pro Lys Val Ile Ala Ala
            20                  25                  30

Ala Gln Val Ser Gly Ile Thr Ala Pro Pro Ala Lys Leu Lys Tyr Thr
        35                  40                  45

Ser Gly Asp Lys Gln His Lys Glu Glu Leu Lys Glu Ser Ile Ser Thr
    50                  55                  60

Pro Gln Asp Ala Phe Lys Phe Leu Leu Gln Arg Cys Ile Ser Asp Pro
65                  70                  75                  80

Glu Leu Ser Glu Val Ala Ser Thr Asp Asp Leu Ala Tyr Ile Cys His
                85                  90                  95

Arg Val Val His Gly Gly Asp Tyr Glu Thr Ser Val Val Ile Thr Asp
            100                 105                 110

Glu Thr Tyr His His Leu Glu Lys Leu Glu Asp Leu Ala Pro Leu His
        115                 120                 125

Asn Tyr Ser Ala Leu Glu Ile Ile Arg His Cys Arg Lys Glu Ile Pro
    130                 135                 140

Ser Val Arg Ser Ile Thr Phe Phe Asp Ser Ala Phe His Gln Thr Leu
145                 150                 155                 160

Pro Glu His Val Lys Thr Tyr Pro Ile Asp Gln Lys Ile Ala Lys Ser
                165                 170                 175

Asn Gly Leu Arg Lys Tyr Gly Phe His Gly Ile Ser Tyr Ser Phe Ile
            180                 185                 190

Leu Arg Ser Val Ala Glu Val Leu Asn Lys Pro Ala Asp Lys Thr Asn
        195                 200                 205

Ile Ile Ala Met His Ile Gly Ser Gly Ala Ser Ile Cys Ala Ile Lys
    210                 215                 220

Asp Gly Lys Ser Val Asp Thr Thr Met Gly Leu Thr Pro Leu Ala Gly
225                 230                 235                 240

Leu Pro Gly Ala Thr Arg Ser Gly Asp Ile Asp Pro Ser Leu Val Phe
                245                 250                 255

His Tyr Thr Asn Asp Ala Gly Lys Leu Ser Pro Ala Ser Thr Lys Glu
            260                 265                 270

Met His Ile Ser Thr Ala Glu Glu Ile Leu Asn Lys Lys Ser Gly Trp
        275                 280                 285

Lys Ala Leu Thr Gly Thr Thr Asp Phe Ala Gln Ile Ala Val Glu Asn
    290                 295                 300

Pro Pro Thr Arg Glu His Lys Leu Ala Phe Asp Ile Leu Val Asp Arg
305                 310                 315                 320

Ile Ala Gly Tyr Leu Gly Asn Tyr Phe Val Lys Leu Asp Gly His Val
                325                 330                 335

Asp Ala Phe Val Phe Ala Gly Gly Ile Gly Glu Lys Ser Ala Leu Leu
            340                 345                 350

Arg Lys Ala Val Thr Glu Lys Cys Arg Cys Leu Gly Cys Ala Val Asp
        355                 360                 365

Pro Gly Lys Asn Asp Lys Gly Ala Gly Asp Gly Glu Thr Val Val Asp
    370                 375                 380

Ile Ser Arg Gly Asp Asp Lys Gly Pro Lys Val Leu Ile Cys Gln Thr
385                 390                 395                 400

Asp Glu Gln Phe Glu Met Ala Tyr Gly Cys Val Asn Gln Tyr Glu Arg
                405                 410                 415

Pro
```

<210> SEQ ID NO 134
<211> LENGTH: 1254
<212> TYPE: DNA
<213> ORGANISM: Aspergillus niger

<400> SEQUENCE: 134

```
atggcgcgca aatccatcct ctccgtcaat gcgggatcct cttcggtcaa gcttaccttc     60

tatacctacg agaaaacccc caaggtcatt gctgcagctc aggtctctgg tatcaccgcc    120

ccgccagcaa agctgaaata caccagtggc gacaagcaac acaaagagga actcaaggaa    180

agcatcagta ctcctcaaga tgccttcaaa ttcctgctcc agcgctgcat ctctgatccc    240

gagctttccg aagtcgccag cacagacgat ctagcctata tctgccaccg tgtggtgcac    300

ggtggagact acgaaacgtc tgttgtaatc actgacgaaa cctatcatca ccttgaaaaa    360

ttggaagacc tagctccatt acacaattac tccgccttgg aaattatccg gcattgcagg    420

aaggagattc catccgtcag gagcatcacc ttctttgact cggcgttcca tcaaaccctc    480

cccgaacacg tcaagaccta ccccatcgac cagaagatag ccaagtccaa cgggcttcgg    540

aaatatggct tccatggaat cagctattcg ttcattctac gctccgtagc cgaggtcctg    600

aacaaacctg ctgacaagac caatatcatt gcaatgcata tcggaagcgg tgcttctatt    660

tgcgccatca aagatggcaa atcagttgat actacgatgg gactcacgcc cctagccgga    720

ctaccaggcg ccacgcgaag cggtgacatt gatccatccc tcgtgttcca ctacaccaac    780

gatgcaggca aacttagccc cgccagcacc aaagaaatgc acatcagcac ggccgaagaa    840

atcctgaaca agaagtccgg ctggaaagcc ttgactggca caaccgactt tgctcaaatc    900

gccgtcgaga acccgccgac acgggaacat aaactggcat tcgacatcct cgttgaccgc    960

atcgccggct acctcggcaa ttactttgtg aaactagacg gccacgtcga cgccttcgtc   1020

ttcgcaggcg gaataggcga gaaaagtgcg ctgcttcgca aagcagttac ggagaagtgt   1080

cgctgcctgg gttgtgcggt cgacccaggg aagaatgaca agggcgcggg ggatggggag   1140

acggtagtgg atatttcgag ggtgatgac aagggcccta aggtgttgat ctgtcagaca   1200

gatgaacagt tcgagatggc atacggatgc gtcaatcagt atgagaggcc gtag          1254
```

<210> SEQ ID NO 135
<211> LENGTH: 437
<212> TYPE: PRT
<213> ORGANISM: Penicillium chrysogenum

<400> SEQUENCE: 135

```
Met Pro Lys Ser Ile Leu Ala Val Asn Ala Gly Ser Ser Ser Val Lys
1               5                   10                  15

Ile Thr Phe Tyr Thr Phe Asp Asn Pro Pro Arg Thr Ile Val Asp Ala
            20                  25                  30

Ala Ile Ser Gly Ile Thr Ala Pro Pro Ser Thr Leu Lys Tyr Gln Ala
        35                  40                  45

Gly Gly Arg Lys His Lys Glu Glu Leu Lys Glu Lys Leu Ser Thr Ala
    50                  55                  60

Gln Asp Ala Phe Lys Tyr Leu Leu Gln Arg Cys Phe Ser Asp Pro Glu
65                  70                  75                  80

Leu Ser Glu Val Ala Ser Ala Asp Asp Val Glu Tyr Ile Cys His Arg
                85                  90                  95

Val Val His Gly Gly Asp Tyr Arg Asp Ala Val Glu Ile Asn Asp Glu
            100                 105                 110

Thr Leu Gly His Leu Lys Gly Leu Glu Asp Leu Ala Pro Leu His Asn
```

```
        115                 120                 125

Phe Ser Ala Leu Glu Ile Val Arg Leu Cys Arg Ser Glu Leu Pro Lys
    130                 135                 140

Val Arg Ser Ile Thr Phe Phe Asp Ser Ser Phe His Gln Thr Ile Pro
145                 150                 155                 160

Glu Ala Val Arg Thr Tyr Pro Ile Asn Gln Glu Ile Ala Lys Ala Asn
                165                 170                 175

Gly Leu Arg Lys Tyr Gly Phe His Gly Ile Ser Tyr Ser Phe Ile Leu
            180                 185                 190

Arg Ser Val Ala Gln Phe Leu Asn Lys Pro Val Glu Lys Thr Asn Leu
        195                 200                 205

Ile Val Met His Ile Gly Ser Gly Ala Ser Ile Cys Ala Ile Lys Asp
    210                 215                 220

Gly Lys Ser Val Asp Thr Ser Met Gly Leu Thr Pro Leu Ala Gly Leu
225                 230                 235                 240

Pro Gly Ala Thr Arg Ser Gly Ser Ile Asp Pro Ser Leu Val Phe His
                245                 250                 255

Tyr Thr Asn Glu Ala Gly Lys Leu Ser Pro Ala Ser Thr Ser Glu Met
            260                 265                 270

His Ile Ser Thr Ala Glu Asp Ile Leu Asn Lys Gln Ser Gly Trp Lys
        275                 280                 285

Ala Leu Thr Gly Thr Thr Asp Phe Ala Gln Ile Ala Val Pro Asn Pro
    290                 295                 300

Pro Ser Glu Ala His Lys Leu Ala Phe Asp Ile Phe Val Asp Arg Ile
305                 310                 315                 320

Gln Gly Tyr Ile Gly Ser Tyr Tyr Val Lys Leu Asn Gly Glu Leu Asp
                325                 330                 335

Gly Val Val Phe Ala Gly Gly Ile Gly Glu Lys Ser Ala Leu Leu Arg
            340                 345                 350

Arg Thr Leu Val Asp Lys Cys Gln Cys Leu Gly Leu Ala Ile Asp Asp
        355                 360                 365

Val Ala Asn Asp Lys Gly Pro Gly Asp Glu Glu Thr Val Lys Asp Ile
    370                 375                 380

Ser Lys Gly Ser Gly Lys Gly Pro Arg Val Leu Ile Cys Gln Thr Asn
385                 390                 395                 400

Glu Gln Val Cys Gly Leu Lys Tyr Trp Val Leu Leu Thr Val Thr Phe
                405                 410                 415

Ala Leu Thr Ser Arg Gly Gly Val Gly Phe Gly Tyr Arg Leu Phe Leu
            420                 425                 430

Tyr Thr Trp Ile Tyr
        435


<210> SEQ ID NO 136
<211> LENGTH: 1314
<212> TYPE: DNA
<213> ORGANISM: Penicillium chrysogenum

<400> SEQUENCE: 136

atgcccaaat ctatcctcgc tgttaacgcg ggttcgtctt ccgtcaaaat caccttctat      60

accttcgaca acccgccaag aaccattgtg gatgcggcga tctctggaat cacagcaccc     120

ccgtctacac tcaagtacca agcaggaggc agaaagcaca aggaggagct caaagaaaaa     180

ctcagtaccg cccaagatgc attcaagtac cttctacagc gctgtttcag cgaccccgaa     240

ctttccgaag tcgccagcgc cgacgatgtg gagtatatct gccaccgagt cgtccacggt     300
```

```
ggagactacc gcgatgcagt cgaaatcaac gacgagacac ttggccacct gaaaggattg    360

gaagatcttg cacctctcca taatttctcc gcgctggaga tagtccgcct gtgcagatca    420

gagctcccca aagtcagaag cataactttt ttcgactctt ctttccacca gactatcccc    480

gaagccgtac gtacataccc aatcaaccag gaaatcgcca aggcgaatgg tctgcgcaag    540

tatggatttc acgggatcag ctactccttc atcctgcggt ccgtagcaca gtttttgaac    600

aaaccggtcg agaagacgaa tctcatcgtg atgcatatcg ggagcggagc ctcgatctgt    660

gcgatcaagg acgggaagtc cgtggatact tcaatgggtc tcactccttt ggcaggatta    720

cccggtgcaa cgcgtagtgg aagcattgat ccatcattgg tcttccacta taccaacgaa    780

gcaggcaaac taagcccagc cagcacgtct gaaatgcaca tcagcacggc ggaggatatc    840

ctcaataaac aatcaggttg gaaagccctc actggaacaa ccgacttcgc ccagattgcg    900

gtgccgaacc caccaagcga agcacataaa ctcgcttttg acattttcgt cgaccgcatc    960

cagggctaca tcggcagcta ctacgtcaaa ctaaatggtg aattagacgg tgtagtcttc   1020

gccggcggga tcggtgagaa gagtgccttg ctgagacgaa cactggtcga taaatgccag   1080

tgtctaggtt tggcaatcga tgatgtggct aatgacaagg ggcctggaga tgaggagacg   1140

gtcaaggata tctccaaggg ttccggcaag gggccccggg ttttaatttg ccagaccaat   1200

gaacaggtat gtggtctcaa atattgggta ttattgaccg tgaccttcgc cttgacctct   1260

cgtggaggtg tagggtttgg ttataggtta tttttgtaca cttggattta ctga         1314
```

```
<210> SEQ ID NO 137
<211> LENGTH: 401
<212> TYPE: PRT
<213> ORGANISM: Clostridium acetobutylicum

<400> SEQUENCE: 137

Met Lys Asn Leu Val Ile Asn Cys Gly Ser Ser Ser Ile Lys Tyr Gln
1               5                   10                  15

Phe Ile Asp Met Lys Asp Glu Thr Val Leu Ala Lys Gly Leu Val Glu
            20                  25                  30

Arg Ile Gly Ile Lys Gly Ser Val Ile Thr His Lys Val Asn Gly Glu
        35                  40                  45

Lys Tyr Val Thr Glu Thr Pro Met Glu Asp His Lys Lys Ala Ile Lys
    50                  55                  60

Leu Val Leu Asp Ala Leu Leu Asn Asp Glu Tyr Gly Val Ile Lys Asn
65                  70                  75                  80

Ile Asp Glu Ile Ser Ala Val Gly His Arg Ile Val His Gly Gly Glu
                85                  90                  95

Lys Tyr Ala Asn Ser Val Leu Ile Asp Glu Asp Val Met Lys Ser Ile
            100                 105                 110

Glu Asp Cys Val Ser Leu Ala Pro Leu His Asn Pro Pro His Ile Ile
        115                 120                 125

Gly Ile Asn Ala Cys Lys Glu Leu Met Pro Asn Val Pro Met Val Ala
    130                 135                 140

Val Phe Asp Thr Ala Phe His Gln Thr Ile Pro Asp Tyr Ala Tyr Met
145                 150                 155                 160

Tyr Ala Ile Pro Tyr Glu Tyr Tyr Asp Lys Tyr Lys Ile Arg Lys Tyr
                165                 170                 175

Gly Phe His Gly Thr Ser His Lys Tyr Val Ser Arg Thr Ala Ala Glu
            180                 185                 190
```

```
Phe Ile Gly Lys Lys Val Glu Asp Leu Lys Met Val Val Cys His Met
        195                 200                 205

Gly Asn Gly Ala Ser Ile Thr Ala Val Glu Asn Gly Lys Ser Val Asp
    210                 215                 220

Thr Ser Met Gly Phe Thr Pro Leu Gly Gly Leu Ala Met Gly Thr Arg
225                 230                 235                 240

Ser Gly Asp Met Asp Pro Ala Val Val Thr Phe Leu Met Asp Lys Leu
                245                 250                 255

Asn Ile Asn Ala Ser Glu Val Asn Asn Leu Leu Asn Lys Lys Ser Gly
            260                 265                 270

Ile Glu Gly Leu Ser Gly Ile Ser Ser Asp Met Arg Asp Ile Lys Lys
        275                 280                 285

Gly Asn Tyr Val Asp Lys Asp Pro Lys Ala Met Leu Ala Tyr Ser Val
    290                 295                 300

Phe Asn Tyr Lys Ile Lys Gln Phe Ile Gly Ser Tyr Thr Ala Val Met
305                 310                 315                 320

Asn Gly Leu Asp Cys Leu Val Phe Thr Gly Gly Ile Gly Glu Asn Ser
                325                 330                 335

Phe Glu Asn Arg Arg Glu Ile Cys Lys Asn Met Asp Tyr Leu Gly Ile
            340                 345                 350

Lys Ile Asp Asp Lys Lys Asn Asp Glu Thr Met Gly Ile Pro Met Asp
        355                 360                 365

Ile Ser Ala Glu Gly Ser Lys Val Arg Val Leu Val Ile Pro Thr Asn
    370                 375                 380

Glu Glu Leu Met Ile Ala Arg Asp Thr Lys Asp Ile Val Gly Lys Leu
385                 390                 395                 400

Lys
```

<210> SEQ ID NO 138
<211> LENGTH: 1206
<212> TYPE: DNA
<213> ORGANISM: Clostridium acetobutylicum

<400> SEQUENCE: 138

```
atgaaaaact tagttattaa ctgcggtagt tcatcaatca aataccagtt tatagatatg     60

aaggatgaaa ctgtactcgc taaaggatta gttgaaagaa ttggaataaa aggatctgta    120

ataacccata aagtaaatgg agaaaaatat gttacagaaa ctcctatgga agatcataaa    180

aaggctataa agcttgtatt agatgcttta ttaaatgatg aatatggtgt tataaaaaat    240

attgatgaga tatcagcagt aggacacaga atcgttcatg gtggagaaaa atatgcaaac    300

tcagttttaa tagatgaaga tgttatgaag tctatagaag attgtgtgag tcttgcaccg    360

cttcataatc caccacacat aataggaatt aatgcttgca aggaattaat gccaaacgtt    420

cctatggttg cagtatttga tacagcattc catcaaacta tacctgatta tgcatatatg    480

tatgctattc catatgaata ttatgataaa tacaaaataa gaaaatatgg ttttcatgga    540

acatcacaca aatatgtatc aagaacagct gcagaattta taggtaaaaa agtagaagat    600

ttaaaaatgg tagtatgcca tatgggaaat ggtgctagta ttacagctgt agaaaatggt    660

aaatcagtag atacaagtat gggatttact cctcttggcg gtcttgctat gggaactaga    720

agtggagata tggacccagc agtagtaact tttttaatgg ataaattaaa tataaatgct    780

tctgaagtaa ataatctatt aaataaaaag tcaggtattg aaggcttaag tggaataagc    840

agcgatatgc gtgatattaa aaaaggaaac tatgtagata aagaccctaa agctatgcta    900
```

-continued

```
gcttacagtg tatttaacta taaaataaag caatttatag gttcatatac tgcagttatg    960

aatggattag actgtttagt attcactggt ggaataggtg aaaattcatt tgaaaataga   1020

agagaaatat gcaaaaacat ggattatcta ggaataaaaa ttgacgataa gaaaaatgat   1080

gaaactatgg gaataccaat ggatataagt gcagaaggtt ctaaagttag ggtacttgta   1140

attccaacta atgaggagtt aatgattgca agggatacca aagatatagt aggcaagtta   1200

aaataa                                                              1206


<210> SEQ ID NO 139
<211> LENGTH: 400
<212> TYPE: PRT
<213> ORGANISM: Thermoanaerobacterium saccharolyticum

<400> SEQUENCE: 139

Met Lys Ile Leu Val Ile Asn Cys Gly Ser Ser Ser Leu Lys Tyr Gln
1               5                   10                  15

Leu Ile Glu Ser Thr Asp Gly Asn Val Leu Ala Lys Gly Leu Ala Glu
            20                  25                  30

Arg Ile Gly Ile Asn Asp Ser Met Leu Thr His Asn Ala Asn Gly Glu
        35                  40                  45

Lys Ile Lys Ile Lys Lys Asp Met Lys Asp His Lys Asp Ala Ile Lys
    50                  55                  60

Leu Val Leu Asp Ala Leu Val Asn Ser Asp Tyr Gly Val Ile Lys Asp
65                  70                  75                  80

Met Ser Glu Ile Asp Ala Val Gly His Arg Val Val His Gly Gly Glu
                85                  90                  95

Ser Phe Thr Ser Ser Val Leu Ile Asn Asp Glu Val Leu Lys Ala Ile
            100                 105                 110

Thr Asp Cys Ile Glu Leu Ala Pro Leu His Asn Pro Ala Asn Ile Glu
        115                 120                 125

Gly Ile Lys Ala Cys Gln Gln Ile Met Pro Asn Val Pro Met Val Ala
    130                 135                 140

Val Phe Asp Thr Ala Phe His Gln Thr Met Pro Asp Tyr Ala Tyr Leu
145                 150                 155                 160

Tyr Pro Ile Pro Tyr Glu Tyr Tyr Thr Lys Tyr Arg Ile Arg Arg Tyr
                165                 170                 175

Gly Phe His Gly Thr Ser His Lys Tyr Val Ser Asn Arg Ala Ala Glu
            180                 185                 190

Ile Leu Asn Lys Pro Ile Glu Asp Leu Lys Ile Ile Thr Cys His Leu
        195                 200                 205

Gly Asn Gly Ser Ser Ile Ala Ala Val Lys Tyr Gly Lys Ser Ile Asp
    210                 215                 220

Thr Ser Met Gly Phe Thr Pro Leu Glu Gly Leu Ala Met Gly Thr Arg
225                 230                 235                 240

Ser Gly Ser Ile Asp Pro Ser Ile Ile Ser Tyr Leu Met Glu Lys Glu
                245                 250                 255

Asn Ile Ser Ala Glu Glu Val Val Asn Ile Leu Asn Lys Lys Ser Gly
            260                 265                 270

Val Tyr Gly Ile Ser Gly Ile Ser Ser Asp Phe Arg Asp Leu Glu Asp
        275                 280                 285

Ala Ala Phe Lys Asn Gly Asp Glu Arg Ala Gln Leu Ala Leu Asn Val
    290                 295                 300

Phe Ala Tyr Arg Val Lys Lys Thr Ile Gly Ala Tyr Ala Ala Ala Met
305                 310                 315                 320
```

```
Gly Gly Val Asp Val Ile Val Phe Thr Ala Gly Val Gly Glu Asn Gly
                325                 330                 335

Pro Glu Ile Arg Glu Phe Ile Leu Asp Gly Leu Glu Phe Leu Gly Phe
            340                 345                 350

Ser Leu Asp Lys Glu Lys Asn Lys Val Arg Gly Lys Glu Thr Ile Ile
        355                 360                 365

Ser Thr Pro Asn Ser Lys Val Ser Val Met Val Val Pro Thr Asn Glu
    370                 375                 380

Glu Tyr Met Ile Ala Lys Asp Thr Glu Lys Ile Val Lys Ser Ile Lys
385                 390                 395                 400


<210> SEQ ID NO 140
<211> LENGTH: 1203
<212> TYPE: DNA
<213> ORGANISM: Thermoanaerobacterium saccharolyticum

<400> SEQUENCE: 140

atgaaaatac tggttattaa ttgcggaagt tcttcgctaa aatatcaact gattgaatca     60

actgatggaa atgtgttggc aaaaggcctt gctgaaagaa tcggcataaa tgattccatg    120

ttgacacata atgctaacgg agaaaaaatc aagataaaaa aagacatgaa agatcacaaa    180

gacgcaataa aattggtttt agatgctttg gtaaacagtg actacggcgt tataaaagat    240

atgtctgaga tagatgctgt aggacataga gttgttcacg gaggagaatc ttttacatca    300

tcagttctca taaatgatga agtgttaaaa gcgataacag attgcataga attagctcca    360

ctgcacaatc ctgctaatat agaaggaatt aaagcttgcc agcaaatcat gccaaacgtt    420

ccaatggtgg cggtatttga tacagccttt catcagacaa tgcctgatta tgcatatctt    480

tatccaatac cttatgaata ctacacaaag tacaggatta gaagatatgg atttcatggc    540

acatcgcata aatatgtttc aaatagggct gcagagattt tgaataaacc tattgaagat    600

ttgaaaatca taacttgtca tcttggaaat ggctccagca ttgctgctgt caaatatggt    660

aaatcaattg acacaagcat gggatttaca ccattagaag gtttggctat gggtacacga    720

tctggaagca tagacccatc catcatttcg tatcttatgg aaaaagaaaa tataagcgct    780

gaagaagtag taaatatatt aaataaaaaa tctggtgttt acggtatttc aggaataagc    840

agcgatttta gagacttaga agatgccgcc tttaaaaatg gagatgaaag agctcagttg    900

gctttaaatg tgtttgcata tcgagtaaag aagacgattg gcgcttatgc agcagctatg    960

ggaggcgtcg atgtcattgt atttacagca ggtgttggtg aaaatggtcc tgagatacga   1020

gaatttatac ttgatggatt agagttttta gggttcagct tggataaaga aaaaaataaa   1080

gtcagaggaa aagaaactat tatatctacg ccgaattcaa aagttagcgt gatggttgtg   1140

cctactaatg aagaatacat gattgctaaa gatactgaaa agattgtaaa gagtataaaa   1200

tag                                                                 1203


<210> SEQ ID NO 141
<211> LENGTH: 2862
<212> TYPE: DNA
<213> ORGANISM: Yarrowia lipolytica

<400> SEQUENCE: 141

atgattgaag gaatctcctt tgcgtcgttt gtgacacacg aaaaacccaa gtttgtgcgc     60

gccctggact tctacaaggc cctgggcttc ctccccacca aggagtacaa gcacggaaca    120

gaccaccatg ccaccgacga agaaggcgcg ggctcgatcc aggaggtctg gctcacgtcg    180
```

```
tcgcgagccg gtgtgccgtc tgtgaccgtc aaattgcgac tctcccgcca cggaaacgaa    240
cacgtgtctc tccccaacct caaacacgac tggcggtcgc tggtgccctc gctggtgtac    300
tacgcccccg acctggacgc ggtgcgagcc gcaatcaccc cgttcttaca cgaggaccac    360
tccacgcttc tggaacgccc ttcccacaca aacttcatcg agctgtacgc cattgacccc    420
atgggaaacc tcgtgggctt ttcccgacga gaaaaccctt actcgtcagc gatgcagaaa    480
cccttctctg ctgacgacat tggcccgcag aacttctcaa agcccaatga aaccaaaatc    540
aagggcaaga agcgtatcgg tgtcatgacc tccggaggag acgcccccgg catgtgtgcg    600
gccgtgcgag ctgtggtccg agccggaatt gcccgcggct gcgaggtcta cgctgtccga    660
gagggctatg agggtcttgt caagggtggc gacctcattg agcccctgtc atgggaagac    720
gtacggggct ggctctccct gggaggaacc cttattggaa ctgctcgatg caaggagttc    780
cgagaacgag agggccgact ggcaggagcc ctcaacatgg tcaagaacgg cattgacgcg    840
ctcattgtca ttggcggaga cggctcgttg accggagccg atctgttccg agaagaatgg    900
ccgtctctaa tcgaggagct agtcaccaat ggctccatca ccgccgagca ggccgaacga    960
caccgacacc tcgacatttg cggtatggta ggctccatcg acaacgacat ggctaccacc   1020
gacgtcacca ttggtgctta ctcatcgctc gaccgaatct gcgagctggt agacttcatc   1080
gatgccaccg cccagtcgca ctcgcgagcc tttgtcgtcg aggttatggg tcggcactgt   1140
ggctggctgg ctctcatggc cggcactgct accggcgccg actacatttt tatccccgag   1200
gctgctcccg atgctactca gtgggccgag aagatgaccc gtgtcgtcaa gagacaccga   1260
agccagggca agcgaaagac cgtggtcatt gtcgccgagg gcgcaatcga ctcggacctc   1320
aaccccatca ctgccaagat ggtcaaggat gtgctagacg gcattggact cgatactcga   1380
atctccaccc tgggtcacgt acagcgagga ggtcccccag ttgccgctga tagagttctg   1440
gcttcactgc agggtgtgga ggctatcgac gccatcctgt ctctcacccc agagacgccc   1500
agtcccatga ttgctctcaa cgagaacaaa atcacccgca agccgctcgt ggagtctgta   1560
gctctcacca agaaggttgc cgatgccatt ggcaacaagg actttgccga ggccatgcgg   1620
cttcgaaacc ccgagtttgt ggagcaattg cagggtttcc tgctcacaaa ctctgctgac   1680
aaggaccggc cccaggagcc tgccaaggat cccctgcgag tcgccattgt gtgcactggc   1740
gctcctgctg gcggaatgaa cgctgccatc cgatctgctg ttctgtacgg tcttgctcga   1800
ggccaccaaa tgtttgccat ccacaatgga tggtccggcc tcgtcaagaa tggtgacgac   1860
gcggtgcggg agctgacttg gctcgaggtc gagcccctgt gtcagaaggg tggctgtgag   1920
attggtacta accgatctct gcccgaatgt gatcttggaa tgattgcata ccactttcag   1980
cgacaacggt ttgacggtct aatcgtcatt ggtggttttg aggctttccg agcgctgaat   2040
cagctcgacg atgcccgtca cgcctaccct gctcttcgaa tccccatggt tggtattcct   2100
gccaccattt cgaacaacgt gcctggaacg gactattctc ttggagccga cacttgtctc   2160
aactctctgg ttcagtactg cgacgtgctc aagacgtctg cttctgccac tcgtctgcgt   2220
ctgtttgtgg tcgaggtgca gggtggaaac tctggttaca tcgccaccgt ggctggtttg   2280
atcaccggcg cctatgtggt gtacacaccc gagagcggta tcaacctgcg acttcttcag   2340
cacgacattt cctaccttaa ggatactttt gctcatcagg cggacgtgaa ccgaaccgga   2400
aagctgcttc tgcgaaacga gcggtcatcc aacgtgttca ccactgatgt catcaccggc   2460
atcatcaacg aggaggccaa gggttcattt gacgcgcgaa ccgccatccc tggccatgtg   2520
```

cagcagggag gacacccctc tcctaccgat cgagtgcgtg ctcagcgatt tgccatcaag 2580
gccgtgcagt ttattgaaga gcaccacggc tccaaaaaca atgccgatca ctgtgtgatt 2640
ctcggtgtgc ggggctccaa gttcaagtac acctctgtgt cgcatctgta cgcccataag 2700
actgagcacg gggctcgacg gcccaagcat tcctactggc acgcgattgg cgacattgcc 2760
aacatgctgg tgggtcgaaa ggcgcctcct ctgcccgaga ctctcaacga cgagattgag 2820
aagaacattg cgaaggagca gggtattatt gatccttgtt ag 2862

<210> SEQ ID NO 142
<211> LENGTH: 3062
<212> TYPE: DNA
<213> ORGANISM: Yarrowia lipolytica

<400> SEQUENCE: 142
aaactctgat atatatatag agagacgtat cccaacagtt gatagtcgac aaacgcaaaa 60
cagacggaca ctgaaccccc cgcgcttcaa aacaccgaca atgattgaag gaatctcctt 120
tgcgtcgttt gtgacacacg aaaaacccaa gtttgtgcgc gccctggact tctacaaggc 180
cctgggcttc ctccccacca aggagtacaa gcacggaaca gaccaccatg ccaccgacga 240
agaaggcgcg ggctcgatcc aggaggtctg gctcacgtcg tcgcgagccg gtgtgccgtc 300
tgtgaccgtc aaattgcgac tctcccgcca cggaaacgaa cacgtgtctc tccccaacct 360
caaacacgac tggcggtcgc tggtgccctc gctggtgtac tacgccccg acctggacgc 420 ggtgcgagcc gcaatcaccc cgttcttaca cgaggaccac tccacgcttc tggaacgccc 480
ttcccacaca aacttcatcg agctgtacgc cattgacccc atgggaaacc tcgtgggctt 540
ttcccgacga gaaaaccctt actcgtcagc gatgcagaaa cccttctctg ctgacgacat 600
tggcccgcag aacttctcaa agcccaatga aaccaaaatc aagggcaaga agcgtatcgg 660
tgtcatgacc tccggaggag acgcccccgg catgtgtgcg gccgtgcgag ctgtggtccg 720
agccggaatt gcccgcggct gcgaggtcta cgctgtccga gagggctatg agggtcttgt 780
caagggtggc gacctcattg agcccctgtc atgggaagac gtacggggct ggctctccct 840
gggaggaacc cttattggaa ctgctcgatg caaggagttc cgagaacgag agggccgact 900
ggcaggagcc ctcaacatgg tcaagaacgg cattgacgcg ctcattgtca ttggcggaga 960
cggctcgttg accggagccg atctgttccg agaagaatgg ccgtctctaa tcgaggagct 1020
agtcaccaat ggctccatca ccgccgagca ggccgaacga caccgacacc tcgacatttg 1080
cggtatggta ggctccatcg acaacgacat ggctaccacc gacgtcacca ttggtgctta 1140
ctcatcgctc gaccgaatct gcgagctggt agacttcatc gatgccaccg cccagtcgca 1200
ctcgcgagcc tttgtcgtcg aggttatggg tcggcactgt ggctggctgg ctctcatggc 1260
cggcactgct accggcgccg actacatttt tatccccgag gctgctcccg atgctactca 1320
gtgggccgag aagatgaccc gtgtcgtcaa gagacaccga agccagggca agcgaaagac 1380
cgtggtcatt gtcgccgagg gcgcaatcga ctcggacctc aaccccatca ctgccaagat 1440
ggtcaaggat gtgctagacg gcattggact cgatactcga atctccaccc tgggtcacgt 1500
acagcgagga ggtcccccag ttgccgctga tagagttctg gcttcactgc agggtgtgga 1560
ggctatcgac gccatcctgt ctctcacccc agagacgccc agtcccatga ttgctctcaa 1620
cgagaacaaa atcacccgca agccgctcgt ggagtctgta gctctcacca agaaggttgc 1680
cgatgccatt ggcaacaagg actttgccga ggccatgcgg cttcgaaacc ccgagtttgt 1740
ggagcaattg cagggtttcc tgctcacaaa ctctgctgac aaggaccggc cccaggagcc 1800
tgccaaggat cccctgcgag tcgccattgt gtgcactggc gctcctgctg gcggaatgaa 1860
cgctgccatc cgatctgctg ttctgtacgg tcttgctcga ggccaccaaa tgtttgccat 1920
ccacaatgga tggtccggcc tcgtcaagaa tggtgacgac gcggtgcggg agctgacttg 1980
gctcgaggtc gagcccctgt gtcagaaggg tggctgtgag attggtacta accgatctct 2040
gcccgaatgt gatcttggaa tgattgcata ccactttcag cgacaacggt ttgacggtct 2100
aatcgtcatt ggtggttttg aggctttccg agcgctgaat cagctcgacg atgcccgtca 2160
cgcctaccct gctcttcgaa tccccatggt tggtattcct gccaccattt cgaacaacgt 2220
gcctggaacg gactattctc ttggagccga cacttgtctc aactctctgg ttcagtactg 2280
cgacgtgctc aagacgtctg cttctgccac tcgtctgcgt ctgtttgtgg tcgaggtgca 2340
gggtggaaac tctggttaca tcgccaccgt ggctggtttg atcaccggcg cctatgtggt 2400
gtacacaccc gagagcggta tcaacctgcg acttcttcag cacgacattt cctaccttaa 2460
ggatactttt gctcatcagg cggacgtgaa ccgaaccgga aagctgcttc tgcgaaacga 2520
gcggtcatcc aacgtgttca ccactgatgt catcaccggc atcatcaacg aggaggccaa 2580
gggttcattt gacgcgcgaa ccgccatccc tggccatgtg cagcagggag gacacccctc 2640
tcctaccgat cgagtgcgtg ctcagcgatt tgccatcaag gccgtgcagt ttattgaaga 2700
gcaccacggc tccaaaaaca atgccgatca ctgtgtgatt ctcggtgtgc ggggctccaa 2760
gttcaagtac acctctgtgt cgcatctgta cgcccataag actgagcacg gggctcgacg 2820
gcccaagcat tcctactggc acgcgattgg cgacattgcc aacatgctgg tgggtcgaaa 2880
ggcgcctcct ctgcccgaga ctctcaacga cgagattgag aagaacattg cgaaggagca 2940
gggtattatt gatccttgtt agggggtttg gtgttggaaa ttaggatatc tatttgatta 3000
atgtagcttg gttttggaca agaatgctga ttgatacatc cggtatcact tgtatacaac 3060
gt 3062

<210> SEQ ID NO 143
<211> LENGTH: 583
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 143
cgcaaaacag acggacactg aacccccgc gcttcaaaac accgacaatg accactctgg 60
atgacaccgc ttaccgatac cgaacttccg ttcctggcga tgccgaggct attgaggctc 120
tggatggatc tttcaccact gacaccgttt tccgagtgac cgctactggc gacggcttca 180
ccctgcgaga ggtgcctgtc gaccctcctc tcaccaaggt tttccctgac gatgagtcgg 240
acgatgagtc tgacgctgga gaggacggcg accctgactc tcgaactttc gtggcttacg 300
gcgacgatgg agacctggcc ggctttgtgg tcgtttctta ctccggatgg aaccgacgac 360
tgaccgtgga ggacatcgag gtcgctcctg agcaccgagg tcatggtgtc ggacgagctc 420
tgatgggtct cgctactgag ttcgctcgag agcgaggtgc tggccacctg tggctcgagg 480
tcaccaacgt taacgcccct gctattcatg cctaccgacg aatgggtttt accctgtgtg 540
gcctcgatac tgccctgtac gacggaaccg cttccgatgg aga 583

<210> SEQ ID NO 144
<211> LENGTH: 2396

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

```
aacttccgtt cctggcgatg ccgaggctat tgaggctctg gatggatctt tcaccactga     60

caccgttttc cgagtgaccg ctactggcga cggcttcacc ctgcgagagg tgcctgtcga    120

ccctcctctc accaaggttt tccctgacga tgagtcggac gatgagtctg acgctggaga    180

ggacggcgac cctgactctc gaactttcgt ggcttacggc gacgatggag acctggccgg    240

ctttgtggtc gtttcttact ccggatggaa ccgacgactg accgtggagg acatcgaggt    300

cgctcctgag caccgaggtc atggtgtcgg acgagctctg atgggtctcg ctactgagtt    360

cgctcgagag cgaggtgctg gccacctgtg gctcgaggtc accaacgtta acgcccctgc    420

tattcatgcc taccgacgaa tgggttttac cctgtgtggc ctcgatactg ccctgtacga    480

cggaaccgct tccgatggag agcaggccct ctacatgtcg atgccctgcc cttaaacagg    540

ccccttttcc tttgtcgata tcatgtaatt agttatgtca cgcttacatt cacgccctcc    600

tcccacatcc gctctaaccg aaaaggaagg agttagacaa cctgaagtct aggtccctat    660

ttattttttt taatagttat gttagtatta agaacgttat ttatatttca aatttttctt    720

ttttttctgt acaaacgcgt gtacgcatgt aacattatac tgaaaacctt gcttgagaag    780

gttttgggac gctcgaaggc tttaatttgc agagaccggg ttggcggcgc atttgtgtcc    840

caaaaaacag ccccaattgc cccaattgac cccaaattga cccagtagcg ggcccaaccc    900

cggcgagagc ccccttctcc ccacatatca aacctccccc ggttcccaca cttgccgtta    960

agggcgtagg gtactgcagt ctggaatcta cgcttgttca gactttgtac tagtttcttt   1020

gtctggccat ccgggtaacc catgccggac gcaaaataga ctactgaaaa ttttttttgct   1080

ttgtggttgg gactttagcc aagggtataa aagaccaccg tccccgaatt acctttcctc   1140

ttcttttctc tctctccttg tcaactcaca cccgaaatcg ttaagcattt ccttctgagt   1200

ataagaatca ttcaaaatgg cttcttaccc ttgccaccag cacgcttccg cttttgacca   1260

ggccgcccga tcccgaggac actccaaccg acgaaccgct ctgcgacccc gacgacagca   1320

ggaggctacc gaggttcgac tggagcagaa gatgcctact ctgctccgag tgtacatcga   1380

cggaccccac ggtatgggca agaccactac cactcagctg ctcgtcgccc tgggttcgcg   1440

agatgacatt gtttacgtgc ctgagcccat gacctactgg caggttctcg gagcttctga   1500

gactatcgcc aacatctaca ccactcagca tcgactggac cagggagaga tctccgctgg   1560

agatgccgct gtggtcatga cctcggccca gattactatg ggcatgcctt acgctgtcac   1620

cgacgctgtt ctggctcctc acatcggtgg agaggctgga tcttcccatg ctcctcctcc   1680

tgctctgacc ctcatcttcg atcgacaccc tattgccgct ctgctctgtt accccgccgc   1740

tcgatacctg atgggctcta tgacccctca ggccgtgctg gcttttgtcg ccctcatccc   1800

tcccaccctg cctggtacta acattgtgct gggtgctctc cctgaggacc gacatatcga   1860

tcgactcgct aagcgacagc gacctggaga gcgactggac ctcgctatgc tggccgctat   1920

tcgacgagtg tacggcctgc tcgctaacac cgtccgatac ctccagggtg gtggatcgtg   1980

gcgagaggac tggggacagc tgtctggtac cgctgtgcct cctcagggtg ctgagcctca   2040

gtccaacgct ggacctcgac cccacatcgg tgacaccctg ttcactctct ttcgagctcc   2100

tgagctgctc gctcctaacg gcgacctgta caacgtcttc gcctgggctc tggatgttct   2160
```

```
cgccaagcga ctccgaccta tgcacgtctt tattctggac tacgatcagt cgcccgctgg   2220

atgtcgagat gccctgctcc agctcacctc tggcatggtt cagactcatg tgaccactcc   2280

tggatccatc cccaccattt gcgatctggc tcgaactttc gcccgagaga tgggagaggc   2340

caactaaggg gtttggtgtt ggaaattagg atatctattt gattaatgta gcttgg       2396


<210> SEQ ID NO 145
<211> LENGTH: 189
<212> TYPE: PRT
<213> ORGANISM: Streptomyces noursei

<400> SEQUENCE: 145

Met Thr Thr Leu Asp Asp Thr Ala Tyr Arg Tyr Arg Thr Ser Val Pro
1               5                   10                  15

Gly Asp Ala Glu Ala Ile Glu Ala Leu Asp Gly Ser Phe Thr Thr Asp
            20                  25                  30

Thr Val Phe Arg Val Thr Ala Thr Gly Asp Gly Phe Thr Leu Arg Glu
        35                  40                  45

Val Pro Val Asp Pro Pro Leu Thr Lys Val Phe Pro Asp Asp Glu Ser
    50                  55                  60

Asp Asp Glu Ser Asp Ala Gly Glu Asp Gly Asp Pro Asp Ser Arg Thr
65                  70                  75                  80

Phe Val Ala Tyr Gly Asp Asp Gly Asp Leu Ala Gly Phe Val Val Val
                85                  90                  95

Ser Tyr Ser Gly Trp Asn Arg Arg Leu Thr Val Glu Asp Ile Glu Val
            100                 105                 110

Ala Pro Glu His Arg Gly His Gly Val Gly Arg Ala Leu Met Gly Leu
        115                 120                 125

Ala Thr Glu Phe Ala Arg Glu Arg Gly Ala Gly His Leu Trp Leu Glu
    130                 135                 140

Val Thr Asn Val Asn Ala Pro Ala Ile His Ala Tyr Arg Arg Met Gly
145                 150                 155                 160

Phe Thr Leu Cys Gly Leu Asp Thr Ala Leu Tyr Asp Gly Thr Ala Ser
                165                 170                 175

Asp Gly Glu Gln Ala Leu Tyr Met Ser Met Pro Cys Pro
            180                 185


<210> SEQ ID NO 146
<211> LENGTH: 570
<212> TYPE: DNA
<213> ORGANISM: Streptomyces noursei

<400> SEQUENCE: 146

atgaccactc tggatgacac cgcttaccga taccgaactt ccgttcctgg cgatgccgag     60

gctattgagg ctctggatgg atctttcacc actgacaccg ttttccgagt gaccgctact    120

ggcgacggct tcaccctgcg agaggtgcct gtcgaccctc ctctcaccaa ggttttccct    180

gacgatgagt cggacgatga gtctgacgct ggagaggacg gcgaccctga ctctcgaact    240

ttcgtggctt acggcgacga tggagacctg gccggctttg tggtcgtttc ttactccgga    300

tggaaccgac gactgaccgt ggaggacatc gaggtcgctc ctgagcaccg aggtcatggt    360

gtcggacgag ctctgatggg tctcgctact gagttcgctc gagagcgagg tgctggccac    420

ctgtggctcg aggtcaccaa cgttaacgcc cctgctattc atgcctaccg acgaatgggt    480

tttaccctgt gtggcctcga tactgccctg tacgacggaa ccgcttccga tggagagcag    540
```

gccctctaca tgtcgatgcc ctgcccttaa 570

<210> SEQ ID NO 147
<211> LENGTH: 189
<212> TYPE: PRT
<213> ORGANISM: Herpes simplex virus

<400> SEQUENCE: 147

Met Thr Thr Leu Asp Asp Thr Ala Tyr Arg Tyr Arg Thr Ser Val Pro
1 5 10 15

Gly Asp Ala Glu Ala Ile Glu Ala Leu Asp Gly Ser Phe Thr Thr Asp
20 25 30

Thr Val Phe Arg Val Thr Ala Thr Gly Asp Gly Phe Thr Leu Arg Glu
35 40 45

Val Pro Val Asp Pro Pro Leu Thr Lys Val Phe Pro Asp Asp Glu Ser
50 55 60

Asp Asp Glu Ser Asp Ala Gly Glu Asp Gly Asp Pro Asp Ser Arg Thr
65 70 75 80

Phe Val Ala Tyr Gly Asp Asp Gly Asp Leu Ala Gly Phe Val Val Val
85 90 95

Ser Tyr Ser Gly Trp Asn Arg Arg Leu Thr Val Glu Asp Ile Glu Val
100 105 110

Ala Pro Glu His Arg Gly His Gly Val Gly Arg Ala Leu Met Gly Leu
115 120 125

Ala Thr Glu Phe Ala Arg Glu Arg Gly Ala Gly His Leu Trp Leu Glu
130 135 140

Val Thr Asn Val Asn Ala Pro Ala Ile His Ala Tyr Arg Arg Met Gly
145 150 155 160

Phe Thr Leu Cys Gly Leu Asp Thr Ala Leu Tyr Asp Gly Thr Ala Ser
165 170 175

Asp Gly Glu Gln Ala Leu Tyr Met Ser Met Pro Cys Pro
180 185

<210> SEQ ID NO 148
<211> LENGTH: 1131
<212> TYPE: DNA
<213> ORGANISM: Herpes simplex virus

<400> SEQUENCE: 148
atggcttctt acccttgcca ccagcacgct tccgcttttg accaggccgc ccgatcccga 60
ggacactcca accgacgaac cgctctgcga ccccgacgac agcaggaggc taccgaggtt 120
cgactggagc agaagatgcc tactctgctc cgagtgtaca tcgacggacc ccacggtatg 180
ggcaagacca ctaccactca gctgctcgtc gccctgggtt cgcgagatga cattgtttac 240
gtgcctgagc ccatgaccta ctggcaggtt ctcggagctt ctgagactat cgccaacatc 300
tacaccactc agcatcgact ggaccaggga gagatctccg ctggagatgc cgctgtggtc 360
atgacctcgg cccagattac tatgggcatg ccttacgctg tcaccgacgc tgttctggct 420
cctcacatcg gtggagaggc tggatcttcc catgctcctc ctcctgctct gaccctcatc 480
ttcgatcgac accctattgc cgctctgctc tgttaccccg ccgctcgata cctgatgggc 540
tctatgaccc ctcaggccgt gctggctttt gtcgccctca tccctcccac cctgcctggt 600
actaacattg tgctgggtgc tctccctgag gaccgacata tcgatcgact cgctaagcga 660
cagcgacctg gagagcgact ggacctcgct atgctggccg ctattcgacg agtgtacggc 720
ctgctcgcta acaccgtccg atacctccag ggtggtggat cgtggcgaga ggactgggga 780
cagctgtctg gtaccgctgt gcctcctcag ggtgctgagc ctcagtccaa cgctggacct 840
cgaccccaca tcggtgacac cctgttcact ctctttcgag ctcctgagct gctcgctcct 900
aacggcgacc tgtacaacgt cttcgcctgg gctctggatg ttctcgccaa gcgactccga 960
cctatgcacg tctttattct ggactacgat cagtcgcccg ctggatgtcg agatgccctg 1020
ctccagctca cctctggcat ggttcagact catgtgacca ctcctggatc catccccacc 1080
atttgcgatc tggctcgaac tttcgcccga gagatgggag aggccaacta a 1131

<210> SEQ ID NO 149
<211> LENGTH: 68
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
cgcaaaacag acggacactg aaccccccgc gcttcaaaac accgacaatg accactctgg 60
atgacacc 68

<210> SEQ ID NO 150
<211> LENGTH: 72
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
ccaagctaca ttaatcaaat agatatccta atttccaaca ccaaacccct tagttggcct 60
ctcccatctc tc 72

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
aacttccgtt cctggcgatg ccg 23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
tctccatcgg aagcggttcc gtc 23

<210> SEQ ID NO 153
<211> LENGTH: 974
<212> TYPE: PRT
<213> ORGANISM: Arxula adeninivorans

<400> SEQUENCE: 153

Met Gly Lys Ala Lys Leu Val Cys Gly Val Thr Phe Ile Ser Phe Pro
1 5 10 15

```
Thr Ser Asp Gln Asp Leu Tyr Gln Lys Ala Val Asp Phe Tyr Gln Arg
            20                  25                  30

Arg Leu Gly Phe Ser Val Ile Gln Glu Tyr Asp His Thr Ser Met Ser
        35                  40                  45

Val Gly Val Lys Ser Val Ala Ser His Cys Ala Ser Ser Val Arg Glu
    50                  55                  60

Thr Trp Leu Asn Val Leu Pro Asp Asp Ala Gln Gln Ala Leu Glu Thr
65                  70                  75                  80

Ala Ala Pro Gly Thr Thr Ile Lys Ile Arg Leu Thr Pro Asp Gly Pro
                85                  90                  95

Gly Ala Ala Gln Val Glu Ala Lys Ile Asp Ala Val Ile Asp Lys Tyr
            100                 105                 110

Lys Asp Lys Asp Trp Arg Gly Ala Ser Ala Ala Met Val Phe His Thr
        115                 120                 125

Glu Asp Leu Ala Asp Val Lys Ser Asp Leu Gly Asp Tyr Pro Ala Glu
    130                 135                 140

Tyr Leu Ser Gly Val Pro Ser Gly Gln Gln Ala Ala Glu Ala Tyr Val
145                 150                 155                 160

Leu Asp Pro Leu Gly Asn Leu Ile Gly Phe Thr Thr Arg His Asn Pro
                165                 170                 175

Phe Ser Ser His Asp Arg Pro Ala Thr Leu Ser Gly Asp Gly Gln Ser
            180                 185                 190

Thr Ser Gly Gly Ile Gln Gln Asn Ser Ser Ser Ser Val Gly Thr Thr
        195                 200                 205

Gly Val Ala Thr Pro Ala Leu Thr Ser Ser Val Gly Gly Gly Ser Lys
    210                 215                 220

Lys Lys Lys Ile Ala Val Met Thr Ser Gly Gly Asp Ala Pro Gly Met
225                 230                 235                 240

Asn Ala Val Val Arg Ala Val Val Arg Thr Ala Ile Ala Arg Gly Cys
                245                 250                 255

Asp Ala Tyr Ala Val Tyr Glu Gly Tyr Gln Gly Leu Val Thr Gly Gly
            260                 265                 270

Asp Tyr Ile Lys Lys Thr Ser Trp Asp Glu Val Arg Gly Tyr Leu Ala
        275                 280                 285

Leu Gly Gly Thr Lys Ile Gly Thr Ala Arg Cys Lys Glu Phe Arg Glu
    290                 295                 300

Arg Asp Gly Arg Leu Gln Ala Cys Val Asn Met Ile Lys Ala Gly Ile
305                 310                 315                 320

Asp Gly Leu Ile Val Cys Gly Gly Asp Gly Ser Leu Thr Gly Ala Asp
                325                 330                 335

Arg Phe Arg Glu Glu Trp Pro Ser Leu Val Gln Glu Ala Lys Glu Lys
            340                 345                 350

Asn Leu Val Thr Pro Gln Glu Leu Ala Gly His Glu His Leu Tyr Ile
        355                 360                 365

Cys Gly Leu Val Gly Ser Ile Asp Asn Asp Met Ser Asn Thr Asp Ala
    370                 375                 380

Thr Ile Gly Ala Tyr Ser Ser Leu Asp Arg Ile Cys Gln Ala Val Asp
385                 390                 395                 400

Phe Ile Asp Ala Thr Ala Glu Ser His Ser Arg Ala Phe Val Ile Glu
                405                 410                 415

Val Met Gly Arg His Cys Gly Trp Leu Gly Leu Met Ala Gly Leu Ala
            420                 425                 430
```

```
Thr Gly Ala Asp Tyr Ile Phe Ile Pro Glu Arg Pro Pro Ser Lys Asp
        435                 440                 445

Glu Trp Arg Arg Lys Met Ser Asp Val Val Val Arg His Arg Lys Asn
    450                 455                 460

Gly Met Arg Arg Thr Ile Val Ile Val Ala Glu Gly Ala Ile Asp Thr
465                 470                 475                 480

Glu Leu Asn Ala Ile Thr Pro Val Met Val Lys Asp Gln Leu Val Asp
                485                 490                 495

Leu Gly Leu Asp Thr Arg Ile Thr Thr Leu Gly His Val Gln Arg Gly
            500                 505                 510

Gly Thr Ala Val Ala Phe Asp Arg Met Leu Ala Thr Leu Gln Gly Val
        515                 520                 525

Glu Ala Val Asp Ala Ile Leu Thr Ser Thr Pro Glu Thr Pro Ser Pro
    530                 535                 540

Met Ile Gly Leu Thr Glu Asn Lys Val Val Arg Arg Asp Leu Ile Glu
545                 550                 555                 560

Ser Val Lys Leu Thr Gly Ser Val Ala Glu Ala Ile Asn Arg Lys Asp
                565                 570                 575

Phe Asp Gly Ala Met Gly Leu Arg Asp Ser Glu Phe Cys Glu His Leu
            580                 585                 590

Asp Asn Phe Tyr Met Ile Asn Ser Ala Asp Lys Asp Lys Pro Leu Ser
        595                 600                 605

Pro Ala Glu Lys Arg Leu Lys Val Ala Ile Val Cys Ile Gly Ala Pro
    610                 615                 620

Ala Gly Gly Met Asn Ala Ala Ile Arg Ala Ala Ala Cys Tyr Cys Phe
625                 630                 635                 640

Ala Arg Gly His Thr Pro Tyr Ala Ile His Asn Gly Phe Thr Gly Leu
                645                 650                 655

Ser Arg His Glu Ser Val Lys Glu Leu Asn Trp Leu Glu Val Glu Gln
            660                 665                 670

Tyr Gly Asn Gln Gly Gly Cys Glu Ile Gly Thr Asn Arg His Thr Pro
        675                 680                 685

Asp Val Asp Leu Gly Met Val Ala Tyr Tyr Phe Gln Lys Tyr Glu Phe
    690                 695                 700

Asp Gly Leu Val Ile Ile Gly Gly Phe Glu Ala Phe Asn Ser Leu His
705                 710                 715                 720

Ile Leu Ser Glu Ala Arg Lys Ser Tyr Pro Ala Phe Arg Met Pro Met
                725                 730                 735

Val Cys Leu Pro Ala Thr Ile Ser Asn Asn Val Pro Gly Thr Glu Tyr
            740                 745                 750

Ser Leu Gly Thr Asp Thr Cys Leu Asn Ala Leu Val Gln Tyr Cys Asp
        755                 760                 765

Val Ile Lys Gln Ser Ala Ser Ser Thr Arg Arg Arg Ala Phe Val Val
    770                 775                 780

Glu Val Gln Gly Gly Asn Ser Gly Tyr Val Ala Ser Tyr Ala Gly Leu
785                 790                 795                 800

Val Thr Gly Ala His Val Val Tyr Thr Pro Glu Glu Gly Ile Ser Leu
                805                 810                 815

Lys Gln Leu Ser Ala Asp Ile Glu Phe Leu Lys His Gln Phe Ala His
            820                 825                 830

Asp Ser Gly Arg Asn Arg Ala Gly Arg Leu Ile Leu Arg Asn Glu Lys
        835                 840                 845

Ala Ser Lys Thr Phe Asn Thr Asp Val Leu Val Ser Ile Leu Gln Asn
```

```
    850                 855                 860

Glu Gly Gly Ser Gln Phe Glu Ala Arg Glu Ala Ile Pro Gly His Val
865                 870                 875                 880

Gln Gln Gly Gly Thr Pro Ser Pro Met Asp Arg Ala Arg Ala Ala Arg
                885                 890                 895

Phe Ala Val Arg Cys Ile Gln Phe Ile Glu Asp Gln Gln Glu Ile Arg
            900                 905                 910

Ser Lys Pro Thr Pro Asp Gln Asp Ser Met Tyr Ser Val Val Gly Val
        915                 920                 925

Arg Lys Ala Lys Leu Val Tyr Thr Pro Val Arg Glu Leu Trp Asp Phe
    930                 935                 940

Glu Thr Glu Val Thr Ser Arg Arg Pro Asn Lys Ile His Trp Asn Arg
945                 950                 955                 960

Met Ile Thr Ile Ala Asp Met Leu Val Gly Arg Thr Lys Val
                965                 970


<210> SEQ ID NO 154
<211> LENGTH: 2925
<212> TYPE: DNA
<213> ORGANISM: Arxula adeninivorans

<400> SEQUENCE: 154

atgggtaaag caaagctggt gtgtggagtg acgtttattt cgtttcccac gtcggaccag     60

gacctgtacc aaaaggcagt ggacttttac cagcgacggt taggattctc ggtgatccag    120

gagtatgacc atacgtccat gtctgtggga gtcaagtcgg tggcttcgca ttgtgcgtcg    180

tcagttcgag aaacttggct caatgtgctt cccgacgacg ctcagcaggc gttggaaacg    240

gccgctccgg gaactacaat taagatccgc ctgactcctg acggtccagg tgctgcgcag    300

gtagaggcca agattgatgc cgttattgac aagtacaagg acaaggactg gcgaggagct    360

tcggcagcaa tggtattcca taccgaagat ttggctgacg tcaagtctga tttgggcgac    420

tatcctgccg aatacctgtc gggagtgccc agcggacagc aggctgcgga ggcctatgtt    480

ttagaccctc tgggaaacct cattggtttc accactagac acaatccctt ttctagccac    540

gaccgccctg ctactttgtc tggggacggc cagtctactt ctggtggtat tcagcagaat    600

tcttcgtcgt cggttggtac tactggagta gctacccctg ccctcacttc gtccgtcgga    660

ggaggcagca agaagaagaa gattgccgtc atgacctccg gaggtgatgc ccccggaatg    720

aacgctgtag tgcgagcggt agttagaacc gcaattgctc gcggatgcga cgcttacgct    780

gtatacgaag gataccaggg tctagtgacc ggcggcgact atattaaaaa gacttcctgg    840

gacgaagtcc gtggatacct ggctctggga ggtaccaaga ttggaactgc gcgatgcaag    900

gagttccggg aacgcgacgg tcgtctgcag gcgtgcgtca acatgatcaa ggctggaatt    960

gacggtctca ttgtgtgcgg aggagatggt tcgctcactg gtgccgaccg attccgagag   1020

gaatggccta gtttggtcca ggaggccaag gaaaagaacc tggtcacccc ccaggagctc   1080

gcgggccacg aacacttgta catttgcggt ctggtgggtt ccattgacaa cgacatgagt   1140

aacaccgatg ctacaattgg agcgtactct tcgctggacc gaatctgcca ggcagtagac   1200

tttatcgatg ccactgccga gtcccattcg cgagcgtttg tcattgaggt catgggtcga   1260

cactgcggtt ggctgggtct gatggccggt ctggccactg gcgctgacta cattttcatt   1320

cctgagcgtc ctccttccaa ggacgaatgg cgacgcaaga tgagcgatgt agtggtacgt   1380

caccgtaaga acggtatgcg tcgaaccatt gtcattgtag ctgagggtgc tattgacacc   1440
```

```
gagcttaacg ccattactcc tgtcatggtc aaagaccagc tggtggacct cggcctggac   1500

actcgtatca ctaccctggg tcacgtccag cgaggaggaa ccgcagttgc ctttgaccgt   1560

atgctggcta ctctgcaggg tgtggaagct gtggacgcta ttctcacttc tacccccgag   1620

actccctctc ctatgatcgg actgaccgag aacaaggttg tgcgccgaga cctgattgaa   1680

tcggtcaagc tcaccgggtc ggtggcagag gcaattaacc gtaaagactt tgatggcgcc   1740

atgggcctgc gagactctga gttctgcgaa cacctggaca atttctacat gatcaactcg   1800

gccgacaagg acaagcctct aagccctgcc gaaaagagac tcaaggtggc cattgtgtgc   1860

attggagctc ccgcgggagg aatgaacgct gccattcgag ctgctgcatg ctactgtttt   1920

gctcgtggcc acactccata cgccatccac aacggtttca ccggtctgtc tcgccacgag   1980

tcggtcaagg agctcaactg gctcgaggtg gagcagtacg gtaaccaggg aggttgcgag   2040

attggtacca accgtcacac ccccgacgtg gacctgggaa tggtggcata ctacttccag   2100

aagtatgagt ttgacggtct ggtcatcatt ggtggttttg aggcattcaa ctcgctgcat   2160

attctgtccg aggcgcgaaa gtcgtaccct gctttccgca tgccaatggt gtgtctgcct   2220

gccacaattt ctaacaatgt tcccggaaca gagtactctc tgggaaccga cacctgtctc   2280

aacgcgctgg tgcagtactg tgacgtgatc aagcagtctg cttcttctac tcgacgacga   2340

gcgtttgtgg tcgaggtcca gggaggaaac tctggttacg tagcttctta cgctggattg   2400

gttactggag ctcacgttgt gtacactcct gaggagggca tctccctcaa gcagctgtcg   2460

gctgacattg agttcctaaa gcatcagttt gctcacgaca gtggccgcaa ccgagccgga   2520

cgactgattc tgcgcaacga aaaggcttca aagacgttta acactgacgt tttggtgtcc   2580

attctgcaga atgaaggagg cagccagttt gaagctcgcg aggccattcc cggtcacgtc   2640

cagcagggag gtactccttc tcctatggac cgtgctcgtg ctgctcgatt tgctgtgcga   2700

tgtatccaat tcattgagga ccagcaggag attcgatcaa agcctactcc tgaccaggat   2760

tcaatgtact ctgtagtggg agtgcgaaag gcaaagcttg tctacacccc tgtccgggaa   2820

ctgtgggact ttgagaccga ggtcacctct cgccgaccaa acaagattca ctggaaccgc   2880

atgattacca ttgctgacat gcttgttggc cgaaccaagg tataa                    2925
```

<210> SEQ ID NO 155
<211> LENGTH: 754
<212> TYPE: PRT
<213> ORGANISM: Arxula adeninivorans

<400> SEQUENCE: 155

```
Met Glu His Lys Thr Thr Arg Ala Leu Ser Glu Ala Leu Lys Ser Thr
1               5                   10                  15

Leu Ala Pro Pro Pro Ser Gln Ser Gly Asp Gly Glu Val Ser Pro His
            20                  25                  30

Thr Val Pro Ala Ala Gly Tyr Gly Ser Ser Ser Ser Ser Gly Ala Gln
        35                  40                  45

Ser Ser Glu Asn Glu Leu Gln Pro Glu Gly Ala Pro Gly Thr Ser Ser
    50                  55                  60

Ser Phe Asn Arg Arg Pro Pro Ser Asp Thr Pro Leu Phe Ser Pro Arg
65                  70                  75                  80

Ser Ala Ser Asp Leu Ser Arg Ile Pro Ile Thr Gln Pro Ser Ser Ser
                85                  90                  95

Gly Ser Ser Arg Asn Asn Ser His Ser Asn Ser Pro Arg Ser Thr Ser
            100                 105                 110
```

```
Ser Ile Pro Pro Leu His Leu Ser Ser Gln Arg Arg Ala Ala Thr Thr
        115                 120                 125

Leu Asp Val Pro Gly Leu Thr Arg Ser Lys Ile Ser Pro Asp Gly Met
    130                 135                 140

Ile Ala Ala Arg Asp Leu Glu Ser Lys Leu Val Ile Val Met Val Gly
145                 150                 155                 160

Leu Pro Ala Arg Gly Lys Ser Tyr Val Thr Lys Lys Leu Cys Arg Tyr
                165                 170                 175

Leu Asn Trp Gln Gln His Gly Ala Arg Ile Phe Asn Val Gly Asn Thr
            180                 185                 190

Arg Arg Asn Ala Asp Arg Thr Val Gly Pro Ala Ser Arg Pro Leu Pro
        195                 200                 205

Asp Glu Gly Val Ala Leu Ala Ser Pro Glu Gln Glu Ala Gln Ala His
    210                 215                 220

Ala Glu His Glu Ala Lys Ala Leu Glu Ala Glu Met Arg Gly Asp Pro
225                 230                 235                 240

Pro Asp His Thr Asp Ser Ala Asp Phe Phe Ser Pro Asp Asn Ala Gln
                245                 250                 255

Thr Ser Gln Leu Arg Glu Lys Trp Ala Met Asp Thr Leu Asp Glu Leu
            260                 265                 270

Leu Asp Tyr Ile Leu Asn Glu Asn Gly Ser Val Gly Val Leu Asp Ala
        275                 280                 285

Thr Asn Thr Thr Arg Ala Arg Arg Lys Lys Val Leu Asp Arg Ile Arg
    290                 295                 300

Glu Arg Thr Gly Gly Arg Leu Lys Val Leu Phe Leu Glu Ser Ile Cys
305                 310                 315                 320

Thr Arg Ser Asp Ile Ile Asp Ala Asn Ile Arg Leu Lys Leu Ser Gly
                325                 330                 335

Pro Asp Tyr Lys Asp Met Asp Gln Glu Lys Ala Leu Lys Asp Phe Val
            340                 345                 350

Ala Arg Leu His Asn Tyr Glu Lys Val Tyr Glu Thr Ile Ser Asp Glu
        355                 360                 365

Glu Glu Glu Asp Asp Asn Phe Gln Tyr Ile Lys Met Ile Asp Val Gly
    370                 375                 380

Arg Lys Val Val Cys Tyr Asn Ile Gln Gly Phe Leu Ala Gly Gln Ala
385                 390                 395                 400

Val Phe Phe Leu Leu Asn Phe Asn Leu Ala Glu Arg Gln Ile Trp Ile
                405                 410                 415

Thr Arg His Gly Glu Ser Glu Asp Asn Ala Ala Gly Arg Ile Gly Gly
            420                 425                 430

Asp Ala Pro Leu Thr Ala Arg Gly Glu Lys Phe Ala Lys Ala Leu Ala
        435                 440                 445

Arg Phe Met Asp Phe Gln Lys Ser Glu Phe Arg Arg Lys Gln Leu Gln
    450                 455                 460

Lys Phe Thr Asp Arg Val Arg Ile Leu Lys Lys Glu Gly Ser Ala Pro
465                 470                 475                 480

Ser Thr Pro Leu Asn Glu Pro Glu Glu Pro Asn Phe Cys Val Trp Thr
                485                 490                 495

Ser Met Met Lys Arg Ser Val Gln Thr Ala Gln Tyr Met Asp Glu Asp
            500                 505                 510

Met Phe Ala Ile Lys Glu Met Arg Met Leu Asn Glu Leu Gly Ala Gly
        515                 520                 525

Val Cys Glu Gly Met Thr Tyr Glu Glu Ile Ser Gln Thr Tyr Pro Glu
```

```
    530                 535                 540

Glu Tyr Ala Ala Arg Ile Ala Asp Lys Ile Gln Tyr Arg Tyr Pro Gly
545                 550                 555                 560

Ile Gly Gly Glu Ser Tyr Leu Asp Val Ile Asn Arg Leu Arg Pro Val
                565                 570                 575

Ile Val Glu Met Glu Arg Met Glu Asp Asn Ala Leu Ile Ile Ala His
            580                 585                 590

Arg Val Val Ala Arg Val Leu Leu Ala Tyr Phe Met Asn Leu Gly Arg
        595                 600                 605

Asp Ala Ile Gly Asp Leu Asp Val Pro Leu His Thr Leu Tyr Met Leu
    610                 615                 620

Glu Pro Lys Pro Tyr Gly Val Asp Trp Ala Val Tyr Glu Tyr Ser Glu
625                 630                 635                 640

Glu Thr Asp Trp Phe Tyr Arg Val Pro Lys Glu Gln Ile Ser Ala Gln
                645                 650                 655

Ile Gln Arg Leu Gln Arg Glu Ser Ser Gln Lys Arg Ser Asn Arg Gly
            660                 665                 670

Ala Pro Ala Val Ile Gly Thr Gly Thr Ala Leu Gly Ser Thr Lys Glu
        675                 680                 685

Arg Asn Phe Ser Val Val Pro Thr Gln Glu Asp Ala Ala Ala Ala Ser
    690                 695                 700

Ala Ala Asn Asn Ile Ser Gln Leu Ser Leu Gly Ala Ser Ser Ala Pro
705                 710                 715                 720

Ser Ser Arg Val Pro Leu Ala Asn Arg Arg Arg Arg Pro Ser Ala Val
                725                 730                 735

Asp Asp Ile Gln Val Lys Gln Ala Asp Tyr His Asp Trp Glu Thr Ala
            740                 745                 750

Ala His


<210> SEQ ID NO 156
<211> LENGTH: 2265
<212> TYPE: DNA
<213> ORGANISM: Arxula adeninivorans

<400> SEQUENCE: 156

atggagcaca agactactag agcgctatca gaagcattga aatcgacgct ggctcctccg      60

ccttctcaaa gtggcgatgg cgaagtgagc ccacacacgg tgccggcggc tgggtatggc     120

agctccagtt ctagtggagc gcagtcttcc gaaaatgaat tacagccaga aggagctcct     180

ggtaccagtt catcgtttaa ccgacggccg ccttccgaca ccccgctgtt ttcgcctcga     240

agcgcgtctg acttgtcccg aatccccatc acacagccat ctagttcggg gtcctctaga     300

aacaattccc attcaaactc ccccagaagt acttccagca ttcctccttt gcatctttca     360

tcccagcgta gggccgccac cactctagat gtgcctgggc tgacccgatc caagatctcc     420

cccgatggta tgatcgcggc aagagacttg gagtccaagc tagtaattgt aatggtaggc     480

cttccggcac gaggaaagtc gtatgtgaca aagaaactgt gccgatacct caactggcag     540

cagcatggcg cacgcatctt caatgttggc aacacccgtc gtaacgcaga ccgtacagta     600

ggtccagcat cccgccccct tcctgatgag ggcgtagcat tagcatcgcc agagcaagaa     660

gcgcaggcgc atgccgagca cgaggcaaag gctttggagg ctgaaatgag aggcgatcct     720

cctgatcata ctgactcggc cgactttttc agccctgaca acgctcagac ttcgcaattg     780

cgggagaagt gggcaatgga tactctagac gaattgcttg actatattct aaatgagaat     840
```

ggctcggttg gagtgctgga cgctaccaac accacccgtg ctcgacgaaa gaaggtgctg 900
gaccgaattc gtgaacgcac cggaggccga ctcaaggttc tgtttctgga gtccatttgc 960
actcgctcgg atataatcga tgcaaacatt cgtctcaagc tgtcgggtcc cgattacaaa 1020
gatatggacc aggagaaggc cctcaaggac ttcgtggctc gtctccacaa ctacgaaaag 1080
gtctacgaga ctattagcga cgaagaggaa gaggacgaca actttcaata tattaagatg 1140
attgacgtag gtcgcaaggt ggtgtgttac aacatccagg gattccttgc tggccaggca 1200
gtctttttcc tgctcaactt taacctggcc gagcgacaga tctggattac ccgtcatgga 1260
gagagtgaag ataatgccgc cggtcgaatt ggcggtgacg cacctctcac tgctcgagga 1320
gaaaagtttg caaaggccct ggctcgattc atggactttc agaagagcga attccgaaga 1380
aagcagctgc aaaagttcac cgaccgggtc cgaatactca agaaggaagg gtcggcacca 1440
tctactcctc ttaacgagcc tgaagagcca aacttctgcg tgtggacttc aatgatgaag 1500
agaagtgtgc agaccgctca atatatggac gaggacatgt ttgccatcaa ggagatgcgt 1560
atgctcaatg agcttggtgc gggagtgtgc gaaggaatga cttacgaaga gatttcccag 1620
acctaccctg aagagtacgc ggcaagaatc gctgacaaga ttcagtacag gtatccaggc 1680
attggcggag agtcctatct cgacgttatc aaccgactgc gtccagtgat tgtggagatg 1740
gagcgaatgg aggataatgc tctgatcatt gcccatagag tggtggccag ggttctgtta 1800
gcatacttta tgaacctggg ccgcgatgcc attggcgacc tagatgtgcc tcttcacacc 1860
ctgtacatgc tagaacccaa gccatatgga gtggattggg ccgtttatga atacagcgaa 1920
gaaaccgact ggttctacag agtgccaaag gagcaaatct ctgcccagat ccaacgtctc 1980
cagcgcgaga gttctcaaaa gagatccaat agaggcgccc ctgccgtcat tggcactggt 2040
actgctttag gatcaacaaa ggagagaaac ttcagtgttg ttcctaccca ggaggatgct 2100
gctgctgcat ctgccgccaa caacatatcg cagctctctc tcggtgcttc ctctgcacct 2160
tcatcaagag taccgctggc taaccgacgc aggcggccaa gcgctgtcga cgacattcaa 2220
gtcaaacaag ccgattatca tgactgggag acggccgccc actaa 2265

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
tcctaacagc tcgcaccgac 20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
gggtcaatgg cgtacagctc 20

<210> SEQ ID NO 159
<211> LENGTH: 822
<212> TYPE: DNA
<213> ORGANISM: Saccharomyces cerevisiae

<400> SEQUENCE: 159
gatccaactg gcaccgctgg cttgaacaac aataccagcc ttccaacttc tgtaaataac 60
ggcggtacgc cagtgccacc agtaccgtta cctttcggta tacctccttt ccccatgttt 120
ccaatgccct tcatgcctcc aacggctact atcacaaatc ctcatcaagc tgacgcaagc 180
cctaagaaat gaataacaat actgacagta ctaaataatt gcctacttgg cttcacatac 240
gttgcatacg tcgatataga taataatgat aatgacagca ggattatcgt aatacgtaat 300
agttgaaaat ctcaaaaatg tgtgggtcat tacgtaaata atgataggaa tgggattctt 360
ctatttttcc tttttccatt ctagcagccg tcgggaaaac gtggcatcct ctctttcggg 420
ctcaattgga gtcacgctgc cgtgagcatc ctctctttcc atatctaaca actgagcacg 480
taaccaatgg aaaagcatga gcttagcgtt gctccaaaaa agtattggat ggttaatacc 540
atttgtctgt tctcttctga ctttgactcc tcaaaaaaaa aaaatctaca atcaacagat 600
cgcttcaatt acgccctcac aaaaactttt ttccttcttc ttcgcccacg ttaaatttta 660
tccctcatgt tgtctaacgg atttctgcac ttgatttatt ataaaaagac aaagacataa 720
tacttctcta tcaatttcag ttattgttct tccttgcgtt attcttctgt tcttcttttt 780
cttttgtcat atataaccat aaccaagtaa tacatattca aa 822

<210> SEQ ID NO 160
<211> LENGTH: 999
<212> TYPE: DNA
<213> ORGANISM: Yarrowia lipolytica

<400> SEQUENCE: 160
gagtttggcg cccgtttttt cgagccccac acgtttcggt gagtatgagc ggcggcagat 60
tcgagcgttt ccggtttccg cggctggacg agagcccatg atgggggctc ccaccaccag 120
caatcagggc cctgattaca cacccacctg taatgtcatg ctgttcatcg tggttaatgc 180
tgctgtgtgc tgtgtgtgtg tgttgtttgg cgctcattgt tgcgttatgc agcgtacacc 240
acaatattgg aagcttatta gcctttctat tttttcgttt gcaaggctta acaacattgc 300
tgtggagagg gatggggata tggaggccgc tggagggagt cggagaggcg ttttggagcg 360
gcttggcctg gcgcccagct cgcgaaacgc acctaggacc ctttggcacg ccgaaatgtg 420
ccacttttca gtctagtaac gccttaccta cgtcattcca tgcatgcatg tttgcgcctt 480
ttttcccttg cccttgatcg ccacacagta cagtgcactg tacagtggag gttttggggg 540
ggtcttagat gggagctaaa agcggcctag cggtacacta gtgggattgt atggagtggc 600
atggagccta ggtggagcct gacaggacgc acgaccggct agcccgtgac agacgatggg 660
tggctcctgt tgtccaccgc gtacaaatgt ttgggccaaa gtcttgtcag ccttgcttgc 720
gaacctaatt cccaattttg tcacttcgca cccccattga tcgagcccta acccctgccc 780
atcaggcaat ccaattaagc tcgcattgtc tgccttgttt agtttggctc ctgcccgttt 840
cggcgtccac ttgcacaaac acaaacaagc attatatata aggctcgtct ctccctccca 900
accacactca cttttttgcc cgtcttccct tgctaacaca aaagtcaaga acacaaacaa 960
ccaccccaac ccccttacac acaagacata tctacagca 999

<210> SEQ ID NO 161
<211> LENGTH: 412
<212> TYPE: DNA
<213> ORGANISM: Saccharomyces cerevisiae

<400> SEQUENCE: 161
atagcttcaa aatgtttcta ctcctttttt actcttccag attttctcgg actccgcgca 60
tcgccgtacc acttcaaaac acccaagcac agcatactaa atttcccctc tttcttcctc 120
tagggtgtcg ttaattaccc gtactaaagg tttggaaaag aaaaaagaga ccgcctcgtt 180
tctttttctt cgtcgaaaaa ggcaataaaa atttttatca cgtttctttt tcttgaaaat 240
tttttttttt gatttttttc tctttcgatg acctcccatt gatatttaag ttaataaacg 300
gtcttcaatt tctcaagttt cagtttcatt tttcttgttc tattacaact ttttttactt 360
cttgctcatt agaaagaaag catagcaatc taatctaagt tttaattaca aa 412

<210> SEQ ID NO 162
<211> LENGTH: 406
<212> TYPE: DNA
<213> ORGANISM: Yarrowia lipolytica

<400> SEQUENCE: 162
agagaccggg ttggcggcgc atttgtgtcc caaaaaacag ccccaattgc cccaattgac 60
cccaaattga cccagtagcg ggcccaaccc cggcgagagc ccccttctcc ccacatatca 120
aacctccccc ggttcccaca cttgccgtta agggcgtagg gtactgcagt ctggaatcta 180
cgcttgttca gactttgtac tagtttcttt gtctggccat ccgggtaacc catgccggac 240
gcaaaataga ctactgaaaa tttttttgct ttgtggttgg gactttagcc aagggtataa 300
aagaccaccg tccccgaatt acctttcctc ttcttttctc tctctccttg tcaactcaca 360
cccgaaatcg ttaagcattt ccttctgagt ataagaatca ttcaaa 406

<210> SEQ ID NO 163
<211> LENGTH: 205
<212> TYPE: DNA
<213> ORGANISM: Saccharomyces cerevisiae

<400> SEQUENCE: 163
gttaattcaa attaattgat atagtttttt aatgagtatt gaatctgttt agaaataatg 60
gaatattatt tttatttatt tatttatatt attggtcggc tcttttcttc tgaaggtcaa 120
tgacaaaatg atatgaagga aataatgatt tctaaaattt tacaacgtaa gatattttta 180
caaaagccta gctcatcttt tgtca 205

<210> SEQ ID NO 164
<211> LENGTH: 300
<212> TYPE: DNA
<213> ORGANISM: Yarrowia lipolytica

<400> SEQUENCE: 164
gcgtctacaa ctggaccctt agcctgtata tatcaattga ttatttaaag atttggtcgg 60
taggcggttc gtattgtaca atgggatctg ttactgaggt ggatctaccc aacttgcgag 120
attcaattgc gagattcaat cgcgagattc aattgcgaga atcagttgcg agttgttcta 180
acactcagct tctacgagcg cttgtattag gacgagtgat actccgtggg gcgacggctt 240
ctcttgcgtc ttctgttgta ttctttctta cactatcgtc catctccaac cacctcgtac 300

<210> SEQ ID NO 165
<211> LENGTH: 300
<212> TYPE: DNA
<213> ORGANISM: Saccharomyces cerevisiae

<400> SEQUENCE: 165

-continued

```
gcgtctacaa ctggaccctt agcctgtata tatcaattga ttatttaaag atttggtcgg     60

taggcggttc gtattgtaca atgggatctg ttactgaggt ggatctaccc aacttgcgag    120

attcaattgc gagattcaat cgcgagattc aattgcgaga atcagttgcg agttgttcta    180

acactcagct tctacgagcg cttgtattag gacgagtgat actccgtggg gcgacggctt    240

ctcttgcgtc ttctgttgta ttctttctta cactatcgtc catctccaac cacctcgtac    300


<210> SEQ ID NO 166
<211> LENGTH: 400
<212> TYPE: DNA
<213> ORGANISM: Yarrowia lipolytica

<400> SEQUENCE: 166

gctgcttgta cctagtgcaa ccccagtttg ttaaaaatta gtagtcaaaa acttctgagt     60

tagaaatttg tgagtgtagt gagattgtag agtatcatgt gtgtccgtaa gtgaagtgtt    120

attgactctt agttagttta tctagtactc gtttagttga cactgatcta gtattttacg    180

aggcgtatga ctttagccaa gtgttgtact tagtcttctc tccaaacatg agagggctct    240

gtcactcagt cggcctatgg gtgagatggc ttggtgagat ctttcgatag tctcgtcaag    300

atggtaggat gatgggggaa tacattactg ctctcgtcaa ggaaaccaca atcagatcac    360

accatcctcc atggtatccg atgactctct tctccacagt                          400
```